United States Patent
Takayanagi et al.

(10) Patent No.: US 10,550,181 B2
(45) Date of Patent: Feb. 4, 2020

(54) ANTI-TIM-3 ANTIBODY

(71) Applicants: KYOWA HAKKO KIRIN CO., LTD, Tokyo (JP); KYUSHU UNIVERSITY, NATIONAL UNIVERSITY CORPORATION, Fukuoka-shi, Fukuoka (JP)

(72) Inventors: Shin-ichiro Takayanagi, Tokyo (JP); Hitomi Tomura, Takasaki (JP); Tomonori Tawara, Tokyo (JP); Yoshimasa Inagaki, Tokyo (JP); Tsuguo Kubota, Tokyo (JP); Koichi Akashi, Fukuoka (JP); Yoshikane Kikushige, Fukuoka (JP)

(73) Assignees: KYOWA KIRIN CO., LTD, Tokyo (JP); Kyushu University, National University Corporation, Fukuoka-shi, Fukuoka (JP)

( * ) Notice: Subject to any disclaimer, the term of this patent is extended or adjusted under 35 U.S.C. 154(b) by 336 days.

(21) Appl. No.: 15/374,265

(22) Filed: Dec. 9, 2016

(65) Prior Publication Data
US 2017/0088616 A1 Mar. 30, 2017

Related U.S. Application Data

(60) Division of application No. 14/019,020, filed on Sep. 5, 2013, now Pat. No. 9,556,270, which is a continuation of application No. 13/158,622, filed on Jun. 13, 2011, now Pat. No. 8,552,156.

(60) Provisional application No. 61/353,836, filed on Jun. 11, 2010.

(51) Int. Cl.
| C07H 21/04 | (2006.01) |
| C12P 21/06 | (2006.01) |
| C12N 15/87 | (2006.01) |
| C12N 1/20 | (2006.01) |
| C12N 15/74 | (2006.01) |
| C07K 16/28 | (2006.01) |
| G01N 33/569 | (2006.01) |

(52) U.S. Cl.
CPC ... *C07K 16/2803* (2013.01); *G01N 33/56972* (2013.01); *C07K 2317/14* (2013.01); *C07K 2317/21* (2013.01); *C07K 2317/24* (2013.01); *C07K 2317/33* (2013.01); *C07K 2317/34* (2013.01); *C07K 2317/56* (2013.01); *C07K 2317/565* (2013.01); *C07K 2317/732* (2013.01); *C07K 2317/92* (2013.01)

(58) Field of Classification Search
None
See application file for complete search history.

(56) References Cited

U.S. PATENT DOCUMENTS

| 5,530,101 A * | 6/1996 | Queen | C07K 16/00 424/133.1 |
| 8,552,156 B2 | 10/2013 | Takayanagi et al. | |
| 2003/0115614 A1 | 6/2003 | Kanda et al. | |
| 2004/0005322 A1 | 1/2004 | Kuchroo et al. | |
| 2005/0262593 A1 | 11/2005 | Kanda et al. | |
| 2005/0272916 A1 | 12/2005 | Hanai et al. | |
| 2005/0276756 A1 | 12/2005 | Hoo et al. | |
| 2005/0276805 A1 | 12/2005 | Hanai et al. | |
| 2006/0024800 A1 | 2/2006 | Hanai et al. | |
| 2006/0063254 A1 | 3/2006 | Kanda et al. | |
| 2006/0064781 A1 | 3/2006 | Kanda et al. | |
| 2006/0078990 A1 | 4/2006 | Kanda et al. | |
| 2006/0078991 A1 | 4/2006 | Kanda et al. | |
| 2007/0010009 A1 | 1/2007 | Kanda et al. | |
| 2007/0166300 A1 | 7/2007 | Hanai et al. | |
| 2007/0166301 A1 | 7/2007 | Hanai et al. | |
| 2007/0166302 A1 | 7/2007 | Hanai et al. | |
| 2007/0166303 A1 | 7/2007 | Hanai et al. | |
| 2007/0166304 A1 | 7/2007 | Hanai et al. | |
| 2007/0166305 A1 | 7/2007 | Hanai et al. | |
| 2007/0207151 A1 | 9/2007 | Hanai et al. | |
| 2008/0177043 A1 | 7/2008 | Hanai et al. | |

(Continued)

FOREIGN PATENT DOCUMENTS

| CN | 101035561 A | 9/2007 |
| EP | 2417984 A1 | 2/2012 |

(Continued)

OTHER PUBLICATIONS

Golden-Mason et al. Negative Immune Regulator Tim-3 Is Overexpressed on T Cells in Hepatitis C Virus Infection and Its Blockade Rescues Dysfunctional CD4+ and CD8+ T Cells. Journal of Virology, Sep. 2009, p. 9122-9130 (Year: 2009).*

(Continued)

Primary Examiner — Maher M Haddad
(74) Attorney, Agent, or Firm — Sughrue Mion, PLLC

(57) ABSTRACT

Disclosed are an anti-human TIM-3 antibody having high ADCC activity or antibody fragment thereof by screening a monoclonal antibody or antibody fragment thereof which binds to the amino acid sequence of the extracellular region of TIM-3 or its three-dimensional structure and exhibits ADCC activity; a hybridoma which produces the antibody; a DNA encoding the antibody; a vector comprising the DNA; a transformant which is obtainable by introducing the vector; a method for producing the antibody or the antibody fragment thereof which comprises using the hybridoma or the transformant; and a therapeutic agent and a diagnostic agent comprising the antibody or the antibody fragment thereof as an active ingredient.

14 Claims, 2 Drawing Sheets

Specification includes a Sequence Listing.

(56) References Cited

U.S. PATENT DOCUMENTS

| | | | |
|---|---|---|---|
| 2008/0227196 | A1 | 9/2008 | Kanda et al. |
| 2008/0261301 | A1 | 10/2008 | Kanda et al. |
| 2009/0110687 | A1 | 4/2009 | Kuchroo et al. |
| 2009/0191199 | A1 | 7/2009 | Kanda et al. |
| 2009/0191592 | A1 | 7/2009 | Kanda et al. |
| 2009/0228994 | A1 | 9/2009 | Kanda et al. |
| 2010/0061992 | A1 | 3/2010 | Anderson et al. |
| 2010/0143388 | A1 | 6/2010 | Kanda et al. |
| 2010/0196371 | A1 | 8/2010 | Hanai et al. |
| 2011/0027271 | A1 | 2/2011 | Kanda et al. |
| 2011/0052610 | A1 | 3/2011 | Kanda et al. |
| 2011/0059115 | A1 | 3/2011 | Kanda et al. |
| 2011/0250643 | A1 | 10/2011 | Kanda et al. |
| 2012/0100131 | A1 | 4/2012 | Takanyagi et al. |

FOREIGN PATENT DOCUMENTS

| | | | |
|---|---|---|---|
| JP | 2005-526018 | A | 9/2005 |
| JP | 2007-530560 | A | 11/2007 |
| JP | 2010-510223 | A | 4/2010 |
| WO | 00/061739 | A1 | 10/2000 |
| WO | 02-031140 | A1 | 4/2002 |
| WO | 03/063792 | A2 | 8/2003 |
| WO | 2008/060617 | A2 | 5/2008 |
| WO | 2010-117057 | A1 | 10/2010 |

OTHER PUBLICATIONS

Darnell et al. Molecular Cell Biology. New York: W H Freeman & Co; pp. 248-255,1986. (Year: 1986).*
Orlandi et al. Cloning immunoglobulin variable domains for expression by the polymerase chain reaction. Proc. Natl. Acad. Sci. USA, 86:3833-3837, 1989 (Year: 1989).*
Lucy Golden-Mason et al. "Negative Immune Regulator Tim-3 Is Overexpressed on T Cells in Hepatitis C Virus Infection and Its Blockade Rescues Dysfunctional CD4 +and CD8+ T Cells", Journal of Virology vol. 83, No. 18, Sep. 2009, (pp. 9122-9130).
Canadian Patent Office; Communication dated Mar. 16, 2018 in counterpart application No. 2,814,155.
Lawrence P. Kane "T Cell Ig and Mucin Domain Proteins and Immunity" The Journal of Immunology, vol. 184, Mar. 15, 2010, (pp. 2743-2749).
Ravindra Majeti; et al.; "Dysregulated gene expression networks in human acute myelogenous leukemia stem cells"; PNAS; Mar. 3, 2009; vol. 106 No. 9; pp. 3396-3401.
Shigeru Iida; et al.; "Nonfucosylated Therapeutic IgG1 Antibody can evade the Inhibitory Effect of Serum Immunoglobin G on Antibody-Dependent Cellular Cytotoxicity through its High Binding to FcyRIIIa";Clin Cacer Res; 2006; vol. 12 No. 9; pp. 2879-2887.
Ana Anderson; "Promotion of tissue Inflammation by the Immune Receptor Tim-3 Expressed on Innate Immune Cells"; Science; Nov. 16, 2007; vol. 318; pp. 1141-1143.
Atsuki Fukushima, et al.; "Antibodies to T-cell Ig and mucin domain-containing proteins (Tim)-1 and -3 suppress the induction and progression of murine allergic conjunctivitis"; Biochemical and Biophysical Research Communications (BBRC); 2007; vol. 353; pp. 211-216.
Ying Ju, et al.; "T Cell immunoglobulin- and mucin-domain-containing molecule-3(TIM-3) mediates natural killer cell suppression in chronic hepatitis B"; European Association for the Study of the Liver, Journal of Hepatology; 2010; vol. 52; pp. 322-329.
William Hastings. et al.; "Tlim-3 is Expressed on Activated Human CD4+ T Cells and Regulates Th1 and Th17 Cytokines"; NIH Public Access; Sep. 2009; vol. 39 No. 9; pp. 2492-2501.
International Searching Authority, International Search Report (PCT/ISA/210) dated Sep. 13, 2011, in corresponding PCT Application No. PCT/JP2011/063396.
The European Patent Office, Extended European Search Report dated Nov. 27, 2013, issued in counterpart European Application No. 11792564.4.
Shitara, Kenya, "Potelligent Antibodies as Next Generation Therapeutic Antibodies," Yakugaku Zasshi vol. 129, No. 1, Jan. 1, 2009, The Pharmaceutical Society of Japan, pp. 3-9.
Hafler, David A. et al, "TIMs: central regulators of immune responses," Journal of Experimental Medicine, Rockefeller University Press, vol. 205, No. 12, Nov. 17, 2008, pp. 2699-2701.
Kikushige, Yoshikane et al, "TIM-3 Is a Promising Target to Selectively Kill Acute Myeloid Leukemia Stem Cells," Cell Stem Cell, Elsevier, Cell Press, vol. 7, No. 6, Oct. 6, 2010, pp. 708-717.
Kikushige, Yoshikane et al, "Leukemogenic Function of TIM-3, a Leukemia Stem Cell Marker, in Acute Myelogenous Leukemia and Myelodysplastic Syndromes," Blood (ASH Annual Meeting Abstracts) 2012, vol. 120, No. 21, Nov. 2012, pp. 1-2.
Kikushige, Yoshikane et al, "TIM-3 as a therapeutic target for malignant stem cells in acute myelogenous leukemia," Annals of the New York Academy of Sciences, Issue: Hematopoietic Stem Cells VIII, vol. 1266, No. 1, Aug. 17, 2012, pp. 118-123.
The State Intellectual Property Office of the People'S Republic of China, Communication dated Jun. 24, 2014 issued in counterpart Chinese Patent Application No. 201180028878.0.

\* cited by examiner

Fig. 1

```
                         1          2          3          4          5          6
                1234567890 1234567890 1234567890 1234567890 1234567890 1234567890
8213 antibody HV0   QVQLVQSGAE VKKPGASVKV SCKASGYTFT SYWMHWVRQA PGQGLEWMGE INPSNGRTNY
8213 antibody HV3                                              K
8213 antibody HV4                                              K          I
8213 antibody HV5                                              K R        I
8213 antibody HV6              V                                          I
8213 antibody HV7                                                         I
8213 antibody HV8              L                               K          I
8213 antibody HV10             V                               K R        I
8213 antibody HV12             V                               K R        I
```

```
                         7          8          9         10         11
                1234567890 1234567890 1234567890 1234567890 1234567890 1234567
8213 antibody HV0   NEKFKTRVTI TADTSTSTAY MELSSLRSED TAVYYCARGY YLYFDYWGQG TLVTVSS
8213 antibody HV3
8213 antibody HV4       K          K
8213 antibody HV5       K
8213 antibody HV6       KA        V K                  G
8213 antibody HV7       K         V K                  G
8213 antibody HV8       A L       V                    G
8213 antibody HV10      KA L      V K                  G                    L
8213 antibody HV12      KA L      V K                  G
```

Fig. 2

```
                    1          2          3          4          5          6
               1234567890 1234567890 1234567890 1234567890 1234567890 1234567890
8213 antibody LV0   DIQMTQSPSS LSASVGDRVT ITCHASQGIR INIGWYQQKP GKAPKLLIYH GTNLEDGVPS
8213 antibody LV2                                         L          F
8213 antibody LV4              L                                     G
8213 antibody LV5                                         L         SF G
8213 antibody LV6              L                          L          F G
8213 antibody LV7            M L                          L          F G
8213 antibody LV9          M V L                          L         SF G 7          8          9         10
               1234567890 1234567890 1234567890 1234567
8213 antibody LV0   RFSGSGSGTD FTLTISSLQP EDFATYYCVQ YGQFPWTFGQ GTKLEIK
8213 antibody LV2
8213 antibody LV4            Y
8213 antibody LV5                      D
8213 antibody LV6            Y         D
8213 antibody LV7            Y         D
8213 antibody LV9            Y         D
```

ANTI-TIM-3 ANTIBODY

CROSS-REFERENCE TO RELATED APPLICATIONS

This application is a divisional of U.S. patent application Ser. No. 14/019,020, filed on Sep. 5, 2013 (now U.S. Pat. No. 9,556,270, issued Jan. 31, 2017), which is a continuation of U.S. patent application Ser. No. 13/158,622 (issued as U.S. Pat. No. 8,552,156), filed on Jun. 13, 2011, which claims the benefit of U.S. Provisional Application No. 61/353,836, filed on Jun. 11, 2010, the disclosures of which are incorporated herein in their entirety by reference.

BACKGROUND OF THE INVENTION

1. Field of the Invention

The present invention relates to a monoclonal antibody or an antibody fragment thereof, which binds to the extracellular region of T-cell immunoglobulin and mucin domain containing molecule-3 (hereinafter referred to as "TIM-3") and exhibits antibody-dependent cellular cytotoxicity (hereinafter referred to as "ADCC"); a hybridoma which produces the antibody; a DNA which encodes the antibody; a vector which comprises the DNA; a transformant obtained by transforming the vector; a process for producing an antibody or an antibody fragment thereof using the hybridoma or the transformant; and a diagnostic agent or a therapeutic agent using the antibody or the antibody fragment thereof.

2. Brief Description of the Background Art

TIM-3 gene family consists of eight genes in mouse and three genes in human, and each of these genes are located at chromosome 11 and at chromosome 5q33 respectively (Non-patent Document 1). These gene regions are known to be related with autoimmune diseases and allergic diseases. TIM protein is a type I transmembrane protein having a structurally conserved immunoglobulin variable (IgV) domain and a mucin domain.

TIM protein was considered to be specifically expressed on T cells and directly regulate the T cell activity, but there are recent reports on expression of TIM-3 protein in antigen-presenting cells and on their functions (Non-patent Document 2). According to the crystal structure analysis, the TIM protein has a conserved protein structure and has a ligand binding site in the IgV domain.

TIM-3 was identified as a molecule specifically expressed on mouse Th1 cells but not on Th2 cells (Non-patent Document 3). The DNA sequence, the amino acid sequence and the three-dimensional structure of TIM-3 is available in the public data base such as the GenBank accession number NM_032782 and NM_134250. TIM-3 is also known as HAVCR2.

In humans, as similar to mice, TIM-3 is expressed on T-cells as well as phagocytic cells such as macrophages and dendritic cells. Binding of TIM-3 to a protein ligand (e.g., galectin-9) can inhibit the Th1 response via mechanism of apoptosis induction, and therefore lead to such as induction of peripheral tolerance.

The reduction in expression of human TIM-3 with siRNA or the inhibition of human TIM-3 by blocking-antibody increased the secretion of interferon γ (IFN-γ) from CD4 positive T-cells, supporting the inhibitory role of TIM-3 in human T cells. In phagocytes, TIM-3 also functions as a receptor for recognizing the apoptosis cells.

Analysis of clinical samples from autoimmune disease patients showed no expression of TIM-3 in CD4 positive cells. In particular, in T cell clones derived from the cerebrospinal fluid of patients with multiple sclerosis, the expression level of TIM-3 was lower and the secretion level of IFN-γ was higher than those of clones derived from normal healthy persons (Non-patent Document 4). There are reports on relation of TIM-3 with allergic diseases or asthma (Patent Documents 1 and 2).

According to the microarray analysis of hematopoietic stem cells from acute myeloid leukemia (hereinafter referred to as "AML") patients and normal hematopoietic stem cells, TIM-3 is expressed on AML stem cells and therefore the analysis suggested involvement of TIM-3 in hematological malignancy (Non-patent Document 5 and Patent Document 3).

Examples of the anti-TIM-3 monoclonal antibodies which were established up to now include anti-human TIM-3 rat monoclonal antibody (Clone 344823, manufactured by R&D Systems) and anti-human TIM-3 mouse monoclonal antibody (Clone F38-2E2, manufactured by R&D Systems).

CITATION LIST

Patent Literature

[Patent Literature 1] WO96/27603
[Patent Literature 2] WO2003/063792
[Patent Literature 3] WO2009/091547

Non-Patent Literature

[Non-Patent Literature 1] Hafler D A et al., *J Exp Med.* 205: 2699-701 (2008)
[Non-Patent Literature 2] Anderson A C et al., *Science* 318: 1141-3 (2007)
[Non-Patent Literature 3] Monney L et al., *Nature* 415: 536-41 (2002)
[Non-Patent Literature 4] Koguchi K et al., *J Exp Med.* 203: 1413-8 (2006)
[Non-Patent Literature 5] Majeti R et al., *Proc Natl Acad Sci USA* 2009 March 3; 106 (9): 3396-401.

SUMMARY OF THE INVENTION

However, there is no report on monoclonal antibody against human TIM-3 having ADCC activity. Therefore, the object of the present invention is to provide a monoclonal antibody or an antibody fragment which binds to the amino acid sequence or the three-dimensional structure of the extracellular region of TIM-3 and expresses ADCC activity. In addition, the object of the present invention is to provide an anti-human TIM-3 antibody having high ADCC activity by screening an anti-human TIM-3 antibody which competes with the monoclonal antibody or the antibody fragment thereof.

In addition, the present invention is to provide a hybridoma which produces the antibody; a DNA which encodes the antibody; a vector which comprises the DNA; a transformant obtained by transforming the vector; a process for producing an antibody or an antibody fragment thereof using the hybridoma or the transformant; and a diagnostic agent or a therapeutic agent using the antibody or the antibody fragment thereof as an active ingredient.

The monoclonal antibody or the antibody fragment of the present invention specifically recognizes the amino acid sequence or the three-dimensional structure of the extracellular region of human TIM-3, and binds to the extracellular region. The amino acid sequence or the three-dimensional structure of the extracellular region of human TIM-3 which is recognized by the monoclonal antibody or the antibody fragment of the present invention is different from those recognized by known anti-TIM-3 monoclonal antibodies. Therefore, the monoclonal antibody or the antibody fragment of the present invention has higher ADCC activity. The monoclonal antibody or the antibody fragment of the present invention which specifically binds to the extracellular region of human TIM-3 and has higher ADCC activity is useful as a therapeutic agent and a diagnostic agent for a disease relating to a human TIM-3 positive cell.

The present invention may provide a hybridoma which produces the antibody; a DNA which encodes the antibody; a vector which comprises the DNA; a transformant obtained by transforming the vector; a process for producing an antibody or an antibody fragment thereof using the hybridoma or the transformant; and a diagnostic agent or a therapeutic agent using the antibody or the antibody fragment thereof.

BRIEF DESCRIPTION OF THE DRAWINGS

FIG. 1 is the amino acid sequences which represent HV0, HV3, HV4, HV5, HV6, HV7, HV8, HV10, and HV12 of the designed H chain variable regions of antibody 8213, respectively.

FIG. 2 is the amino acid sequences which represent LV0, LV2, LV4, LV5, LV6, LV7, and LV9 of the designed L chain variable regions of antibody 8213.

DETAILED DESCRIPTION OF THE INVENTION

The gist of the present invention relates to the followings.

(1) A monoclonal antibody or an antibody fragment thereof, which binds to an extracellular region of human TIM-3 while competing with one antibody selected from the following (i) to (iii):

(i) an antibody which comprises a heavy chain (hereinafter referred to as "H chain") of an antibody which comprises complementary determining regions (hereinafter referred to as "CDR") 1 to 3 comprising the amino acid sequences represented by SEQ ID NOs: 1 to 3, respectively, and comprises a light chain (hereinafter referred to as "L chain") of an antibody which comprises CDRs 1 to 3 comprising the amino acid sequences represented by SEQ ID NOs: 4 to 6, respectively, (ii) an antibody which comprises an H chain of an antibody which comprises CDRs 1 to 3 comprising the amino acid sequences represented by SEQ ID NOs: 11 to 13, respectively, and comprises an L chain of an antibody which comprises CDRs 1 to 3 comprising the amino acid sequences represented by SEQ ID NOs: 14 to 16, respectively, (iii) an antibody which comprises an H chain of an antibody which comprises CDRs1 to 3 comprising the amino acid sequences represented by SEQ ID NOs: 21 to 23, respectively, and comprises an L chain of an antibody which comprises CDRs1 to 3 comprising the amino acid sequences represented by SEQ ID NOs: 24 to 26, respectively.

(2) The monoclonal antibody or the antibody fragment thereof described in the above (1), wherein the monoclonal antibody binds to the same epitope to which one antibody selected from the above (i) to (iii) binds.

(3) A monoclonal antibody or an antibody fragment thereof, which binds to an extracellular region of human TIM-3 while competing with one antibody selected from the following (a) and (b):

(a) an antibody which comprises VH of an antibody comprising the amino acid sequence represented by SEQ ID NO: 8 and comprises VL of an antibody comprising the amino acid sequence represented by SEQ ID NO: 10, (b) an antibody which comprises VH of an antibody comprising the amino acid sequence represented by SEQ ID NO: 18 and comprises VL of an antibody comprising the amino acid sequence represented by SEQ ID NO: 20.

(4) The monoclonal antibody or the antibody fragment thereof described in the above (3), which binds to the same epitope to which one antibody selected from the above (a) or (b) binds.

(5) The monoclonal antibody or the antibody fragment thereof described in any one of the above (1) to (4), which is a recombinant antibody.

(6) The monoclonal antibody or the antibody fragment thereof described in the above (5), which is a recombinant antibody selected from a human chimeric antibody, a humanized antibody and a human antibody.

(7) A monoclonal antibody or an antibody fragment thereof, which is one selected from the following (i) to (iii):

(i) a monoclonal antibody and an antibody fragment thereof which comprises an H chain of an antibody which comprises CDRs 1 to 3 comprising the amino acid sequences represented by SEQ ID NOs: 1 to 3, respectively, and comprises an L chain of an antibody which comprises CDRs 1 to 3 comprising the amino acid sequences represented by SEQ ID NOs: 4 to 6, respectively, (ii) a monoclonal antibody and an antibody fragment thereof which comprises an H chain of an antibody which comprises CDRs 1 to 3 comprising the amino acid sequences represented by SEQ ID NOs: 11 to 13, respectively, and comprises an L chain of an antibody which comprises CDRs 1 to 3 comprising the amino acid sequences represented by SEQ ID NOs: 14 to 16, respectively, (iii) a monoclonal antibody and an antibody fragment thereof which comprises an H chain of an antibody which comprises CDRs 1 to 3 comprising the amino acid sequences represented by SEQ ID NOs: 21 to 23, respectively, and comprises an L chain of an antibody which comprises CDRs 1 to 3 comprising the amino acid sequences represented by SEQ ID NOs: 24 to 26, respectively.

(8) A monoclonal antibody and an antibody fragment thereof, which is one selected from the following (a) and (b):

(a) a monoclonal antibody and an antibody fragment thereof which comprises VH of an antibody comprising the amino acid sequence represented by SEQ ID NO: 8 and comprises VL of an antibody comprising the amino acid sequence represented by SEQ ID NO: 10, (b) a monoclonal antibody and an antibody fragment thereof which comprises VH of an antibody comprising the amino acid sequence represented by SEQ ID NO: 18 and comprises VL of an antibody comprising the amino acid sequence represented by SEQ ID NO: 20.

(9) A monoclonal antibody and an antibody fragment thereof which binds to the amino acid sequences at positions 67 to 105, the amino acid sequences at positions 67 to 96 or the amino acid sequences at positions 67 to 87 in the amino acid sequence of IgV domain of human TIM-3 represented by SEQ ID NO: 53.

(10) The antibody fragment described in any one of the above (1) to (9), wherein the antibody fragment is an antibody fragment selected from Fab, Fab', F(ab')$_2$, a single chain antibody (scFv), a dimerized V region (diabody), a disulfide stabilized V region (dsFv) and a peptide comprising CDR.

(11) A DNA which encodes the monoclonal antibody or the antibody fragment thereof described in any one of the above (1) to (10).

(12) A recombinant vector which comprises the DNA described in the above (11).

(13) A transformant obtainable by introducing the recombinant vector described in the above (12) into a host cell.

(14) A process for producing the monoclonal antibody or the antibody fragment thereof described in any one of the above (1) to (10), which comprises culturing the transformant described in the above (13) in culture to form and accumulate the monoclonal antibody or the antibody fragment thereof described in any one of the above (1) to (10), and recovering the monoclonal antibody or the antibody fragment thereof from the culture.

(15) A method for immunologically detecting or measuring a human TIM-3 which comprises using the monoclonal antibody or the antibody fragment thereof described in any one of the above (1) to (10).

(16) A reagent for detecting or measuring a human TIM-3 which comprises the monoclonal antibody or the antibody fragment thereof described in any one of the above (1) to (10).

(17) A diagnostic agent for a disease relating to a human TIM-3 positive cell which comprises the monoclonal antibody or the antibody fragment thereof described in any one of the above (1) to (10).

(18) A method for diagnosing a disease relating to a human TIM-3 positive cell which comprises detect or measure a human TIM-3 positive cell using the monoclonal antibody or the antibody fragment thereof described in any one of the above (1) to (10).

(19) A method for diagnosing a disease relating to a human TIM-3 positive cell, which comprises detecting or measuring a human TIM-3 using the monoclonal antibody or the antibody fragment thereof described in any one of the above (1) to (10).

(20) Use of the monoclonal antibody or the antibody fragment thereof described in any one of the above (1) to (10) for the manufacture of a diagnostic agent for a disease relating to a human TIM-3 positive cell.

(21) A therapeutic agent for a disease relating to a human TIM-3 positive cell, which comprises the monoclonal antibody or the antibody fragment thereof described in any one of the above (1) to (10).

(22) A therapeutic method for a disease relating to a human TIM-3 positive cell, which comprises inducing cell death of a human TIM-3 positive cell using the monoclonal antibody or the antibody fragment thereof described in any one of the above (1) to (10).

(23) Use of the monoclonal antibody or the antibody fragment thereof described in any one of the above (1) to (10) for the manufacture of a therapeutic agent for a disease relating to a human TIM-3 positive cell.

The human TIM-3 of the present invention include a polypeptide comprising the amino acid sequence represented by SEQ ID NO: 53 or NCBI Accession No. NM_032782, and having a function of TIM-3; a polypeptide comprising an amino acid sequence having at least 60% homology, preferably at least 80% homology, more preferably at least 90% homology, and most preferably at least 95% homology, with the amino acid sequence represented by SEQ ID NO: 53 or NCBI Accession No. NM_032782, and having a function of TIM-3; and the like.

The polypeptide comprising an amino acid sequence wherein one or more amino acid residue(s) is/are deleted, substituted and/or added in the amino acid sequence represented by SEQ ID NO: 53 or NCBI Accession No. NM_032782 can be obtained, for example, by introducing a site-directed mutation into DNA encoding the polypeptide comprising the amino acid sequence represented by SEQ ID NO: 53 by site-directed mutagenesis described in *Molecular Cloning, A Laboratory Manual*, Second Edition (Cold Spring Harbor Laboratory Press, 1989), *Current Protocols in Molecular Biology* (John Wiley & Sons, 1987-1997), *Nucleic Acids Research*, 10, 6487 (1982), *Proc. Natl. Acad. Sci. USA*, 79, 6409 (1982), *Gene*, 34, 315 (1985), *Proc. Natl. Acad. Sci. USA,* 82, 488 (1985), or the like.

The number of amino acid residues which are deleted, substituted or added is not particularly limited, and the number is preferably, 1 to dozens, such as 1 to 20, and more preferably 1 to several, such as 1 to 5.

As a gene which encodes human TIM-3, examples include the nucleotide sequence represented by SEQ ID NO: 52 or NCBI Accession No. NM_032782. Examples also include a gene comprising a nucleotide sequence in which at least one nucleotide is deleted, substituted or added in the nucleotide sequence represented by SEQ ID NO: 52 or NCBI Accession No. NM_032782 and comprising a DNA encoding a polypeptide having a function of TIM-3; a gene comprising an nucleotide sequence having at least 60% homology, preferably at least 80% homology, and more preferably at least 95% homology, with the nucleotide sequence represented by SEQ ID NO: 52 or NCBI Accession No. NM_032782 and comprising a DNA encoding a polypeptide having a function of TIM-3; a gene which hybridizes with the DNA consisting of the nucleotide sequence represented by SEQ ID NO: 52 or NCBI Accession No. NM_032782 under stringent conditions and encodes a polypeptide having a function of TIM-3; and the like.

In the present invention, the DNA which hybridizes under stringent conditions refers to a DNA which is obtained by colony hybridization, plaque hybridization, Southern blot hybridization, DNA microarray analysis, or the like using a DNA consisting of the nucleotide sequence represented by SEQ ID NO: 52 or NCBI Accession No. NM_032782 as a probe.

A specific example of such DNA is a DNA which can be identified by performing hybridization at 65° C. in the presence of 0.7 to 1.0 mol/L sodium chloride using a filter or a slide glass with colony- or plaque-derived DNA, PCR products or oligo DNA encoding the DNA sequence immobilized thereon, and then washing the filter or a slide glass at 65° C. with a 0.1 to 2-fold concentration SSC solution (1-fold concentration SSC solution: 150 mmol/L sodium chloride and 15 mmol/L sodium citrate). Hybridization can be carried out according to the methods described in *Molecular Cloning, A Laboratory Manual*, Second Edition, Cold Spring Harbor Laboratory Press (1989), *Current Protocols in Molecular Biology*, John Wiley & Sons (1987-1997); *DNA Cloning 1: Core Techniques, A Practical Approach*, Second Edition, Oxford University (1995); and the like.

Specifically, the DNA capable of hybridization includes DNA having at least 60% or more homology, preferably 80% or more homology, and more preferably 95% or more homology to the nucleotide sequence represented by SEQ ID NO: 52 or NCBI Accession No. NM_032782.

In the nucleotide sequence of the gene encoding a protein of a eukaryote, genetic polymorphism is often recognized.

The TIM-3 gene used in the present invention also includes a gene in which small modification is generated in the nucleotide sequence by such polymorphism.

The number of the homology described in the present invention may be a number calculated by using a homology search program known by the skilled person, unless otherwise indicated. Regarding the nucleotide sequence, the number may be calculated by using a default parameter in BLAST [*J. Mol. Biol.*, 215, 403 (1990)] or the like, and regarding the amino acid sequence, the number may be calculated by using a default parameter in BLAST2 [*Nucleic Acids Res.*, 25, 3389 (1997); *Genome Res.*, 7, 649 (1997); http://www.ncbi.nlm.nih.gov/Education/BLASTinfo/information3.html] or the like.

As the default parameter, G (cost to open gap) is 5 for the nucleotide sequence and 11 for the amino acid sequence; –E (cost to extend gap) is 2 for the nucleotide sequence and 1 for the amino acid sequence; –q (penalty for nucleotide mismatch) is –3; –r (reward for nucleotide match) is 1; –e (expect value) is 10; –W (wordsize) is 11 residues for the nucleotide sequence and 3 residues for the amino acid sequence; –y (Dropoff (X) for blast extensions in bits) is 20 for blastn and 7 for a program other than blastn; –X (X dropoff value for gapped alignment in bits) is 15; and Z (final X dropoff value for gapped alignment in bits) is 50 for blastn and 25 for a program other than blastn (http://www.ncbi.nlm.nih.gov/blast/html/blastcgihelp.html).

The polypeptide comprising a partial sequence of the amino acid sequence represented by SEQ ID NO: 53 or NCBI Accession No. NM_032782 can be prepared according to a method known by the skilled person. For example, it can be prepared by deleting a part of DNA encoding the amino acid sequence represented by SEQ ID NO: 52 and culturing a transformant into which an expression vector containing the DNA is introduced.

Also, based on the thus prepared polypeptide or DNA, a polypeptide comprising an amino acid sequence in which one or more amino acid(s) is/are deleted, substituted or added in a partial sequence of the amino acid sequence represented by SEQ ID NO: 53 or NCBI Accession No. NM_032782 can be prepared in the same manner as described above.

The polypeptide comprising a parcial sequence of the amino acid sequence represented by SEQ ID NO: 53 or NCBI Accession No. NM_032782; or the polypeptide comprising an amino acid sequence in which at least one amino acid is deleted, substituted or added in a parcial sequence of the amino acid sequence represented by SEQ ID NO: 53 or NCBI Accession No. NM_032782 can also be produced by a chemical synthesis method such as fluorenylmethoxycarbonyl (Fmoc) method or t-butyloxycarbonyl (tBoc) method.

The extracellular region of human TIM-3 of the present invention includes, for example, regions predicted by using the amino acid sequence of the polypeptide represented by SEQ ID NO: 53 with conventionally known transmembrane region prediction program SOSUI (http://bp.nuap.nagoya-u.ac.jp/sosui/sosui_submit.html), TMHMM ver. 2 (http://www.cbs.dtu.dk/services/TMHMM-2.0/), ExPASy Proteomics Server (http://Ca.expasy.org/) or SMART (http://smart.embl-heidelberg.de/).

In the present invention, the amino acid sequence of extracellular region of human TIM-3 includes the amino acid residues at residues at positions 1 to 201 in the amino acid sequence represented by SEQ ID NO: 53, which is the region of the extracellular region predicted by SMART.

In the present invention, the three-dimensional structure of the extracellular region of human TIM-3 is not limited, so long as the extracellular region of human TIM-3 comprising the amino acid sequence represented by SEQ ID NO: 53 or GenBank accession number NM_032782 has the same structure as in the natural state. The three-dimensional structure of the extracellular region of human TIM-3 in the natural state is a natural type of the three-dimensional structure of human TIM-3 expressed on the surface of the cell membrane.

Regarding the function of human TIM-3, binding of TIM-3 with a protein ligand (e.g., galectin 9) can inhibit the Th1 response thorough mechanism such as apoptosis induction in Th1 cells, therefore leading to induction of peripheral tolerance. In phagocytes, human TIM-3 functions as a receptor for recognizing the apoptosis cells.

Binding of the antibody or antibody fragment thereof in the present invention to an amino acid sequence of an extracellular region of human TIM-3 or a three-dimensional structure thereof can be confirmed by a conventionally known immunological immunological detection method using human TIM-3 expressing cells such as a radioimmuno assay with a solid phase sandwich method or enzyme-linked immunosorbent assay (ELISA), and preferably a fluorescent cell staining method in which the binding ability of a cell expressing a specified antigen and an antibody for the specific antigen is confirmed.

Specific examples include a fluorescent antibody staining method using an FMAT8100HTS System (manufactured by Applied Biosystems) [*Cancer Immunol. Immunother.*, 36, 373 (1993)] or the like, a fluorescent cell staining method using flow cytometry, surface plasmon resonance using a Biacore System (manufactured by GE Healthcare) or the like, and the like.

Furthermore, a known immunological detection methods [*Monoclonal Antibodies—Principles and practice*, Third edition, Academic Press (1996), *Antibodies—A Laboratory Manual*, Cold Spring Harbor Laboratory (1988), *Monoclonal Antibody Experimental Manual*, Kodan-sha Scientific (1987)] and the like can be combined to confirm the binding.

In the present invention, the cell expressing human TIM-3 may be any cell, so long as it expresses human TIM-3, and examples include a cell which is naturally present in the human body, a cell line established from the cell which is naturally present in the human body, a cell obtained by a recombinant technique and the like.

Example of the cell which is naturally present in the human body includes a cell expressing the TIM-3 in the body of a patient suffering from cancer, autoimmune disease or allergic disease, concretely, the cells are Th1 cells, macropharges, dendritic cells, and the like.

Example of a cell line established from the cell which is naturally present in the human body include a cell line expressing human TIM-3, among cell lines prepared by establishing the human TIM-3-expressing cells obtained from the above cancer patients, and examples include human acute myeloid leukemia cell line KG-1 (ATCC Accession No: CCL-246), human Burkitt's lymphoma cell line Daudi (ATCC Accession No: CCL-213) which are established from a human cell and the like.

Specific examples of the cell obtained by a recombinant technique may include a human TIM-3-expressing cell obtained by introducing an expression vector comprising a human TIM-3-encoding cDNA into an insect cell, an animal cell or the like, and others.

In addition, the present invention relates to a monoclonal antibody which recognizes an amino acid sequence or a three-dimensional structure of an extracellular region of human TIM-3 and exhibits ADCC activity.

The ADCC activity of the present invention is a reaction in which an antibody which is bound to human TIM-3 on the cell surface is bound to FcγRIIIa on the surface of mainly a natural killer cell (hereinafter referred to as NK cell) through Fc region and therefore a cytotoxic molecule such as molecules perforin, and granzyme released from an NK cell leads to cell lysis [Clark M, Chemical Immunology, 65, 88 (1997); Gorter A et al., Immunol. Today, 20, 576 (1999)].

The antibody of the present invention may be any antibodies as long as it is an antibody or antibody fragment thereof which recognizes an amino acid sequence of an extracellular region of human TIM-3 or a three-dimensional structure thereof and binds to the extracellular region; or an antibody or antibody fragment thereof which binds an extracellular region of human TIM-3 or a three-dimensional structure thereof and have ADCC activity.

Specific example of the antibody of the present invention may include an antibody which binds to the amino acid sequence selected from sequences preferably at positions 67 to 105, more preferably at positions 67 to 96, and most preferably at positions 67 to 87 among the amino acid sequence of extracellular region of human TIM-3 comprising of the residues at positions 1 to 201 in the sequence represented by SEQ ID NO: 53, or the three-dimensional structure thereof.

The example of the antibody includes the monoclonal antibody and the antibody fragment thereof as described in the following (i) to (iii):

(i) a monoclonal antibody or an antibody fragment thereof which comprises a heavy chain (hereinafter referred to as "H chain") of an antibody which comprises complementary determining regions (hereinafter referred to as "CDR") 1 to 3 comprising the amino acid sequences represented by SEQ ID NOs: 1 to 3, respectively, and comprises a light chain (hereinafter referred to as "L chain") of an antibody which comprises CDRs 1 to 3 comprising the amino acid sequences represented by SEQ ID NOs: 4 to 6, respectively.

(ii) a monoclonal antibody or an antibody fragment thereof which comprises an H chain of an antibody which comprises CDRs 1 to 3 comprising the amino acid sequences represented by SEQ ID NOs: 11 to 13, respectively, and comprises an L chain of an antibody which comprises CDRs 1 to 3 comprising the amino acid sequences represented by SEQ ID NOs: 14 to 16, respectively.

(iii) a monoclonal antibody or an antibody fragment thereof which comprises an H chain of an antibody which comprises CDRs 1 to 3 comprising the amino acid sequences represented by SEQ ID NOs: 21 to 23, respectively, and comprises an L chain of an antibody which comprises CDRs 1 to 3 comprising the amino acid sequences represented by SEQ ID NOs: 24 to 26, respectively.

The example of the monoclonal antibody includes a monoclonal antibody and an antibody fragment thereof as described in the following (a) and (b):

(a) a monoclonal antibody and an antibody fragment thereof which comprises VH of an antibody comprising the amino acid sequence represented by SEQ ID NO: 8 and comprises VL of an antibody comprising the amino acid sequence represented by SEQ ID NO: 10, (b) a monoclonal antibody and an antibody fragment thereof which comprises VH of an antibody comprising the amino acid sequence represented by SEQ ID NO: 18 and comprises VL of an antibody comprising the amino acid sequence represented by SEQ ID NO: 20.

In addition, the antibody of the present invention include a monoclonal antibody or an antibody fragment thereof which competes with the above monoclonal antibody in the binding of an amino acid sequence of an extracellular region of human TIM-3 or a three-dimensional structure thereof; and a monoclonal antibody or an antibody fragment thereof which binds to the same epitope existing on the extracellular region of human TIM-3 to which the above monoclonal antibody binds.

In the present invention, an antibody which compete with a monoclonal antibody means an antibody which recognizes the same or a part of the same epitope (also referred to as antigen determinant) on the extracellular region of human TIM-3 as the monoclonal antibody of the present invention, and binds to the epitope. The antibody which binds to the same epitope as the monoclonal antibody of the present invention means an antibody which recognizes and binds to an amino acid sequence of human TIM-3 which the monoclonal antibody of the present invention recognizes.

The monoclonal antibody of the present invention includes an antibody produced by a hybridoma and a recombinant antibody produced by a transformant transformed with an expression vector containing a gene encoding an antibody.

The monoclonal antibody is an antibody secreted by a single clone antibody-producing cell, and recognizes only one epitope (also called antigen determinant) and has uniform amino acid sequence (primary structure).

Examples of the epitope include a single amino acid sequence, a three-dimensional structure comprising the amino acid sequence, a sugar chain-bound amino acid sequence, a three-dimensional structure comprising a sugar chain-bound amino acid sequence, and the like, recognized and bound by a monoclonal antibody.

The monoclonal antibody of the present invention binds preferably to the amino acid residues at positions 22 to 131 of the IgV domain of human TIM-3 in the extracellular sequence of human TIM-3 represented by SEQ ID NO: 53. Specifically, the amino acid sequence to which the monoclonal antibody of the present invention binds is preferably the amino acid residues at positions 67 to 105, more preferably the amino acid residues at positions 67 to 96, and most preferably the amino acid residues at positions 67 to 87 in the amino acid sequence represented by SEQ ID NO: 53.

The epitope to which the monoclonal antibody of the present invention binds may preferably be included in the IgV domain of human TIM-3 represented by the amino acid residues at positions 22 to 131 in the extracellular region of human TIM-3 represented by SEQ ID NO: 53. Specifically, the epitope to which the monoclonal antibody of the present invention binds is preferably included in the amino acid residues at positions 67 to 105, more preferably included in the amino acid residues at positions 67 to 96, and most preferably included in the amino acid residues at positions 67 to 87 in the amino acid sequence represented by SEQ ID NO: 53.

The amino acid sequence of the epitope to which the monoclonal antibody of the present invention binds may preferably include at least one amino acid selected from the amino acid residues at positions 67 to 87 in the amino acid sequence represented by SEQ ID NO: 53 in the IgV domain of human TIM-3, and more preferably include at least one amino acid selected from the amino acids at position 67, position 74, position 76, position 78, position 79, position 81, position 83 and position 85.

The amino acid sequence of the epitope to which the monoclonal antibody of the present invention binds may preferably include at least two or more continuous amino acids selected from positions 67 to 87 of the human TIM-3 IgV domain; and more preferably may include at least one amino acid selected from the amino acids at position 67, position 74, position 76, position 78, position 79, position 81, position 83 and position 85 and include at least two or more continuous amino acids selected from the amino acid residues at positions 67 to 87 in the amino acid sequence represented by SEQ ID NO: 53.

Specifically, examples of the amino acid sequence of the epitope to which the monoclonal antibody of the present invention binds include the amino acid sequence comprising the amino acids at positions 67 to 74, the amino acid sequence comprising the amino acids at positions 67 to 76, the amino acid sequence comprising the amino acids at positions 67 to 78, the amino acid sequence comprising the amino acids at positions 67 to 79, the amino acid sequence comprising the amino acids at positions 67 to 81, the amino acid sequence comprising the amino acids at positions 67 to 83, the amino acid sequence comprising the amino acids at positions 67 to 85, the amino acid sequence comprising the amino acids at positions 74 to 76, the amino acid sequence comprising the amino acids at positions 74 to 78, the amino acid sequence comprising the amino acids at positions 74 to 79, the amino acid sequence comprising the amino acids at positions 74 to 81, the amino acid sequence comprising the amino acids at positions 74 to 83, the amino acid sequence comprising the amino acids at positions 74 to 85, the amino acid sequence comprising the amino acids at positions 76 to 78, the amino acid sequence comprising the amino acids at positions 76 to 79, the amino acid sequence comprising the amino acids at positions 76 to 81, the amino acid sequence comprising the amino acids at positions 76 to 83, the amino acid sequence comprising the amino acids at positions 76 to 85, the amino acid sequence comprising the amino acids at positions 78 to 79, the amino acid sequence comprising the amino acids at positions 78 to 81, the amino acid sequence comprising the amino acids at positions 78 to 83, the amino acid sequence comprising the amino acids at positions 78 to 85, the amino acid sequence comprising the amino acids at positions 79 to 81, the amino acid sequence comprising the amino acids at positions 79 to 83, the amino acid sequence comprising the amino acids at positions 79 to 85, the amino acid sequence comprising the amino acids at position 81 to 83, the amino acid sequence comprising the amino acids at positions 81 to 85, the amino acid sequence comprising the amino acids at positions 83 to 85, and the like, in the amino acid sequence represented by SEQ ID NO: 53.

The hybridoma can be prepared, for example, by preparing the above cell expressing TIM-3 as an antigen, inducing an antibody-producing cell having antigen specificity from an animal immunized with the antigen, and fusing the antibody-producing cell with a myeloma cell. The anti-TIM-3 antibody can be obtained by culturing the hybridoma or administering the hybridoma cell into an animal to cause ascites tumor in the animal and separating and purifying the culture or the ascites.

The animal immunized with an antigen may be any animal, so long as a hybridoma can be prepared, and mouse, rat, hamster, chicken, rabbit or the like is suitably used. Also, the cell having antibody-producing activity can be obtained from such an animal, and the antibody of the present invention includes an antibody produced by a hybridoma obtained by fusion of the cell after in vitro immunization with a myeloma cell.

In the present invention, the recombinant antibody includes an antibody produced by gene recombination, such as a human chimeric antibody, a human CDR grafted antibody, a human antibody and an antibody fragment thereof. Among the recombinant antibodies, one having character of a common monoclonal antibody, low immunogenecity and prolonged half-life in blood is preferable as a therapeutic agent. Examples of the recombinant antibody include an antibody which is prepared by modifying the above monoclonal antibody of the present invention using a recombinant technique.

The human chimeric antibody is an antibody comprising VH and VL of an antibody of a non-human animal, and a heavy chain constant region (hereinafter referred to as CH) and a light chain constant region (hereinafter referred to as CL) of a human antibody. Specifically, the human chimeric antibody of the present invention can be produced by obtaining cDNAs encoding VH and VL from a hybridoma which produces a monoclonal antibody which specifically recognizes human TIM-3 and binds to an amino acid sequence of extracellular region or a three-dimensional structure thereof, inserting each of them into an expression vector for animal cell comprising DNAs encoding CH and CL of human antibody to thereby construct a vector for expression of human chimeric antibody, and then introducing the vector into an animal cell to express the antibody.

As the CH of the human chimeric antibody, any CH can be used, so long as it belongs to human immunoglobulin (hereinafter referred to as "hIg"), and those belonging to the hIgG class are preferred, and any one of the subclasses belonging to the hIgG class, such as hIgG1, hIgG2, hIgG3 and hIgG4, can be used. As the CL of the human chimeric antibody, any CL can be used, so long as it belongs to the hIg class, and those belonging to κ class or λ class can be used.

Specific examples of the human chimeric antibody of the present invention includes a chimeric antibody which comprises VH of the antibody comprising the amino acid sequence represented by SEQ ID NO: 28 and comprises VL of the antibody comprising the amino acid sequence represented by SEQ ID NO: 30.

In addition, the chimeric antibody of the present invention include a chimeric antibody which competes with the above monoclonal antibody in the binding of an extracellular region of human TIM-3 or a three-dimensional structure thereof; and a chimeric antibody which binds to the same epitope existing on the extracellular region of human TIM-3 to which the above chimeric antibody binds.

The human CDR grafted antibody is also called as a humanized antibody and is an antibody in which CDR of VH and VL of a non-human animal antibody were grafted into the appropriate site of VH and VL of a human antibody. The human CDR grafted antibody of the present invention can be produced by constructing cDNAs encoding an antibody V region in which the amino acid sequences of CDRs of VH and VL of an antibody derived from a non-human animal produced by a hybridoma which produces a monoclonal antibody which specifically recognizes three-dimensional structure of TIM-3 and binds to an amino acid sequence of the extracellular region or three-dimensional structure thereof are grafted into frameworks (hereinafter referred to as "FR") of VH and VL of a suitable human antibody, inserting each of them into an expression vector for animal cell comprising genes encoding CH and CL of a human antibody to thereby construct a vector for expression of humanized antibody, and introducing it into an animal cell to thereby express and produce the humanized antibody.

As the CH of the human CDR grafted antibody, any CH can be used, so long as it belongs to human immunoglobulin (hereinafter referred to as "hIg"), and those belonging to the hIgG class are preferred, and any one of the subclasses belonging to the hIgG class, such as hIgG1, hIgG2, hIgG3 and hIgG4, can be used. As the CL of the human CDR grafted antibody, any CL can be used, so long as it belongs to the hIg class, and those belonging to κ class or λ class can be used.

Examples of the CDR grafted antibody of the present invention include a humanized antibody in which CDRs 1 to 3 of VH of the antibody comprises the amino acid sequences represented by SEQ ID NO: 21, 22, and 23, respectively, and CDRs 1 to 3 of VL of the antibody comprises the amino acid sequences represented by SEQ ID NO: 24, 25, and 26, respectively.

Specific examples of the humanized antibody include a humanized antibody comprising at least one of the following (a) VH and (b) VL:

(a) VH of the antibody comprising the amino acid sequence represented by SEQ ID NO: 67, or an amino acid sequence in which at least one amino acid residue selected from Lys at position 12, Val at position 20, Arg at position 38, Ala at position 40, Met at position 48, Arg at position 67, Val at position 68, Be at position 70, Ala at position 72, Thr at position 74, Arg at position 98 and Val at position 113 in the amino acid sequence represented by SEQ ID NO: 67 is substituted with other amino acid residue(s), (b) VL of the antibody comprising the amino acid sequence represented by SEQ ID NO: 69, or an amino acid sequence in which at least one amino acid residue selected from Leu at position 11, Ala at position 13, Val at position 15, Tyr at position 36, Ala at position 43, Pro at position 44, Leu at position 46, Phe at position 71 and Thr at position 85 in the amino acid sequence represented by SEQ ID NO: 69 is substituted with other amino acid residue(s).

As the VH comprised in the humanized antibody, the following (1) to (8) are preferable:

(1) VH comprising an amino acid sequence in which Lys at position 12, Val at position 20, Arg at position 38, Ala at position 40, Met at position 48, Arg at position 67, Val at position 68, Ile at position 70, Ala at position 72, Thr at position 74, Arg at position 98 and Val at position 113 in the amino acid sequence represented by SEQ ID NO: 67 are substituted with other amino acid residues;

(2) VH comprising an amino acid sequence in which Lys at position 12, Arg at position 38, Ala at position 40, Met at position 48, Arg at position 67, Val at position 68, Be at position 70, Ala at position 72, Thr at position 74 and Arg at position 98 in the amino acid sequence represented by SEQ ID NO: 67 are substituted with other amino acid residues;

(3) VH comprising an amino acid sequence in which Val at position 20, Arg at position 38, Met at position 48, Val at position 68, Ile at position 70, Ala at position 72, Arg at position 98 and Val at position 113 in the amino acid sequence represented by SEQ ID NO: 67 are substituted with other amino acid residues;

(4) VH comprising an amino acid sequence in which Arg at position 38, Ala at position 40, Met at position 48, Arg at position 67, Ala at position 72, Thr at position 74 and Arg at position 98 in the amino acid sequence represented by SEQ ID NO: 67 are substituted with other amino acid residues;

(5) VH comprising an amino acid sequence in which Lys at position 12, Arg at position 67, Val at position 68, Ala at position 72, Thr at position 74 and Arg at position 98 in the amino acid sequence represented by SEQ ID NO: 67 are substituted with other amino acid residues;

(6) VH comprising an amino acid sequence in which Arg at position 38, Ala at position 40, Met at position 48, Arg at position 67 and Arg at position 98 in the amino acid sequence represented by SEQ ID NO: 67 are substituted with other amino acid residues, (7) VH comprising an amino acid sequence in which Arg at position 38, Met at position 48, Arg at position 67 and Thr at position 74 in the amino acid sequence represented by SEQ ID NO: 67 are substituted with other amino acid residues; and (8) VH comprising an amino acid sequence in which Arg at position 38, Met at position 48 and Arg at position 98 in the amino acid sequence represented by SEQ ID NO: 67 are substituted with other amino acid residues.

The amino acid sequence of the above VH obtained by the amino acid modifications includes an amino acid sequence in which at least one modification among amino acid modifications for substituting Lys at position 12 with Val, Val at position 20 with Leu, Arg at position 38 with Lys, Ala at position 40 with Arg, Met at position 48 with Ile, Arg at position 67 with Lys, Val at position 68 with Ala, Be at position 70 with Leu, Ala at position 72 with Val, Thr at position 74 with Lys, Arg at position 98 with Gly or Val at position 113 with Leu is introduced in the amino acid sequence represented by SEQ ID NO: 67.

Specific examples of the amino acid sequence of VH in which twelve modifications are introduced include an amino acid sequence in which substitutions of Lys at position 12 with Val, Val at position 20 with Leu, Arg at position 38 with Lys, Ala at position 40 with Arg, Met at position 48 with Be, Arg at position 67 with Lys, Val at position 68 with Ala, Be at position 70 with Leu, Ala at position 72 with Val, Thr at position 74 with Lys, Arg at position 98 with Gly and Val at position 113 with Leu are introduced in the amino acid sequence represented by SEQ ID NO: 67.

Examples of the amino acid sequence of VH in which eleven modifications are introduced include the following amino acid sequence (1) to (12):

(1) an amino acid sequence in which substitutions of Val at position 20 with Leu, Arg at position 38 with Lys, Ala at position 40 with Arg, Met at position 48 with Ile, Arg at position 67 with Lys, Val at position 68 with Ala, Ile at position 70 with Leu, Ala at position 72 with Val, Thr at position 74 with Lys, Arg at position 98 with Gly and Val at position 113 with Leu are introduced in the amino acid sequence represented by SEQ ID NO: 67;

(2) an amino acid sequence in which substitutions of Lys at position 12 with Val, Arg at position 38 with Lys, Ala at position 40 with Arg, Met at position 48 with Ile, Arg at position 67 with Lys, Val at position 68 with Ala, Ile at position 70 with Leu, Ala at position 72 with Val, Thr at position 74 with Lys, Arg at position 98 with Gly and Val at position 113 with Leu are introduced in the amino acid sequence represented by SEQ ID NO: 67;

(3) an amino acid sequence in which substitutions of Lys at position 12 with Val, Val at position 20 with Leu, Ala at position 40 with Arg, Met at position 48 with Ile, Arg at position 67 with Lys, Val at position 68 with Ala, Be at position 70 with Leu, Ala at position 72 with Val, Thr at position 74 with Lys, Arg at position 98 with Gly and Val at position 113 with Leu are introduced in the amino acid sequence represented by SEQ ID NO: 67;

(4) an amino acid sequence in which substitutions of Lys at position 12 with Val, Val at position 20 with Leu, Arg at position 38 with Lys, Met at position 48 with Be, Arg at position 67 with Lys, Val at position 68 with Ala, Ile at position 70 with Leu, Ala at position 72 with Val, Thr at position 74 with Lys, Arg at position 98 with Gly and Val at position 113 with Leu are introduced in the amino acid sequence represented by SEQ ID NO: 67;

(5) an amino acid sequence in which substitutions of Lys at position 12 with Val, Val at position 20 with Leu, Arg at position 38 with Lys, Ala at position 40 with Arg, Arg at position 67 with Lys, Val at position 68 with Ala, Be at position 70 with Leu, Ala at position 72 with Val, Thr at position 74 with Lys, Arg at position 98 with Gly and Val at position 113 with Leu are introduced in the amino acid sequence represented by SEQ ID NO: 67;

(6) an amino acid sequence in which substitutions of Lys at position 12 with Val, Val at position 20 with Leu, Arg at position 38 with Lys, Ala at position 40 with Arg, Met at position 48 with Be, Val at position 68 with Ala, Ile at position 70 with Leu, Ala at position 72 with Val, Thr at position 74 with Lys, Arg at position 98 with Gly and Val at position 113 with Leu are introduced in the amino acid sequence represented by SEQ ID NO: 67;

(7) an amino acid sequence in which substitutions of Lys at position 12 with Val, Val at position 20 with Leu, Arg at position 38 with Lys, Ala at position 40 with Arg, Met at position 48 with Be, Arg at position 67 with Lys, Ile at position 70 with Leu, Ala at position 72 with Val, Thr at position 74 with Lys, Arg at position 98 with Gly and Val at position 113 with Leu are introduced in the amino acid sequence represented by SEQ ID NO: 67;

(8) an amino acid sequence in which substitutions of Lys at position 12 with Val, Val at position 20 with Leu, Arg at position 38 with Lys, Ala at position 40 with Arg, Met at position 48 with Be, Arg at position 67 with Lys, Val at position 68 with Ala, Ala at position 72 with Val, Thr at position 74 with Lys, Arg at position 98 with Gly and Val at position 113 with Leu are introduced in the amino acid sequence represented by SEQ ID NO: 67;

(9) an amino acid sequence in which substitutions of Lys at position 12 with Val, Val at position 20 with Leu, Arg at position 38 with Lys, Ala at position 40 with Arg, Met at position 48 with Be, Arg at position 67 with Lys, Val at position 68 with Ala, Ile at position 70 with Leu, Thr at position 74 with Lys, Arg at position 98 with Gly and Val at position 113 with Leu are introduced in the amino acid sequence represented by SEQ ID NO: 67;

(10) an amino acid sequence in which substitutions of Lys at position 12 with Val, Val at position 20 with Leu, Arg at position 38 with Lys, Ala at position 40 with Arg, Met at position 48 with Be, Arg at position 67 with Lys, Val at position 68 with Ala, Ile at position 70 with Leu, Ala at position 72 with Val, Arg at position 98 with Gly and Val at position 113 with Leu are introduced in the amino acid sequence represented by SEQ ID NO: 67;

(11) an amino acid sequence in which substitutions of Lys at position 12 with Val, Val at position 20 with Leu, Arg at position 38 with Lys, Ala at position 40 with Arg, Met at position 48 with Be, Arg at position 67 with Lys, Val at position 68 with Ala, Ile at position 70 with Leu, Ala at position 72 with Val, Thr at position 74 with Lys and Val at position 113 with Leu are introduced in the amino acid sequence represented by SEQ ID NO: 67; and

(12) an amino acid sequence in which substitutions of Lys at position 12 with Val, Val at position 20 with Leu, Arg at position 38 with Lys, Ala at position 40 with Arg, Met at position 48 with Be, Arg at position 67 with Lys, Val at position 68 with Ala, Ile at position 70 with Leu, Ala at position 72 with Val, Thr at position 74 with Lys and Arg at position 98 with Gly are introduced in the amino acid sequence represented by SEQ ID NO: 67.

Specific examples of the amino acid sequence of VH in which ten modifications are introduced include the following amino acid sequence (1) to (8):

(1) an amino acid sequence in which substitutions of Lys at position 12 with Val, Arg at position 38 with Lys, Ala at position 40 with Arg, Met at position 48 with Ile, Arg at position 67 with Lys, Val at position 68 with Ala, Ile at position 70 with Leu, Ala at position 72 with Val, Thr at position 74 with Lys and Arg at position 98 with Gly are introduced in the amino acid sequence represented by SEQ ID NO: 67;

(2) an amino acid sequence in which substitutions of Lys at position 12 with Val, Val at position 20 with Leu, Arg at position 38 with Lys, Met at position 48 with Ile, Arg at position 67 with Lys, Val at position 68 with Ala, Ile at position 70 with Leu, Ala at position 72 with Val, Thr at position 74 with Lys and Arg at position 98 with Gly are introduced in the amino acid sequence represented by SEQ ID NO: 67;

(3) an amino acid sequence in which substitutions of Val at position 20 with Leu, Arg at position 38 with Lys, Met at position 48 with Be, Arg at position 67 with Lys, Val at position 68 with Ala, Ile at position 70 with Leu, Ala at position 72 with Val, Thr at position 74 with Lys, Arg at position 98 with Gly and Val at position 113 with Leu are introduced in the amino acid sequence represented by SEQ ID NO: 67;

(4) an amino acid sequence in which substitutions of Lys at position 12 with Val, Arg at position 38 with Lys, Met at position 48 with Be, Arg at position 67 with Lys, Val at position 68 with Ala, Ile at position 70 with Leu, Ala at position 72 with Val, Thr at position 74 with Lys, Arg at position 98 with Gly and Val at position 113 with Leu are introduced in the amino acid sequence represented by SEQ ID NO: 67;

(5) an amino acid sequence in which substitutions of Val at position 20 with Leu, Arg at position 38 with Lys, Ala at position 40 with Arg, Met at position 48 with Be, Arg at position 67 with Lys, Val at position 68 with Ala, Ile at position 70 with Leu, Ala at position 72 with Val, Thr at position 74 with Lys and Arg at position 98 with Gly are introduced in the amino acid sequence represented by SEQ ID NO: 67;

(6) an amino acid sequence in which substitutions of Arg at position 38 with Lys, Ala at position 40 with Arg, Met at position 48 with Ile, Arg at position 67 with Lys, Val at position 68 with Ala, Ile at position 70 with Leu, Ala at position 72 with Val, Thr at position 74 with Lys, Arg at position 98 with Gly and Val at position 113 with Leu are introduced in the amino acid sequence represented by SEQ ID NO: 67;

(7) an amino acid sequence in which substitutions of Lys at position 12 with Val, Val at position 20 with Leu, Arg at position 38 with Lys, Ala at position 40 with Arg, Met at position 48 with Be, Val at position 68 with Ala, Ile at position 70 with Leu, Ala at position 72 with Val, Arg at position 98 with Gly and Val at position 113 with Leu are introduced in the amino acid sequence represented by SEQ ID NO: 67; and (8) an amino acid sequence in which substitutions of Lys at position 12 with Val, Arg at position 38 with Lys, Ala at position 40 with Arg, Met at position 48 with Be, Arg at position 67 with Lys, Val at position 68 with Ala, Ile at position 70 with Leu, Ala at position 72 with Val, Thr at position 74 with Lys and Arg at position 98 with Gly are introduced in the amino acid sequence represented by SEQ ID NO: 67.

Examples of the amino acid sequence of VH in which eight modifications are introduced include the following amino acid sequence (1) to (13):

(1) an amino acid sequence in which substitutions of Val at position 20 with Leu, Arg at position 38 with Lys, Met at position 48 with Be, Val at position 68 with Ala, Ile at position 70 with Leu, Ala at position 72 with Val, Arg at position 98 with Gly and Val at position 113 with Leu are introduced in the amino acid sequence represented by SEQ ID NO: 67;

(2) an amino acid sequence in which substitutions of Arg at position 38 with Lys, Met at position 48 with Ile, Val at position 68 with Ala, Be at position 70 with Leu, Ala at position 72 with Val, Thr at position 74 with Lys, Arg at position 98 with Gly and Val at position 113 with Leu are introduced in the amino acid sequence represented by SEQ ID NO: 67;

(3) an amino acid sequence in which substitutions of Arg at position 38 with Lys, Met at position 48 with Ile, Arg at position 67 with Lys, Val at position 68 with Ala, Be at position 70 with Leu, Ala at position 72 with Val, Arg at position 98 with Gly and Val at position 113 with Leu are introduced in the amino acid sequence represented by SEQ ID NO: 67;

(4) an amino acid sequence in which substitutions of Arg at position 38 with Lys, Met at position 48 with Ile, Arg at position 67 with Lys, Val at position 68 with Ala, Ile at position 70 with Leu, Ala at position 72 with Val, Thr at position 74 with Lys and Arg at position 98 with Gly are introduced in the amino acid sequence represented by SEQ ID NO: 67;

(5) an amino acid sequence in which substitutions of Arg at position 38 with Lys, Ala at position 40 with Arg, Met at position 48 with Ile, Val at position 68 with Ala, Ile at position 70 with Leu, Ala at position 72 with Val, Arg at position 98 with Gly and Val at position 113 with Leu are introduced in the amino acid sequence represented by SEQ ID NO: 67;

(6) an amino acid sequence in which substitutions of Arg at position 38 with Lys, Ala at position 40 with Arg, Met at position 48 with Ile, Val at position 68 with Ala, Ile at position 70 with Leu, Ala at position 72 with Val, Thr at position 74 with Lys and Arg at position 98 with Gly are introduced in the amino acid sequence represented by SEQ ID NO: 67;

(7) an amino acid sequence in which substitutions of Arg at position 38 with Lys, Ala at position 40 with Arg, Met at position 48 with Ile, Arg at position 67 with Lys, Val at position 68 with Ala, Ile at position 70 with Leu, Ala at position 72 with Val and Arg at position 98 with Gly are introduced in the amino acid sequence represented by SEQ ID NO: 67;

(8) an amino acid sequence in which substitutions of Val at position 20 with Leu, Arg at position 38 with Lys, Met at position 48 with Be, Val at position 68 with Ala, Ile at position 70 with Leu, Ala at position 72 with Val, Thr at position 74 with Lys and Arg at position 98 with Gly are introduced in the amino acid sequence represented by SEQ ID NO: 67;

(9) an amino acid sequence in which substitutions of Val at position 20 with Leu, Arg at position 38 with Lys, Ala at position 40 with Arg, Met at position 48 with Ile, Val at position 68 with Ala, Ile at position 70 with Leu, Ala at position 72 with Val and Arg at position 98 with Gly are introduced in the amino acid sequence represented by SEQ ID NO: 67;

(10) an amino acid sequence in which substitutions of Val at position 20 with Leu, Arg at position 38 with Lys, Met at position 48 with Be, Val at position 68 with Ala, Ile at position 70 with Leu, Ala at position 72 with Val, Arg at position 98 with Gly and Val at position 113 with Leu are introduced in the amino acid sequence represented by SEQ ID NO: 67;

(11) an amino acid sequence in which substitutions of Lys at position 12 with Val, Arg at position 38 with Lys, Met at position 48 with Be, Val at position 68 with Ala, Be at position 70 with Leu, Ala at position 72 with Val, Thr at position 74 with Lys and Arg at position 98 with Gly are introduced in the amino acid sequence represented by SEQ ID NO: 67;

(12) an amino acid sequence in which substitutions of Lys at position 12 with Val, Arg at position 38 with Lys, Ala at position 40 with Arg, Met at position 48 with Be, Val at position 68 with Ala, Ile at position 70 with Leu, Ala at position 72 with Val and Arg at position 98 with Gly are introduced in the amino acid sequence represented by SEQ ID NO: 67; and

(13) an amino acid sequence in which substitutions of Lys at position 12 with Val, Val at position 20 with Leu, Arg at position 38 with Lys, Met at position 48 with Be, Val at position 68 with Ala, Ile at position 70 with Leu, Ala at position 72 with Val and Arg at position 98 with Gly are introduced in the amino acid sequence represented by SEQ ID NO: 67.

Specific examples of the amino acid sequence of VH in which seven modifications are introduced include the following amino acid sequence (1) to (11):

(1) an amino acid sequence in which substitutions of Arg at position 38 with Lys, Ala at position 40 with Arg, Met at position 48 with Ile, Arg at position 67 with Lys, Ala at position 72 with Val, Thr at position 74 with Lys and Arg at position 98 with Gly are introduced in the amino acid sequence represented by SEQ ID NO: 67;

(2) an amino acid sequence in which substitutions of Arg at position 38 with Lys, Met at position 48 with Ile, Val at position 68 with Ala, Be at position 70 with Leu, Ala at position 72 with Val, Thr at position 74 with Lys and Arg at position 98 with Gly are introduced in the amino acid sequence represented by SEQ ID NO: 67;

(3) an amino acid sequence in which substitutions of Arg at position 38 with Lys, Met at position 48 with Ile, Arg at position 67 with Lys, Be at position 70 with Leu, Ala at position 72 with Val, Thr at position 74 with Lys and Arg at position 98 with Gly are introduced in the amino acid sequence represented by SEQ ID NO: 67;

(4) an amino acid sequence in which substitutions of Arg at position 38 with Lys, Met at position 48 with Ile, Arg at position 67 with Lys, Val at position 68 with Ala, Ala at position 72 with Val, Thr at position 74 with Lys and Arg at position 98 with Gly are introduced in the amino acid sequence represented by SEQ ID NO: 67;

(5) an amino acid sequence in which substitutions of Arg at position 38 with Lys, Met at position 48 with Ile, Arg at position 67 with Lys, Val at position 68 with Ala, Be at position 70 with Leu, Ala at position 72 with Val and Arg at position 98 with Gly are introduced in the amino acid sequence represented by SEQ ID NO: 67;

(6) an amino acid sequence in which substitutions of Arg at position 38 with Lys, Ala at position 40 with Arg, Met at position 48 with Ile, Be at position 70 with Leu, Ala at position 72 with Val, Thr at position 74 with Lys and Arg at position 98 with Gly are introduced in the amino acid sequence represented by SEQ ID NO: 67;

(7) an amino acid sequence in which substitutions of Arg at position 38 with Lys, Ala at position 40 with Arg, Met at position 48 with Ile, Val at position 68 with Ala, Ala at position 72 with Val, Thr at position 74 with Lys and Arg at position 98 with Gly are introduced in the amino acid sequence represented by SEQ ID NO: 67;

(8) an amino acid sequence in which substitutions of Arg at position 38 with Lys, Ala at position 40 with Arg, Met at position 48 with Ile, Val at position 68 with Ala, Be at position 70 with Leu, Ala at position 72 with Val and Arg at position 98 with Gly are introduced in the amino acid sequence represented by SEQ ID NO: 67;

(9) an amino acid sequence in which substitutions of Arg at position 38 with Lys, Ala at position 40 with Arg, Met at position 48 with Ile, Arg at position 67 with Lys, Ala at position 72 with Val, Thr at position 74 with Lys and Arg at position 98 with Gly are introduced in the amino acid sequence represented by SEQ ID NO: 67;

(10) an amino acid sequence in which substitutions of Arg at position 38 with Lys, Ala at position 40 with Arg, Met at position 48 with Ile, Arg at position 67 with Lys, Ile at position 70 with Leu, Ala at position 72 with Val and Arg at position 98 with Gly are introduced in the amino acid sequence represented by SEQ ID NO: 67; and

(11) an amino acid sequence in which substitutions of Arg at position 38 with Lys, Ala at position 40 with Arg, Met at position 48 with Ile, Arg at position 67 with Lys, Val at position 68 with Ala, Ala at position 72 with Val and Arg at position 98 with Gly are introduced in the amino acid sequence represented by SEQ ID NO: 67.

Specific Examples of the amino acid sequence of VH in which six modifications are introduced include the following amino acid sequence (1) to (16):

(1) an amino acid sequence in which substitutions of Lys at position 12 with Val, Arg at position 67 with Lys, Val at position 68 with Ala, Ala at position 72 with Val, Thr at position 74 with Lys and Arg at position 98 with Gly are introduced in the amino acid sequence represented by SEQ ID NO: 67;

(2) an amino acid sequence in which substitutions of Lys at position 12 with Val, Val at position 20 with Leu, Arg at position 38 with Lys, Met at position 48 with Ile, Arg at position 67 with Lys and Arg at position 98 with Gly are introduced in the amino acid sequence represented by SEQ ID NO: 67;

(3) an amino acid sequence in which substitutions of Lys at position 12 with Val, Arg at position 38 with Lys, Ala at position 40 with Arg, Met at position 48 with Be, Arg at position 67 with Lys and Arg at position 98 with Gly are introduced in the amino acid sequence represented by SEQ ID NO: 67;

(4) an amino acid sequence in which substitutions of Lys at position 12 with Val, Arg at position 38 with Lys, Met at position 48 with Be, Arg at position 67 with Lys, Val at position 68 with Ala and Arg at position 98 with Gly are introduced in the amino acid sequence represented by SEQ ID NO: 67;

(5) an amino acid sequence in which substitutions of Lys at position 12 with Val, Arg at position 38 with Lys, Met at position 48 with Be, Arg at position 67 with Lys, Ala at position 72 with Val and Arg at position 98 with Gly are introduced in the amino acid sequence represented by SEQ ID NO: 67;

(6) an amino acid sequence in which substitutions of Lys at position 12 with Val, Arg at position 38 with Lys, Met at position 48 with Be, Arg at position 67 with Lys, Thr at position 74 with Lys and Arg at position 98 with Gly are introduced in the amino acid sequence represented by SEQ ID NO: 67;

(7) an amino acid sequence in which substitutions of Val at position 20 with Leu, Arg at position 38 with Lys, Ala at position 40 with Arg, Met at position 48 with Ile, Arg at position 67 with Lys and Arg at position 98 with Gly are introduced in the amino acid sequence represented by SEQ ID NO: 67;

(8) an amino acid sequence in which substitutions of Val at position 20 with Leu, Arg at position 38 with Lys, Met at position 48 with Be, Arg at position 67 with Lys, Val at position 68 with Ala and Arg at position 98 with Gly are introduced in the amino acid sequence represented by SEQ ID NO: 67;

(9) an amino acid sequence in which substitutions of Val at position 20 with Leu, Arg at position 38 with Lys, Met at position 48 with Be, Arg at position 67 with Lys, Ala at position 72 with Val and Arg at position 98 with Gly are introduced in the amino acid sequence represented by SEQ ID NO: 67;

(10) an amino acid sequence in which substitutions of Val at position 20 with Leu, Arg at position 38 with Lys, Met at position 48 with Be, Arg at position 67 with Lys, Thr at position 74 with Lys and Arg at position 98 with Gly are introduced in the amino acid sequence represented by SEQ ID NO: 67;

(11) an amino acid sequence in which substitutions of Arg at position 38 with Lys, Ala at position 40 with Arg, Met at position 48 with Ile, Arg at position 67 with Lys, Val at position 68 with Ala and Arg at position 98 with Gly are introduced in the amino acid sequence represented by SEQ ID NO: 67;

(12) an amino acid sequence in which substitutions of Arg at position 38 with Lys, Ala at position 40 with Arg, Met at position 48 with Ile, Arg at position 67 with Lys, Ala at position 72 with Val and Arg at position 98 with Gly are introduced in the amino acid sequence represented by SEQ ID NO: 67;

(13) an amino acid sequence in which substitutions of Arg at position 38 with Lys, Ala at position 40 with Arg, Met at position 48 with Ile, Arg at position 67 with Lys, Thr at position 74 with Lys and Arg at position 98 with Gly are introduced in the amino acid sequence represented by SEQ ID NO: 67;

(14) an amino acid sequence in which substitutions of Arg at position 38 with Lys, Met at position 48 with Ile, Arg at position 67 with Lys, Val at position 68 with Ala, Ala at position 72 with Val and Arg at position 98 with Gly are introduced in the amino acid sequence represented by SEQ ID NO: 67;

(15) an amino acid sequence in which substitutions of Arg at position 38 with Lys, Met at position 48 with Ile, Arg at position 67 with Lys, Val at position 68 with Ala, Thr at position 74 with Lys and Arg at position 98 with Gly are introduced in the amino acid sequence represented by SEQ ID NO: 67; and

(16) an amino acid sequence in which substitutions of Arg at position 38 with Lys, Met at position 48 with Ile, Arg at position 67 with Lys, Ala at position 72 with Val, Thr at position 74 with Lys and Arg at position 98 with Gly are introduced in the amino acid sequence represented by SEQ ID NO: 67.

Specific examples of the amino acid sequence of VH in which five modifications are introduced include the following amino acid sequence (1) to (7):

(1) an amino acid sequence in which substitutions of Arg at position 38 with Lys, Ala at position 40 with Arg, Met at position 48 with Ile, Arg at position 67 with Lys and Arg at position 98 with Gly are introduced in the amino acid sequence represented by SEQ ID NO: 67;

(2) an amino acid sequence in which substitutions of Lys at position 12 with Val, Arg at position 38 with Lys, Met at position 48 with Be, Arg at position 67 with Lys and Arg at position 98 with Gly are introduced in the amino acid sequence represented by SEQ ID NO: 67;

(3) an amino acid sequence in which substitutions of Val at position 20 with Leu, Arg at position 38 with Lys, Met at position 48 with Be, Arg at position 67 with Lys and Arg at position 98 with Gly are introduced in the amino acid sequence represented by SEQ ID NO: 67;

(4) an amino acid sequence in which substitutions of Arg at position 38 with Lys, Met at position 48 with Ile, Arg at position 67 with Lys, Val at position 68 with Ala and Arg at position 98 with Gly are introduced in the amino acid sequence represented by SEQ ID NO: 67;

(5) an amino acid sequence in which substitutions of Arg at position 38 with Lys, Met at position 48 with Ile, Arg at position 67 with Lys, Be at position 70 with Leu and Arg at position 98 with Gly are introduced in the amino acid sequence represented by SEQ ID NO: 67;

(6) an amino acid sequence in which substitutions of Arg at position 38 with Lys, Met at position 48 with Ile, Arg at position 67 with Lys, Ala at position 72 with Val and Arg at position 98 with Gly are introduced in the amino acid sequence represented by SEQ ID NO: 67; and (7) an amino acid sequence in which substitutions of Arg at position 38 with Lys, Met at position 48 with Ile, Arg at position 67 with Lys, Thr at position 74 with Lys and Arg at position 98 with Gly are introduced in the amino acid sequence represented by SEQ ID NO: 67.

Specific examples of the amino acid sequence of VH in which four modifications are introduced include the following amino acid sequence (1) to (8):

(1) an amino acid sequence in which substitutions of Arg at position 38 with Lys, Met at position 48 with Ile, Arg at position 67 with Lys and Thr at position 74 with Lys are introduced in the amino acid sequence represented by SEQ ID NO: 67;

(2) an amino acid sequence in which substitutions of Lys at position 12 with Val, Arg at position 38 with Lys, Met at position 48 with Be and Arg at position 67 with Lys are introduced in the amino acid sequence represented by SEQ ID NO: 67;

(3) an amino acid sequence in which substitutions of Val at position 20 with Leu, Arg at position 38 with Lys, Met at position 48 with Be and Arg at position 67 with Lys are introduced in the amino acid sequence represented by SEQ ID NO: 67;

(4) an amino acid sequence in which substitutions of Arg at position 38 with Lys, Ala at position 40 with Arg, Met at position 48 with Ile and Arg at position 67 with Lys are introduced in the amino acid sequence represented by SEQ ID NO: 67;

(5) an amino acid sequence in which substitutions of Arg at position 38 with Lys, Met at position 48 with Ile, Arg at position 67 with Lys and Val at position 68 with Ala are introduced in the amino acid sequence represented by SEQ ID NO: 67;

(6) an amino acid sequence in which substitutions of Arg at position 38 with Lys, Met at position 48 with Ile, Arg at position 67 with Lys and Ile at position 70 with Leu are introduced in the amino acid sequence represented by SEQ ID NO: 67;

(7) an amino acid sequence in which substitutions of Arg at position 38 with Lys, Met at position 48 with Ile, Arg at position 67 with Lys and Ala at position 72 with Val are introduced in the amino acid sequence represented by SEQ ID NO: 67; and (8) an amino acid sequence in which substitutions of Arg at position 38 with Lys, Met at position 48 with Ile, Arg at position 67 with Lys and Arg at position 98 with Gly are introduced in the amino acid sequence represented by SEQ ID NO: 67.

Specific examples of the amino acid sequence of VH in which three modifications are introduced include the following amino acid sequence (1) to (9):

(1) an amino acid sequence in which substitutions of Arg at position 38 with Lys, Met at position 48 with Ile and Arg at position 98 with Gly are introduced in the amino acid sequence represented by SEQ ID NO: 67;

(2) an amino acid sequence in which substitutions of Lys at position 12 with Val, Arg at position 38 with Lys and Met at position 48 with Be are introduced in the amino acid sequence represented by SEQ ID NO: 67;

(3) an amino acid sequence in which substitutions of Val at position 20 with Leu, Arg at position 38 with Lys and Met at position 48 with Be are introduced in the amino acid sequence represented by SEQ ID NO: 67;

(4) an amino acid sequence in which substitutions of Arg at position 38 with Lys, Ala at position 40 with Arg and Met at position 48 with Be are introduced in the amino acid sequence represented by SEQ ID NO: 67;

(5) an amino acid sequence in which substitutions of Arg at position 38 with Lys, Met at position 48 with Ile and Arg at position 67 with Lys are introduced in the amino acid sequence represented by SEQ ID NO: 67;

(6) an amino acid sequence in which substitutions of Arg at position 38 with Lys, Met at position 48 with Ile and Val at position 68 with Ala are introduced in the amino acid sequence represented by SEQ ID NO: 67;

(7) an amino acid sequence in which substitutions of Arg at position 38 with Lys, Met at position 48 with Ile and Ile at position 70 with Leu are introduced in the amino acid sequence represented by SEQ ID NO: 67;

(8) an amino acid sequence in which substitutions of Arg at position 38 with Lys, Met at position 48 with Ile and Ala at position 72 with Val are introduced in the amino acid sequence represented by SEQ ID NO: 67; and (9) an amino acid sequence in which substitutions of Arg at position 38 with Lys, Met at position 48 with Ile and Thr at position 74 with Lys are introduced in the amino acid sequence represented by SEQ ID NO: 67;

Specific examples of the amino acid sequence of VH in which two modifications are introduced include the following amino acid sequence (1) to (21):

(1) an amino acid sequence in which substitutions of Lys at position 12 with Val and Arg at position 38 with Lys are introduced in the amino acid sequence represented by SEQ ID NO: 67;

(2) an amino acid sequence in which substitutions of Val at position 20 with Leu and Arg at position 38 with Lys are introduced in the amino acid sequence represented by SEQ ID NO: 67;

(3) an amino acid sequence in which substitutions of Arg at position 38 with Lys and Ala at position 40 with Arg are introduced in the amino acid sequence represented by SEQ ID NO: 67;

(4) an amino acid sequence in which substitutions of Arg at position 38 with Lys and Met at position 48 with Be are introduced in the amino acid sequence represented by SEQ ID NO: 67;

(5) an amino acid sequence in which substitutions of Arg at position 38 with Lys and Arg at position 67 with Lys are introduced in the amino acid sequence represented by SEQ ID NO: 67;

(6) an amino acid sequence in which substitutions of Arg at position 38 with Lys and Val at position 68 with Ala are introduced in the amino acid sequence represented by SEQ ID NO: 67;

(7) an amino acid sequence in which substitutions of Arg at position 38 with Lys and Ile at position 70 with Leu are introduced in the amino acid sequence represented by SEQ ID NO: 67;

(8) an amino acid sequence in which substitutions of Arg at position 38 with Lys and Ala at position 72 with Val are introduced in the amino acid sequence represented by SEQ ID NO: 67;

(9) an amino acid sequence in which substitutions of Arg at position 38 with Lys and Thr at position 74 with Lys are introduced in the amino acid sequence represented by SEQ ID NO: 67;

(10) an amino acid sequence in which substitutions of Arg at position 38 with Lys and Arg at position 98 with Gly are introduced in the amino acid sequence represented by SEQ ID NO: 67;

(11) an amino acid sequence in which substitutions of Arg at position 38 with Lys and Val at position 113 with Leu are introduced in the amino acid sequence represented by SEQ ID NO: 67;

(12) an amino acid sequence in which substitutions of Lys at position 12 with Val and Met at position 48 with Be are introduced in the amino acid sequence represented by SEQ ID NO: 67;

(13) an amino acid sequence in which substitutions of Val at position 20 with Leu and Met at position 48 with Ile are introduced in the amino acid sequence represented by SEQ ID NO: 67;

(14) an amino acid sequence in which substitutions of Ala at position 40 with Arg and Met at position 48 with Ile are introduced in the amino acid sequence represented by SEQ ID NO: 67;

(15) an amino acid sequence in which substitutions of Met at position 48 with Be and Arg at position 67 with Lys are introduced in the amino acid sequence represented by SEQ ID NO: 67;

(16) an amino acid sequence in which substitutions of Met at position 48 with Be and Val at position 68 with Ala are introduced in the amino acid sequence represented by SEQ ID NO: 67;

(17) an amino acid sequence in which substitutions of Met at position 48 with Be and Ile at position 70 with Leu are introduced in the amino acid sequence represented by SEQ ID NO: 67;

(18) an amino acid sequence in which substitutions of Met at position 48 with Ile and Ala at position 72 with Val are introduced in the amino acid sequence represented by SEQ ID NO: 67;

(19) an amino acid sequence in which substitutions of Met at position 48 with Ile and Thr at position 74 with Lys are introduced in the amino acid sequence represented by SEQ ID NO: 67;

(20) an amino acid sequence in which substitutions of Met at position 48 with Ile and Arg at position 98 with Gly are introduced in the amino acid sequence represented by SEQ ID NO: 67; and

(21) an amino acid sequence in which substitutions of Met at position 48 with Ile and Val at position 113 with Leu are introduced in the amino acid sequence represented by SEQ ID NO: 67.

Specific examples of the amino acid sequence of VH in which one modification is introduced include the following amino acid sequence (1) to (12):

(1) an amino acid sequence in which substitution of Lys at position 12 with Val is introduced in the amino acid sequence represented by SEQ ID NO: 67;

(2) an amino acid sequence in which substitution of Val at position 20 with Leu is introduced in the amino acid sequence represented by SEQ ID NO: 67;

(3) an amino acid sequence in which substitution of Arg at position 38 with Lys is introduced in the amino acid sequence represented by SEQ ID NO: 67;

(4) an amino acid sequence in which substitution of Ala at position 40 with Arg is introduced in the amino acid sequence represented by SEQ ID NO: 67;

(5) an amino acid sequence in which substitution of Met at position 48 with Ile is introduced in the amino acid sequence represented by SEQ ID NO: 67;

(6) an amino acid sequence in which substitution of Arg at position 67 with Lys is introduced in the amino acid sequence represented by SEQ ID NO: 67;

(7) an amino acid sequence in which substitution of Val at position 68 with Ala is introduced in the amino acid sequence represented by SEQ ID NO: 67;

(8) an amino acid sequence in which substitution of Be at position 70 with Leu is introduced in the amino acid sequence represented by SEQ ID NO: 67;

(9) an amino acid sequence in which substitution of Ala at position 72 with Val is introduced in the amino acid sequence represented by SEQ ID NO: 67;

(10) an amino acid sequence in which substitution of Thr at position 74 with Lys is introduced in the amino acid sequence represented by SEQ ID NO: 67;

(11) an amino acid sequence in which substitution of Arg at position 98 with Gly is introduced in the amino acid sequence represented by SEQ ID NO: 67; and

(12) an amino acid sequence in which substitution of Val at position 113 with Leu is introduced in the amino acid sequence represented by SEQ ID NO: 67.

As the VL comprised in the humanized antibody, the following (1) to (6) are preferable:

(1) VL comprising an amino acid sequence in which Leu at position 11, Ala at position 13, Val at position 15, Tyr at position 36, Ala at position 43, Pro at position 44, Leu at position 46, Phe at position 71 and Thr at position 85 in the amino acid sequence represented by SEQ ID NO: 69 are substituted with other amino acid residues.

(2) VL comprising an amino acid sequence in which Leu at position 11, Val at position 15, Tyr at position 36, Pro at position 44, Leu at position 46, Phe at position 71 and Thr at position 85 in the amino acid sequence represented by SEQ ID NO: 69 are substituted with other amino acid residues.

(3) VL comprising an amino acid sequence in which Val at position 15, Tyr at position 36, Pro at position 44, Leu at position 46, Phe at position 71 and Thr at position 85 in the amino acid sequence represented by SEQ ID NO: 69 are substituted with other amino acid residues.

(4) VL comprising an amino acid sequence in which Tyr at position 36, Ala at position 43, Pro at position 44, Leu at position 46 and Thr at position 85 in the amino acid sequence represented by SEQ ID NO: 69 are substituted with other amino acid residues.

(5) VL comprising an amino acid sequence in which Val at position 15, Tyr at position 36, Leu at position 46 and Phe at position 71 in the amino acid sequence represented by SEQ ID NO: 69 are substituted with other amino acid residues.

(6) VL comprising an amino acid sequence in which Tyr at position 36 and Pro at position 44 in the amino acid sequence represented by SEQ ID NO: 69 are substituted with other amino acid residues.

The amino acid sequence of the above VL obtained by the amino acid modifications includes an amino acid sequence in which at least one modification among amino acid modifications for substituting Leu at position 11 with Met, Ala at position 13 with Val, Val at position 15 with Leu, Tyr at position 36 with Leu, Ala at position 43 with Ser, Pro at position 44 with Phe, Leu at position 46 with Gly, Phe at position 71 with Tyr, and Thr at position 85 with Asp is introduced in the amino acid sequence represented by SEQ ID NO: 69.

Examples of the amino acid sequence of VL in which nine modifications are introduced include an amino acid sequence in which substitutions of Leu at position 11 with Met, Ala at position 13 with Val, Val at position 15 with Leu, Tyr at position 36 with Leu, Ala at position 43 with Ser, Pro at position 44 with Phe, Leu at position 46 with Gly, Phe at position 71 with Tyr, and Thr at position 85 with Asp are introduced in the amino acid sequence represented by SEQ ID NO: 69.

Specific examples of the amino acid sequence of VL in which eight modifications are introduced include the following amino acid sequence (1) to (9):

(1) an amino acid sequence in which substitutions of Ala at position 13 with Val, Val at position 15 with Leu, Tyr at position 36 with Leu, Ala at position 43 with Ser, Pro at position 44 with Phe, Leu at position 46 with Gly, Phe at position 71 with Tyr and Thr at position 85 with Asp are introduced in the amino acid sequence represented by SEQ ID NO: 69;

(2) an amino acid sequence in which substitutions of Leu at position 11 with Met, Val at position 15 with Leu, Tyr at position 36 with Leu, Ala at position 43 with Ser, Pro at position 44 with Phe, Leu at position 46 with Gly, Phe at position 71 with Tyr and Thr at position 85 with Asp are introduced in the amino acid sequence represented by SEQ ID NO: 69;

(3) an amino acid sequence in which substitutions of Leu at position 11 with Met, Ala at position 13 with Val, Tyr at position 36 with Leu, Ala at position 43 with Ser, Pro at position 44 with Phe, Leu at position 46 with Gly, Phe at position 71 with Tyr and Thr at position 85 with Asp are introduced in the amino acid sequence represented by SEQ ID NO: 69;

(4) an amino acid sequence in which substitutions of Leu at position 11 with Met, Ala at position 13 with Val, Val at position 15 with Leu, Ala at position 43 with Ser, Pro at position 44 with Phe, Leu at position 46 with Gly, Phe at position 71 with Tyr and Thr at position 85 with Asp are introduced in the amino acid sequence represented by SEQ ID NO: 69;

(5) an amino acid sequence in which substitutions of Leu at position 11 with Met, Ala at position 13 with Val, Val at position 15 with Leu, Tyr at position 36 with Leu, Pro at position 44 with Phe, Leu at position 46 with Gly, Phe at position 71 with Tyr and Thr at position 85 with Asp are introduced in the amino acid sequence represented by SEQ ID NO: 69;

(6) an amino acid sequence in which substitutions of Leu at position 11 with Met, Ala at position 13 with Val, Val at position 15 with Leu, Tyr at position 36 with Leu, Ala at position 43 with Ser, Leu at position 46 with Gly, Phe at position 71 with Tyr and Thr at position 85 with Asp are introduced in the amino acid sequence represented by SEQ ID NO: 69;

(7) an amino acid sequence in which substitutions of Leu at position 11 with Met, Ala at position 13 with Val, Val at position 15 with Leu, Tyr at position 36 with Leu, Ala at position 43 with Ser, Pro at position 44 with Phe, Phe at position 71 with Tyr and Thr at position 85 with Asp are introduced in the amino acid sequence represented by SEQ ID NO: 69;

(8) an amino acid sequence in which substitutions of Leu at position 11 with Met, Ala at position 13 with Val, Val at position 15 with Leu, Tyr at position 36 with Leu, Ala at position 43 with Ser, Pro at position 44 with Phe, Leu at position 46 with Gly and Thr at position 85 with Asp are introduced in the amino acid sequence represented by SEQ ID NO: 69; and (9) an amino acid sequence in which substitutions of Leu at position 11 with Met, Ala at position 13 with Val, Val at position 15 with Leu, Tyr at position 36 with Leu, Ala at position 43 with Ser, Pro at position 44 with Phe, Leu at position 46 with Gly and Phe at position 71 with Tyr are introduced in the amino acid sequence represented by SEQ ID NO: 69.

Specific example of the amino acid sequence of VL in which seven modifications are introduced include the following amino acid sequence (1) to (9):

(1) an amino acid sequence in which substitutions of Leu at position 11 with Met, Val at position 15 with Leu, Tyr at position 36 with Leu, Pro at position 44 with Phe, Leu at position 46 with Gly, Phe at position 71 with Tyr and Thr at position 85 with Asp are introduced in the amino acid sequence represented by SEQ ID NO: 69;

(2) an amino acid sequence in which substitutions of Val at position 15 with Leu, Tyr at position 36 with Leu, Ala at position 43 with Ser, Pro at position 44 with Phe, Leu at position 46 with Gly, Phe at position 71 with Tyr and Thr at position 85 with Asp are introduced in the amino acid sequence represented by SEQ ID NO: 69;

(3) an amino acid sequence in which substitutions of Leu at position 11 with Met, Tyr at position 36 with Leu, Ala at position 43 with Ser, Pro at position 44 with Phe, Leu at position 46 with Gly, Phe at position 71 with Tyr and Thr at position 85 with Asp are introduced in the amino acid sequence represented by SEQ ID NO: 69;

(4) an amino acid sequence in which substitutions of Leu at position 11 with Met, Val at position 15 with Leu, Ala at position 43 with Ser, Pro at position 44 with Phe, Leu at position 46 with Gly, Phe at position 71 with Tyr and Thr at position 85 with Asp are introduced in the amino acid sequence represented by SEQ ID NO: 69;

(5) an amino acid sequence in which substitutions of Leu at position 11 with Met, Val at position 15 with Leu, Tyr at position 36 with Leu, Pro at position 44 with Phe, Leu at position 46 with Gly, Phe at position 71 with Tyr and Thr at position 85 with Asp are introduced in the amino acid sequence represented by SEQ ID NO: 69;

(6) an amino acid sequence in which substitutions of Leu at position 11 with Met, Val at position 15 with Leu, Tyr at position 36 with Leu, Ala at position 43 with Ser, Leu at position 46 with Gly, Phe at position 71 with Tyr and Thr at position 85 with Asp are introduced in the amino acid sequence represented by SEQ ID NO: 69;

(7) an amino acid sequence in which substitutions of Leu at position 11 with Met, Val at position 15 with Leu, Tyr at position 36 with Leu, Ala at position 43 with Ser, Pro at position 44 with Phe, Phe at position 71 with Tyr and Thr at position 85 with Asp are introduced in the amino acid sequence represented by SEQ ID NO: 69;

(8) an amino acid sequence in which substitutions of Leu at position 11 with Met, Val at position 15 with Leu, Tyr at position 36 with Leu, Ala at position 43 with Ser, Pro at position 44 with Phe, Leu at position 46 with Gly and Thr at position 85 with Asp are introduced in the amino acid sequence represented by SEQ ID NO: 69; and (9) an amino acid sequence in which substitutions of Leu at position 11 with Met, Val at position 15 with Leu, Tyr at position 36 with Leu, Ala at position 43 with Ser, Pro at position 44 with Phe, Leu at position 46 with Gly and Phe at position 71 with Tyr are introduced in the amino acid sequence represented by SEQ ID NO: 69.

Specific example of the amino acid sequence of VL in which six modifications are introduced include the following amino acid sequence (1) to (6):

(1) an amino acid sequence in which substitutions of Val at position 15 with Leu, Tyr at position 36 with Leu, Pro at position 44 with Phe, Leu at position 46 with Gly, Phe at position 71 with Tyr and Thr at position 85 with Asp are introduced in the amino acid sequence represented by SEQ ID NO: 69;

(2) an amino acid sequence in which substitutions of Tyr at position 36 with Leu, Ala at position 43 with Ser, Pro at position 44 with Phe, Leu at position 46 with Gly, Phe at position 71 with Tyr and Thr at position 85 with Asp are introduced in the amino acid sequence represented by SEQ ID NO: 69;

(3) an amino acid sequence in which substitutions of Val at position 15 with Leu, Tyr at position 36 with Leu, Ala at position 43 with Ser, Pro at position 44 with Phe, Leu at position 46 with Gly and Thr at position 85 with Asp are introduced in the amino acid sequence represented by SEQ ID NO: 69;

(4) an amino acid sequence in which substitutions of Leu at position 11 with Met, Tyr at position 36 with Leu, Pro at position 44 with Phe, Leu at position 46 with Gly, Phe at position 71 with Tyr and Thr at position 85 with Asp are introduced in the amino acid sequence represented by SEQ ID NO: 69;

(5) an amino acid sequence in which substitutions of Leu at position 11 with Met, Tyr at position 36 with Leu, Ala at position 43 with Ser, Pro at position 44 with Phe, Leu at position 46 with Gly and Thr at position 85 with Asp are introduced in the amino acid sequence represented by SEQ ID NO: 69; and (6) an amino acid sequence in which substitutions of Leu at position 11 with Met, Ala at position 13 with Val, Tyr at position 36 with Leu, Pro at position 44 with Phe, Leu at position 46 with Gly and Thr at position 85 with Asp are introduced in the amino acid sequence represented by SEQ ID NO: 69.

Specific example of the amino acid sequence of VL in which five modifications are introduced include the following amino acid sequence (1) to (7):

(1) an amino acid sequence in which substitutions of Tyr at position 36 with Leu, Ala at position 43 with Ser, Pro at position 44 with Phe, Leu at position 46 with Gly and Thr at position 85 with Asp are introduced in the amino acid sequence represented by SEQ ID NO: 69;

(2) an amino acid sequence in which substitutions of Val at position 15 with Leu, Tyr at position 36 with Leu, Ala at position 43 with Ser, Pro at position 44 with Phe and Leu at position 46 with Gly are introduced in the amino acid sequence represented by SEQ ID NO: 69;

(3) an amino acid sequence in which substitutions of Val at position 15 with Leu, Tyr at position 36 with Leu, Pro at position 44 with Phe, Leu at position 46 with Gly and Phe at position 71 with Tyr are introduced in the amino acid sequence represented by SEQ ID NO: 69;

(4) an amino acid sequence in which substitutions of Val at position 15 with Leu, Tyr at position 36 with Leu, Pro at position 44 with Phe, Leu at position 46 with Gly and Thr at position 85 with Asp are introduced in the amino acid sequence represented by SEQ ID NO: 69;

(5) an amino acid sequence in which substitutions of Tyr at position 36 with Leu, Ala at position 43 with Ser, Pro at position 44 with Phe, Leu at position 46 with Gly and Phe at position 71 with Tyr are introduced in the amino acid sequence represented by SEQ ID NO: 69;

(6) an amino acid sequence in which substitutions of Tyr at position 36 with Leu, Ala at position 43 with Ser, Pro at position 44 with Phe, Leu at position 46 with Gly and Thr at position 85 with Asp are introduced in the amino acid sequence represented by SEQ ID NO: 69; and (7) an amino acid sequence in which substitutions of Tyr at position 36 with Leu, Pro at position 44 with Phe, Leu at position 46 with Gly, Phe at position 71 with Tyr and Thr at position 85 with Asp are introduced in the amino acid sequence represented by SEQ ID NO: 69.

Specific example of the amino acid sequence of VL in which four modifications are introduced include the following amino acid sequence (1) to (10):

(1) an amino acid sequence in which substitutions of Val at position 15 with Leu, Tyr at position 36 with Leu, Leu at position 46 with Gly and Phe at position 71 with Tyr are introduced in the amino acid sequence represented by SEQ ID NO: 69;

(2) an amino acid sequence in which substitutions of Val at position 15 with Leu, Tyr at position 36 with Leu, Pro at position 44 with Phe and Leu at position 46 with Gly are introduced in the amino acid sequence represented by SEQ ID NO: 69;

(3) an amino acid sequence in which substitutions of Val at position 15 with Leu, Tyr at position 36 with Leu, Pro at position 44 with Phe and Phe at position 71 with Tyr are introduced in the amino acid sequence represented by SEQ ID NO: 69;

(4) an amino acid sequence in which substitutions of Val at position 15 with Leu, Tyr at position 36 with Leu, Pro at position 44 with Phe and Thr at position 85 with Asp are introduced in the amino acid sequence represented by SEQ ID NO: 69;

(5) an amino acid sequence in which substitutions of Val at position 15 with Leu, Tyr at position 36 with Leu, Leu at position 46 with Gly and Thr at position 85 with Asp are introduced in the amino acid sequence represented by SEQ ID NO: 69;

(6) an amino acid sequence in which substitutions of Val at position 15 with Leu, Tyr at position 36 with Leu, Phe at position 71 with Tyr and Thr at position 85 with Asp are introduced in the amino acid sequence represented by SEQ ID NO: 69;

(7) an amino acid sequence in which substitutions of Tyr at position 36 with Leu, Pro at position 44 with Phe, Leu at position 46 with Gly and Phe at position 71 with Tyr are introduced in the amino acid sequence represented by SEQ ID NO: 69;

(8) an amino acid sequence in which substitutions of Tyr at position 36 with Leu, Pro at position 44 with Phe, Leu at position 46 with Gly and Thr at position 85 with Asp are introduced in the amino acid sequence represented by SEQ ID NO: 69;

(9) an amino acid sequence in which substitutions of Tyr at position 36 with Leu, Pro at position 44 with Phe, Phe at position 71 with Tyr and Thr at position 85 with Asp are introduced in the amino acid sequence represented by SEQ ID NO: 69; and

(10) an amino acid sequence in which substitutions of Tyr at position 36 with Leu, Leu at position 46 with Gly, Phe at position 71 with Tyr and Thr at position 85 with Asp are introduced in the amino acid sequence represented by SEQ ID NO: 69.

Specific example of the amino acid sequence of VL in which three modifications are introduced include the following amino acid sequence (1) to (7):

(1) an amino acid sequence in which substitutions of Leu at position 11 with Met, Tyr at position 36 with Leu and Pro at position 44 with Phe are introduced in the amino acid sequence represented by SEQ ID NO: 69;

(2) an amino acid sequence in which substitutions of Ala at position 13 with Val, Tyr at position 36 with Leu and Pro at position 44 with Phe are introduced in the amino acid sequence represented by SEQ ID NO: 69;

(3) an amino acid sequence in which substitutions of Val at position 15 with Leu, Tyr at position 36 with Leu and Pro at position 44 with Phe are introduced in the amino acid sequence represented by SEQ ID NO: 69;

(4) an amino acid sequence in which substitutions of Tyr at position 36 with Leu, Ala at position 43 with Ser and Pro at position 44 with Phe are introduced in the amino acid sequence represented by SEQ ID NO: 69;

(5) an amino acid sequence in which substitutions of Tyr at position 36 with Leu, Pro at position 44 with Phe and Leu at position 46 with Gly are introduced in the amino acid sequence represented by SEQ ID NO: 69;

(6) an amino acid sequence in which substitutions of Tyr at position 36 with Leu, Pro at position 44 with Phe and Phe at position 71 with Tyr are introduced in the amino acid sequence represented by SEQ ID NO: 69; and (7) an amino acid sequence in which substitutions of Tyr at position 36 with Leu, Pro at position 44 with Phe and Thr at position 85 with Asp are introduced in the amino acid sequence represented by SEQ ID NO: 69.

Specific example of the amino acid sequence of VL in which two modifications are introduced include the following amino acid sequence (1) to (15):

(1) an amino acid sequence in which substitutions of Tyr at position 36 with Leu and Pro at position 44 with Phe are introduced in the amino acid sequence represented by SEQ ID NO: 69;

(2) an amino acid sequence in which substitutions of Leu at position 11 with Met and Tyr at position 36 with Leu are introduced in the amino acid sequence represented by SEQ ID NO: 69;

(3) an amino acid sequence in which substitutions of Ala at position 13 with Val and Tyr at position 36 with Leu are introduced in the amino acid sequence represented by SEQ ID NO: 69;

(4) an amino acid sequence in which substitutions of Val at position 15 with Leu and Tyr at position 36 with Leu are introduced in the amino acid sequence represented by SEQ ID NO: 69;

(5) an amino acid sequence in which substitutions of Tyr at position 36 with Leu and Ala at position 43 with Ser are introduced in the amino acid sequence represented by SEQ ID NO: 69;

(6) an amino acid sequence in which substitutions of Tyr at position 36 with Leu and Leu at position 46 with Gly are introduced in the amino acid sequence represented by SEQ ID NO: 69;

(7) an amino acid sequence in which substitutions of Tyr at position 36 with Leu and Phe at position 71 with Tyr are introduced in the amino acid sequence represented by SEQ ID NO: 69;

(8) an amino acid sequence in which substitutions of Tyr at position 36 with Leu and Thr at position 85 with Asp are introduced in the amino acid sequence represented by SEQ ID NO: 69;

(9) an amino acid sequence in which substitutions of Leu at position 11 with Met and Pro at position 44 with Phe are introduced in the amino acid sequence represented by SEQ ID NO: 69;

(10) an amino acid sequence in which substitutions of Ala at position 13 with Val and Pro at position 44 with Phe are introduced in the amino acid sequence represented by SEQ ID NO: 69;

(11) an amino acid sequence in which substitutions of Val at position 15 with Leu and Pro at position 44 with Phe are introduced in the amino acid sequence represented by SEQ ID NO: 69;

(12) an amino acid sequence in which substitutions of Ala at position 43 with Ser and Pro at position 44 with Phe are introduced in the amino acid sequence represented by SEQ ID NO: 69;

(13) an amino acid sequence in which substitutions of Pro at position 44 with Phe and Leu at position 46 with Gly are introduced in the amino acid sequence represented by SEQ ID NO: 69;

(14) an amino acid sequence in which substitutions of Pro at position 44 with Phe and Phe at position 71 with Tyr are introduced in the amino acid sequence represented by SEQ ID NO: 69; and

(15) an amino acid sequence in which substitutions of Pro at position 44 with Phe and Thr at position 85 with Asp are introduced in the amino acid sequence represented by SEQ ID NO: 69.

Specific example of the amino acid sequence of VH in which one modification is introduced include the following amino acid sequence (1) to (9):

(1) an amino acid sequence in which substitution of Leu at position 11 with Met is introduced in the amino acid sequence represented by SEQ ID NO: 69;

(2) an amino acid sequence in which substitution of Ala at position 13 with Val is introduced in the amino acid sequence represented by SEQ ID NO: 69;

(3) an amino acid sequence in which substitution of Val at position 15 with Leu is introduced in the amino acid sequence represented by SEQ ID NO: 69;

(4) an amino acid sequence in which substitution of Tyr at position 36 with Leu is introduced in the amino acid sequence represented by SEQ ID NO: 69;

(5) an amino acid sequence in which substitution of Ala at position 43 with Ser is introduced in the amino acid sequence represented by SEQ ID NO: 69;

(6) an amino acid sequence in which substitution of Pro at position 44 with Phe is introduced in the amino acid sequence represented by SEQ ID NO: 69;

(7) an amino acid sequence in which substitution of Leu at position 46 with Gly is introduced in the amino acid sequence represented by SEQ ID NO: 69;

(8) an amino acid sequence in which substitution of Phe at position 71 with Tyr is introduced in the amino acid sequence represented by SEQ ID NO: 69; and (9) an amino acid sequence in which substitution of Thr at position 85 with Asp is introduced in the amino acid sequence represented by SEQ ID NO: 69.

In addition, examples of the humanized antibody of the present invention include a humanized antibody in which VH of the antibody comprises the amino acid sequence represented by SEQ ID NO: 67 and/or VL of the antibody comprises the amino acid sequence represented by SEQ ID: 69, a humanized antibody in which VH of the antibody comprises the amino acid sequence represented by SEQ ID NO: 67 and/or VL of the antibody comprises any one of the amino acid sequences shown in FIG. 2, or a humanized antibody in which VH of the antibody comprises any one of the amino acid sequences shown in FIG. 1 and/or VL of the antibody comprises the amino acid sequence represented by SEQ ID: 69.

Furthermore, examples of the humanized antibody of the present invention include a humanized antibody which competes with the monoclonal antibody of the present invention in the binding of an amino acid sequence of an extracellular region of human TIM-3 or a three-dimensional structure thereof; and a humanized antibody which binds to the same epitope existing on the extracellular region of human TIM-3 to which the above humanized antibody binds.

A human antibody is originally an antibody naturally existing in the human body, and it also includes an antibody obtained from a human antibody phage library or a human antibody-producing transgenic animal, which is prepared based on the recent advanced techniques in genetic engineering, cell engineering and developmental engineering.

The antibody existing in the human body can be prepared, for example, by isolating a human peripheral blood lymphocyte, immortalizing it by infecting with EB virus or the like, and then cloning it to thereby obtain lymphocytes capable of producing the antibody, culturing the lymphocytes thus obtained, and purifying the antibody from the supernatant of the culture.

The human antibody phage library is a library in which antibody fragments such as Fab and scFv are expressed on the phage surface by inserting a gene encoding an antibody prepared from a human B cell into a phage gene. A phage expressing an antibody fragment having the desired antigen binding activity can be recovered from the library, using its activity to bind to an antigen-immobilized substrate as the index. The antibody fragment can be converted further into a human antibody molecule comprising two full H chains and two full L chains by genetic engineering techniques.

A human antibody-producing transgenic animal is an animal in which a human antibody gene is integrated into cells. Specifically, a human antibody-producing transgenic animal can be prepared by introducing a gene encoding a human antibody into a mouse ES cell, grafting the ES cell into an early embryo of mouse and then developing it. A human antibody is prepared from the human antibody-producing transgenic non-human animal by obtaining a human antibody-producing hybridoma by a hybridoma preparation method usually carried out in non-human mammals, culturing the obtained hybridoma and forming and accumulating the human antibody in the supernatant of the culture.

In the amino acid sequence constituting the above antibody or antibody fragment thereof, an antibody or antibody fragment thereof in which one or more amino acids are deleted, substituted, inserted or added, having activity similar to the above antibody or antibody fragment thereof is also included in the antibody or antibody fragment of the present invention.

The number of amino acids which are deleted, substituted, inserted and/or added is one or more, and is not specifically limited, but it is within the range where deletion, substitution or addition is possible by known methods such as the site-directed mutagenesis described in *Molecular Cloning*, Second Edition, Cold Spring Harbor Laboratory Press (1989); *Current Protocols in Molecular Biology*, John Wiley & Sons (1987-1997); *Nucleic Acids Research,* 10, 6487 (1982), *Proc. Natl. Acad. Sci. USA,* 79, 6409 (1982); *Gene,* 34, 315 (1985), *Nucleic Acids Research,* 13, 4431 (1985); *Proc. Natl. Acad. Sci. USA,* 82, 488 (1985) or the like. For example, the number is preferably 1 to dozens, more preferably 1 to 20, furthermore preferably 1 to 10, and most preferably 1 to 5.

The expression "one or more amino acid residue(s) is/are deleted, substituted, inserted and/or added" in the amino acid sequence of the above antibody means the followings. That is, it means there is deletion, substitution, insertion or addition of one or plural amino acids at optional positions in the same sequence and in one or plural amino acid sequences. Also, the deletion, substitution, insertion or addition may occur at the same time and the amino acid which is substituted, inserted or added may be either a natural type or a non-natural type.

The natural type amino acid includes L-alanine, L-asparagine, L-aspartic acid, L-glutamine, L-glutamic acid, glycine, L-histidine, L-isoleucine, L-leucine, L-lysine, L-methionine, L-phenylalanine, L-proline, L-serine, L-threonine, L-tryptophan, L-tyrosine, L-valine, L-cysteine and the like.

Preferable examples of mutually substitutable amino acids are shown below. The amino acids in the same group are mutually substitutable.

Group A: leucine, isoleucine, norleucine, valine, norvaline, alanine, 2-aminobutanoic acid, methionine, O-methylserine, t-butylglycine, t-butylalanine, cyclohexylalanine Group B: aspartic acid, glutamic acid, isoaspartic acid, isoglutamic acid, 2-aminoadipic acid, 2-aminosuberic acid Group C: asparagine, glutamine Group D: lysine, arginine, ornithine, 2,4-diaminobutanoic acid, 2,3-diaminopropionic acid Group E: proline, 3-hydroxyproline, 4-hydroxyproline Group F: serine, threonine, homoserine Group G: phenylalanine, tyrosine The antibody fragment of the present invention includes Fab, F(ab')$_2$, Fab', a single chain antibody (scFv), a dimerized V region (diabody), a disulfide stabilized V region (dsFv), a peptide comprising CDR and the like.

An Fab is an antibody fragment among fragments obtained by treating an IgG antibody molecule with a protease, papain (cleaved at an amino acid residue at position 224 of the H chain), having a molecular weight of about 50,000 and having antigen binding activity, in which about a half of the N-terminal side of H chain and the entire L chain are bound together through a disulfide bond.

The Fab of the present invention can be produced by treating the monoclonal antibody of the present invention which specifically recognizes human TIM-3 and binds to an amino acid sequence of the extracellular region or three-dimensional structure thereof with papain. Also, the Fab can be produced by inserting DNA encoding Fab of the antibody into an expression vector for prokaryote or an expression vector for eukaryote, and introducing the vector into a prokaryote or eukaryote to express the Fab.

An F(ab')$_2$ is an antibody fragment having a molecular weight of about 100,000 and having antigen binding activity and comprising two Fab regions which are bound in the hinge position obtained by digesting the lower part of two disulfide bonds in the hinge region of IgG with an enzyme, pepsin.

The F(ab')$_2$ of the present invention can be produced by treating the monoclonal antibody of the present invention which specifically recognizes human TIM-3 and binds to an amino acid sequence of the extracellular region or three-dimensional structure thereof with pepsin. Also, the F(ab')$_2$ can be produced by binding Fab' described below via a thioether bond or a disulfide bond.

An Fab' is an antibody fragment having a molecular weight of about 50,000 and antigen binding activity, which is obtained by cleaving a disulfide bond at the hinge region of the above F(ab')$_2$. The Fab' of the present invention can be produced by treating the F(ab')$_2$ of the present invention which specifically recognizes TIM-3 and binds to an amino acid sequence of the extracellular region or three-dimensional structure thereof with a reducing agent, such as dithiothreitol. Also, the Fab' can be produced by inserting DNA encoding Fab' fragment of the antibody into an expression vector for prokaryote or an expression vector for eukaryote, and introducing the vector into a prokaryote or eukaryote to express the Fab'.

An scFv is a VH-P-VL or VL-P-VH polypeptide in which one chain VH and one chain VL are linked using an appropriate peptide linker (hereinafter referred to as "P") and is an antibody fragment having antigen binding activity.

The scFv of the present invention can be produced by obtaining cDNAs encoding VH and VL of the monoclonal antibody of the present invention which specifically recognizes human TIM-3 and binds to an amino acid sequence of the extracellular region or three-dimensional structure thereof, constructing DNA encoding scFv, inserting the DNA into an expression vector for prokaryote or an expression vector for eukaryote, and then introducing the expression vector into a prokaryote or eukaryote to express the scFv.

A diabody is an antibody fragment wherein scFv is dimerized, is an antibody fragment having divalent antigen binding activity. In the divalent antigen binding activity, two antigens may be the same or different.

The diabody of the present invention can be produced by obtaining cDNAs encoding VH and VL of the monoclonal antibody of the present invention which specifically recognizes human TIM-3 and binds to an amino acid sequence of the extracellular region or three-dimensional structure thereof, constructing DNA encoding scFv so that the length of the amino acid sequence of the peptide linker is 8 or less residues, inserting the DNA into an expression vector for prokaryote or an expression vector for eukaryote, and then introducing the expression vector into a prokaryote or eukaryote to express the diabody.

A dsFv is obtained by binding polypeptides in which one amino acid residue of each of VH and VL is substituted with a cysteine residue via a disulfide bond between the cysteine residues. The amino acid residue to be substituted with a cysteine residue can be selected based on a three-dimensional structure estimation of the antibody in accordance with a known methods [*Protein Engineering*, 7, 697 (1994)].

The dsFv of the present invention can be produced by obtaining cDNAs encoding VH and VL of the monoclonal antibody of the present invention which specifically recognizes human TIM-3 and binds to an amino acid sequence of the extracellular region or three-dimensional structure thereof, constructing DNA encoding dsFv, inserting the DNA into an expression vector for prokaryote or an expression vector for eukaryote, and then introducing the expression vector into a prokaryote or eukaryote to express the dsFv.

A peptide comprising CDR is constituted by including one or more regions of CDRs of VH or VL. Peptide comprising plural CDRs can be bound directly or via an appropriate peptide linker.

The peptide comprising CDR of the present invention can be produced by constructing DNA encoding CDRs of VH and VL of the monoclonal antibody of the present invention which specifically recognizes human TIM-3 and binds to an amino acid sequence of the extracellular region or three-dimensional structure thereof, inserting the DNA into an expression vector for prokaryote or an expression vector for eukaryote, and then introducing the expression vector into a prokaryote or eukaryote to express the peptide. The peptide comprising CDR can also be produced by a chemical synthesis method such as Fmoc method or tBoc method.

The monoclonal antibody of the present invention includes an antibody conjugate in which the monoclonal antibody or the antibody fragment of the present invention which specifically recognizes human TIM-3 and binds to an amino acid sequence of the extracellular region or three-dimensional structure thereof is chemically or genetically bound to a radioisotope, an agent having a low molecular weight, an agent having a high molecular weight, a protein, a therapeutic antibody or the like.

The antibody conjugate of the present invention can be produced by chemically conjugating a radioisotope, an agent having a low molecular weight, an agent having a high molecular weight, an adjuvant, a protein, a therapeutic antibody or the like to the N-terminal side or C-terminal side of an H chain or an L chain, adequate substituent or sidechain, sugarchain, and the like of the monoclonal antibody or the antibody fragment of the present invention which specifically recognizes human TIM-3 and binds to an amino acid sequence of the extracellular region or three-dimensional structure thereof [*Kotai Kogaku Nyumon*, published by Chijin Shokan (1994)].

Also, the antibody conjugate can be genetically produced by linking a DNA encoding the monoclonal antibody or the antibody fragment of the present invention which specifically recognizes human TIM-3 and binds to an amino acid sequence of the extracellular region or three-dimensional structure thereof to other DNA encoding a protein or a therapeutic antibody to be conjugated, inserting the DNA into a vector for expression, and introducing the expression vector into an appropriate host cell.

The radioisotope includes $^{131}$I, $^{125}$I, $^{90}$Y, $^{64}$Cu, $^{199}$Tc, $^{77}$Lu, $^{211}$At and the like. The radioisotope can directly be conjugated with the antibody by Chloramine-T method or the like. Also, a substance chelating the radioisotope can be conjugated with the antibody. The chelating agent includes 1-isothiocyanatobenzyl-3-methyldiethylene-triaminepentaacetic acid (MX-DTPA) and the like.

The agent having a low molecular weight includes an anti-tumor agent such as an alkylating agent, a nitrosourea agent, a metabolism antagonist, an antibiotic substance, an alkaloid derived from a plant, a topoisomerase inhibitor, an agent for hormonotherapy, a hormone antagonist, an aromatase inhibitor, a P glycoprotein inhibitor, a platinum complex derivative, an M-phase inhibitor and a kinase inhibitor [*Rinsho Syuyo-gaku* (Clinical Oncology), Gan to Kagakuryoho-Sha (1996)], a steroid agent such as hydrocortisone and prednisone, a nonsteroidal agent such as aspirin and indomethacin, immunomodulatory agent such as aurothiomalate, penicillamine, immuno-suppressing agent such as cyclophosphamide and azathioprine, anti-inflammatory agent such as anti-histamine agent, for example, chlorpheniramine maleate and clemastine [*Ensho to Kouensho-Ryoho* (*Inflammation and Anti-inflammation Therapy*), Ishiyaku Shuppann (1982)] and the like.

Examples of the antitumor agent include amifostine (Ethyol), cisplatin, dacarbazine (DTIC), dactinomycin, mecloretamin (nitrogen mustard), streptozocin, cyclophosphamide, iphosphamide, carmustine (BCNU), lomustine (CCNU), doxorubicin (adriamycin), epirubicin, gemcitabine (Gemsal), daunorubicin, procarbazine, mitomycin, cytarabine, etoposide, methotrexate, 5-fluorouracil, fluorouracil, vinblastine, vincristine, bleomycin, daunomycin, peplomycin, estramustine, paclitaxel (Taxol), docetaxel (Taxotea), aldesleukin, asparaginase, busulfan, carboplatin, oxaliplatin, nedaplatin, cladribine, camptothecin, 10-hydroxy-7-ethyl-camptothecin (SN38), floxuridine, fludarabine, hydroxyurea, iphosphamide, idarubicin, mesna, irinotecan (CPT-11), nogitecan, mitoxantrone, topotecan, leuprolide, megestrol, melfalan, mercaptopurine, hydroxycarbamide, plicamycin, mitotane, pegasparagase, pentostatin, pipobroman, streptozocin, tamoxifen, goserelin, leuprorelin, flutamide, teniposide, testolactone, thioguanine, thiotepa, uracil mustard, vinorelbine, chlorambucil, hydrocortisone, prednisolone, methylprednisolone, vindesine, nimustine, semustine, capecitabine, Tomudex, azacytidine, UFT, oxaliplatin, gefitinib (Iressa), imatinib (STI 571), elrotinib, FMS-like tyrosine kinase 3 (Flt3) inhibitor, vascular endothelial growth facotr receptor (VEGFR) inhibitor, fibroblast growth factor receptor (FGFR) inhibitor, Epidermal Growth Factor Receptor (EGFR) inhibitor such as Iressa and Tarceva, radicicol, 17-allylamino-17-demethoxygeldanamycin, rapamycin, amsacrine, all-trans-retinoic acid, thalidomide, anastrozole, fadrozole, letrozole, exemestane, gold thiomalate, D-penicillamine, bucillamine, azathioprine, mizoribine, cyclosporine, rapamycin, hydrocortisone, bexarotene (Targretin), tamoxifen, dexamethasone, progestin substances, estrogen substances, anastrozole (Arimidex), Leuplin, aspirin, indomethacin, celecoxib, azathioprine, penicillamine, gold thiomalate, chlorpheniramine maleate, chlorpheniramine, clemastine, tretinoin, bexarotene, arsenic, voltezomib, allopurinol, calicheamicin, ibritumomab tiuxetan, Targretin, ozogamine, clarithromycin, leucovorin, ifosfamide, ketoconazole, aminoglutethimide, suramin, methotrexate, maytansinoid and derivatives thereof.

The method for conjugating the agent having low molecular weight with the antibody includes a method in which the agent and an amino group of the antibody are conjugated through glutaraldehyde, a method in which an amino group of the agent and a carboxyl group of the antibody are conjugated through water-soluble carbodiimide, and the like.

The agent having a high molecular weight includes polyethylene glycol (hereinafter referred to as "PEG"), albumin, dextran, polyoxyethylene, styrene-maleic acid copolymer, polyvinylpyrrolidone, pyran copolymer, hydroxypropyl-methacrylamide, and the like. By binding these compounds having a high molecular weight to an antibody or antibody fragment, the following effects are expected: (1) improvement of stability against various chemical, physical or biological factors, (2) remarkable prolongation of half life in blood, (3) disappearance of immunogenicity or suppression of antibody production, and the like [*Bioconjugate Drug*, Hirokawa Shoten (1993)]. For example, the method for binding PEG to an antibody includes a method in which an antibody is allowed to react with a PEG-modifying reagent [*Bioconjugate Drug*, Hirokawa Shoten (1993)]. The PEG-modifying reagent includes a modifying agent of ε-amino group of lysine (Japanese Published Unexamined Patent Application No. 178926/86), a modifying agent of a carboxyl group of aspartic acid and glutamic acid (Japanese Published Unexamined Patent Application No. 23587/81), a modifying agent of a guanidino group of arginine (Japanese Published Unexamined Patent Application No. 117920/90) and the like.

The immunostimulator may be any natural products known as immunoadjuvants. Examples of an agent enhancing immunogen include β(1→3)glucan (lentinan, schizophyllan), α-galactosylceramide and the like.

The protein includes a cytokine or a growth factor which activates a immunocompetent cell, such as NK cell, macrophage or neutrophil, a toxic protein, and the like.

Examples of the cytokine or the growth factor include interferon (hereinafter referred to as "IFN")-α, IFN-β, IFN-γ, interleukin (hereinafter referred to as "IL")-2, IL-12, IL-15, IL-18, IL-21, IL-23, granulocyte-colony stimulating factor (G-CSF), granulocyte macrophage-colony stimulating factor (GM-CSF), macrophage-colony stimulating factor (M-CSF) and the like.

The toxic protein includes ricin, diphtheria toxin, ONTAK and the like, and also includes a toxic protein wherein mutation is introduced into a protein in order to control the toxicity.

The therapeutic antibody includes an antibody against an antigen in which apoptosis is induced by binding of the antibody, an antibody against an antigen participating in formation of pathologic state of tumor, an antibody against an antigen regulating immunological function and an antibody against an antigen relating to angiogenesis in the pathologic part.

The antigen in which apoptosis is induced by binding of the antibody includes cluster of differentiation (hereinafter "CD") 19, CD20, CD21, CD22, CD23, CD24, CD37, CD53, CD72, CD73, CD74, CDw75, CDw76, CD77, CDw78, CD79a, CD79b, CD80 (B7.1), CD81, CD82, CD83, CDw84, CD85, CD86 (B7.2), human leukocyte antigen (HLA)-Class II, epidermal growth factor receptor (EGFR) and the like.

The antigen participating in formation of pathologic state of tumor or the antigen regulating immunological function includes CD40, CD40 ligand, B7 family molecule (CD80, CD86, CD274, B7-DC, B7-H2, B7-H3, B7-H4), ligand of B7 family molecule (CD28, CTLA-4, ICOS, PD-1, BTLA), OX-40, OX-40 ligand, CD137, tumor necrosis factor (TNF) receptor family molecule (DR4, DR5, TNFR1, TNFR2), TNF-related apoptosis-inducing ligand receptor (TRAIL) family molecule, receptor family of TRAIL family molecule (TRAIL-R1, TRAIL-R2, TRAIL-R3, TRAIL-R4), receptor activator of nuclear factor kappa B (RANK), RANK ligand, CD25, folic acid receptor 4, cytokine [IL-1α, IL-1β, IL-4, IL-5, IL-6, IL-10, IL-13, transforming growth factor (TGF)

β, TNFα, etc.], receptors of these cytokines, chemokine (SLC, ELC, 1-309, TARC, MDC, CTACK, etc.) and receptors of these chemokines.

The antigen for the antibody which inhibits angiogenesis in the pathologic part includes vascular endothelial growth factor (VEGF), angiopoietin, fibroblast growth factor (FGF), EGF, platelet-derived growth factor (PDGF), insulin-like growth factor (IGF), erythropoietin (EPO), TGFβ, IL-8, Ephilin, SDF-1, receptors thereof and the like.

A fusion antibody with a protein or therapeutic antibody can be produced by linking a cDNA encoding a monoclonal antibody or antibody fragment to a cDNA encoding the protein, constructing a DNA encoding the fusion antibody, inserting the DNA into an expression vector for prokaryote or eukaryote, and then introducing the expression vector into a prokaryote or eukaryote to express the fusion antibody.

In the case where the above antibody conjugate is used for the detection method, method for quantitative determination, detection reagent, reagent for quantitative determination or diagnostic agent in the present invention, examples of the agent to which the monoclonal antibody or the antibody fragment of the present invention which specifically recognizes human TIM-3 and binds to an amino acid sequence of the extracellular region or three-dimensional structure thereof is bound includes a label used in routine immunological detecting or measuring method.

The label includes enzymes such as alkaline phosphatase, peroxidase and luciferase, luminescent materials such as acridinium ester and lophine, fluorescent materials such as fluorescein isothiocyanate (FITC) and tetramethyl rhodamine isothiocyanate (RITC), and the like.

Furthermore, the present invention includes an agent for treating a disease relating to a TIM-3 positive cell, comprising the monoclonal antibody of the present invention or the antibody fragment thereof as an active ingredient.

The disease relating to the TIM-3 positive cell is not limited, so long as it is a disease relating to a cell expressing TIM-3, such as cancer, autoimmune disease, and allergic disease.

The cancer includes blood cancer, breast cancer, uterine cancer, colorectal cancer, esophageal cancer, gastric cancer, ovarian cancer, lung cancer, renal cancer, rectal cancer, thyroid cancer, uterine cervix cancer, small intestinal cancer, prostate cancer and pancreatic cancer. Preferable examples of the cancer include blood cancer, esophageal cancer, gastric cancer, colorectal cancer, liver cancer and prostate cancer.

Examples of the blood cancer include acute myeloid leukemia (AML), chronic myeloid leukemia (CML), myelodysplasticsyndromes (MDS), multiple myeloma, cutaneous T cell lymphoma (CTCL), peripheral T-cell lymphoma (PTCL), anaplastic large cell lymphoma (ALCL), acute lymphocytic leukemia (ALL), chronic lymphocytic leukemia (CLL), other lymphoid leukemia, NK cell lymphoma, Hodgkin lymphoma, non-Hodgkin's lymphoma such as Burkitt's lymphoma, and the like.

Specific examples of the autoimmune diseases include rheumatoid arthritis, psoriasis, Crohn's disease, Ankylosing spondylitis, multiple sclerosis, type I diabetes, hepatitis, myocarditis, Sjogren's syndrome, autoimmune hemolytic anemia after transplant rejection, blisters pemphigoid, Graves disease, Hashimoto's thyroiditis, systemic lupus erythematosus (SLE), myasthenia gravis, pemphigus, pernicious anemia, and the like.

Examples of the allergic diseases include acute or chronic reactive airway disease, bronchial asthma, atopic dermatitis, allergic rhinitis, urticaria, PIE syndrome, food allergies, hay fever, allergic nose, bronchial asthma, atopic dermatitis, anaphylactic shock and the like.

The therapeutic agent of the present invention comprises the above monoclonal antibody or the antibody fragment of the present invention as an active ingredient.

The therapeutic agent comprising the monoclonal antibody of the present invention or antibody fragment thereof, or conjugate thereof may comprise only the antibody or antibody fragment thereof, or conjugate thereof as an active ingredient. It is generally preferred that the therapeutic agent is prepared as a pharmaceutical preparation produced by an appropriate method well known in the technical field of pharmaceutics, and by mixing it with one or more pharmaceutically acceptable carriers.

It is preferred to administer the therapeutic agent by the route that is most effective for the treatment. Examples include oral administration and parenteral administration, such as buccal, tracheal, rectal, subcutaneous, intramuscular or intravenous administration and intravenous administration is preferred.

The pharmaceutical preparation includes sprays, capsules, tablets, powders, granules, syrups, emulsions, suppositories, injections, ointments, tapes and the like.

Although the dose or the frequency of administration varies depending on the objective therapeutic effect, administration method, treating period, age, body weight and the like, it is usually 10 μg/kg to 10 mg/kg per day and per adult.

Further, the present invention relates to a method for immunologically detecting or measuring TIM-3, a reagent for immunologically detecting or measuring TIM-3, a method for immunologically detecting or measuring a cell expressing TIM-3, and a diagnostic agent for diagnosing a disease relating to a TIM-3 positive cell, comprising the monoclonal antibody or the antibody fragment of the present invention which specifically recognizes human TIM-3 and binds to an amino acid sequence of the extracellular region or three-dimensional structure thereof as an active ingredient.

In the present invention, the method for detecting or measuring the amount of TIM-3 may be any known method. For example, it includes an immunological detecting or measuring method.

The immunological detecting or measuring method is a method in which an antibody amount or an antigen amount is detected or determined using a labeled antigen or antibody. Examples of the immunological detecting or measuring method include radioactive substance-labeled immunoantibody method (RIA), enzyme immunoassay (EIA or ELISA), fluorescent immunoassay (FIA), luminescent immunoassay, Western blotting method, physicochemical method and the like.

The above disease relating to a TIM-3 positive cell can be diagnosed by detecting or measuring a cell expressing TIM-3 by using the monoclonal antibody or antibody fragment of the present invention.

For the detection of the cell expressing the polypeptide, known immunological detection methods can be used, and an immunoprecipitation method, a fluorescent cell staining method, an immune tissue staining method and the like are preferably used. Also, a fluorescent antibody staining method using FMAT 8100 HTS system (Applied Biosystem) and the like can be used.

In the present invention, the living body sample to be used for detecting or measuring TIM-3 is not particularly limited, so long as it has a possibility of containing a cell expressing TIM-3, such as tissue cells, blood, blood plasma, serum, pancreatic fluid, urine, fecal matter, tissue fluid or culture fluid.

The diagnostic agent containing the monoclonal antibody of the present invention or antibody fragment thereof, or conjugate thereof may further contain a reagent for carrying out an antigen-antibody reaction or a reagent for detection of the reaction depending on the desired diagnostic method. The reagent for carrying out the antigen-antibody reaction includes a buffer, a salt, and the like. The reagent for detection includes a reagent generally used for the immunological detecting or measuring method, such as labeled secondary antibody which recognizes the monoclonal antibody, antibody fragment thereof or conjugates thereof and substrate corresponding to the labeling and the like.

A process for producing the antibody of the present invention, a method for treating the disease and a method for diagnosing the disease are specifically described below.

1. Preparation Method of Monoclonal Antibody (1) Preparation of Antigen

TIM-3 or a cell expressing TIM-3 as an antigen can be obtained by introducing an expression vector comprising cDNA encoding a full length of TIM-3 or a partial length thereof is introduced into *Escherichia coli*, yeast, an insect cell, an animal cell or the like. In addition, TIM-3 can be purified and obtained from various human tumor cell lines, human tissue and the like which express a large amount of TIM-3. The tumor cell line and the tissue can be directly allowed to use as antigens. Furthermore, a synthetic peptide having a partial sequence of the TIM-3 can be prepared by a chemical synthesis method such as Fmoc method or tBoc method and used as an antigen.

TIM-3 used in the present invention can be produced, for example, by expressing a DNA encoding TIM-3 in a host cell using a method described in *Molecular Cloning, A Laboratory Manual*, Second Edition, Cold Spring Harbor Laboratory Press (1989), *Current Protocols in Molecular Biology*, John Wiley & Sons (1987-1997) or the like according to the following method.

Firstly, a recombinant vector is prepared by inserting a full length cDNA comprising the region encoding TIM-3 into downstream of a promoter of an appropriate expression vector. At this time, if necessary, a DNA fragment having an appropriate length containing a region encoding the polypeptide prepared based on the full length cDNA may be used instead of the above full length cDNA. Next, a transformant producing polypeptide can be obtained by introducing the recombinant vector into a host cell suitable for the expression vector.

The expression vector may be any one, so long as it can replicate autonomously in the host cell to be used or it can be integrated into a chromosome comprising an appropriate promoter at such a position that the DNA encoding the polypeptide can be transcribed.

The host cell may be any one, so long as it can express the objective gene. Examples include a microorganism which belongs to the genera *Escherichia*, such as *Escherichia coli*, yeast, an insect cell, an animal cell and the like.

When a prokaryote such as *Escherichia coli* is used as the host cell, it is preferred that the recombinant vector used in the present invention is autonomously replicable in the prokaryote and comprising a promoter, a ribosome binding sequence, the DNA encoding TIM-3 and a transcription termination sequence. The recombinant vector is not necessary to have a transcription termination sequence, but a transcription termination sequence is preferably set just below the structural gene. The recombinant vector may further comprise a gene regulating the promoter.

Also, the above recombinant vector is preferably a plasmid in which the space between Shine-Dalgarno sequence, which is the ribosome binding sequence, and the initiation codon is adjusted to an appropriate distance (for example, 6 to 18 nucleotides).

Furthermore, the nucleotide sequence of the DNA encoding TIM-3 can be substituted with another base so as to be a suitable codon for expressing in a host cell, thereby improve the productivity of the objective TIM-3.

Any expression vector can be used, so long as it can function in the host cell to be used. Examples of the expression vector includes pBTrp2, pBTac1, pBTac2 (all manufactured by Roche Diagnostics), pKK233-2 (manufactured by Pharmacia), pSE280 (manufactured by Invitrogen), pGEMEX-1 (manufactured by Promega), pQE-8 (manufactured by QIAGEN), pKYP10 (Japanese Published Unexamined Patent Application No. 110600/83), pKYP200 [*Agricultural Biological Chemistry*, 48, 669 (1984)], pLSA1 [*Agric. Biol. Chem.*, 53, 277 (1989)], pGEL1 [*Proc. Natl. Acad. Sci. USA*, 82, 4306 (1985)], pBluescript II SK(−) (manufactured by Stratagene), pTrs30 [prepared from *Escherichia coli* JM109/pTrS30 (FERM BP-5407)], pTrs32 [prepared from *Escherichia coli* JM109/pTrS32 (FERM BP-5408)], pGHA2 [prepared from *Escherichia coli* IGHA2 (FERM BP-400), Japanese Published Unexamined Patent Application No. 221091/85], pGKA2 [prepared from *Escherichia coli* IGKA2 (FERM BP-6798), Japanese Published Unexamined Patent Application No. 221091/85], pTerm2 (U.S. Pat. Nos. 4,686,191, 4,939,094, 5,160,735), pSupex, pUB110, pTP5, pC194, pEG400 [*J. Bacteriol.*, 172, 2392 (1990)], pGEX (manufactured by Pharmacia), pET system (manufactured by Novagen), pME18SFL3 and the like.

Any promoter can be used, so long as it can function in the host cell to be used. Examples include promoters derived from *Escherichia coli*, phage and the like, such as trp promoter (Ptrp), lac promoter, PL promoter, PR promoter and T7 promoter and the like. Also, artificially designed and modified promoters, such as a promoter in which two Ptrp are tandemly linked, tac promoter, lacT7 promoter and letI promoter, can be used.

Examples of host cell include *Escherichia coli* XL1-Blue, *Escherichia coli* XL2-Blue, *Escherichia coli* DH1, *Escherichia coli* MC1000, *Escherichia coli* KY3276, *Escherichia coli* W1485, *Escherichia coli* JM109, *Escherichia coli* HB101, *Escherichia coli* No. 49, *Escherichia coli* W3110, *Escherichia coli* NY49, *Escherichia coli* DH5a and the like.

Any introduction method of the recombinant vector can be used, so long as it is a method for introducing DNA into the host cell, and examples include a method using a calcium ion described in *Proc. Natl. Acad. Sci. USA*, 69, 2110 (1972), *Gene*, 17, 107 (1982) and *Molecular & General Genetics*, 168, 111 (1979) and the like.

When an animal cell is used as the host cell, any expression vector can be used, so long as it can function in the animal cell. Examples include pcDNAI, pcDM8 (manufactured by Funakoshi), pAGE107 [Japanese Published Unexamined Patent Application No. 22979/91; *Cytotechnology*, 3, 133 (1990)], pAS3-3 (Japanese Published Unexamined Patent Application No. 227075/90), pCDM8 [*Nature*, 329, 840, (1987)], pcDNAI/Amp (manufactured by Invitrogen), pcDNA3.1 (manufactured by Invitrogen), pREP4 (manufactured by Invitrogen), pAGE103 [*J. Biochemistry*, 101, 1307 (1987)], pAGE210, pME18SFL3, pKANTEX93 (WO 97/10354) and the like.

Any promoter can be used, so long as it can function in an animal cell. Examples include a promoter of immediate early (IE) gene of cytomegalovirus (CMV), SV40 early promoter, a promoter of retrovirus, a metallothionein promoter, a heat shock promoter, SRα promoter, Molony murine leukemia virus promoter or enhancer, and the like. Also, the enhancer of the IE gene of human CMV can be used together with the promoter.

The host cell includes human Namalwa leukemia cell, monkey COS cell, Chinese hamster ovary (CHO) cell [Journal of Experimental Medicine, 108, 945 (1958); Proc. Natl. Acad. Sci. USA, 60, 1275 (1968); Genetics, 55, 513(1968); Chromosoma, 41, 129 (1973); Methods in Cell Science, 18, 115 (1996); Radiation Research, 148, 260 (1997); Proc. Natl. Acad. Sci. USA, 77, 4216 (1980); Proc. Natl. Acad. Sci. USA, 60, 1275 (1968); Cell, 6, 121 (1975); Molecular Cell genetics, Appendix I, II (pp. 883-900)], CHO/DG44, CHO-K1 (ATCC accession NO: CCL-61), DUkXB11 (ATCC accession NO:CCL-9096), Pro-5 (ATCC accession NO: CCL-1781), CHO-S (Life Technologies, Cat#11619), Pro-3, rat myeloma cell YB2/3HL.P2.G11.16Ag.20 (also called as YB2/0), mouse myeloma cell NS0, mouse myeloma cell SP2/0-Ag14, Syrian hamster cell BHK or HBT5637 (Japanese Published Unexamined Patent Application No. 299/88) and the like.

Any introduction method of the recombinant vector can be used, so long as it is a method for introducing DNA into an animal cell, and examples include electroporation [Cytotechnology, 3, 133 (1990)], the calcium phosphate method (Japanese Published Unexamined Patent Application No. 227075/90), the lipofection method [Proc. Natl. Acad. Sci. USA, 84, 7413 (1987)], and the like.

TIM-3 can be produced by culturing the transformant derived from a microorganism, an animal cell or the like having a recombinant vector comprising the DNA encoding TIM-3 in a medium to form and accumulate TIM-3 in the culture, and recovering it from the culture. The method for culturing the transformant in the medium is carried out according to the usual method used in culturing of hosts.

When TIM-3 is expressed in a cell derived from eukaryote, TIM-3 to which sugars or sugar chains bind can be obtained.

When a microorganism transformed with a recombinant vector containing an inducible promoter is cultured, an inducer can be added to the medium, if necessary. For example, isopropyl-β-D-thiogalactopyranoside or the like can be added to the medium when a microorganism transformed with a recombinant vector using lac promoter is cultured; or indoleacrylic acid or the like can be added thereto when a microorganism transformed with a recombinant vector using trp promoter is cultured.

When a transformant obtained using an animal cell as the host cell is cultured, the medium includes generally used RPMI 1640 medium [The Journal of the American Medical Association, 199, 519 (1967)], Eagle's MEM medium [Science, 122, 501 (1952)], Dulbecco's modified MEM medium [Virology, 8, 396 (1959)] and 199 medium [Proceeding of the Society for the Biological Medicine, 73, 1 (1950)], Iscove's modified Dulbecco's medium (IMDM), the media to which fetal calf serum, etc. is added, and the like. Culture is carried out generally at a pH of 6 to 8 and 30 to 40° C. for 1 to 7 days in the presence of 5% $CO_2$. If necessary, an antibiotic such as kanamycin or penicillin can be added to the medium during the culturing.

Regarding the expression method of the gene encoding TIM-3, in addition to direct expression, secretory production, fusion protein expression and the like can be carried out according to the method described in Molecular Cloning, A Laboratory Manual, Second Edition, Cold Spring Harbor Laboratory Press (1989).

The process for producing TIM-3 includes a method of intracellular expression in a host cell, a method of extracellular secretion from a host cell, a method of producing on a host cell outer membrane, and the like. The appropriate method can be selected by changing the host cell used and the structure of the TIM-3 produced.

When the TIM-3 is produced in a host cell or on a host cell membrane outer envelope, TIM-3 can be positively secreted extracellularly in accordance with the method of Paulson et al. [J. Biol. Chem., 264, 17619 (1989)], the method of Lowe et al. [Proc. Natl. Acad. Sci. USA, 86, 8227 (1989), Genes Develop., 4, 1288 (1990)], the methods described in Japanese Published Unexamined Patent Application No. 336963/93 and WO 94/23021, and the like.

Also, the production amount of TIM-3 can be increased in accordance with the method described in Japanese Published Unexamined Patent Application No. 227075/90 utilizing a gene amplification system using a dihydrofolate reductase gene.

The resulting TIM-3 can be isolated and purified, for example, as follows.

When TIM-3 is intracellularly expressed in a dissolved state, the cells after culturing are recovered by centrifugation, suspended in an aqueous buffer and then disrupted using ultrasonicator, French press, Manton Gaulin homogenizer, dynomill or the like to obtain a cell-free extract.

The cell-free extract is centrifuged to obtain a supernatant, and a purified preparation can be obtained by subjecting the supernatant to a general protein isolation and purification techniques such as solvent extraction; salting out with ammonium sulfate etc.; desalting; precipitation with an organic solvent; anion exchange chromatography using a resin such as diethylaminoethyl (DEAE)-sepharose, DIAION HPA-75 (manufactured by Mitsubishi Chemical); cation exchange chromatography using a resin such as S-Sepharose FF (manufactured by Pharmacia); hydrophobic chromatography using a resin such as butyl-Sepharose or phenyl-Sepharose; gel filtration using a molecular sieve; affinity chromatography; chromatofocusing; electrophoresis such as isoelectric focusing; and the like which may be used alone or in combination.

When TIM-3 is expressed intracellularly by forming an inclusion body, the cells are recovered, disrupted and centrifuged in the same manner, and the inclusion body of TIM-3 are recovered as a precipitation fraction. The recovered inclusion body of the TIM-3 protein is solubilized with a protein denaturing agent. The protein is made into a normal three-dimensional structure by diluting or dialyzing the solubilized solution, and then a purified preparation of polypeptide is obtained by the same isolation purification method as above.

When TIM-3 or the derivative such as a glycosylated product is secreted extracellularly, TIM-3 or the derivative such as a glycosylated product can be recovered from the culture supernatant. That is, the culture is treated by a method such as centrifugation in the same manner as above to obtain a soluble fraction, a purified preparation of TIM-3 can be obtained from the soluble fraction by the same isolation purification method as above.

Also, TIM-3 used in the present invention can be produced by a chemical synthesis method, such as Fmoc method or tBoc method. Also, it can be chemically synthesized using a peptide synthesizer manufactured by Advanced ChemTech, Perkin-Elmer, Pharmacia, Protein Technology Instrument, Synthecell-Vega, PerSeptive, Shimadzu Corporation, or the like.

(2) Immunization of Animal and Preparation of Antibody-Producing Cell for Fusion A mouse, rat or hamster and the like which is 3 to 20-weeks-old is immunized with the antigen prepared in the above (1), and antibody-producing cells within the spleen, lymph node or peripheral blood of the animal are collected. Also, when the increase of a sufficient titer in the above animal is not recognized due to low immunogenecity, a TIM-3 knockout mouse may by used as an animal to be immunized.

The immunization is carried out by administering the antigen to the animal through subcutaneous, intravenous or intraperitoneal injection together with an appropriate adjuvant (for example, complete Freund's adjuvant, combination of aluminum hydroxide gel with pertussis vaccine, or the like). When the antigen is a partial peptide, a conjugate is produced with a carrier protein such as BSA (bovine serum albumin), KLH (keyhole limpet hemocyanin) or the like, which is used as the antigen.

The administration of the antigen is carried out 5 to 10 times every one week or every two weeks after the first administration. On the 3rd to 7th day after each administration, a blood sample is collected from the fundus of the eye, the reactivity of the serum with the antigen is tested, for example, by enzyme immunoassay [*Antibodies—A Laboratory Manual*, Cold Spring Harbor Laboratory (1988)] or the like. An animal showing a sufficient antibody titer in their sera against the antigen used for the immunization is used as the source of antibody-producing cells for fusion.

Three to seven days after final administration of the antigen, tissue containing the antibody-producing cells such as the spleen is excised from the immunized animal to collect the antibody-producing cells. When the spleen cells are used, the spleen is cut out and loosened, followed by centrifugation. Then, antibody-producing cells for fusion are obtained by removing erythrocytes.

(3) Preparation of Myeloma Cell

An established cell line obtained from mouse is used as myeloma cells. Examples include 8-azaguanine-resistant mouse (derived from BALB/c) myeloma cell line P3-X63Ag8-U1 (P3-U1) [*Current Topics in Microbiology and Immunology*, 18, 1 (1978)], P3-NS1/1-Ag41 (NS-1) [*European J. Immunology*, 6, 511 (1976)], SP2/0-Ag14 (SP-2) [*Nature*, 276, 269 (1978)], P3-X63-Ag8653 (653) [*J. Immunology*, 123, 1548 (1979)], P3-X63-Ag8 (X63) [*Nature*, 256, 495 (1975)] and the like.

The myeloma cells are subcultured in a normal medium [a medium in which glutamine, 2-mercaptoethanol, gentamicin, FBS and 8-azaguanine are added to RPMI-1640 medium] and they are subcultured in the normal medium 3 or 4 days before cell fusion to ensure the cell number of $2 \times 10^7$ or more on the day for fusion.

(4) Cell Fusion and Preparation of Hybridoma for Producing Monoclonal Antibody

The antibody-producing cells for fusion obtained by the above (2) and myeloma cells obtained by the above (3) were sufficiently washed with a minimum essential medium (MEM) or PBS (1.83 g of disodium hydrogen phosphate, 0.21 g of potassium dihydrogen phosphate, 7.65 g of sodium chloride, 1 liter of distilled water, pH 7.2) and mixed to give a ratio of the antibody-producing cells: the myeloma cells=5 to 10:1, followed by centrifugation. Then, the supernatant is discarded.

The precipitated cell group is sufficiently loosened. After loosening the precipitated cell, the mixture of polyethylene glycol-1000 (PEG-1000), MEM and dimethylsulfoxide is added to the cell under stirring at 37° C. In addition, 1 to 2 mL of MEM medium is added several times every one or two minutes, and MEM is added to give a total amount of 50 mL. After centrifugation, the supernatant is discarded. After the cells are gently loosened, the cells are gently suspended in HAT medium [a normal medium containing hypoxanthine, thymidine and aminopterin]. The suspension is cultured in a 5% $CO_2$ incubator for 7 to 14 days at 37° C.

After the culturing, a portion of the culture supernatant is sampled and a hybridoma which is reactive to an antigen containing TIM-3 and is not reactive to an antigen not containing TIM-3 is selected by binding assay as described below. Then, cloning is carried out twice by a limiting dilution method [Firstly, HT medium (HAT medium from which aminopterin is removed) is used, and secondly, the normal medium is used], and a hybridoma which stably shows a high antibody titer is selected as the monoclonal antibody-producing hybridoma.

(5) Preparation of Purified Monoclonal Antibody

The hybridoma cells producing a monoclonal antibody obtained by the above (4) are administered by intraperitoneal injection into 8- to 10-week-old mice or nude mice treated with 0.5 mL of pristane (2,6,10,14-tetramethylpentadecane (pristane) is intraperitoneally administered, followed by feeding for 2 weeks). The hybridoma develops ascites tumor in 10 to 21 days. The ascitic fluid is collected from the mice, centrifuged to remove solids, subjected to salting out with 40 to 50% ammonium sulfate and then precipitated by caprylic acid, passed through a DEAE-Sepharose column, a protein A column or a gel filtration column to collect an IgG or IgM fraction as a purified monoclonal antibody.

Furthermore, a monoclonal antibody-producing hybridoma obtained by the above (4) is cultured in RPMI1640 medium containing 10% FBS or the like and the supernatant is removed by centrifugation. The precipitated cells are suspended in Hybridoma-SFM medium and cultured for 3 to 7 days. The purified monoclonal antibody can be obtained by centrifusing the obtained cell suspension, followed by purification from the resulting supernatant with Protein A column or Protein G column to collect the IgG fractions. Additionally, Hybridoma-SFM medium can contain 5% DIGO GF21.

The subclass of the antibody can be determined using a subclass typing kit by enzyme immunoassay. The amount of the protein can be determined by the Lowry method or from the absorbance at 280 nm.

(6) Selection of Monoclonal Antibody

Selection of monoclonal antibody is carried out by the following binding assay using an enzyme immunoassay method and inhibition assay of intracellular uptake of amino acids.

(6-a) Binding Assay

As the antigen, a gene-introduced cell obtained by introducing an expression vector containing a cDNA encoding TIM-3 obtained in (1) into *Escherichia coli*, yeast, an insect cell, an animal cell or the like, a recombinant protein, or a purified polypeptide or partial peptide obtained from a human tissue is used. When the antigen is a partial peptide, a conjugate is prepared with a carrier protein such as BSA or KLH is prepared and is used.

After making these antigens into a solid layer by dispensing in a 96-well plate, a substance to be tested such as serum, a culture supernatant of a hybridoma or a purified monoclonal antibody is dispensed therein as the primary antibody and allowed to react. After thoroughly washing with PBS, PBS-Tween and the like, an anti-immunoglobulin antibody labeled with biotin, an enzyme, a chemiluminescent material, a radiation compound or the like is dispensed therein as the secondary antibody and allowed to react. After thoroughly washing with PBS-Tween, the reaction appropriate to the label of the secondary antibody is carried out to select a monoclonal antibody which specifically reacts with the antigen.

In addition, a monoclonal antibody which competes with the anti-TIM-3 monoclonal antibody of the present invention in the binding of an extracellular region of human TIM-3 can be obtained by adding a subject antibody to the above binding assay system to allow to react. Namely, a monoclonal antibody which competes with the obtained monoclonal antibody in the binding of an amino acid sequence of the extracellular region of human TIM-3 or a three-dimensional structure thereof can be obtained by screening a subject antibody which inhibits the binding of the monoclonal antibody upon adding to the antibody.

Furthermore, an antibody which binds to the same epitope to which the monoclonal antibody of the present invention which binds to an amino acid sequence of the extracellular region of TIM-3 or three-dimensional structure thereof can be obtained by identifying an epitope of the antibody obtained by the above binding assay system, preparing a partial synthetic peptide of the epitope or a synthetic peptide which mimics the three-dimensional structure of the epitope and immunizing with the peptide.

(6-b) Kinetic Analysis with Biacore

The kinetics between an antigen and a test substance is measured using Biacore T100 and then the obtained results are analyzed using analysis software accompanied with the apparatus. After anti-mouse IgG antibody is immobilized onto to a CM 5 sensor chip by an amine coupling method, a test substance such as culture supernatant of a hybridoma, a purified monoclonal antibody is allowed to flow and bind at an appropriate amount, and an antigen at plural known concentrations is further allowed to flow. And then, the binding and dissociation are measured.

Using the obtained data and the software accompanied with the apparatus, the kinetics analysis is carried out using the 1:1 binding model to obtain necessary parameters. Otherwise, after human TIM-3 is immobilized onto the sensor chip by an amino coupling method, a purified monoclonal antibody is allowed to flow at plural known concentrations followed by measuring the binding and dissociation. Using the obtained data and the software accompanied with the apparatus, the kinetics analysis is carried out using bivalent analyte model to obtain necessary parameters.

2. Preparation of Recombinant Antibody

As production examples of recombinant antibodies, processes for producing a human chimeric antibody and a human CDR grafted antibody are shown below.

(1) Construction of Vector for Expression of Recombinant Antibody

A vector for expression of recombinant antibody is an expression vector for animal cell into which DNAs encoding CH and CL of a human antibody have been inserted, and is constructed by cloning each of DNAs encoding CH and CL of a human antibody into an expression vector for animal cell.

The C region of a human antibody may be used CH and CL of any human antibody. Examples include CH belonging to γ1 subclass, CL belonging to κ class, and the like. As the DNAs encoding CH and CL of a human antibody, the cDNA may be generally used and a chromosomal DNA comprising an exon and an intron can be also used.

As the expression vector for animal cell, any expression vector can be used, so long as a gene encoding the C region of a human antibody can be inserted thereinto and expressed therein. Examples include pAGE107 [*Cytotechnol.*, 3, 133 (1990)], pAGE103 [*J. Biochem.*, 101, 1307 (1987)], pHSG274 [*Gene*, 27, 223 (1984)], pKCR [*Proc. Natl. Acad. Sci. USA*, 78, 1527 (1980), pSG1bd2-4 [*Cytotechnol.*, 4, 173 (1990)], pSE1UK1Sed1-3 [*Cytotechnol.*, 13, 79 (1993)] and the like.

Examples of a promoter and enhancer used for an expression vector for animal cell include an SV40 early promoter [*J. Biochem.*, 101, 1307 (1987)], a Moloney mouse leukemia virus LTR [*Biochem. Biophys. Res. Commun.*, 149, 960 (1987)], an immunoglobulin H chain promoter [*Cell*, 41, 479 (1985)] and enhancer [*Cell*, 33, 717 (1983)] and the like.

The vector for expression of recombinant antibody may be either of a type in which a gene encoding an antibody H chain and a gene encoding an antibody L chain exist on separate vectors or of a type in which both genes exist on the same vector (tandem type). In respect of easiness of construction of a vector for expression of recombinant antibody, easiness of introduction into animal cells, and balance between the expression amounts of antibody H and L chains in animal cells, a tandem type of the vector for expression of recombinant antibody is more preferred [*J. Immunol. Methods*, 167, 271 (1994)]. Examples of the tandem type of the vector for expression of recombinant antibody include pKANTEX93 (WO 97/10354), pEE18 [*Hybridoma*, 17, 559 (1998)], and the like.

(2) Obtaining of cDNA Encoding V Region of Antibody Derived from Non-Human Animal and Analysis of Amino Acid Sequence Obtaining of cDNAs encoding VH and VL of a non-human antibody and analysis of amino acid sequence are carried out as follows.

mRNA is extracted from hybridoma cells producing a non-human antibody to synthesize cDNA. The synthesized cDNA is cloned into a vector such as a phage or a plasmid, to prepare a cDNA library.

Each of a recombinant phage or recombinant plasmid containing cDNA encoding VH or VL is isolated from the library using DNA encoding a part of the C region or V region of a mouse antibody as the probe. The full length of the nucleotide sequences of VH and VL of a mouse antibody of interest on the recombinant phage or recombinant plasmid are determined, and the full length of the amino acid sequences of VH and VL are deduced from the nucleotide sequences, respectively.

Examples of the non-human animal for preparing a hybridoma cell which produces a non-human antibody include mouse, rat, hamster, rabbit or the like. Any animals can be used so long as a hybridoma cell can be produced therefrom.

Examples of the method for preparing total RNA from a hybridoma cell include a guanidine thiocyanate-cesium trifluoroacetate method [*Methods in Enzymol.*, 154, 3 (1987)], the use of a kit such as RNA easy kit (manufactured by Qiagen) and the like.

Examples of the method for preparing mRNA from total RNA include an oligo (dT) immobilized cellulose column method [*Molecular Cloning, A Laboratory Manual*, Second Edition, Cold Spring Harbor Laboratory Press (1989)], a method using a kit such as Oligo-dT30<Super> mRNA Purification Kit (manufactured by Takara Bio) and the like. Additionary, examples of the method for preparing mRNA include method using a kit Fast Track mRNA Isolation kit (manufactured by Invitrogen) or QuickPrep mRNA Purification Kit (manufactured by Pharmacia) and the like.

Examples of the method for synthesizing cDNA and preparing a cDNA library include known methods [*Molecular Cloning, A Laboratory Manual*, Second Edition, Cold Spring Harbor Laboratory Press (1989); *Current Protocols in Molecular Biology*, Supplement 1, John Wiley & Sons (1987-1997)]; a method using a kit such as Super Script Plasmid System for cDNA Synthesis and Plasmid Cloning (manufactured by Invitrogen), ZAP-cDNA Synthesis Kit (manufactured by Stratagene), etc.; and the like.

The vector into which the synthesized cDNA using mRNA extracted from a hybridoma cell as the template is inserted for preparing a cDNA library may be any vector, so long as the cDNA can be inserted. Examples include ZAP ExPress [*Strategies*, 5, 58 (1992)], pBluescript II SK(+) [*Nucleic Acids Research*, 17, 9494 (1989)], λZAPII (manufactured by Stratagene), λgt10 and λgt11 [*DNA Cloning: A Practical Approach*, I, 49 (1985)], Lambda BlueMid (manufactured by Clontech), λExCell and pT7T3-18U (manufactured by Pharmacia), pcD2 [*Mol. Cell. Biol.*, 3, 280 (1983)], pUC18 [*Gene*, 33, 103 (1985)], and the like.

Any *Escherichia coli* for introducing the cDNA library constructed by a phage or plasmid vector may be used, so long as the cDNA library can be introduced, expressed and maintained. Examples include XL1-Blue MRF' [*Strategies*, 5, 81 (1992)], C600 [*Genetics*, 39, 440 (1954)], Y1088 and Y1090 [*Science*, 222: 778 (1983)], NM522 [*J. Mol. Biol.*, 166, 1 (1983)], K802 [*J. Mol. Biol.*, 16, 118 (1966)], JM105 [*Gene*, 38, 275 (1985)], and the like.

A colony hybridization or plaque hybridization method using an isotope- or fluorescence-labeled probe may be used for selecting cDNA clones encoding VH or VL of a non-human antibody or the like from the cDNA library [*Molecular Cloning, A Laboratory Manual*, Second Edition, Cold Spring Harbor Laboratory Press (1989)].

Also, the cDNAs encoding VH and VL can be prepared through polymerase chain reaction (hereinafter referred to as "PCR"; *Molecular Cloning, A Laboratory Manual*, Second Edition, Cold Spring Harbor Laboratory Press (1989); *Current Protocols in Molecular Biology*, Supplement 1, John Wiley & Sons (1987-1997)) by preparing primers and using cDNA prepared from mRNA or a cDNA library as the template.

The nucleotide sequence of the cDNA can be determined by digesting the cDNA selected with appropriate restriction enzymes and the like, cloning the fragments into a plasmid such as pBluescript SK(−) (manufactured by Stratagene), carrying out the reaction by a usually used nucleotide sequence analyzing method. For example, a nucleotide sequence analyzing method is carried out by using an automatic nucleotide sequence analyzer such as ABI PRISM3700 (manufactured by PE Biosystems) and A.L.F. DNA sequencer (manufactured by Pharmacia) after a reaction such as the dideoxy method [*Proc. Natl. Acad. Sci. USA*, 74, 5463 (1977)].

Whether the obtained cDNAs encode the full amino acid sequences of VH and VL of the antibody containing a secretory signal sequence can be confirmed by estimating the full length of the amino acid sequences of VH and VL from the determined nucleotide sequence and comparing them with the full length of the amino acid sequences of VH and VL of known antibodies [A.L.F. DNA sequencer, US Dept. Health and Human Services (1991)].

With regard to the full amino acid sequences of VH and VL of the antibody containing a secretory signal sequence, the length of the secretory signal sequence and N-terminal amino acid sequence can be estimated by comparing them with the full length of the amino acid sequences of VH and VL of known antibodies [A.L.F. DNA sequencer, US Dept. Health and Human Services (1990], and furthermore the subgroup to which they belong can be determined. In addition, the amino acid sequence of each CDR of VH and VL can be determined by comparing them with the full length of the amino acid sequences of VH and VL of known antibodies [A.L.F. DNA sequencer, US Dept. Health and Human Services (1991)].

Moreover, the novelty of the full length of the amino acid sequence of VH and VL can be examined by carrying out a homology search with sequences in any database, for example, SWISS-PROT, PIR-Protein or the like using the obtained full length of the amino acid sequences of VH and VL, for example, according to the BLAST method [*J. Mol. Biol.*, 215, 403 (1990)] or the like.

(3) Construction of Vector for Expression of Human Chimeric Antibody cDNA encoding each of VH and VL of antibody of non-human animal is cloned in the upstream of genes encoding CH or CL of human antibody of vector for expression of recombinant antibody mentioned in the above (1) to thereby construct a vector for expression of human chimeric antibody.

In order to ligate cDNA comprising a nucleotide sequence of 3'-terminal of VH or VL of antibody of non-human animal and a nucleotide sequence of 5'-terminal of CH or CL of human antibody, each cDNA encoding VH or VL of a non-human animal antibody is prepared so as to encodes appropriate amino acids and have an appropriate recognition sequence of a restriction enzyme at a linkage portion.

The prepared cDNAs encoding VH and VL of antibody are respectively cloned so that each of them is expressed in an appropriate form in the upstream of gene encoding CH or CL of the human antibody of the vector for expression of the human CDR-grafted antibody mentioned in the above (1) to construct a vector for expression of human chimeric antibody.

In addition, cDNA encoding VH or VL of a non-human animal antibody is amplified by PCR using a synthetic DNA having a recognition sequence of an appropriate restriction enzyme at both ends and each of them is cloned to the vector for expression of recombinant antibody obtained in the above (1).

(4) Construction of cDNA Encoding V Region of Human CDR-Grafted Antibody cDNAs encoding VH or VL of a human CDR-grafted antibody can be obtained as follows.

Amino acid sequences of framework region (hereinafter referred to as "FR") in VH or VL of a human antibody to which amino acid sequences of CDRs in VH or VL of an antibody derived from a non-human animal antibody are transplanted are respectively selected. Any amino acid sequences of FR of a human antibody can be used, so long as they are derived from human.

Examples include amino acid sequences of FRs of human antibodies registered in database such as Protein Data Bank or the like, and amino acid sequences common to subgroups of FRs of human antibodies [*Sequences of Proteins of Immunological Interest*, US Dept. Health and Human Services (1990], and the like. In order to inhibit the decrease in the binding activity of the antibody, amino acid sequences having high homology (at least 60% or more) with the amino acid sequence of FR in VH or VL of the original antibody is selected.

Then, amino acid sequences of CDRs of the original antibody are grafted to the selected amino acid sequence of FR in VH or VL of the human antibody, respectively, to design each amino acid sequence of VH or VL of a humanized antibody. The designed amino acid sequences are converted to DNA sequences by considering the frequency of codon usage found in nucleotide sequences of genes of antibodies [*Sequence of Proteins of Immunological Interest*, US Dept. Health and Human Services (1991)], and the DNA sequence encoding the amino acid sequence of VH or VL of a humanized antibody is designed.

Based on the designed nucleotide sequences, several synthetic DNAs having a length of about 100 nucleotides are synthesized, and PCR is carried out using them. In this case, it is preferred that 6 synthetic DNAs per each of the H chain and the L chain are designed in view of the reaction efficiency of PCR and the lengths of DNAs which can be synthesized.

Furthermore, the cDNA encoding VH or VL of a human CDR-grafted antibody can be easily cloned into the vector for expression of human CDR-grafted antibody constructed in (1) by introducing the recognition sequence of an appropriate restriction enzyme to the 5' terminal of the synthetic DNAs existing on the both ends.

Otherwise, it can be carried out using a synthetic DNA as one DNA encoding each of the full-length H chain and the full-length L chain based on the designed DNA sequence.

After the PCR, an amplified product is cloned into a plasmid such as pBluescript SK(−) (manufactured by Stratagene) or the like, and the nucleotide sequence is determined according to a method similar to the method described in (2) to obtain a plasmid having a DNA sequence encoding the amino acid sequence of VH or VL of a desired humanized antibody.

(5) Modification of Amino Acid Sequence of V Region of Human CDR-Grafted Antibody It is known that when a human CDR-grafted antibody is produced by simply grafting only CDRs in VH and VL of an antibody derived from a non-human animal into FRs of VH and VL of a human antibody, its antigen binding activity is lower than that of the original antibody derived from a non-human animal [*BIO/TECHNOLOGY*, 9, 266 (1991)].

In human CDR-grafted antibodies, among the amino acid sequences of FRs in VH and VL of a human antibody, an amino acid residue which directly relates to binding to an antigen, an amino acid residue which interacts with an amino acid residue in CDR, and an amino acid residue which maintains the three-dimensional structure of an antibody and indirectly relates to binding to an antigen are identified and modified to an amino acid residue which is found in the original non-humanized antibody to thereby increase the antigen binding activity which has been decreased.

In order to identify the amino acid residues relating to the antigen binding activity in FR, constructing the three-dimensional structure of an antibody and analyzing can be done by X-ray crystallography [*J. Mol. Biol.*, 112, 535 (1977)], computer-modeling [*Protein Engineering*, 7, 1501 (1994)] or the like. In addition, modified human CDR-grafted antibody having sufficient binding activity against antigen can be obtained by various attempts, such as producing several modified antibodies of each antibody and examining their binding activities.

The modification of the amino acid sequence of FR in VH and VL of a human antibody can be accomplished using various synthetic DNA for modification according to PCR as described in (4). With regard to the amplified product obtained by the PCR, the nucleotide sequence is determined according to the method as described in (2) so that whether the objective modification has been carried out is confirmed.

(6) Construction of Vector for Expression of Human CDR-Grafted Antibody

A vector for expression of human CDR-grafted antibody can be constructed by cloning each cDNA encoding VH or VL of a constructed recombinant antibody into upstream of each gene encoding CH or CL of the human antibody in the vector for expression of recombinant antibody as described in (1).

For example, when recognizing sequences of an appropriate restriction enzymes are introduced to the 5'-terminal of synthetic DNAs positioned at both ends among synthetic DNAs used in the construction of VH or VL of the human CDR-grafted antibody in (4) and (5), cloning can be carried out so that they are expressed in an appropriate form in the upstream of each gene encoding CH or CL of the human antibody in the vector for expression of a human CDR-grafted antibody as described in (1).

(7) Transient Expression of Recombinant Antibody

In order to efficiently evaluate the antigen binding activity of various human CDR-grafted antibodies produced, the recombinant antibodies can be expressed transiently using the vector for expression of antibody as described in (3) and (6) or the modified expression vector thereof.

Any cell can be used as a host cell, so long as the host cell can express a recombinant antibody. For example, COS-7 cell (ATCC CRL1651) is used in view of its high expression amount [*Methods in Nucleic Acids Res.*, CRC Press, 283 (1991)].

Examples of the method for introducing the expression vector into COS-7 cell include a DEAE-dextran method [*Methods in Nucleic Acids Res.*, CRC Press, 283 (1990], a lipofection method [*Proc. Natl. Acad. Sci. USA*, 84, 7413 (1987)], and the like.

After introduction of the expression vector, the expression amount and antigen binding activity of the recombinant antibody in the culture supernatant can be determined by the enzyme immunoassay [*Monoclonal Antibodies—Principles and practice*, Third edition, Academic Press (1996), *Antibodies—A Laboratory Manual*, Cold Spring Harbor Laboratory (1988), *Monoclonal Antibody Experiment Manual*, Kodansha Scientific (1987)] and the like.

(8) Obtaining Transformant which Stably Expresses Recombinant Antibody and Preparation of Recombinant Antibody A transformant which stably expresses a recombinant antibody can be obtained by introducing the vector for expression of recombinant antibody described in (3) and (6) into an appropriate host cell.

Examples of the method for introducing the expression vector into a host cell include electroporation [Japanese Published Unexamined Patent Application No. 257891/90, *Cytotechnology*, 3, 133 (1990)] and the like.

As the host cell into which a vector for expression of a recombinant antibody is introduced, any cell can be used, so long as it is a host cell which can produce the recombinant antibody. Examples include CHO-K1 (ATCC CCL-61), DUkXB11 (ATCC CCL-9096), Pro-5 (ATCC CCL-1781), CHO-S (Life Technologies, Cat # 11619), rat myeloma cell YB2/3HL.P2.G11.16Ag.20 (also referred to as YB2/0), mouse myeloma cell NSO, mouse myeloma cell SP2/0-Ag14 (ATCC No. CRL1581), mouse P3X63-Ag8653 cell (ATCC No. CRL1580), CHO cell in which a dihydrofolate reductase gene (hereinafter referred to as "dhfr") is defective [*Proc. Natl. Acad. Sci. U.S.A.*, 77, 4216 (1980)], lection resistance-acquired Lec13 [*Somatic Cell and Molecular*

*genetics,* 12, 55 (1986)], CHO cell in which α1,6-fucosyltransaferse gene is defected (WO 2005/35586, WO 02/31140), rat YB2/3HL.P2.G11.16Ag.20 cell (ATCC No. CRL1662), and the like.

In addition, host cells in which activity of a protein such as an enzyme relating to synthesis of an intracellular sugar nucleotide, GDP-fucose, a protein such as an enzyme relating to the modification of a sugar chain in which 1-position of fucose is bound to 6-position of N-acetylglucosamine in the reducing end through α-bond in a complex type N-glycoside-linked sugar chain, or a protein relating to transport of an intracellular sugar nucleotide, GDP-fucose, to the Golgi body is decreased or deleted, preferably CHO cell in which α1,6-fucosyltransferase gene is defected as described in WO2005/35586, WO02/31140 or the like, can also be used.

After introduction of the expression vector, transformants which express a recombinant antibody stably are selected by culturing in a medium for animal cell culture containing an agent such as G418 sulfate (hereinafter referred to as "G418") or the like (Japanese Published Unexamined Patent Application No. 257891/90).

Examples of the medium for animal cell culture include RPMI1640 medium (manufactured by Invitrogen), GIT medium (manufactured by Nihon Pharmaceutical), EX-CELL301 medium (manufactured by JRH), IMDM medium (manufactured by Invitrogen), Hybridoma-SFM medium (manufactured by Invitrogen), media obtained by adding various additives such as FBS to these media, and the like.

The recombinant antibody can be produced and accumulated in a culture supernatant by culturing the obtained transformants in a medium. The expression amount and antigen binding activity of the recombinant antibody in the culture supernatant can be measured by ELISA or the like. Also, in the transformant, the expression amount of the recombinant antibody can be increased by using DHFR amplification system or the like according to the method disclosed in Japanese Published Unexamined Patent Application No. 257891/90.

The recombinant antibody can be purified from the culture supernatant of the transformant by using a protein A column [Monoclonal *Antibodies—Principles and practice*, Third edition, Academic Press (1996), *Antibodies—A Laboratory Manual*, Cold Spring Harbor Laboratory (1988)]. In addition, the recombinant antibody can be purified by a combination of the methods for purification such as gel filtration, ion-exchange chromatography, ultrafiltration and the like.

The molecular weight of the H chain or the L chain of the purified recombinant antibody or the antibody molecule as a whole is determined by polyacrylamide gel electrophoresis (hereinafter referred to as "SDS-PAGE") [*Nature*, 227, 680 (1970)], Western blotting [*Monoclonal Antibodies—Principles and practice*, Third edition, Academic Press (1996), *Antibodies—A Laboratory Manual*, Cold Spring Harbor Laboratory (1988)], and the like.

3. Activity Evaluation of the Monoclonal Antibody or Antibody Fragment

The activity of the purified monoclonal antibody or antibody fragment of the present invention can be evaluated in the following manner.

The binding activity to TIM-3-expressing cell is evaluated by the binding assay described in the above 1-(6a) and a surface plasmon resonance method using such as the Biacore system described in the above (6b). Furthermore, it can be measured by fluorescent antibody technique [*Cancer Immunol. Immunother.*, 36, 373 (1993)] and the like.

Complement-Dependent Cytotoxicity (hereinafter, referred to as "CDC activity") or ADCC activity against an antigen positive cell line is evaluated by a known method [*Cancer Immunol. Immunother.*, 36, 373 (1993)].

4. Method of Controlling Effector Activity of Antibody

As a method for controlling an effector activity of the monoclonal antibody of the present invention, a method for controlling an amount of fucose (hereinafter, referred to also as "core fucose") which is bound in α-1,6 linkage to N-acetylglucosamine (GlcNAc) present in a reducing end of a complex type N-linked sugar chain which is bound to asparagine (Asn) at position 297 of an Fc region of an antibody (WO2005/035586, WO2002/31140, and WO00/61739), a method for controlling an effector activity of a monoclonal antibody by modifying amino acid group(s) of an Fc region of the antibody, and the like are known. The effector activity of the anti-TIM-3 monoclonal antibody of the present invention can be controlled by using any of the methods.

The "effector activity" means an antibody-dependent activity which is induced via an Fc region of an antibody. As the effector activity, ADCC activity, CDC activity, an antibody-dependent phagocytosis (ADP activity) by phagocyte such as macrophages or dendritic cells, and the like are known.

By controlling a content of core fucose of a complex type N-linked sugar chain of Fc of an antibody, an effector activity of the antibody can be increased or decreased.

According to a method for lowering a content of fucose which is bound to a complex type N-linked sugar chain bound to Fc of the antibody, an antibody to which fucose is not bound can be obtained by the expression of an antibody using a CHO cell which is deficient in a gene encoding α1,6-fucosyltransferase. The antibody to which fucose is not bound has a high ADCC activity.

On the other hand, according to a method for increasing a content of fucose which is bound to a complex type N-linked sugar chain bound to Fc of an antibody, an antibody to which fucose is bound can be obtained by the expression of an antibody using a host cell into which a gene encoding α1,6-fucosyltransferase is introduced. The antibody to which fucose is bound has a lower ADCC activity than the antibody to which fucose is not bound.

Further, by modifying amino acid residue(s) in an Fc region of an antibody, the ADCC activity or CDC activity can be increased or decreased. For example, the binding activity to an antibody can be increased by using the amino acid sequence of the Fc region described in US2007/0148165. Further, the ADCC activity or CDC activity can be increased or decreased by modifying the amino acid as described in U.S. Pat. No. 6,737,056, or 7,297,775 or 7,317,091.

Furthermore, an antibody in which the effector activity is controlled can be obtained by combining the above method within one antibody.

5. Method for Treating Disease Using the Anti-TIM-3 Monoclonal Antibody or Antibody Fragment of the Present Invention The monoclonal antibody or an antibody fragment thereof of the present invention can be used for treating a disease relating to a TIM-3 positive cell.

The therapeutic agent comprising the antibody or antibody fragment of the present invention or derivatives thereof may be only the antibody or antibody fragment or derivatives thereof as an active ingredient, and is preferably supplied as a pharmaceutical preparation produced by an appropriate method well known in the technical field of pharmaceutics, by mixing it with one or more pharmaceutically acceptable carriers.

Examples of a route of administration include oral administration and non-oral administration, such as buccal, tracheal, rectal, subcutaneous, intramuscular or intravenous administration. Examples of the dosage form includes sprays, capsules, tablets, powder, granules, syrups, emulsions, suppositories, injections, ointments, tapes and the like.

The pharmaceutical preparation suitable for oral administration includes emulsions, syrups, capsules, tablets, powders, granules and the like.

Liquid preparations such as emulsions and syrups can be produced using, as additives, water; sugars such as sucrose, sorbitol and fructose; glycols such as polyethylene glycol and propylene glycol; oils such as sesame oil, olive oil and soybean oil; antiseptics such as p-hydroxybenzoic acid esters; flavors such as strawberry flavor and peppermint; and the like.

Capsules, tablets, powders, granules and the like can be produced using, as additives, excipients such as lactose, glucose, sucrose and mannitol; disintegrating agents such as starch and sodium alginate; lubricants such as magnesium stearate and talc; binders such as polyvinyl alcohol, hydroxypropylcellulose and gelatin; surfactants such as fatty acid ester; plasticizers such as glycerin; and the like.

The pharmaceutical preparation suitable for parenteral administration includes injections, suppositories, sprays and the like.

Injections can be prepared using a carrier such as a salt solution, a glucose solution or a mixture of both thereof.

Suppositories can be prepared using a carrier such as cacao butter, hydrogenated fat or carboxylic acid.

Sprays can be prepared using the antibody or antibody fragment as such or using it together with a carrier which does not stimulate the buccal or airway mucous membrane of the patient and can facilitate absorption of the compound by dispersing it as fine particles. The carrier includes lactose, glycerol and the like. It is possible to produce pharmaceutical preparations such as aerosols and dry powders.

In addition, the components exemplified as additives for oral preparations can also be added to the parenteral preparations.

6. Method for Diagnosing Disease Using the Anti-TIM-3 Monoclonal Antibody or Antibody Fragment Thereof in the Present Invention A disease relating to TIM-3 can be diagnosed by detecting or determining TIM-3 or a cell expressing TIM-3 using the monoclonal antibody or antibody fragment of the present invention.

A diagnosis of cancer which is one of the diseases relating to TIM-3 can be carried out by, for example, the following detection or measurement of TIM-3.

The diagnosis of cancer can be carried out by detecting TIM-3 expression on the cell in a patient's body by an immunological method such as a flow cytometry.

An immunological method is a method in which an antibody amount or an antigen amount is detected or determined using a labeled antigen or antibody. Examples of the immunological method include radioactive substance-labeled immunoantibody method, enzyme immunoassay, fluorescent immunoassay, luminescent immunoassay, Western blotting method, physico-chemical means and the like.

Examples of the radioactive substance-labeled immunoantibody method include a method, in which the antibody or antibody fragment of the present invention is allowed to react with an antigen, a cell expressing an antigen or the like, then anti-immunoglobulin antibody subjected to a radioactive labeling or a binding fragment thereof is allowed to react therewith, followed by determination using a scintillation counter or the like.

Examples of the enzyme immunoassay include a method, in which the antibody or antibody fragment of the present invention is allowed to react with an antigen, a cell expressing an antigen or the like, then an anti-immunoglobulin antibody or an binding fragment thereof subjected to antibody labeling is allowed to react therewith and the colored pigment is measured by a spectrophotometer, and, for example, sandwich ELISA may be used.

As a label used in the enzyme immunoassay, any known enzyme label (*Enzyme Immunoassay*, published by Igaku Shoin, 1987) can be used as described previously. Examples include alkaline phosphatase labeling, peroxidase labeling, luciferase labeling, biotin labeling and the like.

Sandwich ELISA is a method in which an antibody is bound to a solid phase, antigen to be detected or measured is trapped and another antibody is allowed to react with the trapped antigen. In the ELISA, two kinds of antibody which recognizes the antigen to be detected or measured or the antibody fragment thereof in which antigen recognizing site is different are prepared and the first antibody or antibody fragments is previously adsorbed on a plate (such as a 96-well plate) and the second antibody or antibody fragment is labeled with a fluorescent substance such as FITC, an enzyme such as peroxidase, or biotin.

The plate to which the above antibody is adsorbed is allowed to react with the cell separated from living body or disrupted cell suspension thereof, tissue or disintegrated solution thereof, supernatant of cell culture, serum, pleural effusion, ascites, eye solution or the like, then allowed to react with a labeled monoclonal antibody or an antibody fragment and a detection reaction corresponding to the labeled substance is carried out. The antigen concentration in the sample to be tested can be calculated from a calibration curve prepared by a stepwise dilution of antigen of known concentration.

As antibody used for sandwich ELISA, any of polyclonal antibody and monoclonal antibody may be used or antibody fragments such as Fab, Fab' and F(ab)$_2$ may be used. As a combination of 2 kinds of antibodies used in sandwich ELISA, a combination of monoclonal antibodies or antibody fragments recognizing different epitopes may be used or a combination of polyclonal antibody with monoclonal antibody or antibody fragments may be used.

A fluorescent immunoassay includes a method described in the literatures [*Monoclonal Antibodies—Principles and practice*, Third Edition, Academic Press (1996); *Manual for Monoclonal Antibody Experiments*, Kodansha Scientific (1987)] and the like. As a label for the fluorescent immunoassay, any of known fluorescent labels [*Fluorescent Immunoassay*, by Akira Kawao, Soft Science, (1983)] may be used. Examples of the label include FITC, RITC and the like.

The luminescent immunoassay can be carried out using the methods described in the literature [*Bioluminescence and Chemical Luminescence, Rinsho Kensa*, 42, Hirokawa Shoten (1998)] and the like. As a label used for luminescent immunoassay, any of known luminescent labels can be included. Examples include acridinium ester, lophine or the like may be used.

Western blotting is a method in which an antigen or a cell expressing an antigen is fractionated by SDS (Sodium dodecyl sulfate)-PAGE [*Antibodies—A Laboratory Manual*

(Cold Spring Harbor Laboratory, 1988)], the gel is blotted onto PVDF membrane or nitrocellulose membrane, the membrane is allowed to react with antigen-recognizing antibody or antibody fragment, further allowed to react with an anti-mouse IgG antibody or antibody fragment which is labeled with a fluorescent substance such as FITC, an enzyme label such as peroxidase, a biotin labeling, or the like, and the label is visualized to confirm the reaction. An example thereof is described below.

Cells or tissues in which a polypeptide having the amino acid sequence represented by SEQ ID NO: 53 is expressed are dissolved in a solution and, under reducing conditions, 0.1 to 30 µg as a protein amount per lane is electrophoresed by an SDS-PAGE method. The electrophoresed protein is transferred onto a PVDF membrane and allowed to react with PBS containing 1 to 10% of BSA (hereinafter referred to as "BSA-PBS") at room temperature for 30 minutes for blocking.

Here, the monoclonal antibody of the present invention is allowed to react therewith, washed with PBS containing 0.05 to 0.1% Tween 20 (hereinafter referred to as "Tween-PBS") and allowed to react with goat anti-mouse IgG labeled with peroxidase at room temperature for 2 hours. It is washed with Tween-PBS and a band to which the monoclonal antibody is bound is detected using ECL Western Blotting Detection Reagents (manufactured by Amersham) or the like to thereby detect a polypeptide having the amino acid sequence represented by SEQ ID NO: 1. As an antibody used for the detection in Western blotting, an antibody which can be bound to a polypeptide having no three-dimensional structure of a natural type is used.

The physicochemical method is specifically carried out by reacting TIM-3 as the antigen with the antibody or antibody fragment of the present invention to form an aggregate, and detecting this aggregate. Other examples of the physicochemical methods include a capillary method, a one-dimensional immunodiffusion method, an immunoturbidimetry, a latex immunoturbidimetry [*Handbook of Clinical Test Methods*, Kanehara Shuppan, (1988)] and the like.

For example, in a latex immunodiffusion method, a carrier such as polystyrene latex having a particle size of about of 0.1 to 1 µm sensitized with antibody or antigen may be used and when an antigen-antibody reaction is carried out using the corresponding antigen or antibody, scattered light in the reaction solution increases while transmitted light decreases. When such a change is detected as absorbance or integral sphere turbidity, it is possible to measure antigen concentration, etc. in the sample to be tested.

In addition, for the detection of the cell expressing TIM-3, known immunological detection methods can be used, and an immunoprecipitation method, an immuno cell staining method, an immune tissue staining method, a fluorescent antibody staining method and the like are preferably used.

An immunoprecipitation method is a method in which a cell expressing TIM-3 is allowed to react with the monoclonal antibody or antibody fragment of the present invention and then a carrier having specific binding ability to immunoglobulin such as protein G-Sepharose is added so that an antigen-antibody complex is precipitated. Also, the following method can be carried out. The above-described antibody or antibody fragment of the present invention is solid-phased on a 96-well plate for ELISA and then blocked with BSA-PBS.

When the antibody is in a non-purified state such as a culture supernatant of hybridoma cell, anti-mouse immunoglobulin or rat immunoglobulin or protein A or Protein G or the like is previously adsorbed on a 96-well plate for ELISA and blocked with BSA-PBS and a culture supernatant of hybridoma cell is dispensed thereto for binding. After BSA-PBS is discarded and the residue is sufficiently washed with PBS, reaction is carried out with a dissolved solution of cells or tissues expressing TIM-3. An immune precipitate is extracted from the well-washed plate with a sample buffer for SDS-PAGE and detected by the above-described Western blotting.

An immune cell staining method or an immune tissue staining method are a method where cells or tissues in which antigen is expressed are treated, if necessary, with a surfactant, methanol or the like to make an antibody easily permeate to the cells or tissues, then the monoclonal antibody of the present invention is allowed to react therewith, then further allowed to react with an anti-immunoglobulin antibody or binding fragment thereof subjected to fluorescent labeling such as FITC, enzyme label such as peroxidase or biotin labeling and the label is visualized and observed under a microscope.

In addition, cells can be detected by an immunofluorescent staining method where cells are allowed to react with a fluorescence-labeled antibody and analyzed by a flow cytometer [*Monoclonal Antibodies—Principles and practice*, Third Edition, Academic Press (1996), *Manual for Experiments of Monoclonal Antibodies*, Kodansha Scientific (1987)] in which cells are allowed to react with a fluorescence-labeled antibody and analyzed by a flow cytometer.

Particularly, the monoclonal antibody or antibody fragment of the present invention which binds to amino acids sequences of an extracellular region of the TIM-3 or a three-dimensional structure thereof can detect a cell expressing the polypeptide maintaining a natural three-dimensional structure by a fluorescence antibody method.

In addition, in the case of using FMAT8100HTS system (manufactured by Applied Biosystems) and the like among fluorescent antibody staining methods, the antigen quantity or antibody quantity can be measured without separating the formed antibody-antigen complex and the free antibody or antigen which is not concerned in the formation of the antibody-antigen complex.

The present invention can provide a monoclonal antibody or an antibody fragment of thereof, which binds to amino acids sequences of an extracellular region of TIM-3 or a three-dimensional structure and expresses ADCC activity; a hybridoma which produces the antibody; a DNA which encodes the antibody; a vector which comprises the DNA; a transformant obtained by transforming the vector; a process for producing an antibody or an antibody fragment thereof using the hybridoma or the transformant; and a therapeutic agent or a diagnostic agent comprising the antibody or the antibody fragment thereof as an active ingredient.

Hereinafter, exemplary embodiments of the present invention will be described specifically. However, the present invention is not limited to the exemplary embodiments described below.

EXAMPLE

Example 1

(Molecular Cloning of Human TIM-3 cDNA and Establishment of Stable Expression Cell)

Human TIM-3 cDNA was amplified by PCR using ExTaq (manufactured by Takara Bio Inc.) and Human MTC panel (manufactured by Clontech) as a template. For primers, TIM-3 Fw2 (SEQ ID NO: 31) and TIM-3 Re2 (SEQ ID NO: 32) were used. The obtained PCR product was inserted into pGEM-T Easy vector (manufactured by Promega Corp.), and the plasmid was introduced into TOP10 One shot competent cells (manufactured by Invitrogen) to amplify. The plasmid DNA was extracted by the miniprep method.

By analyzing the sequence of purified DNA using primers TIM-3 Fw and TIM-3 Re2, the clone having the same sequence as the coding region of GenBank accession number NM_032782 was selected. A human TIM-3 retrovirus (hTIM-3/pMCs-IG) was constructed by recombination of the insert of the selected clone into pMCs-IRES-GFP vector (manufactured by Cell Biolabs Inc.) using Retrovirus Constructive System Ampho (manufactured by Takara Bio Inc.).

The human TIM-3 retrovirus was infected into Jurkat cell (ATCC accession NO: CRL-2063), EoL-1 cell (RIKEN CELL BANK NO: RCB0641) and L929 cell (manufactured by Sigma-Aldrich Co., LLC.) which were confirmed not to endogenously express TIM-3 was confirmed by flow cytometry analysis. After several passages, TIM-3 positive cells were collected by FACSAria (manufactured by BD Biosciences). Human TIM-3 stable expression cell line was established by recollecting the TIM-3 positive cells by FACSAria after several passages.

Example 2

(Preparation of Expression Vector of Fusion Protein of Soluble Extracellular Human TIM-3-Human Fc)

The cDNA encoding the extracellular region of human TIM-3 was amplified by PCR using ExTaq (manufactured by Takara Bio Inc.) and hTIM-3/pMCs-Ig constructed in Example 1 as a template. For primers, pMCs-Fw (SEQ ID NO: 33) and TIM3ED-FcReXba 2 (SEQ ID NO: 34) were used.

The amplified PCR product was inserted into pTracer-CMV-FLAG-human Fc vetctor [modified vector in which FLAG and Fc domain of human IgG1 were inserted into pTracer-CMV (manufactured by Invitrogen) vector between XbaI site and ApaI site]. After the plasmid was introduced into TOP10 One shot competent cells (manufactured by Invitrogen) to amplify, the plasmid DNA (sTIM-3-FLAG-Fc/pTracerCMV) was extracted by miniprep method.

By the analysis of the DNA sequence using T7 (SEQ ID NO: 35) and hTIM-3 Fw1 (SEQ ID NO: 36) as a primer, the purified sTIM-3-FLAG-Fc/pTracerCMV was confirmed to have the same nucleotide sequence as the corresponding region in GenBank accession number NM_032782. The nucleotide sequence (from EcoRI recognition site to ApaI recognition site) was identical to the nucleotide sequence represented by SEQ ID NO: 37.

Example 3

(Preparation of Expression Vector of Soluble Extracellular Human TIM-3)

The cDNA encoding the extracellular region of human TIM-3 was amplified by PCR using ExTaq (manufactured by Takara Bio Inc.) and sTIM-3-FLAG-Fc/pTracerCMV established in Example 2 as a template. As primers, TIM-3 Fw2 (SEQ ID NO: 31) and TIM3ED-FLAG4aa (SEQ ID NO: 39) were used.

Next, FLAG epitope was ligated by PCR method using ExTaq (manufactured by Takara Bio Inc.), TIM-3 Fw2 (SEQ ID NO: 31) and C-FLAG-NotR2 (SEQ ID NO: 40) as primers and the obtained PCR product as a template. The PCR product was inserted into pGEM-T Easy vector (manufactured by Promega Corp.). After the plasmid was introduced into TOP10 One shot competent cells (manufactured by Invitrogen) to amplify the plasmid DNA (sTIM-3-FLAG/pEF6Myc_HisC) was extracted by the miniprep method.

By the DNA sequence analysis using T7 (SEQ ID NO: 35) and BGH-R (SEQ ID NO: 41) as a primer, the purified sTIM-3-FLAG-Fc/pEF6 Myc_HisC was confirmed to have the same nucleotide sequence as the corresponding region in GenBank accession number NM_032782.

Example 4

(Preparation of the Fusion Protein of Soluble Extracellular Human TIM-3-Human Fc and Soluble Extracellular Human TIM-3)

Each of sTIM-3-FLAG-Fc/pTracerCMV plasmid DNA and sTIM-3-FLAG-Fc/pEF6 Myc_HisC plasmid DNA obtained in Example 2 and Example 3, respectively, was introduced into HEK293F cells (manufactured by Invitrogen) and was transiently expressed. Six days after, each of the cell supernatant was recovered and used for protein purification.

The culture supernatant containing the fusion protein of soluble extracellular human TIM-3-human Fc or soluble extracellular human TIM-3 was recovered by centrifugation six days after transfection. The fusion proteins were purified by an anti-FLAG column prepared using Anti-FLAG M2 Agarose Affinity gel (manufactured by Sigma-Aldrich Co., LLC.) and by FLAG peptides (manufactured by Sigma-Aldrich Co., LLC.) according to the manufacturer's protocols.

The eluted samples were fractionated and then each fraction was analyzed by SDS-PAGE under reduced conditions, and then silver staining and Western blotting were carried out. For Western blotting, an anti-FLAG M2 antibody (manufactured by Sigma-Aldrich Co., LLC.) and an alkaline phosphatase labeled rabbit anti-mouse immunoglobulin antibody was used (manufactured by Dako). The fraction containing the target protein was concentrated using Amicon Ultra 4 10K (manufactured by Millipore) and was applied for gel filtration chromatography using Superdex 200 gp column (manufactured by GE Healthcare).

After fractionation, each fraction was applied to SDS-PAGE under reduced condition, silver stained and then Western blotted. The fraction in which the target protein was found was concentrated and washed with 0.5 ml of PBS. The soluble extracellular human TIM-3-human Fc fusion protein or soluble extracellular human TIM-3 was collected after filtering through the MILLEX-GV sterilizing filter (manufactured by Millipore) having a pore diameter of 0.22 μm. The purity of the protein was measured by Limulus ES-II kit Wako (manufactured by Wako Pure Chemical Industries, Ltd.) which is a kit to detect endotoxin and confirmed that the fraction was sufficiently purified.

Example 5

(Preparation of Human Antibody Expressing Mouse)

The mice used for immunization has a genetic background in which both of endogenous Ig heavy chain locus and κ light chain locus were homozygously disrupted and maintained a chromosome 14 fragment (SC20) comprising a human heavy chain transchromosome, and a human Igκ chain transgene (KCo5) at the same time. This mouse strain was established by cross breeding mice strain A which had human Ig heavy chain loci and mice strain B which maintained human Igκ chain transgene.

Mouse strain A is a homozygote in which both of the endogenous Ig heavy chain locus and κ light chain locus are homozygously disrupted, and maintains a chromosome 14 fragment (SC20) which can be transmitted to the progeny and for example, described in Tomizuka et al. (Tomizuka, K. et al., 2000, *Proc. Natl. Acad. Sci. U.S.A.* 97:722-727).

Mouse Strain B is a mouse strain (transgenic mouse) in which both of the endogenous Ig heavy chain locus and κ light chain locus are homozygously disrupted, and maintains a human Igκ light chain transgene (KCo5), and is, for example, described in Fishwild et al. (1996) [*Nature Biotechnology* 14:845-851].

The animal individual was obtained by cross-breeding male mouse of strain A and female mouse of strain B, or female mouse of strain A and male mouse of strain B and was a mouse in which human Ig heavy chain and Igκ light chain could be detected at the same time in their serum [Ishida & Lonberg, *IBC's* 11*th Antibody Engineering*, Abstract 2000] was further used for immunological experiments. For your information, the human antibody expressing mouse (hereinafter referred to as "KM mouse") can be obtained from Kyowa Hakko Kirin by establishing a license.

Example 6

(Preparation of Anti-Human TIM-3 Monoclonal Antibody)

The preparation of monoclonal antibody in the present Example was carried out according to the general methods, such as published in *Monoclonal Antibody Experiment Manual*, (Yasuhigashi Tamie et al., Kodansha, 1991). Either TIM-3 expressing L929 cell prepared in Example 1 or the soluble extracellular human TIM-3-human Fc fusion protein prepared in Example 4 was used as a TIM-3 immunogen. The immunized animal was KM mouse described above.

The TIM-3 expressing L929 cell was intraperitoneally injected into mice at a dose of $1 \times 10^7$ cells/animal. After the first immunization, the same cell was further administered for another three times or more thereafter. Three days before obtaining the spleen, the soluble extracellular human TIM-3-human Fc fusion protein prepared in Example 4 was administered from caudal vein at 20 μg/mouse. The spleen was surgically removed from the immunized mouse, put into 4 ml of PBS and mashed on a mesh (cell strainer: manufactured by Falcon) using a syringe piston.

The cells were precipitated by centrifuging the cell suspension which was passed through the mesh, and the cells were resuspended in 1 ml of Red Blood Cell Lysis Buffer (manufactured by Sigma-Aldrich Co., LLC.). After incubating for 5 min at room temperature, 10 ml of serum free DMEM medium (manufactured by Invitrogen) (hereinafter referred to as "serum free DMEM medium") containing 50 unit/ml penicillin and 50 μg/ml streptomycin was added, and the cells were precipitated by centrifugation.

The cell pellets were resuspended in serum free DMEM medium. On the other hand, myeloma cell line SP2/0 (ATCC NO: CRL-1581) was cultured in DMEM medium containing 10% FBS, 50 unit/ml penicillin and 50 μg/ml streptomycin (hereinafter referred to as "DMEM medium containing serum") and incubated at 37° C. under 5% $CO_2$ so as not exceed the cell number of $1 \times 10^6$ cells/ml.

The SP2/0 cells were washed with 10 ml of serum free DMEM medium and suspended in serum free DMEM medium as in the case of the spleen derived cells. These suspension of spleen derived cells and suspension of myeloma cell were mixed at a ratio of 5:1, centrifuged, and the supernatant was completely removed. To fuse the cells, 1 ml of 50% (w/v) of polyethylene glycol (manufactured by Boehringer Mannheim Corp.) was slowly added while stirring the pellet with the pipette tip, and then 1 ml of serum free DMEM medium preheated at 37° C. was added. Slowly, 5 ml and 10 ml of serum free DMEM was added followed by 5 min incubation at 37° C. under 5% $CO_2$.

After the centrifugation and removal of supernatant, the fused cells were resuspended in 50 ml of DMEM medium containing 10% FBS (manufactured by Invitrogen), penicillin-streptomycin-glutamine (manufactured by Invitrogen, 100-fold dilution of Catalog No. 10378-016), IL-6 (5 ng/ml), and 2-mercaptoethanol (manufactured by Invitrogen, 1000-fold dilution of Catalog No. 21985-023) (hereinafter referred to as "DMEM medium containing IL-6") and incubated at 37° C. under 5% $CO_2$.

The next day, cells were harvested by pipetting, centrifuged and the pellet was resuspended in 10 ml of DMEM medium containing IL-6. On the next day, Hypoxanthine-aminopterin-thymidine (hereinafter referred to as "HAT", manufactured by Sigma-Aldrich Co., LLC.) was added. After incubating for about 7 to 10 days, the culture supernatant was collected for hybridoma screening.

Example 7

(Preparation of Anti-Human TIM-3 Mouse Monoclonal Antibody)

The preparation of monoclonal antibody in the present Example was carried out according to the general methods published in Introduction to Monoclonal Antibody Experiment (Yasuhigashi Tamie et al., Kodansha, 1991). Either TIM-3 expressing L929 cell prepared in Example 1 or soluble extracellular human TIM-3 prepared in Example 4 was used as a TIM-3 immunogen. The immunized animal was Balb/c mouse (purchased from Nihon Charles River).

First, a Balb/c mouse was immunized by injecting TIM-3 expressing L929 cells intraperitoneallyat a dose of $1 \times 10^7$ cells/animal. After the first immunization, the same cell was further administered for another three times or more thereafter. Three days before extracting the spleen, the soluble extracellular human TIM-3 protein prepared in Example 4 was administered from caudal vein at 20 μg/mouse. The spleen was surgically removed from the immunized mouse, put into 4 ml of PBS and mashed on a mesh (cell strainer: manufactured by Falcon) using a syringe piston.

The cells were precipitated by centrifuging the cell suspension which was passed through the mesh, and the cells were resuspended in 1 ml of Red Blood Cell Lysis Buffer (manufactured by Sigma-Aldrich Co., LLC.). After incubating for 5 min at room temperature, 10 ml of serum free DMEM medium was added, and then cells were precipitated by centrifugation. The pellets were resuspended in serum free DMEM medium. On the other hand, myeloma cell line SP2/0 (ATCC NO: CRL-1581) were cultured in DMEM medium by incubating at 37° C. under 5% $CO_2$ to the cell number of $1 \times 10^6$ cells/ml or less.

Similar to the spleen derived cells, the SP2/0 cells were washed with 10 ml of serum free DMEM medium and suspended in serum free DMEM medium. The suspension of spleen cell and the suspension of myeloma cell were mixed at a ratio of 5:1. After centrifugation, the supernatant was removed. To this pellet, 1 ml of 50% (w/v) of polyethylene glycol (manufactured by Boehringer Mannheim Corp.) was slowly added while stirring the pellet with the pipette tip, and then 1 ml of serum free DMEM medium preheated to 37° C. was added.

To this suspension, 5 ml of DMEM medium was slowly added. After further adding 10 ml of serum free DMEM, the suspension was incubated for 5 min at 37° C. under 5% $CO_2$.

After the suspension was centrifuged, the cell pellets were resuspended in 50 ml of DMEM medium containing IL-6 and cultured at 37° C. under 5% $CO_2$. After incubation for one day, cells were collected by pipetting. After centrifugation, the pellet was resuspended in 10 ml of DMEM medium containing IL-6. On the next day, HAT medium (manufactured by Sigma-Aldrich Co., LLC.) was added. After incubation for about 7 to 10 days, the culture supernatant was recovered and used for hybridoma screening.

Example 8

(Screening of Hybridoma Producing a Human or Mouse Monoclonal Antibody which Binds to Human TIM-3)

The hybridoma was screened using the cell supernatant prepared in Example 6 and Example 7. The method to be used was a flow cytometry method using human TIM-3 expressing cell lines. First, the human TIM-3 expressing Jurkat cell or EoL-1 cell prepared in Example 1 were washed with staining medium (PBS containing 2% FBS and 0.05% sodium azide), and then resuspended in 1 ml of staining medium to give a cell density of $1 \times 10^6$ cells/ml. The cell suspension was dispensed at 10 μl/well into a 96-well culture plate.

Then, 50 μl of the hybridoma supernatant was added and incubated for 30 min at 4° C. After the cells were washed twice with the staining medium, 50 μl of labeled antibody which was diluted 200-fold with staining medium was added to each well and incubated for 30 min at 4° C. As for labeled antibodies, Goat F(ab')$_2$ Anti-Human IgG (γ chain specific)-R-PE (manufactured by SouthernBiotech) were used for the human monoclonal antibody and Goat F(ab')$_2$ Anti-Mouse IgG(H+L)R-PE (manufactured by SouthernBiotech) was used for the mouse monoclonal antibody.

After washing twice with staining medium, the cells were analysed using FACSCalibur (manufactured by BD Biosciences) as a primary screening. After positive clones were picked and expanded, the hybridoma cells were clone-sorted by FACSAria (manufactured by BD Biosciences) and cultured for seven days in DMEM medium containing IL-6 which further contains Hypoxanthine-thymidine (hereinafter referred to as "HT", manufactured by Sigma-Aldrich Co., LLC.).

Harvested supernatants were screened as the same as in the primary screening method for cloning of hybridomas expressing anti-human TIM-3 human monoclonal antibody and hybridomas expressing anti-human TIM-3 mouse monoclonal antibody and selected hybridoma clone was used for purification of monoclonal antibody.

Example 9

(Purification of Hybridoma Derived Monoclonal Antibody)

An anti-TIM-3 human or mouse monoclonal antibody was purified from the anti-human TIM-3 human or mouse monoclonal antibody expressing hybridoma prepared in Example 8. Briefly, hybridoma supernatant containing a high concentration of the anti-TIM-3 antibody was prepared using a CELLine antibody production system (manufactured by BD Biosciences) and the anti-human TIM-3 monoclonal antibody was purified from the supernatant. First, to adapt the cloned hybridoma to the serum free medium, the hybridomas were cultured for several days in a medium mixing DMEM medium containing HT and IL-6 and BD Cell MAb serum free medium (manufactured by BD Biosciences) at a ratio of 1:1, and then cultured for several days in a medium having a mixing ratio of 1:2.

Next, the hybridomas were cultured in a BD Cell MAb serum free medium (manufactured by BD Biosciences) and adapted hybridomas to the serum free medium. The hybridoma cells adapted to the serum free medium were cultured in CL-1000 flasks according to the manufacturer's instructions and the supernatant of the hybridoma containing high concentration of the anti-TIM-3 antibody was collected from the flasks. The antibody from the supernatant of the hybridoma was purified in accordance with the standard procedures using Protein A.

Specifically, MabSelect (manufactured by GE Healthcare) were packed in an open column and the supernatant diluted 2-fold by PBS was loaded and then eluted with 0.1 mol/L Glycine-HCl (pH 2.7), followed by concentration with Amicon Ultra (manufactured by Millipore). Next, by using a NAP-5 column (manufactured by GE Healthcare), the obtained solution was equilibrated with PBS buffer, and then sterilized by filtration to obtain 4 clones of the anti-human TIM-3 human monoclonal antibodies (antibody 512, antibody 644, antibody 4545 and antibody 4177) and one clone (antibody 8213) of the anti-human TIM-3 mouse monoclonal antibody.

Example 10

(Identification of Isotype of Anti-TIM-3 Human Monoclonal Antibody)

Each of the isotype of anti-TIM-3 human monoclonal antibodies which was prepared in Example 9 was determined by a solid-phase ELISA and flow cytometry.

Specifically, as for the solid-phase ELISA, soluble extracellular human TIM-3 obtained by Example 4 was diluted with a Carbonate-Biacarbonate Buffer (manufactured by Sigma-Aldrich Co., LLC.) to give a concentration of 1 μg/ml and dispensed at 50 μl/well into a 96-well culture plate (Maxisorp, manufactured by Nunc). The soluble extracellular human TIM-3 was adsorbed to the microplate by incubating overnight at 4° C.

After the supernatant was discarded, SuperBlock Blocking Buffer in TBS (manufactured by PIERCE) was added to the plate and then incubated for 10 min at room temperature and 50 μl of the culture supernatant of the hybridoma was added and then incubated for 30 min at room temperature. After washing each well with Tris-buffered saline containing 0.1% Tween20 (TBS-T), 50 μl of each of HRP-labeled mouse anti-human IgG1, anti-human IgG2, anti-human IgG3 or anti-human IgG4 antibodies, each antibody was diluted 2000, 2000, 2000 and 4000-fold with TBS-T containing 10% SuperBlock Blocking Buffer, respectively; manufactured by SouthernBiotech), were added and incubated for 30 minutes at room temperature.

After washing each well with TBS-T, 50 μl of substrate buffer (TMB, manufactured by DAKO) was added and then incubated for 20 min at room temperature. The reaction was stopped by adding 50 μl of 0.5 mol/L sulfuric acid (manufactured by Wako Pure Chemical Industries, Ltd.). The absorbance at wavelength of 450 nm (reference wavelength: 570 nm) was measured on a microplate reader (VersaMax, manufactured by Molecular Devices, LLC.).

In addition, in flow cytometry method, the Jurkat cell which expressed human TIM-3 prepared in Example 1 was washed with staining medium, and then 50 μl of the supernatant of the hybridoma was added and incubated for 30 min at 4° C. After washing, 50 μl of each of Mouse anti-Human IgG1-PE, Mouse anti-Human IgG2-PE, Mouse anti-Human IgG3 (Hinge)-PE and Mouse anti-Human IgG4(Fc)-PE (manufactured by SouthernBiotech) which was diluted 100-fold with staining medium was added, allowed to stand still for 30 min at 4° C. and then analyzed using FACSCalibur flow cytometer (manufactured by BD Biosciences).

Based on the result, the isotypes of antibody 512, antibody 644, and antibody 4545 were IgG1, IgG4 and IgG2, respectively.

Example 11

(Identification of the Isotype of the Mouse Monoclonal Antibody for Human TIM-3)

The isotype of the anti-human TIM-3 mouse monoclonal antibody prepared in Example 9 was determined using Iso Strip Mouse Monoclonal Antibody Isotyping Kit (manufactured by Roche-diagnostics). By using the supernatant of the hybridoma containing the anti-TIM-3 antibody prepared in Example 8, the isotype was determined according to the manufacturer's instructions. As a result, the isotype of antibody 8213 was determined as IgG2b.

Example 12

(Isolation of Anti-TIM-3 Monoclonal Antibody Gene)

The gene of anti TIM-3 human or mouse monoclonal antibody which was prepared in Example 9 was isolated from the hybridoma which produced anti-human TIM-3 human or mouse monoclonal antibody prepared in Example 9. Total RNA was extracted from the cloned hybridoma using High Pure RNA Isolation Kit (manufactured by Roche-Diagnostics), according to the manufacturer's instructions. The cloning of the cDNA encoding the variable region was carried out using SMART RACE cDNA amplification Kit (manufactured by Clontech) in accordance with the instructions attached thereto.

The heavy chain (VH) of the human monoclonal antibody was amplified by PCR using UPM (SMART RACE cDNA amplification Kit; manufactured by Clontech) and primer hh-6 (SEQ ID NO: 44). Using part of the reaction product as a template, PCR was carried out using NUP (SMART RACE cDNA amplification Kit; manufactured by Clontech) and primer hh-3 (SEQ ID NO: 45). The cloning of the PCR product was carried out using Zero Blunt TOPO PCR Cloning Kit (manufactured by Invitrogen). The nucleotide sequence was analyzed by universal primers of the vector (e.g., T7 or M13R primer) and the amino acid sequence was deduced from the nucleotide sequence.

As a result, the nucleotide sequence and the amino acid sequence of VH of antibody 512 were represented by SEQ ID NO: 54, was and SEQ ID NO: 55, respectively, the nucleotide sequence and the amino acid sequence of VH of antibody 644 were represented by SEQ ID NO: 58 and SEQ ID NO: 59, respectively, the nucleotide sequence and the amino acid sequence of VH of antibody 4545 were represented by SEQ ID NO: 7 and SEQ ID NO: 8, respectively, and the nucleotide sequence and the amino acid sequence of VH of antibody 4177 were represented by SEQ ID NO: 17 and SEQ ID NO: 18, respectively. The protein sequences of SEQ ID NOS: 8 and 18 are shown to contain the signal sequence which consists of the first 19 amino acid residues. The mature protein sequence of the proteins of SEQ ID NOS: 8 and 18 are shown as SEQ ID NO: 116 and 118, respectively. Each of the obtained variable regions obtained and the constant region of human IgG1 were inserted and ligated into the expression vector, N5KG1 (manufactured by Biogen IDEC Inc.).

Human monoclonal antibody light chain (VL) was amplified by PCR using UPM (SMART RACE cDNA amplification Kit; manufactured by Clontech) and primer hk-2 (SEQ ID NO: 46). Using part of the reaction product as a template, PCR was carried out using NUP (SMART RACE cDNA amplification Kit; manufactured by Clontech) and primer hk-6 (SEQ ID NO: 47). The PCR product was cloned using Zero Blunt TOPO PCR Cloning Kit (manufactured by Invitrogen). The nucleotide sequence was analyzed by universal primers of the vector (e.g., T7 or M13R) and the amino acid sequence was deduced from the nucleotide sequence.

As a result, the nucleotide sequence and the amino acid sequence of VL of antibody 512 were represented by SEQ ID NO: 56 and SEQ ID NO: 57, respectively, the nucleotide sequence and the amino acid sequence of VL of antibody 644 were represented by SEQ ID NO: 60 and SEQ ID NO: 61, respectively, the nucleotide sequence and the amino acid sequence of VL of antibody 4545 were represented by SEQ ID NO: 9 and SEQ ID NO: 10, respectively, and the nucleotide sequence and the amino acid sequence of VL of antibody 4177 were represented by SEQ ID NO: 19 and SEQ ID NO: 20, respectively. The protein sequences of SEQ ID NOS: 10 and 20 are shown to contain the signal sequence which consists of the first 20 amino acid residues. The mature protein sequence of the proteins of SEQ ID NOS: 10 and 20 are shown as SEQ ID NO: 117 and 119, respectively. Each of the obtained variable regions and constant region of κ chain were inserted and ligated into the expression vector, N5KG1 (manufactured by Biogen IDEC Inc.).

The heavy chain (VH) of mouse monoclonal antibody was amplified by PCR using UPM (SMART RACE cDNA amplification Kit; manufactured by Clontech) and a primer, mH_Rv1 (SEQ ID NO: 48). Using part of the reaction product e as template, PCR was carried out using NUP (SMART RACE cDNA amplification Kit; manufactured by Clontech) and primer mH_Rv2 (SEQ ID NO: 49).

The cloning of the PCR product was carried out using Zero Blunt TOPO PCR Cloning Kit (manufactured by Invitrogen). The nucleotide sequence was analyzed by universal primers of the vector (e.g., T7 or M13R) and the amino acid sequence was deduced from the nucleotide sequence.

As a result, the nucleotide sequence and the amino acid sequence of VH of antibody 8213 were represented by SEQ ID NO: 27 and SEQ ID NO: 28, respectively. The obtained variable region and the constant region of mouse IgG2a were ligated and inserted into the expression vector, N5KG1 (manufactured by Biogen IDEC Inc.).

The light chain (VL) of the mouse monoclonal antibody was amplified by PCR using UPM (SMART RACE cDNA amplification Kit; manufactured by Clontech) and primer mK_Rv1 (SEQ ID NO: 50). Additionally, part of the reaction product was used as a template, and PCR was carried out using NUP (SMART RACE cDNA amplification Kit; manufactured by Clontech) and primer mK_Rv2 (SEQ ID NO: 51). The PCR product was cloned using Zero Blunt TOPO PCR Cloning Kit (manufactured by Invitrogen). Nucleotide sequences were analyzed by universal primers of the vector (e.g., T7 or M13R) and the amino acid sequence was deduced from the nucleotide sequence.

As a result, the nucleotide sequence and the amino acid sequence of the VL of antibody 8213 were represented by SEQ ID NO: 29 and SEQ ID NO: 30, respectively. The variable region obtained and the constant region of κ chain were ligated and inserted into the above mentioned expression vector encoding VH of antibody 8213.

In addition, in order to obtain anti-dinitrophenyl (DNP) human IgG1 antibody as a negative control, the nucleotide sequence of the heavy chain (VH) of the antibody (SEQ ID NO: 62), the nucleotide sequence of the light chain of the antibody (SEQ ID NO: 64), and the constant region of human IgG1 and the κ chain were inserted into expression vector N5KG1 (manufactured by Biogen IDEC Inc.).

Example 13

(Purification of Recombinant Anti-TIM-3 Human Monoclonal Defucose Antibody)

A cell expressing a recombinant antibody was produced by introducing the recombinant antibody expression vector prepared in Example 12 into the host cell. As the host cell for expression, FUT8$^{-/-}$CHO cells were used in accordance with a published report (*Clin Cancer Res* 2006: 12(9) Iida et al.). Briefly, the expression vectors for each of 512, 644, 4545 and 4177 prepared in Example 12 were introduced into FUT8$^{-/-}$ CHO cell using FreeStyle™ MAX Reagent (manufactured by Invitrogen). The FUT8$^{-/-}$CHO cells were cultured on a shaker at 37° C. under 5% $CO_2$. The culture supernatant was recovered after about five days.

The recovered supernatant was purified using Protein A (manufactured by GE Healthcare) and further using 0.8×40 cm column (manufactured by BioRad) and the like, depending on the sample amount. Antibodies were affinity purified using PBS as the binding buffer and 0.02 mol/L sodium citrate (pH 2.7, 50 mmol/L NaCl) buffer as the elution buffer. The elution fraction was added with 0.2 mol/L of sodium phosphate buffer (pH 7.0).

The prepared antibody solution was equilibrated with PBS using NAP-25 column (manufactured by GE Healthcare) and concentrated with Amicon Ultra (10000 cut, manufactured by Millipore). After sterilization by filtration, the recombinant anti-TIM-3 human monoclonal defucose antibodies (antibody 512, antibody 644, antibody 4545 and antibody 4177) were obtained. The purity of the protein was determined by Limulus ES-II kit Wako (manufactured by Wako Pure Chemical Industries, Ltd.) and found that these antibodies were sufficiently purified.

The vector for expressing anti-DNP prepared in Example 12 was introduced into CHO-DG44 cells. The CHO-DG44 cells were cultured on a shaker at 37° C. under 5% $CO_2$. The cultured supernatant was recovered following incubation for 5 days. The collected supernatant was purified using Protein A (manufactured by GE Healthcare) and further using 0.8×40 cm column (manufactured by BioRad) and the like, depending on the sample amount. The affinity purification of the antibodies was carried out using PBS as the binding buffer and 0.02 mol/L of sodium citrate (pH 2.7, 50 mmol/L NaCl) buffer as the elution buffer. The elution fraction was added with 0.2 mol/L of sodium phosphate buffer (pH 7.0). The prepared antibody solution was equilibrated with PBS and concentrated using NAP-25 column (manufactured by GE Healthcare) with Amicon Ultra (10000 cut, manufactured by Millipore) respectively. After sterilization by filtration, the recombinant anti-DNP antibody was obtained. The purity of the protein was determined using a Limulus ES-II kit Wako (manufactured by Wako Pure Chemical Industries, Ltd.) and found that the antibody was sufficiently purified.

Example 14

(Purification of Recombinant Anti-TIM-3 Mouse Monoclonal Antibody)

The vector for expressing antibody 8213 prepared in Example 12 was introduced into HEK293F cells (manufactured by Invitrogen) using 293 fectin (manufactured by Invitrogen). HEK293F cells were incubated on a shaker at 37° C. under 5% $CO_2$. The cultured supernatant was collected after incubation for five days. The collected supernatant was purified using Protein A (manufactured by GE Healthcare) and further using 0.8×40 cm column (manufactured by BioRad) and the like, depending on the sample amount. The affinity purification of the antibody was carried out using PBS as a binding buffer and 0.02 mol/L sodium citrate buffer (pH 2.7, 50 mmol/L NaCl) as an elution buffer.

To the elution fraction, 0.2 mol/L of sodium phosphate buffer (pH 7.0) was added. The prepared antibody solution was equilibrated with PBS using NAP-25 column (manufactured by GE Healthcare) and concentrated with Amicon Ultra (10000 cut, manufactured by Millipore). After sterilization by filtration, the recombinant anti-TIM-3 mouse monoclonal antibody (8213 antibody) was obtained. The purity of the protein was determined using a Limulus ES-II kit Wako (manufactured by Wako Pure Chemical Industries, Ltd.) and found that the antibody was sufficiently purified.

Example 15

(Fluorescent Labeling of Purified Monoclonal Antibody)

The fluorescent labeling of the hybridoma derived monoclonal antibody and recombinant monoclonal antibody was carried out by using Alexa Fluor 647 Monoclonal Antibody Labeling Kit (manufactured by Invitrogen) according to the manufacturer's instructions. After the labeling, each antibody was confirmed to be positively labeled with Alexa Fluor 647 (hereinafter referred to as "Alexa-647") by FACSCalibur (manufactured by BD Biosciences) analysis for TIM-3 expressing cells.

Example 16

(Classification of Epitopes Using Competition Test-1)

The relation of epitopes between antibodies prepared in Example 13 and Example 14, and commercially available anti-TIM-3 antibody 344823 (Clone 344823, manufactured by R&D Systems) was analyzed by a competition test. In brief, the test antibody was allowed to interact with the TIM-3 expression cell prepared in Example 1, and then whether another anti-TIM-3 antibody could further bind to TIM-3 expressing cells was evaluated by flow cytometry method.

In the first step, whether or not the competition between each of the monoclonal antibodies prepared in Example 13 and Example 14 (antibody 512, antibody 644, antibody 4177 and antibody 8213) and antibody 34823 were examined. First, human TIM-3 expressing EoL-1 cells and the parent cell, EoL-1 cells were washed with staining medium and then allowed to react with each of the purified subjective monoclonal antibodies (antibody 512, antibody 644, antibody 4177 and antibody 8213) (4° C., 30 min). The final concentration was 10 μg/ml. Next, the PE labeled antibody 344823 (Clone 344823, manufactured by R&D Systems) was added and allowed to react (4° C., 30 min). After washing with staining medium, 7-ADD (manufactured by BD Biosciences) was added and analyzed using FACSCalibur (manufactured by BD Biosciences).

As a result, the goat derived anti-human TIM-3 polyclonal antibody (manufactured by R&D Systems) used as a positive control and antibody 644 almost completely blocked the binding of PE-labeled antibody 344823 to TIM-3 expressing cell. However, antibody 512, 4545 and 8213 did not inhibit the binding of PE-labeled antibody 344823 to TIM-3 expressing cell. Antibody 4177 inhibited the binding of PE-labeled antibody 344823 to TIM-3 expressing cells, but this inhibition was weaker than that of antibody 644. Accordingly, antibody 644 competed with antibody 344823, but antibodies 512, 4545 and 8213 did not compete with antibody 344823. It was found that the antibody 4177 and antibody 344823 competed with each other, but they competed partially.

In the second step, among the anti-TIM-3 monoclonal antibodies tested, antibodies 512, 4545 and 8213 which did not interact with antibody 344823 were examined whether or not they competed. The experiment was carried out in the same manner as the first step except for using Alexa-647 labeled antibody 512 or Alexa-647 labeled antibody 8213 prepared in Example 15 as a labeled antibody. As a result, antibody 4545 and antibody 8213 did not inhibit the binding of Alexa-647 labeled antibody 512 to the TIM-3 expressing cells.

However, antibody 4545 inhibited the binding of Alexa-647 labeled antibody 8213 to TIM-3 expressing cells. Therefore, it was found that antibody 4545 and antibody 8213 competed with each other, but these two antibodies did not compete with antibody 512. This result suggested that antibody 512 recognized different epitope from antibody 344823 and antibody 8213.

In the third step, a competitive assay with antibody 512 and antibody 8213 was carried out on antibody 4177 which was shown to partially compete with antibody 344823 in the first step. The experiment was performed in the same manner as described in second step. As a result, antibody 4177 did not inhibit the binding of the Alexa-647 labeled antibody 512 to the TIM-3 expressing cells, but inhibited the binding of the Alexa-647 labeled antibody 8213 to the TIM-3 expressing cells. Therefore, it was found that antibody 4177 did not compete with antibody 512, but only with antibody 8213.

Based on these results, among the 5 antibodies prepared in Example 13 and Example 14, antibody 644 recognized an epitope which was near the epitope to which antibody 344823 recognized; antibody 512 recognized an epitope different from of the epitope to which antibody 344823 and other four antibodies (antibody 644, antibody 4545, antibody 4177 and antibody 8213) recognized.

It was suggested that antibody 8213 recognized epitope different from of the epitope to which antibodies 344823 or 512 recognized. It was suggested that antibody 4545 recognized an epitope which was near the epitope to which antibody 8213 recognized. However, antibody 4177 recognized the epitope which was near the epitope to which antibody 8213 recognized, and also weakly recognized an epitope which was near the epitope to which antibody 344823 recognized.

Example 17

(Antibody Dependent Cellular Cytotoxicity Test of Recombinant Anti-TIM-3 Human Monoclonal Defucose Antibody)

Regarding the cellular cytotoxic activity via antibody, the ADCC activity against the target cell was measured by using human Peripheral Blood Mononuclear Cells (hereinafter referred to as "PBMC") as an effector in the presence of the antibody. First, peripheral blood was collected from the healthy human donor and mixed with anticoagulant. The obtained blood was loaded onto Ficoll-Plaque Plus (manufactured by GE Healthcare), and centrifuged at 2000 rpm for 20 min using a large scale centrifuge (CF9RX, manufactured by Hitachi Koki Co., Ltd.) so as not to disturb the boundary.

The middle fraction containing cells were collected and washed with PBS, and then centrifuged at 900 rpm for 20 min to remove the platelets. Thus obtained PBMC was used for the measurement. Next, the Daudi cell used as a target cell and the PBMC were mixed at the ratio of effector/target=50.

Each of the recombinant anti-human monoclonal defucose antibodies (antibody 512, antibody 644, antibody 4545 and antibody 4177) prepared in Example 13 and Example 14, and anti-DNP antibody as a human IgG1 control was suspended in the medium to give a final concentration of 1 μg/ml and a total volume of 100 μl. After mixing, the solution was incubated at 37° C. under 5% $CO_2$ for 4 hr. The lysis ratio of the target cell was evaluated based on the amount of LDH released into the medium. The LDH activity and lysis ratio were calculated using CytoTox 96 Non-Radioactive Cytotoxicity Assay (manufactured by Promega Corp.) in accordance with the instructions attached thereto. As statistical analysis, standard Student's t-test was used wherein a sample having a risk rate (p) of less than 0.05 was considered as one which was significantly different.

As the result that the ADCC activity on Daudi cells was measured, it was found that antibody 4545 and antibody 4177 exhibited the significant increase in the lysis ratio of the target cell as compared to anti-DNP antibody. This result suggests that anti-TIM-3 mouse antibody 8213 and anti-TIM-3 antibody which competes with anti-TIM-3 mouse antibody 8213 have high ADCC activity.

Similarly, the ADCC activity was measured by using recombinant anti-TIM-3 human monoclonal defucose antibodies (antibody 4545 and antibody 4177) prepared in Example 13, commercially available anti-TIM-3 monoclonal antibody 344823, and anti-DNP antibody as a negative control.

First, peripheral blood was collected from the healthy human donor and mixed with anticoagulant. The obtained blood was then loaded onto Ficoll-Plaque Plus (manufactured by GE Healthcare), and centrifuged at 2000 rpm for 20 min using a large scale centrifuge (CF9RX, manufactured by Hitachi Koki Co., Ltd.) so as not to disturb the boundary. The middle fraction containing cells were collected and washed with PBS, and then centrifuged at 900 rpm for 20 min to remove the platelets. Thus obtained PBMC fraction was used for the measurement of t the ADCC activity.

Next, the Daudi cell used as a target cell and the PBMC were mixed at the ratio of effector/target=25. Each of the antibody 4545, antibody 4177, antibody 344823, anti-DNP antibody and PBS were suspended in the medium to give a final concentration of 1 μg/ml and a total volume of 100 μl. After mixing, the solution was incubated at 37° C. under 5% $CO_2$ for 4 hr. The lysis ratio of the target cell was evaluated based on using the amount of LDH released into the medium.

The LDH activity and the lysis ratio were calculated using CytoTox 96 Non-Radioactive Cytotoxicity Assay (manufactured by Promega Corp.) in accordance with the instructions attached thereto. As statistical analysis, standard Student's t-test was used wherein a sample having a risk rate (p) of less than 0.05 was considered as one which was significantly different. As the result of the ADCC activity on Daudi cells was measured, it was found that antibody 4545 and antibody 4177 exhibited the significant increase in the lysis ratio of the target cell as compared to anti-DNP antibody. On the other hand, antibody 344823 exhibited no significant increase in the lysis ratio of the target cell as compared to anti-DNP antibody and PBS.

Example 18

(Calculating the Bound/Dissociation Constant Using Anti-TIM-3 Antibody)

The bound/dissociation constant was analyzed using surface plasmon resonance based biosensor (Biacore, manufactured by GE Healthcare). In brief, an anti-human antibody or an anti-mouse antibody was immobilized on the CM5 sensor chips. Next, the anti-TIM-3 human or mouse antibody were made to flow to bind the chip, and then soluble extracellular human TIM-3 prepared in Example 4 was made to flow to examine the bound/association constant of TIM-3 to the anti-TIM-3 antibody. Throughout the experimental process, basically the experimental method provided by GE Healthcare for calculating bound/dissociation constant was used.

Specifically, CM5 was used as the sensor chip (Research grade, manufactured by GE Healthcare). First, CM5 chip was activated by flowing through a mixed solution of equal parts of 400 mmol/L EDC (N-ethyl-N'-(3-dimethylaminopropyl)carbodiimide hydrocholoride) and 100 mmol/L NHS (N-hyderoxysuccinimide). Next, the anti-human antibody attached to the Human Antibody Capture Kit (manufactured by GE Healthcare) was diluted with the solution attached to the kit and the obtained solution was made to flow so that the required amount of the antibody to an antibody for a human antibody was immobilized on the CM5 chip.

For the mouse antibody, the antibody against mouse antibody was immobilized on the CM5 surface by diluting in the solution, which was provided in the Mouse Antibody Capture Kit (manufactured by GE Healthcare antibody). The activated chip surface was blocked by the passing through 1 mol/L for ethanolamide hydrochloride and inactivated.

Next, one kind of the anti-TIM-3 antibodies was diluted with HBS-EP buffer (manufactured by GE Healthcare) per one flow cell and passed through so as to bind the antibody for the human antibody or antibody for the mouse antibody immobilized on the chip surface. Then soluble extracellular human TIM-3 was flown through. To dissociate the bound anti-TIM-3 antibody from the soluble extracellular human TIM-3, either the total volume of 3 mol/L of $MgCl_2$ which was attached to the Human Antibody Capture Kit or Glycine-HCl (pH 1.7) which was attached to the Mouse Antibody Capture Kit were flown through the cell.

The above described procedures were considered as one step, and the similar procedure was repeated using different concentrations of the soluble extracellular human TIM-3, to collect data (sensorgram) for calculating the bound/association constant. The concentration of soluble extracellular human TIM-3 used as an analyte was calculated by measuring the absorbance at 280 nm and then converting the value of 1.4 OD to 1 mg/mL.

The molecular weight of the soluble extracellular human TIM-3 was calculated as 42.8 kDa based on the mobility on electrophoresis. The data was analyzed using Biaevaluation soft-ware (manufactured by GE Healthcare) according to the Biaevaluation Software Handbook. Specifically, the simultaneous Kinetics analysis was performed and the association rate constant (Ka) and dissociation rate constant (Kd) was calculated, by basically adopting a 1:1 Langmuir Binding reaction model was used for fitting. Then the value of the dissociation constant ($K_D$) was calculated from Kd/Ka.

Most of the anti-human TIM-3 human monoclonal antibody had the $K_D$ value of the order of $10^{-9}$ mol/L. In this aspect, there was no correlation between ADCC activity and binding affinity targeting for TIM-3.

When the anti-human TIM-3 monoclonal antibody was monitored (e.g., monitored the dissociation state for 30 min), there was no dissociation detected with the antigen soluble extracellular human TIM-3 as an antigen. As a result, it was found that it was possible to produce a monoclonal antibody having a very high affinity for human TIM-3.

Example 19

(Classification of Epitopes Using Competition Test-2)

The epitopes of anti-TIM-3 antibodies, i.e., antibody 512, antibody 644, antibody 4545, antibody 8213, antibody 344823, antibody F38-2E2 and anti-DNP antibody as a control were analyzed by a competitive assay. In brief, the unlabeled target antibody was allowed to interact with the TIM-3 expression cell prepared in Example 1, and whether or not other fluorescence labeled anti-TIM-3 antibody was further bound to TIM-3 expression cells were evaluated by flow cytometry method.

Human TIM-3 expressing EoL-1 cells were washed with staining medium and allowed to react with purified test monoclonal antibodies [antibody 512, antibody 644, antibody 4545, antibody 8213, antibody 344823 (manufactured by R&D Systems), antibody F38-2E2 (manufactured by Imgenex)] (4° C., 30 min). The final concentration was 10 µg/ml. Next, the Alexa-647 or APC labeled anti-TIM-3 antibodies [antibody 344823 (manufactured by R&D Systems) and antibody F38-2E2 (manufactured by eBiosciences)] were added and were allowed to react (4° C., 30 min). After washing with staining medium, 7-ADD (manufactured by BD Biosciences) was added before analyzing with FACSCalibur (manufactured by BD Biosciences).

The results are shown in Table 1. As shown in Table 1, the case the degree of the binding to the TIM-3 expression cell to which the unlabeled anti-TIM-3 antibody was bound was similar to that of a negative control were indicated as "+", the case where the degree to the binding to the TIM-3 expression cell to which the unlabeled anti-TIM-3 antibody was bound was found but was lower than that of a negative control was indicated as "+/−" and the case where the binding to the TIM-3 expression cell to which the unlabeled anti-TIM-3 antibody was bound was not detected, it was indicated as "−".

TABLE 1

| | | Unlabeled antibody | | | | | |
|---|---|---|---|---|---|---|---|
| | | DNP | 512 | 644 | 4545 | 8213 | 344823 | F38-2E2 |
| Alexa-647 or APC labeled antibody | DNP | − | − | − | − | − | − | − |
| | 512 | + | − | + | + | + | + | + |
| | 644 | + | + | +/− | + | + | +/− | +/− |
| | 4545 | + | + | + | − | − | + | + |
| | 8213 | + | + | + | − | − | + | + |
| | 344823 | + | + | − | + | + | − | +/− |
| | F38-2E2 | + | + | − | + | + | − | − |

As shown in Table 1, since Alexa-647 labeled antibody 512 was found to bind to the TIM-3 expressing cell to which the other unlabeled anti-TIM-3 antibodies were bound, this antibody was suggested to recognize an independent epitope with which antibody 644, antibody 4545, antibody 8213, antibody 344823 and antibody F38-2E2 did not compete.

Since it was found that Alexa-647 labeled antibody 644 did not bind or reduced in binding to the TIM-3 expressing cell to which the unlabeled anti-TIM-3 antibody 344823 or F38-2E2 was bound, it was indicated that this antibody competed with antibody 344823 or F38-E2E in the recognition of the epitope close to each other.

Since it was found that Alexa-647 labeled antibody 4545 did not bind to the TIM-3 expressing cell to which the unlabeled anti-TIM-3 antibody 8213 was bound, it was indicated that this antibody competed with antibody 8213 in the recognition of the epitope close to each other.

Since it was found that Alexa-647 labeled antibody 8213 did not bind to the TIM-3 expressing cell to which the unlabeled anti-TIM-3 antibody 4545 was bound, it was indicated that this antibody competed with antibody 4545 in the recognition of the epitope close to each other.

Since it was found that APC labeled antibody 344823 did not bind to the TIM-3 expressing cell to which the unlabeled anti-TIM-3 antibody 644 or F38-2E2 was bound, it was indicated that this antibody competed with antibody 644 or F38-E2E antibody in the recognition of the epitope close to each other.

Since it was found that APC labeled Antibody F38-2E2 did not bind to the TIM-3 expressing cell to which the unlabeled anti-TIM-3 antibody 644 or 344823 was bound, it was indicated that this antibody competed with antibody 644 or antibody 344823 in the recognition of the epitope close to each other.

Example 20

(Molecular Cloning of Mouse TIM-3 cDNA)

The cDNA of mouse TIM-3 was prepared in the same manner as described in Example 1. Total RNA was extracted from Balb/c mouse derived bone marrow cells using High Pure RNA isolation Kit (manufactured by Roche). Template cDNA was synthesized using ThermoScript RT-PCR system (manufactured by Invitrogen). For primers, mTim-3 Fw3 (SEQ ID NO: 70) and mTim-3 Re3 (SEQ ID NO: 71) were used. The cDNA was inserted into pGEM-T Easy Vector (manufactured by Promega Corp.), and the sequence was analyzed. The clone having identical nucleotide sequence with the coding region of GenBank accession number AF450241 was selected.

PCR was carried out using the selected clone as the template and inserting the DNA into NotI site of the pEF6/Myc-HisC vector (manufactured by Invitrogen) (mTim-3/pEF6 Myc_HisC). For PCR primers, mTim-3 Fw4NotI (SEQ ID NO: 72) and mTim-3 Re4NotI (SEQ ID NO: 73) were used.

Example 21

(Construction of hTim-3/pEF6 Myc_HisC)

The plasmid DNA hTIM-3/pMCs-IG prepared in Example 1 and pEF6 Myc_HisC were both digested with NotI to construct human TIM-3 expressing pEF6 Myc_HisC vector (hTim-3/pEF6 Myc_HisC). DNA sequence analysis confirmed that the vector sequence matched the coding region of the GenBank accession number NM_032782.

Example 22

(Cross-Reactivity of Anti-Human TIM-3 Antibody to Anti-Mouse TIM-3 Antibody)

Each of the plasmid DNAs, mTim-3/pEF6 Myc_HisC and hTim-3/pEF6 Myc_HisC prepared in Example 20 and Example 21, and an empty vector control was introduced into HEK293F cell in the same manner as Example 4. Two days later, in the same manner as Example 15, the binding activity of Alexa-647 labeled antibodies (antibody 512, antibody 644, antibody 4545 and antibody 8213), commercially available APC labeled anti-human TIM-3 antibodies (antibody 344823 and antibody F38-2E2) and commercially available PE labeled anti-mouse TIM-3 antibody (RMT3-23 antibody, manufactured by BioLegend Inc.) to human TIM-3 and mouse TIM-3 was evaluated using flow cytometry analysis.

As a result, antibody 512, antibody 644, antibody 4545, antibody 8213, antibody 344823 and antibody F38-2E2 exclusively interacted with human TIM-3 expressing 293F cells. However, RMT3-23 antibody interacted exclusively with mouse TIM-3 expressing 293F cells. Therefore, it was found that antibody 512, antibody 644, antibody 4545, antibody 8213, antibody 344823 and antibody F38-2E2 did not cross-react with mouse TIM-3.

Example 23

(Construction of Expression System for TIM-3 Chimeric Protein with IgV Domain Substituted for Mouse TIM-3)

The objective sequence was amplified by the PCR using hTim-3/pEF6 Myc_HisC plasmid DNA as a template, hTIM3+mIgV_vecR1 primer (SEQ ID NO: 74) and hTIM3+mIgV_vecF1 primer (SEQ ID NO: 75), and PrimeSTAR GXL DNA Polymerase (manufactured by Takara Bio Inc.). The objective sequence was amplified by PCR using mTim-3/pEF6 Myc_HisC plasmid DNA as a template, hTIM3+mIgV_insF1 primer (SEQ ID NO: 76) and hTIM3+mIgV_insR1 primer (SEQ ID NO: 77), and PrimeSTAR GXL DNA Polymerase (manufactured by Takara Bio Inc.).

The two PCR products obtained were ligated using GENEART seamless cloning and assembly kit (manufactured by Invitrogen). The sequence from the transformant was analyzed and it was found that the PCR products had the objective sequences (IgV chimeraTIM-3/pEF6 Myc_HisC, SEQ ID NO: 78).

Example 24

(Construction of Expression System for TIM-3 Chimeric Protein with Mucin Domain Substituted for Mouse TIM-3)

The objective sequence was amplified by PCR using hTim-3/pEF6 Myc_HisC plasmid DNA as a template, hTIM3+mMucin_vecR2 primer (SEQ ID NO: 80) and hTIM3+mMucin_vecF2 primer (SEQ ID NO: 81), and PrimeSTAR GXL DNA Polymerase (manufactured by Takara Bio Inc.). The objective sequence was amplified by PCR using mTim-3/pEF6 Myc_HisC plasmid DNA as a template, hTIM3+mMuicn_insF2 primer (SEQ ID NO: 82) and hTIM3+mMucin_insR2 primer (SEQ ID NO: 83), and PrimeSTAR GXL DNA Polymerase (manufactured by Takara Bio Inc.).

The two PCR products obtained were ligated using GENEART seamless cloning and assembly kit (manufactured by Invitrogen). The sequence from the transformant was analyzed and it was found that the PCR products had the objective sequences (Mucin chimeraTIM-3/pEF6 Myc_HisC, SEQ ID NO: 84).

Example 25

(Binding Assay of Anti-TIM-3 Antibody to TIM-3 Chimeric Protein in which IgV Domain was Substituted with Mouse TIM-3 and TIM-3 Chimeric Protein in which Mucin Domain was Substituted with Mouse TIM-3)

Each of the plasmid DNAs prepared in Example 23 and Example 24, IgV chimeraTIM-3/pEF6 Myc_HisC, Mucin chimeraTIM-3/pEF6 Myc_HisC, hTim-3/pEF6 Myc_HisC, mTim-3/pEF6 Myc_HisC, and an empty vector control was introduced into HEK293F cell in the same manner as Example 4. Two days later, in the same manner as Example 22, the binding activity of anti-TIM-3 antibody was evaluated using flow cytometry.

As a result, antibody 512, antibody 644, antibody 4545, antibody 8213, antibody 4177, antibody 344823 and antibody F38-2E2 bound to the human TIM-3 expressing cells and Mucin chimeraTIM-3 expressing cells only. However, RMT-23 antibody bound to the mouse TIM-3 expressing cells and the IgV chimeraTIM-3 expressing cells only.

Therefore, as a result, it was found that all of the anti-human TIM-3 antibodies tested (antibody 512, antibody 644, antibody 4545, antibody 8213, antibody 344823 and antibody F38-2E2) and mouse TIM-3 antibody (antibody RMT3-23) recognized the IgV domain.

Example 26

(Construction of TIM-3 Chimera 22-47/pEF6 Myc_HisC)

A vector which expressed TIM-3 chimeric protein in which the amino acid of human TIM-3 (SEQ ID NO: 53) at position 22 to position 47 were substituted with the corresponding amino acid of mouse TIM-3 (hereinafter referred to as "TIM-3 chimera 22-47") was constructed. By using hTim-3/pEF6 Myc_HisC plasmid DNA prepared in Example 21 as a template, and hTIM3chimera22-47F1 primer (SEQ ID NO: 86) and hTIM3chimera22-47R1 primer (SEQ ID NO: 87), and PCR was carried out using PrimeSTAR GXL DNA Polymerase (manufactured by Takara Bio Inc.).

Using the obtained PCR product as a template, the objective sequence was amplified by PCR using hTIM3chimera22-47F2 primer (SEQ ID NO: 88) and hTIM3chimera22-47R2 primer (SEQ ID NO: 89) and using PrimeSTAR GXL DNA Polymerase (manufactured by Takara Bio Inc.).

Using the obtained PCR product as a template, the objective sequence was amplified by PCR using hTIM3chimera22-47F3 primer (SEQ ID NO: 90) and hTIM3chimera22-47R3 primer (SEQ ID NO: 91), and using PrimeSTAR GXL DNA Polymerase (manufactured by Takara Bio Inc.).

After the obtained PCR product obtained from the third PCR was digested with DpnI (manufactured by New England Biolabs), it was subjected to agarose gel electrophoresis. The DNA was extracted and ligated using GENEART seamless cloning and assembly kit (manufactured by Invitrogen). The sequence of the clone obtained from the transformant was analyzed and confirmed that the clone had the objective sequence (TIM-3 chimera 22-47/pEF6 Myc_HisC, SEQ ID NO: 92).

Example 27

(Construction of TIM-3 Chimera 57-66/pEF6 Myc_HisC)

A vector which expressed TIM-3 chimeric protein in which the amino acid of human TIM-3 (SEQ ID NO: 53) at position 57 to position 66 were substituted with the corresponding amino acid of mouse TIM-3 (hereinafter referred to as "TIM-3 chimera 57-66") was constructed. PCR was carried out using hTim-3/pEF6 Myc_HisC plasmid DNA prepared in Example 21 as a template, hTIM3chimera57-66F primer (SEQ ID NO: 94) and hTIM3chimera57-66R primer (SEQ ID NO: 95) phosphorylated by T4 Polynucleotide Kinase (manufactured by New England Biolabs) and PrimeSTAR GXL DNA Polymerase (manufactured by Takara Bio Inc.) to amplify the objective sequence.

After the obtained PCR product was digested with DpnI (manufactured by New England Biolabs), it was subjected to the agarose gel electrophoresis. The DNA was extracted and ligated with LigaFast™ Rapid DNA Ligation System (manufactured by Promega Corp.). The sequence of the clone obtained from the transformant was analyzed and confirmed that it was the objective sequence (TIM-3 chimera 57-66/pEF6 Myc_HisC, SEQ ID NO: 96).

Example 28

(Construction of TIM-3 Chimera 67-105/pEF6 Myc_HisC)

A vector which expressed TIM-3 chimeric protein in which the amino acid of human TIM-3 (SEQ ID NO: 53) at position 67 to position 105 were substituted with the corresponding amino acid of mouse TIM-3 (hereinafter referred to as "TIM-3 chimera 67-105") was constructed. PCR was carried out using hTim-3/pEF6 Myc_HisC plasmid DNA as a template, hTIM3chimera67-105F primer (SEQ ID NO: 98) and hTIM3chimera67-105R primer (SEQ ID NO: 99) and using PrimeSTAR GXL DNA Polymerase (manufactured by Takara Bio Inc.) to amplify the objective sequence.

PCR was carried out using mTim-3/pEF6 Myc_HisC plasmid DNA as a template, mTIM3chimera67-105F primer (SEQ ID NO: 100) and mTIM3chimera67-105R primer (SEQ ID NO: 101) and using PrimeSTAR GXL DNA Polymerase (manufactured by Takara Bio Inc.). The two PCR products were ligated by GENEART seamless cloning and assembly kit (manufactured by Invitorgen). The sequence of the clone obtained from the transformant was analyzed and confirmed that it was the objective sequence (TIM-3 chimera 67-105/pEF6 Myc_HisC, SEQ ID NO: 102).

Example 29

(Construction of TIM-3 Chimera 74-81/pEF6 Myc_HisC)

A vector which expressed TIM-3 chimeric protein in which the amino acid of human TIM-3 (SEQ ID NO: 53) at position 74 to position 81 were substituted with the corresponding amino acid of mouse TIM-3 (hereinafter referred to as "TIM-3 chimera 74-81") was constructed. PCR was carried out using hTim-3/pEF6 Myc_HisC plasmid DNA prepared in Example 21 as a template, hTIM3chimera74-81F primer (SEQ ID NO: 104) and hTIM3chimera74-81R primer (SEQ ID NO: 105) and using PrimeSTAR GXL DNA Polymerase (manufactured by Takara Bio Inc.).

After the PCR product was digested with DpnI (manufactured by New England Biolabs), it was subjected to agarose gel electrophoresis. The DNA was extracted and ligated with GENEART seamless cloning and assembly kit (manufactured by Invitorgen). The sequence of the clone obtained from the transformant was analyzed and confirmed that it was the objective sequence (TIM-3 chimera 74-81/pEF6 Myc_HisC, SEQ ID NO: 106).

Example 30

(Construction of TIM-3 Chimera 88-96/pEF6 Myc_HisC)

A vector which expressed TIM-3 chimeric protein in which the amino acid of human TIM-3 (SEQ ID NO: 53) at position 88 to position 96 were substituted with the corresponding amino acid of mouse TIM-3 (hereinafter referred to as "TIM-3 chimera 88-96") was constructed. The PCR was carried out by preparing a reaction solution containing hTim-3/pEF6 Myc_HisC plasmid DNA prepared in Example 21 as a template, hTIM3chimera88-96F primer (SEQ ID NO: 108) and hTIM3chimera88-96R primer (SEQ ID NO: 109) and using PrimeSTAR GXL DNA Polymerase (manufactured by Takara Bio Inc.).

After the obtained PCR product was digested with DpnI (manufactured by New England Biolabs), it was subjected to agarose gel electrophoresis. The DNA was extracted and ligated with GENEART seamless cloning and assembly kit (manufactured by Invitrogen). The sequence of the clone obtained from the transformant was analyzed and confirmed that it was the objective sequence (TIM-3 chimera 88-96/pEF6 Myc_HisC, SEQ ID NO: 110).

Example 31

(Construction of TIM-3 Chimera 96-105/pEF6 Myc_HisC)

A vector which expressed TIM-3 chimeric protein in which the amino acid of human TIM-3 (SEQ ID NO: 53) at position 96 to position 105 were substituted with the corresponding amino acid of mouse TIM-3 (hereinafter referred to as "TIM-3 chimera 96-105") was constructed. The PCR was carried out by preparing a reaction solution containing hTim-3/pEF6 Myc_HisC plasmid DNA prepared in Example 21 as a template, hTIM3chimera96-105F primer (SEQ ID NO: 112) and hTIM3chimera96-105R primer (SEQ ID NO: 113) and using PrimeSTAR GXL DNA Polymerase (manufactured by Takara Bio Inc.).

After the obtained PCR product was digested with DpnI (manufactured by New England Biolabs), it was subjected to agarose gel electrophoresis. The DNA was extracted and ligated with GENEART seamless cloning and assembly kit (manufactured by Invitrogen). The sequence of the clone obtained from the transformant was analyzed and confirmed that it was the objective sequence (TIM-3 chimera 96-105/pEF6 Myc_HisC, SEQ ID NO: 114).

Example 32

(Binding Assay of Anti-TIM-3 Antibody to TIM-3 Chimeric Protein in which Part of the IgV Domain was Substituted with Mouse TIM-3)

Each of various TIM-3 vectors prepared in Examples 26 to 31 and an empty vector as a control were introduced into HEK293F in the same manner as Example 4. The introduced vectors and the expressed TIM-3 chimeric proteins thereof were as follows:

(1) TIM-3 chimera 22-47: TIM-3 chimeric protein in which the amino acid residues at position 22 to position 47 of human TIM-3 (SEQ ID NO: 53) were substituted with the corresponding amino acids of mouse TIM-3;

(2) TIM-3 chimera 57-66: TIM-3 chimeric protein in which the amino acid residues at position 57 to position 66 of human TIM-3 (SEQ ID NO: 53) were substituted with the corresponding amino acids of mouse TIM-3;

(3) TIM-3 chimera 67-105: TIM-3 chimeric protein in which the amino acid residues at position 67 to position 105 of human TIM-3 (SEQ ID NO: 53) were substituted with the corresponding amino acids of mouse TIM-3;

(4) TIM-3 chimera 74-81: TIM-3 chimeric protein in which the amino acid residues at position 74 to position 81 of human TIM-3 (SEQ ID NO: 53) were substituted with the corresponding amino acids of mouse TIM-3;

(5) TIM-3 chimera 88-96: TIM-3 chimeric protein in which the amino acid residues at position 88 to position 96 of human TIM-3 (SEQ ID NO: 53) were substituted with the corresponding amino acids of mouse TIM-3; and (6) TIM-3 chimera 96-105: TIM-3 chimeric protein in which the amino acid residues at position 96 to position 105 of human TIM-3 (SEQ ID NO: 53) were substituted with the corresponding amino acids of mouse TIM-3.

Two days after transfection, in the same manner as Example 22, the binding activity of anti-TIM-3 antibody was evaluated using flow cytometry.

The results are shown in Table 2. As shown in Table 2, the case where the binding of the antibody to the transfected cell was detected was indicated as "+", the case where the binding of the antibody to the transfected cell was detected but the degree of the binding was reduced was indicated as "+/−" and the case where the binding of the antibody to the transfected cell was not detected was indicated as "−".

TABLE 2

| Vector name | 4545 | 8213 | 4177 | 512 | 644 | 344823 | F38-2E2 |
|---|---|---|---|---|---|---|---|
| TIM-3 chimera 22-47 | + | + | +/− | − | + | + | + |
| TIM-3 chimera 57-66 | + | + | +/− | + | − | − | − |
| TIM-3 chimera 67-105 | − | − | +/− | + | + | + | + |
| TIM-3 chimera 74-81 | − | − | + | + | + | + | + |
| TIM-3 chimera 88-96 | + | + | + | + | + | + | + |
| TIM-3 chimera 96-105 | + | + | + | + | + | + | + |

As shown in Table 2, antibody 4545 and antibody 8213 bound to the cells transfected with TIM3-chimera 22-47, TIM3-chimera 57-66, TIM3-chimera 88-96 or TIM3-chimera 96-105 transfected cells. However, these antibodies did not bind to the cell into which TIM-3 chimera 67-105 were introduced.

The antibody 512 bound to the cells transfected with TIM3-chimera 57-66, TIM3-chimera 88-96, TIM3-chimera 96-105, TIM-3 chimera 67-105 or TIM-3 chimera 74-81. However, antibody 512 did not bind to the cells transfected with TIM-3 chimera 22-47.

The antibody 644, antibody 344823 and antibody F38-2E2 bound to the cells transfected with TIM3-chimera 22-47, TIM3-chimera 88-96, TIM3-chimera 96-105, TIM-3 chimera 67-105 or TIM-3 chimera 74-81. However, these antibodies did not bind to the cells transfected with to TIM-3 chimera 57-66.

The antibody 4177 bound to the cells transfected with TIM3-chimera 88-96, TIM3-chimera 96-105 or TIM-3 chimera 74-81. Antibody 4177 weakly bound to TIM-3 the cells transfected with chimera 22-47, TIM-3 chimera 57-66 or TIM-3 chimera 67-105.

Based on the above result and results from Example 16 and Example 19, it was suggested that antibody 4545 and antibody 8213 bound to the amino acid residues at position 67 to 87 of human TIM-3. Since antibody 4545 and antibody 8213 did not bind to the cells transfected with TIM-3 chimera 74-81, it was suggested that the amino acids required for binding of antibody 4545 and antibody 8213 to human TIM-3 were included in the amino acid at position 74 to 81.

In addition, it was suggested that antibody 512 bound to the amino acids up to at position 47 of human TIM-3 and that antibody 644, antibody 344823 and antibody F38-2E2 bound to the amino acid residues at position 57 to 66 of human TIM-3.

Furthermore, it was suggested that antibody 4177 bound to the amino acids other than at position 74 to 81 within the amino acids at position 67 to 87 of human TIM-3 to which antibody 4545 and antibody 8213 bind although antibody 512, antibody 644, antibody 344823 and antibody F38-2E2 did not bind.

Example 33

(Preparation of Anti-Human TIM-3 Antibody 8213 Humanized Antibody)
(1) Design of Amino Acid Sequences of VH and VL of Antibody 8213 Humanized Antibody The amino acid sequence of VH of antibody 8213 humanized antibody was designed in the following manner. The amino acid sequences of FRs in VH of human antibody which is suitable for the grafting of the amino acid sequences (SEQ ID NOs: 21 to 23) of CDRs1 to 3 of antibody 8213 were selected as follows.

Kabat et al., have classified the VH of conventionally known various human antibodies into three subgroups (HSG I to III) based on the homology of their amino acid sequences and reported the consensus sequences for each of the subgroups [*Sequences of Proteins of Immunological Interest*, US Dept. Health and Human Services (1991)]. Therefore, the homology search of the amino acid consensus sequences of FR of VH subgroups I to III of human antibodies with the amino sequence of FR of VH of antibody 8213 was conducted.

As a result of the homology search, the homologies of HSGI, HSGII, and HSGIII were 77.0%, 55.2%, and 58.6%, respectively. Therefore, the amino acid sequence of FR of the VH region of antibody 8213 had the highest homology to the subgroup I.

Based on the above results, the amino acid sequence of CDR of the VH of antibody 8213 (SEQ ID NOs: 21 to 23) was grafted to an appropriate position of the FR amino acid sequence of the consensus sequence of subgroup I of human antibody VH. In this manner, the 8213 antibody HV0 represented by SEQ ID NO: 67, i.e., the amino acid sequence of VH of an anti-human TIM-3 antibody 8213 humanized antibody was designed.

Next, the amino acid sequence of VL of antibody 8213 humanized antibody was designed in the following manner. The amino acid sequences of FR in VL of human antibody which were suitable for the grafting of the amino acid sequences (SEQ ID NOs: 24 to 26) of CDRs1 to 3 in VL of antibody 8213 were selected as follows.

Kabat et al., have classified the VL of various known human antibodies into four subgroups (HSG I to IV) based on the homology of their amino acid sequences and reported the consensus sequences for each of the subgroups [*Sequences of Proteins of Immunological Interest*, US Dept. Health and Human Services (1991)]. Therefore, the homology search among the FR amino acid consensus sequences of VL subgroup I to IV of human antibodies were searched for sequence homology with FR amino sequence of VL of antibody 8213.

As a result of the homology search, the homologies of HSGI, HSGII, HSGIII and HSGIV were 76.3%, 61.3%, 61.3%, and 68.8%, respectively. Therefore, the amino acid sequence of FR of the VL region of antibody 8213 had the highest homology to the subgroup I.

Based on the above results, each of the amino acid sequences of CDRs of the VL of antibody 8213 (SEQ ID NOs: 24 to 26) was grafted into an appropriate position in the amino acid sequence of FR of the consensus sequence of subgroup I of VL of an human antibody. In this manner, the 8213 antibody LV0 represented by SEQ ID NO: 69, i.e., the amino acid sequence of VL of an anti-human TIM-3 antibody 8213 humanized antibody, was designed.

The amino acid sequence of 8213 antibody HV0 which was VH of antibody 8213 humanized antibody; and the amino acid sequence of 8213 antibody LV0 which was VL of antibody 8213 humanized antibody designed in the above were the sequences in which only the amino acid sequences of CDRs of the mouse monoclonal antibody 8213 were grafted into the amino acid sequence of the selected FR of human antibody.

However, in general, it is known that a humanized antibody prepared merely by grafting CDRs of a mouse antibody to FRs of a human antibody has a lower binding activity. In order to avoid decreasing of the binding activity, attempts have been made in the preparation of a humanized antibody to raise the lowered binding activity by modifying the amino acid residues which were considered to have influence on the binding activity among the amino acid sequences of FRs of a human antibody which are different from a mouse antibody as well as grafting amino acid sequences of CDRs. Therefore, in Examples, the inventors decided to identify and modify the amino acid residues of FR which were considered to have influence on the binding activity in the following manner.

First, three-dimensional structure of the above designed antibody V region (hereinafter referred to as "HV0LV0") comprising the amino acid sequence of antibody 8213 HV0 which was VH of the antibody 8213 humanized antibody and the amino acid sequence of antibody 8213 LV0 which was VL of antibody 8213 humanized antibody was constructed using a computer modeling technique. Discovery Studio (manufactured by Accelrys Inc.) was used for preparation of the three-dimensional structure and display of the three-dimensional structure. A computer model of the three-dimensional structure of V region of antibody 8213 was constructed in the same manner.

Furthermore, amino acid residues which were different from those of antibody 8213 in the amino acid sequence of FRs of VH and VL of HV0LV0 were selected, prepared an amino acid sequence in which such amino acid residues were substituted with the corresponding amino acid residues of 8213 antibody and then a three-dimensional structure model was constructed in the same manner. The amino acids which were considered to have influence on the binding activity were selected by comparing the three-dimensional structures of the V regions of antibody 8213 and HV0LV0 and the modified product.

As a result, as amino acid residues of FR in HV0LV0 which were considered to change the three-dimensional structure of the antigen binding region and have influence on the binding activity, Lys at position 12, Val at position 20, Arg at position 38, Ala at position 40, Met at position 48, Arg at position 67, Val at position 68, Ile at position 70, Ala at position 72, Thr at position 74, Arg at position 98 and Val at position 113 were selected in antibody 8213 HV0; and Leu at position 11, Ala at position 13, Val at position 15, Tyr at position 36, Ala at position 43, Pro at position 44, Leu at position 46, Phe at position 71 and Thr at position 85 were selected in antibody 8213 LV0.

Among the selected amino acid residues, at least one or more amino acid residues was substituted with amino acid residues which were present at the corresponding sites of antibody 8213 and VHs and VLs of the humanized antibody comprising various modifications were constructed.

Specifically, as for VH, at least one modification was introduced among the amino acid modifications for substituting Lys at position 12 with Val, Val at position 20 with Leu, Arg at position 38 with Lys, Ala at position 40 with Arg, Met at position 48 with Ile, Arg at position 67 with Lys, Val at position 68 with Ala, Be at position 70 with Leu, Ala at position 72 with Val, Thr at position 74 with Lys, Arg at position 98 with Gly, or Val at position 113 with Leu in the amino acid sequence represented by SEQ ID NO: 67.

As for VL, at least one modification was introduced among the amino acid modifications for substituting Leu at position 11 with Met, Ala at position 13 with Val, Val at position 15 with Leu, Tyr at position 36 with Leu, Ala at position 43 with Ser, Pro at position 44 with Phe, Leu at position 46 with Gly, Phe at position 71 with Tyr and Thr at position 85 with Asp in the amino acid sequence represented by SEQ ID NO: 69.

As the antibody V region of 8213 antibody-humanized antibody in which at least one amino acid existing in FR in HV0LV0 was modified, HV0LV0, HV0LV2, HV0LV4, HV0LV5, HV0LV6, HV0LV7, HV0LV9, HV3LV0, HV3LV2, HV3LV4, HV3LV5, HV3LV6, HV3LV7, HV3LV9, HV4LV0, HV4LV2, HV4LV4, HV4LV5, HV4LV6, HV4LV7, HV4LV9, HV5LV0, HV5LV2, HV5LV4, HV5LV5, HV5LV6, HV5LV7, HV5LV9, HV6LV0, HV6LV2, HV6LV4, HV6LV5, HV6LV6, HV6LV7, HV6LV9, HV0LV0, HV7LV2, HV7LV4, HV7LV5, HV7LV6, HV7LV7, HV7LV9, HV8LV0, HV8LV2, HV8LV4, HV8LV5, HV8LV6, HV8LV7, HV8LV9, HV10LV0, HV10LV2, HV10LV4, HV10LV5, HV10LV6, HV10LV7, HV10LV9, HV12LV0, HV12LV2, HV12LV4, HV12LV5, HV12LV6, HV12LV7, and HV12LV9 were designed.

The amino acid sequences of each of the H chain variable regions, HV3, HV4, HV5, HV6, HV7, HV8, HV10 and HV12; and the amino acid sequence of the L chain variable region, LV2, LV4, LV5, LV6, LV7 and LV9 were shown in FIG. 1 and FIG. 2, respectively.

(2) Preparation of 8213 Antibody-Humanized Antibody

DNA encoding the amino acid sequence of the variable region of 8213 antibody-humanized antibody was designed using codons used in the DNAs (SEQ ID NO: 27 and 29) encoding the amino acid sequence of VH of 8213 antibody and VL of 8213 antibody, respectively. When the amino acid modification was introduced, DNA was designed using a codon which was used in a mammal cell with a high frequency.

Using these DNA sequences, vectors for expressing an antibody were constructed and humanized antibodies were expressed.

While the invention has been described in detail and with reference to specific embodiments thereof, it will be apparent to one skill in the art that various changes and modifications can be made therein without departing from the spirit and scope thereof.

This application is based on U.S. provisional application No. 61/353,836, filed on Jun. 11, 2010, the entire contents of which are incorporated hereinto by reference. All references cited herein are incorporated in their entirety.

FREE TEXT OF SEQUENCE LISTING

SEQ ID NO: 1: The amino acid sequence of Human 4545 H chain CDR1
SEQ ID NO: 2: The amino acid sequence of Human 4545 H chain CDR2
SEQ ID NO: 3: The amino acid sequence of Human 4545 H chain CDR3
SEQ ID NO: 4: The amino acid sequence of Human 4545 L chain CDR1
SEQ ID NO: 5: The amino acid sequence of Human 4545 L chain CDR2
SEQ ID NO: 6: The amino acid sequence of Human 4545 L chain CDR3
SEQ ID NO: 11: The amino acid sequence of Human 4177 H chain CDR1
SEQ ID NO: 12: The amino acid sequence of Human 4177 H chain CDR2
SEQ ID NO: 13: The amino acid sequence of Human 4177 H chain CDR3
SEQ ID NO: 14: The amino acid sequence of Human 4177 L chain CDR1
SEQ ID NO: 15: The amino acid sequence of Human 4177 L chain CDR2
SEQ ID NO: 16: The amino acid sequence of Human 4177 L chain CDR3
SEQ ID NO: 21: The amino acid sequence of Mouse 8213 H chain CDR1
SEQ ID NO: 22: The amino acid sequence of Mouse 8213 H chain CDR2
SEQ ID NO: 23: The amino acid sequence of Mouse 8213 H chain CDR3
SEQ ID NO: 24: The amino acid sequence of Mouse 8213 L chain CDR1
SEQ ID NO: 25: The amino acid sequence of Mouse 8213 L chain CDR2
SEQ ID NO: 26: The amino acid sequence of Mouse 8213 L chain CDR3
SEQ ID NO: 31: The nucleotide sequence of primer TIM-3 Fw2
SEQ ID NO: 32: The nucleotide sequence of primer TIM-3 Re2
SEQ ID NO: 33: The nucleotide sequence of primer pMCs-Fw
SEQ ID NO: 34: The nucleotide sequence of primer TIM3ED-FcReXba
SEQ ID NO: 35: The nucleotide sequence of primer T7
SEQ ID NO: 36: The nucleotide sequence of primer hTIM-3 Fw1
SEQ ID NO: 37: The nucleotide sequence of insert hTIM-3 ECD Fc fusion
SEQ ID NO: 38: The amino acid sequence of insert hTIM-3 ECD Fc fusion
SEQ ID NO: 39: The nucleotide sequence of primer TIM3ED-FLAG4aa
SEQ ID NO: 40: The nucleotide sequence of primer C-FLAG-NotR2
SEQ ID NO: 41: The nucleotide sequence of primer BGH-R SEQ ID NO: 42: The nucleotide sequence of insert hTIM-3 ECD
SEQ ID NO: 43: The amino acid sequence of insert hTIM-3 ECD
SEQ ID NO: 44: The nucleotide sequence of primer hh-6
SEQ ID NO: 45: The nucleotide sequence of primer hh-3
SEQ ID NO: 46: The nucleotide sequence of primer hk-2
SEQ ID NO: 47: The nucleotide sequence of primer hk-6
SEQ ID NO: 48: The nucleotide sequence of primer mH_Rv1
SEQ ID NO: 49: The nucleotide sequence of primer mH_Rv2
SEQ ID NO: 50: The nucleotide sequence of primer mK_Rv1
SEQ ID NO: 51: The nucleotide sequence of primer mK_Rv2
SEQ ID NO: 66: The nucleotide sequence of 8213 antibody HV0 variable region
SEQ ID NO: 67: The amino acid sequence of 8213 antibody HV0 variable region
SEQ ID NO: 68: The nucleotide sequence of 8213 antibody LV0 variable region
SEQ ID NO: 69: The amino acid sequence of 8213 antibody LV0 variable region
SEQ ID NO: 70: The nucleotide sequence of primer mTim-3 Fw3
SEQ ID NO: 71: The nucleotide sequence of primer mTim-3 Re3
SEQ ID NO: 72: The nucleotide sequence of primer mTim-3 Fw4NotI
SEQ ID NO: 73: The nucleotide sequence of primer mTim-3 Re4NotI
SEQ ID NO: 74: The nucleotide sequence of primer hTIM3+mIgV_vecR1
SEQ ID NO: 75: The nucleotide sequence of primer hTIM3+mIgV_vecF1
SEQ ID NO: 76: The nucleotide sequence of primer hTIM3+mIgV_insF1
SEQ ID NO: 77: The nucleotide sequence of primer hTIM3+mIgV_insR1
SEQ ID NO: 78: The nucleotide sequence of insert IgV chimeraTIM-3/pEF6 Myc_HisC
SEQ ID NO: 79: The amino acid sequence of insert IgV chimeraTIM-3/pEF6 Myc_HisC
SEQ ID NO: 80: The nucleotide sequence of primer hTIM3+mMucin_vecR2
SEQ ID NO: 81: The nucleotide sequence of primer hTIM3+mMucin_vecF2
SEQ ID NO: 82: The nucleotide sequence of primer hTIM3+mMucin_insF2
SEQ ID NO: 83: The nucleotide sequence of primer hTIM3+mMucin_insR2
SEQ ID NO: 84: The nucleotide sequence of insert Mucin chimeraTIM-3/pEF6 Myc_HisC
SEQ ID NO: 85: The amino acid sequence of insert Mucin chimeraTIM-3/pEF6 Myc_HisC
SEQ ID NO: 86: The nucleotide sequence of primer hTIM3chimera22-47F1
SEQ ID NO: 87: The nucleotide sequence of primer hTIM3chimera22-47R1
SEQ ID NO: 88: The nucleotide sequence of primer hTIM3chimera22-47F2
SEQ ID NO: 89: The nucleotide sequence of primer hTIM3chimera22-47R2
SEQ ID NO: 90: The nucleotide sequence of primer hTIM3chimera22-47F3
SEQ ID NO: 91: The nucleotide sequence of primer hTIM3chimera22-47R3
SEQ ID NO: 92: The nucleotide sequence of insert TIM-3 chimera 22-47/pEF6 Myc_HisC
SEQ ID NO: 93: The amino acid sequence of insert TIM-3 chimera 22-47/pEF6 Myc_HisC
SEQ ID NO: 94: The nucleotide sequence of primer hTIM3chimera57-66F
SEQ ID NO: 95: The nucleotide sequence of primer hTIM3chimera57-66R
SEQ ID NO: 96: The nucleotide sequence of insert TIM-3 chimera 57-66/pEF6 Myc_HisC
SEQ ID NO: 97: The amino acid sequence of insert TIM-3 chimera 57-66/pEF6 Myc_HisC
SEQ ID NO: 98: The nucleotide sequence of primer hTIM3chimera67-105F
SEQ ID NO: 99: The nucleotide sequence of primer hTIM3chimera67-105R
SEQ ID NO: 100: The nucleotide sequence of primer mTIM3chimera67-105F
SEQ ID NO: 101: The nucleotide sequence of primer mTIM3chimera67-105R
SEQ ID NO: 102: The nucleotide sequence of insert TIM-3 chimera 67-105/pEF6 Myc_HisC
SEQ ID NO: 103: The amino acid sequence of insert TIM-3 chimera 67-105/pEF6 Myc_HisC
SEQ ID NO: 104: The nucleotide sequence of primer hTIM3chimera74-81F
SEQ ID NO: 105: The nucleotide sequence of primer hTIM3chimera74-81R
SEQ ID NO: 106: The nucleotide sequence of insert TIM-3 chimera 74-81/pEF6 Myc_HisC
SEQ ID NO: 107: The amino acid sequence of insert TIM-3 chimera 74-81/pEF6 Myc_HisC
SEQ ID NO: 108: The nucleotide sequence of primer hTIM3chimera88-96F
SEQ ID NO: 109: The nucleotide sequence of primer hTIM3chimera88-96R
SEQ ID NO: 110: The nucleotide sequence of insert TIM-3 chimera 88-96/pEF6 Myc_HisC
SEQ ID NO: 111: The amino acid sequence of insert TIM-3 chimera 88-96/pEF6 Myc_HisC
SEQ ID NO: 112: The nucleotide sequence of primer hTIM3chimera96-105F
SEQ ID NO: 113: The nucleotide sequence of primer hTIM3chimera96-105R
SEQ ID NO: 114: The nucleotide sequence of insert TIM-3 chimera 96-105/pEF6 Myc_HisC
SEQ ID NO: 115: The amino acid sequence of insert TIM-3 chimera 96-105/pEF6 Myc_HisC

What is claimed is:

1. A nucleic acid encoding a heavy chain variable region or a light chain variable region of an antibody or an antigen-binding fragment thereof capable of specifically binding to an extracellular region of human T-cell immunoglobulin and mucin domain containing molecule-3 (anti-TIM-3 antibody), wherein the anti-TIM-3 antibody or the antigen-binding fragment thereof is one selected from the following (a) to (e):
   (a) a monoclonal antibody or an antigen-binding fragment thereof comprising a heavy chain (H chain) and a light chain (L chain), wherein complementarity determining regions (CDRs) 1 to 3 of said H chain comprise the amino acid sequences of SEQ ID NOs: 1 to 3, respectively, and CDRs 1 to 3 of said L chain comprise the amino acid sequences of SEQ ID NOs: 4 to 6, respectively,
   (b) a monoclonal antibody or an antigen-binding fragment thereof comprising a H chain and a L chain, wherein CDRs 1 to 3 of said H chain comprise the amino acid sequences of SEQ ID NOs: 11 to 13, respectively, and CDRs 1 to 3 of said L chain comprise the amino acid sequences of SEQ ID NOs: 14 to 16, respectively,
   (c) a monoclonal antibody or an antigen-binding fragment thereof comprising a H chain and a L chain, wherein CDRs 1 to 3 of said H chain comprise the amino acid sequences of SEQ ID NOs: 21 to 23, respectively, and CDRs 1 to 3 of said L chain comprise the amino acid sequences of SEQ ID NOs: 24 to 26, respectively,
   (d) a monoclonal antibody or an antigen-binding fragment thereof comprising a H chain variable region (VH) and a L chain variable region (VL), wherein said VH and VL comprise the amino acid sequences of SEQ ID NO: 8 and SEQ ID NO: 10, respectively, and
   (e) a monoclonal antibody or an antigen-binding fragment thereof comprising VH and VL, wherein said VH and VL comprise the amino acid sequences of SEQ ID NO: 18 and SEQ ID NO: 20, respectively.

2. The nucleic acid according to claim 1, wherein the anti-TIM-3 antibody is a recombinant antibody.

3. The nucleic acid according to claim 2, wherein the recombinant antibody is a recombinant antibody selected from a human chimeric antibody, a humanized antibody and a human antibody.

4. The nucleic acid according to claim 1, wherein the antigen-binding fragment is a Fab, a Fab', a F(ab')$_2$, a single chain antibody (scFv), a dimerized V region (diabody), or a disulfide stabilized V region (dsFv).

5. A vector comprising the nucleic acid according to claim 1.

6. A transformant cell comprising the vector according to claim 5.

7. The nucleic acid according to claim 1, wherein the anti-TIM-3 antibody comprises a heavy chain (H chain) and a light chain (L chain), wherein complementarity determining regions (CDRs) 1 to 3 of said H chain comprise the amino acid sequences of SEQ ID NOs: 1 to 3, respectively, and CDRs 1 to 3 of said L chain comprise the amino acid sequences of SEQ ID NOs: 4 to 6, respectively.

8. The nucleic acid according to claim 1, wherein the anti-TIM-3 antibody comprises a H chain and a L chain, wherein CDRs 1 to 3 of said H chain comprises the amino acid sequences of SEQ ID NOs: 21 to 23, respectively, and CDRs 1 to 3 of said L chain comprises the amino acid sequences of SEQ ID NOs: 24 to 26, respectively.

9. A nucleic acid encoding a heavy chain variable region or a light chain variable region of an antibody or an antigen-binding fragment thereof capable of specifically binding to an extracellular region of human T-cell immunoglobulin and mucin domain containing molecule-3 (anti-TIM-3 antibody), wherein the anti-TIM-3 antibody or the antigen-binding fragment thereof is (a) or (b):
   (a) an antibody or an antigen-binding fragment thereof comprising a H chain variable region (VH) and a L chain variable region (VL), wherein said VH and VL comprise the amino acid sequences of SEQ ID NO: 116 and SEQ ID NO: 117, respectively, or
   (b) an antibody or an antigen-binding fragment thereof comprising VH and VL comprise the amino acid sequences of SEQ ID NO: 118 and SEQ ID NO: 119, respectively.

10. The nucleic acid according to claim 9, wherein the anti-TIM-3 antibody is a recombinant antibody.

11. The nucleic acid according to claim 10, wherein the recombinant antibody is a recombinant antibody selected from a human chimeric antibody, a humanized antibody and a human antibody.

12. The nucleic acid according to claim 9, wherein the antigen-binding fragment is a Fab, a Fab', a F(ab')$_2$, a single chain antibody (scFv), a dimerized V region (diabody), or a disulfide stabilized V region (dsFv).

13. A vector comprising the nucleic acid according to claim 9.

14. A transformant cell comprising the vector according to claim 13.

* * * * *

SEQUENCE LISTING

```
<160> NUMBER OF SEQ ID NOS: 119

<210> SEQ ID NO 1
<211> LENGTH: 7
<212> TYPE: PRT
```

<213> ORGANISM: Artificial
<220> FEATURE:
<223> OTHER INFORMATION: Human4545 H-chain CDR1

<400> SEQUENCE: 1

Arg Gly Gly Tyr Tyr Trp Asn
1               5

<210> SEQ ID NO 2
<211> LENGTH: 16
<212> TYPE: PRT
<213> ORGANISM: Artificial
<220> FEATURE:
<223> OTHER INFORMATION: Human4545 H-chain CDR2

<400> SEQUENCE: 2

Tyr Ile Tyr Tyr Ser Gly Ser Thr Asn Tyr Asn Pro Ser Leu Lys Ser
1               5                   10                  15

<210> SEQ ID NO 3
<211> LENGTH: 11
<212> TYPE: PRT
<213> ORGANISM: Artificial
<220> FEATURE:
<223> OTHER INFORMATION: Human4545 H-chain CDR3

<400> SEQUENCE: 3

Asp His Tyr Ser Ser Ser Trp Thr Phe Asp Tyr
1               5                   10

<210> SEQ ID NO 4
<211> LENGTH: 11
<212> TYPE: PRT
<213> ORGANISM: Artificial
<220> FEATURE:
<223> OTHER INFORMATION: Human4545 L-chain CDR1

<400> SEQUENCE: 4

Arg Ala Ser Gln Ser Val Ser Ser Tyr Leu Ala
1               5                   10

<210> SEQ ID NO 5
<211> LENGTH: 7
<212> TYPE: PRT
<213> ORGANISM: Artificial
<220> FEATURE:
<223> OTHER INFORMATION: Human4545 L-chain CDR2

<400> SEQUENCE: 5

Asp Ala Ser Asn Arg Ala Thr
1               5

<210> SEQ ID NO 6
<211> LENGTH: 9
<212> TYPE: PRT
<213> ORGANISM: Artificial
<220> FEATURE:
<223> OTHER INFORMATION: Human4545 L-chain CDR3

<400> SEQUENCE: 6

Gln Gln Arg Ser Asn Trp Pro Pro Thr
1               5

<210> SEQ ID NO 7
<211> LENGTH: 420
<212> TYPE: DNA
<213> ORGANISM: Homo sapiens

```
<220> FEATURE:
<221> NAME/KEY: CDS
<222> LOCATION: (1)..(420)

<400> SEQUENCE: 7 atg aaa cac ctg tgg ttc ttc ctc ctc ctg gcg gca gct ccc aga tgg        48
Met Lys His Leu Trp Phe Phe Leu Leu Leu Ala Ala Ala Pro Arg Trp
1               5                   10                  15 gtc ctg tcc cag gtg cag ctg cag gag tcg ggc cca gga ctg gtg aag        96
Val Leu Ser Gln Val Gln Leu Gln Glu Ser Gly Pro Gly Leu Val Lys
            20                  25                  30 cct tcg gag acc ctg tcc ctc acc tgc act gtc tct ggt ggc tcc ttc       144
Pro Ser Glu Thr Leu Ser Leu Thr Cys Thr Val Ser Gly Gly Ser Phe
        35                  40                  45 agc cgt ggt ggt tat tac tgg aac tgg atc cgg cag ccc cca ggg aag       192
Ser Arg Gly Gly Tyr Tyr Trp Asn Trp Ile Arg Gln Pro Pro Gly Lys
    50                  55                  60 gga ctg gag tgg att ggg tat atc tat tac agt ggg agc acc aac tac       240
Gly Leu Glu Trp Ile Gly Tyr Ile Tyr Tyr Ser Gly Ser Thr Asn Tyr
65                  70                  75                  80 aac ccc tcc ctc aag agt cga gtc acc atc tca cta gac acg tcc aag       288
Asn Pro Ser Leu Lys Ser Arg Val Thr Ile Ser Leu Asp Thr Ser Lys
                85                  90                  95 aac cag ttc tcc ctg aag ctg agc tct gtg acc gct gcg gac acg gcc       336
Asn Gln Phe Ser Leu Lys Leu Ser Ser Val Thr Ala Ala Asp Thr Ala
            100                 105                 110 gtg tat tac tgt gcg aga gat cat tat agc agc agc tgg acc ttt gac       384
Val Tyr Tyr Cys Ala Arg Asp His Tyr Ser Ser Ser Trp Thr Phe Asp
        115                 120                 125 tac tgg ggc cag gga acc ctg gtc acc gtc tcc tca                       420
Tyr Trp Gly Gln Gly Thr Leu Val Thr Val Ser Ser
    130                 135                 140

<210> SEQ ID NO 8
<211> LENGTH: 140
<212> TYPE: PRT
<213> ORGANISM: Homo sapiens
<220> FEATURE:
<221> NAME/KEY: Signal sequence
<222> LOCATION: (1)..(19)
<220> FEATURE:
<221> NAME/KEY: Mature protein
<222> LOCATION: (20)..(140)

<400> SEQUENCE: 8

Met Lys His Leu Trp Phe Phe Leu Leu Leu Ala Ala Ala Pro Arg Trp
1               5                   10                  15

Val Leu Ser Gln Val Gln Leu Gln Glu Ser Gly Pro Gly Leu Val Lys
            20                  25                  30

Pro Ser Glu Thr Leu Ser Leu Thr Cys Thr Val Ser Gly Gly Ser Phe
        35                  40                  45

Ser Arg Gly Gly Tyr Tyr Trp Asn Trp Ile Arg Gln Pro Pro Gly Lys
    50                  55                  60

Gly Leu Glu Trp Ile Gly Tyr Ile Tyr Tyr Ser Gly Ser Thr Asn Tyr
65                  70                  75                  80

Asn Pro Ser Leu Lys Ser Arg Val Thr Ile Ser Leu Asp Thr Ser Lys
                85                  90                  95

Asn Gln Phe Ser Leu Lys Leu Ser Ser Val Thr Ala Ala Asp Thr Ala
            100                 105                 110

Val Tyr Tyr Cys Ala Arg Asp His Tyr Ser Ser Ser Trp Thr Phe Asp
        115                 120                 125
```

```
Tyr Trp Gly Gln Gly Thr Leu Val Thr Val Ser Ser
        130                 135                 140

<210> SEQ ID NO 9
<211> LENGTH: 381
<212> TYPE: DNA
<213> ORGANISM: Homo sapiens
<220> FEATURE:
<221> NAME/KEY: CDS
<222> LOCATION: (1)..(381)

<400> SEQUENCE: 9 atg gaa gcc cca gct cag ctt ctc ttc ctc ctg cta ctc tgg ctc cca      48
Met Glu Ala Pro Ala Gln Leu Leu Phe Leu Leu Leu Leu Trp Leu Pro
1               5                   10                  15 gat acc acc gga gaa att gtg ttg aca cag tct cca gcc acc ctg tct      96
Asp Thr Thr Gly Glu Ile Val Leu Thr Gln Ser Pro Ala Thr Leu Ser
                20                  25                  30 ttg tct cca ggg gaa aga gcc acc ctc tcc tgc agg gcc agt cag agt     144
Leu Ser Pro Gly Glu Arg Ala Thr Leu Ser Cys Arg Ala Ser Gln Ser
            35                  40                  45 gtt agc agc tac tta gcc tgg tac caa cag aaa cct ggc cag gct ccc     192
Val Ser Ser Tyr Leu Ala Trp Tyr Gln Gln Lys Pro Gly Gln Ala Pro
        50                  55                  60 agg ctc ctc atc tat gat gca tcc aac agg gcc act ggc atc cca gcc     240
Arg Leu Leu Ile Tyr Asp Ala Ser Asn Arg Ala Thr Gly Ile Pro Ala
65                  70                  75                  80 agg ttc agt ggc agt ggg tct ggg aca gac ttc act ctc acc atc agc     288
Arg Phe Ser Gly Ser Gly Ser Gly Thr Asp Phe Thr Leu Thr Ile Ser
                85                  90                  95 agc cta gag cct gaa gat ttt gca gtt tat tac tgt cag cag cgt agc     336
Ser Leu Glu Pro Glu Asp Phe Ala Val Tyr Tyr Cys Gln Gln Arg Ser
                100                 105                 110 aac tgg cct ccg acg ttc ggc cag ggg acc aag ctg gag atc aaa         381
Asn Trp Pro Pro Thr Phe Gly Gln Gly Thr Lys Leu Glu Ile Lys
        115                 120                 125

<210> SEQ ID NO 10
<211> LENGTH: 127
<212> TYPE: PRT
<213> ORGANISM: Homo sapiens
<220> FEATURE:
<221> NAME/KEY: Signal sequence
<222> LOCATION: (1)..(20)
<220> FEATURE:
<221> NAME/KEY: Mature protein
<222> LOCATION: (21)..(127)

<400> SEQUENCE: 10

Met Glu Ala Pro Ala Gln Leu Leu Phe Leu Leu Leu Leu Trp Leu Pro
1               5                   10                  15

Asp Thr Thr Gly Glu Ile Val Leu Thr Gln Ser Pro Ala Thr Leu Ser
                20                  25                  30

Leu Ser Pro Gly Glu Arg Ala Thr Leu Ser Cys Arg Ala Ser Gln Ser
            35                  40                  45

Val Ser Ser Tyr Leu Ala Trp Tyr Gln Gln Lys Pro Gly Gln Ala Pro
        50                  55                  60

Arg Leu Leu Ile Tyr Asp Ala Ser Asn Arg Ala Thr Gly Ile Pro Ala
65                  70                  75                  80

Arg Phe Ser Gly Ser Gly Ser Gly Thr Asp Phe Thr Leu Thr Ile Ser
                85                  90                  95
```

Ser Leu Glu Pro Glu Asp Phe Ala Val Tyr Tyr Cys Gln Gln Arg Ser
            100                 105                 110

Asn Trp Pro Pro Thr Phe Gly Gln Gly Thr Lys Leu Glu Ile Lys
        115                 120                 125

<210> SEQ ID NO 11
<211> LENGTH: 5
<212> TYPE: PRT
<213> ORGANISM: Artificial
<220> FEATURE:
<223> OTHER INFORMATION: Human4177 H-chain CDR1

<400> SEQUENCE: 11

Ser Tyr Tyr Trp Ser
1               5

<210> SEQ ID NO 12
<211> LENGTH: 16
<212> TYPE: PRT
<213> ORGANISM: Artificial
<220> FEATURE:
<223> OTHER INFORMATION: Human4177 H-chain CDR2

<400> SEQUENCE: 12

Tyr Ile Phe His Ser Gly Ser Thr Asn Tyr Asn Pro Ser Leu Lys Ser
1               5                   10                  15

<210> SEQ ID NO 13
<211> LENGTH: 13
<212> TYPE: PRT
<213> ORGANISM: Artificial
<220> FEATURE:
<223> OTHER INFORMATION: Human4177 H-chain CDR3

<400> SEQUENCE: 13

Asp Gly Glu Tyr Phe Asp Met Leu Thr Gly Phe Asp Tyr
1               5                   10

<210> SEQ ID NO 14
<211> LENGTH: 11
<212> TYPE: PRT
<213> ORGANISM: Artificial
<220> FEATURE:
<223> OTHER INFORMATION: Human4177 L-chain CDR1

<400> SEQUENCE: 14

Arg Ala Ser Gln Gly Ile Ser Ser Trp Leu Ala
1               5                   10

<210> SEQ ID NO 15
<211> LENGTH: 7
<212> TYPE: PRT
<213> ORGANISM: Artificial
<220> FEATURE:
<223> OTHER INFORMATION: Human4177 L-chain CDR2

<400> SEQUENCE: 15

Ala Ala Ser Ser Leu Gln Ser
1               5

<210> SEQ ID NO 16
<211> LENGTH: 9
<212> TYPE: PRT
<213> ORGANISM: Artificial
<220> FEATURE:
<223> OTHER INFORMATION: Human4177 L-chain CDR3

<400> SEQUENCE: 16

Gln Gln Tyr Asn Ser Tyr Pro Arg Thr
1               5

<210> SEQ ID NO 17
<211> LENGTH: 420
<212> TYPE: DNA
<213> ORGANISM: Homo sapiens
<220> FEATURE:
<221> NAME/KEY: CDS
<222> LOCATION: (1)..(420)

<400> SEQUENCE: 17

```
atg aaa cat ctg tgg ttc ttc ctt ctc ctg gtg gca gct ccc aga tgg        48
Met Lys His Leu Trp Phe Phe Leu Leu Leu Val Ala Ala Pro Arg Trp
1               5                   10                  15 gtc ctg tcc cag gtg cag ttg cag gag tcg ggc cca gga ctg gtg aag        96
Val Leu Ser Gln Val Gln Leu Gln Glu Ser Gly Pro Gly Leu Val Lys
                20                  25                  30 cct tcg gag acc ctg tcc ctc acc tgc act gtc tct ggt ggc tcc atc       144
Pro Ser Glu Thr Leu Ser Leu Thr Cys Thr Val Ser Gly Gly Ser Ile
            35                  40                  45 agt agt tac tac tgg agc tgg atc cgg cag ccc cca ggg aag gga ctg       192
Ser Ser Tyr Tyr Trp Ser Trp Ile Arg Gln Pro Pro Gly Lys Gly Leu
        50                  55                  60 gag tgg att ggg tat atc ttt cac agt ggg agc acc aac tac aac ccc       240
Glu Trp Ile Gly Tyr Ile Phe His Ser Gly Ser Thr Asn Tyr Asn Pro
65                  70                  75                  80 tcc ctc aag agt cga gtc acc ata tca gta gac acg tcc aag aac cag       288
Ser Leu Lys Ser Arg Val Thr Ile Ser Val Asp Thr Ser Lys Asn Gln
                85                  90                  95 ttc tcc ctg aag ctg agc tct gtg acc gct gcg gac acg gcc gtg tat       336
Phe Ser Leu Lys Leu Ser Ser Val Thr Ala Ala Asp Thr Ala Val Tyr
            100                 105                 110 tac tgt gcg aga gat ggg gag tat ttc gat atg ttg act ggt ttt gac       384
Tyr Cys Ala Arg Asp Gly Glu Tyr Phe Asp Met Leu Thr Gly Phe Asp
        115                 120                 125 tac tgg ggc cag gga acc ctg gtc acc gtc tcc tca                        420
Tyr Trp Gly Gln Gly Thr Leu Val Thr Val Ser Ser
    130                 135                 140
```

<210> SEQ ID NO 18
<211> LENGTH: 140
<212> TYPE: PRT
<213> ORGANISM: Homo sapiens
<220> FEATURE:
<221> NAME/KEY: Signal sequence
<222> LOCATION: (1)..(19)
<220> FEATURE:
<221> NAME/KEY: Mature protein
<222> LOCATION: (20)..(140)

<400> SEQUENCE: 18

Met Lys His Leu Trp Phe Phe Leu Leu Leu Val Ala Ala Pro Arg Trp
1               5                   10                  15

Val Leu Ser Gln Val Gln Leu Gln Glu Ser Gly Pro Gly Leu Val Lys
                20                  25                  30

Pro Ser Glu Thr Leu Ser Leu Thr Cys Thr Val Ser Gly Gly Ser Ile
            35                  40                  45

Ser Ser Tyr Tyr Trp Ser Trp Ile Arg Gln Pro Pro Gly Lys Gly Leu
        50                  55                  60

Glu Trp Ile Gly Tyr Ile Phe His Ser Gly Ser Thr Asn Tyr Asn Pro 65                  70                  75                  80
Ser Leu Lys Ser Arg Val Thr Ile Ser Val Asp Thr Ser Lys Asn Gln
                85                  90                  95

Phe Ser Leu Lys Leu Ser Ser Val Thr Ala Ala Asp Thr Ala Val Tyr
            100                 105                 110

Tyr Cys Ala Arg Asp Gly Glu Tyr Phe Asp Met Leu Thr Gly Phe Asp
        115                 120                 125

Tyr Trp Gly Gln Gly Thr Leu Val Thr Val Ser Ser
    130                 135                 140

<210> SEQ ID NO 19
<211> LENGTH: 387
<212> TYPE: DNA
<213> ORGANISM: Homo sapiens
<220> FEATURE:
<221> NAME/KEY: CDS
<222> LOCATION: (1)..(387)

<400> SEQUENCE: 19 atg gac atg agg gtc ctc gct cag ctc ctg ggg ctc ctg ctg ctc tgt       48
Met Asp Met Arg Val Leu Ala Gln Leu Leu Gly Leu Leu Leu Leu Cys
1               5                   10                  15 ttc cca ggt gcc aga tgt gac atc cag atg acc cag tct cca tcc tca       96
Phe Pro Gly Ala Arg Cys Asp Ile Gln Met Thr Gln Ser Pro Ser Ser
                20                  25                  30 ctg tct gca tct gta gga gac aga gtc acc atc act tgt cgg gcg agt      144
Leu Ser Ala Ser Val Gly Asp Arg Val Thr Ile Thr Cys Arg Ala Ser
            35                  40                  45 cag ggt att agc agc tgg tta gcc tgg tat cag cag aaa cca gag aaa      192
Gln Gly Ile Ser Ser Trp Leu Ala Trp Tyr Gln Gln Lys Pro Glu Lys
        50                  55                  60 gcc cct aag tcc ctg atc tat gct gca tcc agt ttg caa agt ggg gtc      240
Ala Pro Lys Ser Leu Ile Tyr Ala Ala Ser Ser Leu Gln Ser Gly Val
65                  70                  75                  80 cca tca agg ttc agc ggc agt gga tct ggg aca gat ttc act ctc acc      288
Pro Ser Arg Phe Ser Gly Ser Gly Ser Gly Thr Asp Phe Thr Leu Thr
                85                  90                  95 atc agc agc ctg cag cct gaa gat ttt gca act tat tac tgc caa cag      336
Ile Ser Ser Leu Gln Pro Glu Asp Phe Ala Thr Tyr Tyr Cys Gln Gln
                100                 105                 110 tat aat agt tac cct cgg acg ttc ggc caa ggg acc aag gtg gaa atc      384
Tyr Asn Ser Tyr Pro Arg Thr Phe Gly Gln Gly Thr Lys Val Glu Ile
            115                 120                 125 aaa                                                                   387
Lys

<210> SEQ ID NO 20
<211> LENGTH: 129
<212> TYPE: PRT
<213> ORGANISM: Homo sapiens
<220> FEATURE:
<221> NAME/KEY: Signal sequence
<222> LOCATION: (1)..(20)
<220> FEATURE:
<221> NAME/KEY: Mature protein
<222> LOCATION: (21)..(129)

<400> SEQUENCE: 20

Met Asp Met Arg Val Leu Ala Gln Leu Leu Gly Leu Leu Leu Leu Cys
1               5                   10                  15

Phe Pro Gly Ala Arg Cys Asp Ile Gln Met Thr Gln Ser Pro Ser Ser
                20                  25                  30

```
Leu Ser Ala Ser Val Gly Asp Arg Val Thr Ile Thr Cys Arg Ala Ser
        35                  40                  45

Gln Gly Ile Ser Ser Trp Leu Ala Trp Tyr Gln Gln Lys Pro Glu Lys
 50                  55                  60

Ala Pro Lys Ser Leu Ile Tyr Ala Ala Ser Ser Leu Gln Ser Gly Val
 65                  70                  75                  80

Pro Ser Arg Phe Ser Gly Ser Gly Ser Gly Thr Asp Phe Thr Leu Thr
                 85                  90                  95

Ile Ser Ser Leu Gln Pro Glu Asp Phe Ala Thr Tyr Tyr Cys Gln Gln
                100                 105                 110

Tyr Asn Ser Tyr Pro Arg Thr Phe Gly Gln Gly Thr Lys Val Glu Ile
                115                 120                 125

Lys

<210> SEQ ID NO 21
<211> LENGTH: 5
<212> TYPE: PRT
<213> ORGANISM: Artificial
<220> FEATURE:
<223> OTHER INFORMATION: Mouse8213 H-chain CDR1

<400> SEQUENCE: 21

Ser Tyr Trp Met His
1               5

<210> SEQ ID NO 22
<211> LENGTH: 17
<212> TYPE: PRT
<213> ORGANISM: Artificial
<220> FEATURE:
<223> OTHER INFORMATION: Mouse8213 H-chain CDR2

<400> SEQUENCE: 22

Glu Ile Asn Pro Ser Asn Gly Arg Thr Asn Tyr Asn Glu Lys Phe Lys
1               5                   10                  15

Thr

<210> SEQ ID NO 23
<211> LENGTH: 8
<212> TYPE: PRT
<213> ORGANISM: Artificial
<220> FEATURE:
<223> OTHER INFORMATION: Mouse8213 H-chain CDR3

<400> SEQUENCE: 23

Gly Tyr Tyr Leu Tyr Phe Asp Tyr
1               5

<210> SEQ ID NO 24
<211> LENGTH: 11
<212> TYPE: PRT
<213> ORGANISM: Artificial
<220> FEATURE:
<223> OTHER INFORMATION: Mouse8213 L-chain CDR1

<400> SEQUENCE: 24

His Ala Ser Gln Gly Ile Arg Ile Asn Ile Gly
1               5                   10

<210> SEQ ID NO 25
<211> LENGTH: 7
<212> TYPE: PRT
```

```
<213> ORGANISM: Artificial
<220> FEATURE:
<223> OTHER INFORMATION: Mouse8213 L-chain CDR2

<400> SEQUENCE: 25

His Gly Thr Asn Leu Glu Asp
1               5

<210> SEQ ID NO 26
<211> LENGTH: 9
<212> TYPE: PRT
<213> ORGANISM: Artificial
<220> FEATURE:
<223> OTHER INFORMATION: Mouse8213 L-chain CDR3

<400> SEQUENCE: 26

Val Gln Tyr Gly Gln Phe Pro Trp Thr
1               5

<210> SEQ ID NO 27
<211> LENGTH: 408
<212> TYPE: DNA
<213> ORGANISM: Mus musculus
<220> FEATURE:
<221> NAME/KEY: CDS
<222> LOCATION: (1)..(408)

<400> SEQUENCE: 27 atg gga tgg agc tat atc atc ctc ttt ttg gta gca aca gcg aca gat        48
Met Gly Trp Ser Tyr Ile Ile Leu Phe Leu Val Ala Thr Ala Thr Asp
1               5                   10                  15 gtc cac tcc cag gtc caa ctg cag cag cct ggg gct gaa ctg gtg aag        96
Val His Ser Gln Val Gln Leu Gln Gln Pro Gly Ala Glu Leu Val Lys
                20                  25                  30 cct ggg gct tca gtg aag ctg tcc tgc aag gct tct ggc tac acc ttc       144
Pro Gly Ala Ser Val Lys Leu Ser Cys Lys Ala Ser Gly Tyr Thr Phe
            35                  40                  45 acc agc tac tgg atg cac tgg gtg aag cag agg cct gga caa ggc ctt       192
Thr Ser Tyr Trp Met His Trp Val Lys Gln Arg Pro Gly Gln Gly Leu
        50                  55                  60 gag tgg att gga gag att aat cct agc aac ggt cgt act aac tac aat       240
Glu Trp Ile Gly Glu Ile Asn Pro Ser Asn Gly Arg Thr Asn Tyr Asn
65                  70                  75                  80 gag aag ttc aag acc aag gcc aca ctg act gta gac aaa tcc tcc agc       288
Glu Lys Phe Lys Thr Lys Ala Thr Leu Thr Val Asp Lys Ser Ser Ser
                85                  90                  95 aca gcc tac atg caa ctc agc agc ctg aca tct gag gac tct gcg gtc       336
Thr Ala Tyr Met Gln Leu Ser Ser Leu Thr Ser Glu Asp Ser Ala Val
                100                 105                 110 tat tac tgt gcg ggg ggt tac tac ctc tac ttt gac tac tgg ggc caa       384
Tyr Tyr Cys Ala Gly Gly Tyr Tyr Leu Tyr Phe Asp Tyr Trp Gly Gln
            115                 120                 125 ggc acc act ctc aca gtc tcc tca                                       408
Gly Thr Thr Leu Thr Val Ser Ser
        130                 135

<210> SEQ ID NO 28
<211> LENGTH: 136
<212> TYPE: PRT
<213> ORGANISM: Mus musculus

<400> SEQUENCE: 28

Met Gly Trp Ser Tyr Ile Ile Leu Phe Leu Val Ala Thr Ala Thr Asp
1               5                   10                  15
```

```
Val His Ser Gln Val Gln Leu Gln Gln Pro Gly Ala Glu Leu Val Lys
         20                  25                  30

Pro Gly Ala Ser Val Lys Leu Ser Cys Lys Ala Ser Gly Tyr Thr Phe
         35                  40                  45

Thr Ser Tyr Trp Met His Trp Val Lys Gln Arg Pro Gly Gln Gly Leu
 50                  55                  60

Glu Trp Ile Gly Glu Ile Asn Pro Ser Asn Gly Arg Thr Asn Tyr Asn
 65                  70                  75                  80

Glu Lys Phe Lys Thr Lys Ala Thr Leu Thr Val Asp Lys Ser Ser Ser
             85                  90                  95

Thr Ala Tyr Met Gln Leu Ser Ser Leu Thr Ser Glu Asp Ser Ala Val
             100                 105                 110

Tyr Tyr Cys Ala Gly Tyr Tyr Leu Tyr Phe Asp Tyr Trp Gly Gln
             115                 120                 125

Gly Thr Thr Leu Thr Val Ser Ser
         130                 135

<210> SEQ ID NO 29
<211> LENGTH: 387
<212> TYPE: DNA
<213> ORGANISM: Mus musculus
<220> FEATURE:
<221> NAME/KEY: CDS
<222> LOCATION: (1)..(387)

<400> SEQUENCE: 29 atg gac atg atg gtc ctt gct cag ttt ctt gca ttc ttg ttg ctt tgg     48
Met Asp Met Met Val Leu Ala Gln Phe Leu Ala Phe Leu Leu Leu Trp
 1               5                   10                  15 ttt cca ggt gca aca tgt gac atc ctg atg acc caa tct cca tcc tcc     96
Phe Pro Gly Ala Thr Cys Asp Ile Leu Met Thr Gln Ser Pro Ser Ser
                 20                  25                  30 atg tct gta tct ctg gga gac aca gtc aac atc act tgc cat gca agt    144
Met Ser Val Ser Leu Gly Asp Thr Val Asn Ile Thr Cys His Ala Ser
             35                  40                  45 cag ggc att agg att aat ata ggg tgg ttg cag cag aag cca ggg aaa    192
Gln Gly Ile Arg Ile Asn Ile Gly Trp Leu Gln Gln Lys Pro Gly Lys
         50                  55                  60 tca ttt aag ggc ctg atc tat cat gga acc aac ttg gaa gat gga gtt    240
Ser Phe Lys Gly Leu Ile Tyr His Gly Thr Asn Leu Glu Asp Gly Val
 65                  70                  75                  80 cca tca agg ttc agt ggc agt gga tct gga cca gat tat tct ctc acc    288
Pro Ser Arg Phe Ser Gly Ser Gly Ser Gly Pro Asp Tyr Ser Leu Thr
                 85                  90                  95 atc agc agc ctg gaa tct gaa gat ttt gca gac tat tac tgt gta cag    336
Ile Ser Ser Leu Glu Ser Glu Asp Phe Ala Asp Tyr Tyr Cys Val Gln
             100                 105                 110 tat ggt cag ttt ccg tgg acg ttc ggt gga ggc acc aag ctg gaa atg    384
Tyr Gly Gln Phe Pro Trp Thr Phe Gly Gly Gly Thr Lys Leu Glu Met
         115                 120                 125 aaa                                                                387
Lys

<210> SEQ ID NO 30
<211> LENGTH: 129
<212> TYPE: PRT
<213> ORGANISM: Mus musculus

<400> SEQUENCE: 30
```

```
Met Asp Met Met Val Leu Ala Gln Phe Leu Ala Phe Leu Leu Leu Trp
1               5                   10                  15

Phe Pro Gly Ala Thr Cys Asp Ile Leu Met Thr Gln Ser Pro Ser Ser
            20                  25                  30

Met Ser Val Ser Leu Gly Asp Thr Val Asn Ile Thr Cys His Ala Ser
        35                  40                  45

Gln Gly Ile Arg Ile Asn Ile Gly Trp Leu Gln Gln Lys Pro Gly Lys
    50                  55                  60

Ser Phe Lys Gly Leu Ile Tyr His Gly Thr Asn Leu Glu Asp Gly Val
65                  70                  75                  80

Pro Ser Arg Phe Ser Gly Ser Gly Ser Gly Pro Asp Tyr Ser Leu Thr
                85                  90                  95

Ile Ser Ser Leu Glu Ser Glu Asp Phe Ala Asp Tyr Tyr Cys Val Gln
                100                 105                 110

Tyr Gly Gln Phe Pro Trp Thr Phe Gly Gly Gly Thr Lys Leu Glu Met
            115                 120                 125
Lys
```

<210> SEQ ID NO 31
<211> LENGTH: 26
<212> TYPE: DNA
<213> ORGANISM: Artificial
<220> FEATURE:
<223> OTHER INFORMATION: Primer TIM-3 Fw2

<400> SEQUENCE: 31
gccaccatgt tttcacatct tccctt                     26

<210> SEQ ID NO 32
<211> LENGTH: 20
<212> TYPE: DNA
<213> ORGANISM: Artificial
<220> FEATURE:
<223> OTHER INFORMATION: Primer TIM-3 Re2

<400> SEQUENCE: 32
ctatggcatt gcaaagcgac                            20

<210> SEQ ID NO 33
<211> LENGTH: 21
<212> TYPE: DNA
<213> ORGANISM: Artificial
<220> FEATURE:
<223> OTHER INFORMATION: Primer pMCs-Fw

<400> SEQUENCE: 33
tcaaagtaga cggcatcgca g                          21

<210> SEQ ID NO 34
<211> LENGTH: 27
<212> TYPE: DNA
<213> ORGANISM: Artificial
<220> FEATURE:
<223> OTHER INFORMATION: Primer TIM3ED-FcReXba

<400> SEQUENCE: 34
ttttctagat ctgatggttg ctccaga                    27

<210> SEQ ID NO 35
<211> LENGTH: 20
<212> TYPE: DNA
<213> ORGANISM: Artificial

```
<220> FEATURE:
<223> OTHER INFORMATION: Primer T7

<400> SEQUENCE: 35
taatacgact cactataggg                                                 20

<210> SEQ ID NO 36
<211> LENGTH: 18
<212> TYPE: DNA
<213> ORGANISM: Artificial
<220> FEATURE:
<223> OTHER INFORMATION: Primer hTIM-3 Fw1

<400> SEQUENCE: 36
actctggagc aaccatca                                                   18

<210> SEQ ID NO 37
<211> LENGTH: 1333
<212> TYPE: DNA
<213> ORGANISM: Artificial
<220> FEATURE:
<223> OTHER INFORMATION: Insert hTIM-3 ECD Fc fusion
<220> FEATURE:
<221> NAME/KEY: CDS
<222> LOCATION: (11)..(1333)

<400> SEQUENCE: 37
gattgccacc atg ttt tca cat ctt ccc ttt gac tgt gtc ctg ctg ctg       49
            Met Phe Ser His Leu Pro Phe Asp Cys Val Leu Leu Leu
              1               5                   10 ctg ctg cta cta ctt aca agg tcc tca gaa gtg gaa tac aga gcg gag       97
Leu Leu Leu Leu Leu Thr Arg Ser Ser Glu Val Glu Tyr Arg Ala Glu
         15                  20                  25 gtc ggt cag aat gcc tat ctg ccc tgc ttc tac acc cca gcc gcc cca      145
Val Gly Gln Asn Ala Tyr Leu Pro Cys Phe Tyr Thr Pro Ala Ala Pro
     30                  35                  40                  45 ggg aac ctc gtg ccc gtc tgc tgg ggc aaa gga gcc tgt cct gtg ttt      193
Gly Asn Leu Val Pro Val Cys Trp Gly Lys Gly Ala Cys Pro Val Phe
                 50                  55                  60 gaa tgt ggc aac gtg gtg ctc agg act gat gaa agg gat gtg aat tat      241
Glu Cys Gly Asn Val Val Leu Arg Thr Asp Glu Arg Asp Val Asn Tyr
             65                  70                  75 tgg aca tcc aga tac tgg cta aat ggg gat ttc gca aaa gga gat gtg      289
Trp Thr Ser Arg Tyr Trp Leu Asn Gly Asp Phe Arg Lys Gly Asp Val
         80                  85                  90 tcc ctg acc ata gag aat gtg act cta gca gac agt ggg atc tac tgc      337
Ser Leu Thr Ile Glu Asn Val Thr Leu Ala Asp Ser Gly Ile Tyr Cys
     95                 100                 105 tgc cgg atc caa atc cca ggc ata atg aat gat gaa aaa ttt aac ctg      385
Cys Arg Ile Gln Ile Pro Gly Ile Met Asn Asp Glu Lys Phe Asn Leu
110                 115                 120                 125 aag ttg gtc atc aaa cca gcc aag gtc acc cct gca ccg act cgg cag      433
Lys Leu Val Ile Lys Pro Ala Lys Val Thr Pro Ala Pro Thr Arg Gln
                130                 135                 140 aga gac ttc act gca gcc ttt cca agg atg ctt acc acc agg gga cat      481
Arg Asp Phe Thr Ala Ala Phe Pro Arg Met Leu Thr Thr Arg Gly His
            145                 150                 155 ggc cca gca gag aca cag aca ctg ggg agc ctc cct gat ata aat cta      529
Gly Pro Ala Glu Thr Gln Thr Leu Gly Ser Leu Pro Asp Ile Asn Leu
        160                 165                 170 aca caa ata tcc aca ttg gcc aat gag tta cgg gac tct aga ttg gcc      577
Thr Gln Ile Ser Thr Leu Ala Asn Glu Leu Arg Asp Ser Arg Leu Ala
    175                 180                 185
```

```
aat gac tta cgg gac tct gga gca acc atc aga tct aga gca gac tac       625
Asn Asp Leu Arg Asp Ser Gly Ala Thr Ile Arg Ser Arg Ala Asp Tyr
190                 195                 200                 205 aag gac gac gat gac aag act agt gac aaa act cac aca tgc cca ccg       673
Lys Asp Asp Asp Asp Lys Thr Ser Asp Lys Thr His Thr Cys Pro Pro
                    210                 215                 220 tgc cca gca cct gaa ctc ctg ggg gga ccg tca gtc ttc ctc ttc ccc       721
Cys Pro Ala Pro Glu Leu Leu Gly Gly Pro Ser Val Phe Leu Phe Pro
                225                 230                 235 cca aaa ccc aag gac acc ctc atg atc tcc cgg acc cct gag gtc aca       769
Pro Lys Pro Lys Asp Thr Leu Met Ile Ser Arg Thr Pro Glu Val Thr
            240                 245                 250 tgc gtg gtg gtg gac gtg agc cac gaa gac cct gag gtc aag ttc aac       817
Cys Val Val Val Asp Val Ser His Glu Asp Pro Glu Val Lys Phe Asn
        255                 260                 265 tgg tac gtg gac ggc gtg gag gtg cat aat gcc aag aca aag ccg cgg       865
Trp Tyr Val Asp Gly Val Glu Val His Asn Ala Lys Thr Lys Pro Arg
270                 275                 280                 285 gag gag cag tac aac agc acg tac cgt gtg gtc agc gtc ctc acc gtc       913
Glu Glu Gln Tyr Asn Ser Thr Tyr Arg Val Val Ser Val Leu Thr Val
                    290                 295                 300 ctg cac cag gac tgg ctg aat ggc aag gag tac aag tgc aag gtc tcc       961
Leu His Gln Asp Trp Leu Asn Gly Lys Glu Tyr Lys Cys Lys Val Ser
                305                 310                 315 aac aaa gcc ctc cca gcc ccc atc gag aaa acc atc tcc aaa gcc aaa      1009
Asn Lys Ala Leu Pro Ala Pro Ile Glu Lys Thr Ile Ser Lys Ala Lys
            320                 325                 330 ggg cag ccc cga gaa cca cag gtg tac acc ctg ccc cca tcc cgg gag      1057
Gly Gln Pro Arg Glu Pro Gln Val Tyr Thr Leu Pro Pro Ser Arg Glu
        335                 340                 345 gag atg acc aag aac cag gtc agc ctg acc tgc ctg gtc aaa ggc ttc      1105
Glu Met Thr Lys Asn Gln Val Ser Leu Thr Cys Leu Val Lys Gly Phe
350                 355                 360                 365 tat ccc agc gac atc gcc gcg gag tgg gag agc aat ggg cag ccg gag      1153
Tyr Pro Ser Asp Ile Ala Ala Glu Trp Glu Ser Asn Gly Gln Pro Glu
                    370                 375                 380 aac aac tac aag acc acg cct ccc gtg ctg gac tcc gac ggc tcc ttc      1201
Asn Asn Tyr Lys Thr Thr Pro Pro Val Leu Asp Ser Asp Gly Ser Phe
                385                 390                 395 ttc ctc tac agc aag ctc acc gtg gac aag agc agg tgg cag cag ggg      1249
Phe Leu Tyr Ser Lys Leu Thr Val Asp Lys Ser Arg Trp Gln Gln Gly
            400                 405                 410 aac gtc ttc tca tgc tcc gtg atg cat gag gct ctg cac aac cac tac      1297
Asn Val Phe Ser Cys Ser Val Met His Glu Ala Leu His Asn His Tyr
        415                 420                 425 acg cag aag agc ctc tcc ctg tct ccg ggt aaa tga                      1333
Thr Gln Lys Ser Leu Ser Leu Ser Pro Gly Lys
430                 435                 440

<210> SEQ ID NO 38
<211> LENGTH: 440
<212> TYPE: PRT
<213> ORGANISM: Artificial
<220> FEATURE:
<223> OTHER INFORMATION: Synthetic Construct

<400> SEQUENCE: 38

Met Phe Ser His Leu Pro Phe Asp Cys Val Leu Leu Leu Leu Leu Leu
1               5                   10                  15

Leu Leu Thr Arg Ser Ser Glu Val Glu Tyr Arg Ala Glu Val Gly Gln
```

-continued

```
                20                  25                  30
Asn Ala Tyr Leu Pro Cys Phe Tyr Thr Pro Ala Ala Pro Gly Asn Leu
            35                  40                  45
Val Pro Val Cys Trp Gly Lys Gly Ala Cys Pro Val Phe Glu Cys Gly
        50                  55                  60
Asn Val Val Leu Arg Thr Asp Glu Arg Asp Val Asn Tyr Trp Thr Ser
65                  70                  75                  80
Arg Tyr Trp Leu Asn Gly Asp Phe Arg Lys Gly Asp Val Ser Leu Thr
                85                  90                  95
Ile Glu Asn Val Thr Leu Ala Asp Ser Gly Ile Tyr Cys Cys Arg Ile
            100                 105                 110
Gln Ile Pro Gly Ile Met Asn Asp Glu Lys Phe Asn Leu Lys Leu Val
        115                 120                 125
Ile Lys Pro Ala Lys Val Thr Pro Ala Pro Thr Arg Gln Arg Asp Phe
130                 135                 140
Thr Ala Ala Phe Pro Arg Met Leu Thr Thr Arg Gly His Gly Pro Ala
145                 150                 155                 160
Glu Thr Gln Thr Leu Gly Ser Leu Pro Asp Ile Asn Leu Thr Gln Ile
                165                 170                 175
Ser Thr Leu Ala Asn Glu Leu Arg Asp Ser Arg Leu Ala Asn Asp Leu
            180                 185                 190
Arg Asp Ser Gly Ala Thr Ile Arg Ser Arg Ala Asp Tyr Lys Asp Asp
        195                 200                 205
Asp Asp Lys Thr Ser Asp Lys Thr His Thr Cys Pro Pro Cys Pro Ala
210                 215                 220
Pro Glu Leu Leu Gly Gly Pro Ser Val Phe Leu Phe Pro Pro Lys Pro
225                 230                 235                 240
Lys Asp Thr Leu Met Ile Ser Arg Thr Pro Glu Val Thr Cys Val Val
                245                 250                 255
Val Asp Val Ser His Glu Asp Pro Glu Val Lys Phe Asn Trp Tyr Val
            260                 265                 270
Asp Gly Val Glu Val His Asn Ala Lys Thr Lys Pro Arg Glu Glu Gln
        275                 280                 285
Tyr Asn Ser Thr Tyr Arg Val Val Ser Val Leu Thr Val Leu His Gln
        290                 295                 300
Asp Trp Leu Asn Gly Lys Glu Tyr Lys Cys Lys Val Ser Asn Lys Ala
305                 310                 315                 320
Leu Pro Ala Pro Ile Glu Lys Thr Ile Ser Lys Ala Lys Gly Gln Pro
                325                 330                 335
Arg Glu Pro Gln Val Tyr Thr Leu Pro Pro Ser Arg Glu Glu Met Thr
            340                 345                 350
Lys Asn Gln Val Ser Leu Thr Cys Leu Val Lys Gly Phe Tyr Pro Ser
        355                 360                 365
Asp Ile Ala Ala Glu Trp Glu Ser Asn Gly Gln Pro Glu Asn Asn Tyr
        370                 375                 380
Lys Thr Thr Pro Pro Val Leu Asp Ser Asp Gly Ser Phe Phe Leu Tyr
385                 390                 395                 400
Ser Lys Leu Thr Val Asp Lys Ser Arg Trp Gln Gln Gly Asn Val Phe
                405                 410                 415
Ser Cys Ser Val Met His Glu Ala Leu His Asn His Tyr Thr Gln Lys
            420                 425                 430
Ser Leu Ser Leu Ser Pro Gly Lys
        435                 440
```

<210> SEQ ID NO 39
<211> LENGTH: 30
<212> TYPE: DNA
<213> ORGANISM: Artificial
<220> FEATURE:
<223> OTHER INFORMATION: Primer TIM3ED-FLAG4aa

<400> SEQUENCE: 39
gtccttgtag tctctgatgg ttgctccaga                                    30

<210> SEQ ID NO 40
<211> LENGTH: 39
<212> TYPE: DNA
<213> ORGANISM: Artificial
<220> FEATURE:
<223> OTHER INFORMATION: Primer C-FLAG-NotR2

<400> SEQUENCE: 40
aaaagcggcc gctcacttgt cgtcatcgtc cttgtagtc                          39

<210> SEQ ID NO 41
<211> LENGTH: 18
<212> TYPE: DNA
<213> ORGANISM: Artificial
<220> FEATURE:
<223> OTHER INFORMATION: Primer BGH-R

<400> SEQUENCE: 41
tagaaggcac agtcgagg                                                 18

<210> SEQ ID NO 42
<211> LENGTH: 645
<212> TYPE: DNA
<213> ORGANISM: Artificial
<220> FEATURE:
<223> OTHER INFORMATION: Insert hTIM-3 ECD
<220> FEATURE:
<221> NAME/KEY: CDS
<222> LOCATION: (19)..(645)

<400> SEQUENCE: 42

```
gggaattcga ttgccacc atg ttt tca cat ctt ccc ttt gac tgt gtc ctg      51
                   Met Phe Ser His Leu Pro Phe Asp Cys Val Leu
                    1               5                      10 ctg ctg ctg ctg cta cta ctt aca agg tcc tca gaa gtg gaa tac aga      99
Leu Leu Leu Leu Leu Leu Leu Thr Arg Ser Ser Glu Val Glu Tyr Arg
             15                  20                  25 gcg gag gtc ggt cag aat gcc tat ctg ccc tgc ttc tac acc cca gcc    147
Ala Glu Val Gly Gln Asn Ala Tyr Leu Pro Cys Phe Tyr Thr Pro Ala
         30                  35                  40 gcc cca ggg aac ctc gtg ccc gtc tgc tgg ggc aaa gga gcc tgt cct    195
Ala Pro Gly Asn Leu Val Pro Val Cys Trp Gly Lys Gly Ala Cys Pro
     45                  50                  55 gtg ttt gaa tgt ggc aac gtg gtg ctc agg act gat gaa agg gat gtg    243
Val Phe Glu Cys Gly Asn Val Val Leu Arg Thr Asp Glu Arg Asp Val
 60                  65                  70                  75 aat tat tgg aca tcc aga tac tgg cta aat ggg gat ttc cgc aaa gga    291
Asn Tyr Trp Thr Ser Arg Tyr Trp Leu Asn Gly Asp Phe Arg Lys Gly
                 80                  85                  90 gat gtg tcc ctg acc ata gag aat gtg act cta gca gac agt ggg atc    339
Asp Val Ser Leu Thr Ile Glu Asn Val Thr Leu Ala Asp Ser Gly Ile
             95                 100                 105 tac tgc tgc cgg atc caa atc cca ggc ata atg aat gat gaa aaa ttt    387
Tyr Cys Cys Arg Ile Gln Ile Pro Gly Ile Met Asn Asp Glu Lys Phe
```

```
            Tyr Cys Cys Arg Ile Gln Ile Pro Gly Ile Met Asn Asp Glu Lys Phe
                    110                 115                 120 aac ctg aag ttg gtc atc aaa cca gcc aag gtc acc cct gca ccg act          435
Asn Leu Lys Leu Val Ile Lys Pro Ala Lys Val Thr Pro Ala Pro Thr
        125                 130                 135 cgg cag aga gac ttc act gca gcc ttt cca agg atg ctt acc acc agg          483
Arg Gln Arg Asp Phe Thr Ala Ala Phe Pro Arg Met Leu Thr Thr Arg
140                 145                 150                 155 gga cat ggc cca gca gag aca cag aca ctg ggg agc ctc cct gat ata          531
Gly His Gly Pro Ala Glu Thr Gln Thr Leu Gly Ser Leu Pro Asp Ile
                    160                 165                 170 aat cta aca caa ata tcc aca ttg gcc aat gag tta cgg gac tct aga          579
Asn Leu Thr Gln Ile Ser Thr Leu Ala Asn Glu Leu Arg Asp Ser Arg
                175                 180                 185 ttg gcc aat gac tta cgg gac tct gga gca acc atc aga gac tac aag          627
Leu Ala Asn Asp Leu Arg Asp Ser Gly Ala Thr Ile Arg Asp Tyr Lys
                190                 195                 200 gac gat gac gac aag tga                                                  645
Asp Asp Asp Asp Lys
        205

<210> SEQ ID NO 43
<211> LENGTH: 208
<212> TYPE: PRT
<213> ORGANISM: Artificial
<220> FEATURE:
<223> OTHER INFORMATION: Synthetic Construct

<400> SEQUENCE: 43

Met Phe Ser His Leu Pro Phe Asp Cys Val Leu Leu Leu Leu Leu Leu
1               5                   10                  15

Leu Leu Thr Arg Ser Ser Glu Val Glu Tyr Arg Ala Glu Val Gly Gln
            20                  25                  30

Asn Ala Tyr Leu Pro Cys Phe Tyr Thr Pro Ala Ala Pro Gly Asn Leu
        35                  40                  45

Val Pro Val Cys Trp Gly Lys Gly Ala Cys Pro Val Phe Glu Cys Gly
    50                  55                  60

Asn Val Val Leu Arg Thr Asp Glu Arg Asp Val Asn Tyr Trp Thr Ser
65                  70                  75                  80

Arg Tyr Trp Leu Asn Gly Asp Phe Arg Lys Gly Asp Val Ser Leu Thr
                85                  90                  95

Ile Glu Asn Val Thr Leu Ala Asp Ser Gly Ile Tyr Cys Cys Arg Ile
            100                 105                 110

Gln Ile Pro Gly Ile Met Asn Asp Glu Lys Phe Asn Leu Lys Leu Val
        115                 120                 125

Ile Lys Pro Ala Lys Val Thr Pro Ala Pro Thr Arg Gln Arg Asp Phe
    130                 135                 140

Thr Ala Ala Phe Pro Arg Met Leu Thr Thr Arg Gly His Gly Pro Ala
145                 150                 155                 160

Glu Thr Gln Thr Leu Gly Ser Leu Pro Asp Ile Asn Leu Thr Gln Ile
                165                 170                 175

Ser Thr Leu Ala Asn Glu Leu Arg Asp Ser Arg Leu Ala Asn Asp Leu
            180                 185                 190

Arg Asp Ser Gly Ala Thr Ile Arg Asp Tyr Lys Asp Asp Asp Asp Lys
        195                 200                 205

<210> SEQ ID NO 44
<211> LENGTH: 27
```

<212> TYPE: DNA
<213> ORGANISM: Artificial
<220> FEATURE:
<223> OTHER INFORMATION: Primer hh-6

<400> SEQUENCE: 44
ggtccgggag atcatgaggg tgtcctt                                            27

<210> SEQ ID NO 45
<211> LENGTH: 26
<212> TYPE: DNA
<213> ORGANISM: Artificial
<220> FEATURE:
<223> OTHER INFORMATION: Primer hh-3

<400> SEQUENCE: 45
gtgcacgccg ctggtcaggg cgcctg                                             26

<210> SEQ ID NO 46
<211> LENGTH: 26
<212> TYPE: DNA
<213> ORGANISM: Artificial
<220> FEATURE:
<223> OTHER INFORMATION: Primer hk-2

<400> SEQUENCE: 46
gttgaagctc tttgtgacgg gcgagc                                             26

<210> SEQ ID NO 47
<211> LENGTH: 26
<212> TYPE: DNA
<213> ORGANISM: Artificial
<220> FEATURE:
<223> OTHER INFORMATION: Primer hk-6

<400> SEQUENCE: 47
tggcgggaag atgaagacag atggtg                                             26

<210> SEQ ID NO 48
<211> LENGTH: 32
<212> TYPE: DNA
<213> ORGANISM: Artificial
<220> FEATURE:
<223> OTHER INFORMATION: Primer mH_Rv1

<400> SEQUENCE: 48
attttgtcga cckyggtsyt gctggcyggg tg                                      32

<210> SEQ ID NO 49
<211> LENGTH: 30
<212> TYPE: DNA
<213> ORGANISM: Artificial
<220> FEATURE:
<223> OTHER INFORMATION: Primer mH_Rv2

<400> SEQUENCE: 49
gcacacyrct ggacagggat ccagagttcc                                         30

<210> SEQ ID NO 50
<211> LENGTH: 30
<212> TYPE: DNA
<213> ORGANISM: Artificial
<220> FEATURE:
<223> OTHER INFORMATION: Primer mK_Rv1

<400> SEQUENCE: 50

-continued

```
ttgaagctct tgacaatggg tgaagttgat                                           30
```

<210> SEQ ID NO 51
<211> LENGTH: 30
<212> TYPE: DNA
<213> ORGANISM: Artificial
<220> FEATURE:
<223> OTHER INFORMATION: Primer mK_Rv2

<400> SEQUENCE: 51

```
gtaggtgctg tctttgctgt cctgatcagt                                           30
```

<210> SEQ ID NO 52
<211> LENGTH: 906
<212> TYPE: DNA
<213> ORGANISM: Homo sapiens
<220> FEATURE:
<221> NAME/KEY: CDS
<222> LOCATION: (1)..(906)

<400> SEQUENCE: 52

```
atg ttt tca cat ctt ccc ttt gac tgt gtc ctg ctg ctg ctg cta          48
Met Phe Ser His Leu Pro Phe Asp Cys Val Leu Leu Leu Leu Leu
1               5                   10                  15 cta ctt aca agg tcc tca gaa gtg gaa tac aga gcg gag gtc ggt cag       96
Leu Leu Thr Arg Ser Ser Glu Val Glu Tyr Arg Ala Glu Val Gly Gln
            20                  25                  30 aat gcc tat ctg ccc tgc ttc tac acc cca gcc gcc cca ggg aac ctc      144
Asn Ala Tyr Leu Pro Cys Phe Tyr Thr Pro Ala Ala Pro Gly Asn Leu
        35                  40                  45 gtg ccc gtc tgc tgg ggc aaa gga gcc tgt cct gtg ttt gaa tgt ggc      192
Val Pro Val Cys Trp Gly Lys Gly Ala Cys Pro Val Phe Glu Cys Gly
    50                  55                  60 aac gtg gtg ctc agg act gat gaa agg gat gtg aat tat tgg aca tcc      240
Asn Val Val Leu Arg Thr Asp Glu Arg Asp Val Asn Tyr Trp Thr Ser
65                  70                  75                  80 aga tac tgg cta aat ggg gat ttc cgc aaa gga gat gtg tcc ctg acc      288
Arg Tyr Trp Leu Asn Gly Asp Phe Arg Lys Gly Asp Val Ser Leu Thr
                85                  90                  95 ata gag aat gtg act cta gca gac agt ggg atc tac tgc tgc cgg atc      336
Ile Glu Asn Val Thr Leu Ala Asp Ser Gly Ile Tyr Cys Cys Arg Ile
            100                 105                 110 caa atc cca ggc ata atg aat gat gaa aaa ttt aac ctg aag ttg gtc      384
Gln Ile Pro Gly Ile Met Asn Asp Glu Lys Phe Asn Leu Lys Leu Val
        115                 120                 125 atc aaa cca gcc aag gtc acc cct gca ccg act cgg cag aga gac ttc      432
Ile Lys Pro Ala Lys Val Thr Pro Ala Pro Thr Arg Gln Arg Asp Phe
    130                 135                 140 act gca gcc ttt cca agg atg ctt acc acc agg gga cat ggc cca gca      480
Thr Ala Ala Phe Pro Arg Met Leu Thr Thr Arg Gly His Gly Pro Ala
145                 150                 155                 160 gag aca cag aca ctg ggg agc ctc cct gat ata aat cta aca caa ata      528
Glu Thr Gln Thr Leu Gly Ser Leu Pro Asp Ile Asn Leu Thr Gln Ile
                165                 170                 175 tcc aca ttg gcc aat gag tta cgg gac tct aga ttg gcc aat gac tta      576
Ser Thr Leu Ala Asn Glu Leu Arg Asp Ser Arg Leu Ala Asn Asp Leu
            180                 185                 190 cgg gac tct gga gca acc atc aga ata ggc atc tac atc gga gca ggg      624
Arg Asp Ser Gly Ala Thr Ile Arg Ile Gly Ile Tyr Ile Gly Ala Gly
        195                 200                 205 atc tgt gct ggg ctg gct ctg gct ctt atc ttc ggc gct tta att ttc      672
Ile Cys Ala Gly Leu Ala Leu Ala Leu Ile Phe Gly Ala Leu Ile Phe
```

| | | | | | | | | | | | | | | | | |
|---|---|---|---|---|---|---|---|---|---|---|---|---|---|---|---|---|
| | 210 | | | | 215 | | | | | 220 | | | | | | |
| aaa | tgg | tat | tct | cat | agc | aaa | gag | aag | ata | cag | aat | tta | agc | ctc | atc | 720 |
| Lys | Trp | Tyr | Ser | His | Ser | Lys | Glu | Lys | Ile | Gln | Asn | Leu | Ser | Leu | Ile | |
| 225 | | | | | 230 | | | | | 235 | | | | | 240 | |
| tct | ttg | gcc | aac | ctc | cct | ccc | tca | gga | ttg | gca | aat | gca | gta | gca | gag | 768 |
| Ser | Leu | Ala | Asn | Leu | Pro | Pro | Ser | Gly | Leu | Ala | Asn | Ala | Val | Ala | Glu | |
| | | | | 245 | | | | | 250 | | | | | 255 | | |
| gga | att | cgc | tca | gaa | gaa | aac | atc | tat | acc | att | gaa | gag | aac | gta | tat | 816 |
| Gly | Ile | Arg | Ser | Glu | Glu | Asn | Ile | Tyr | Thr | Ile | Glu | Glu | Asn | Val | Tyr | |
| | | | 260 | | | | | 265 | | | | | 270 | | | |
| gaa | gtg | gag | gag | ccc | aat | gag | tat | tat | tgc | tat | gtc | agc | agc | agg | cag | 864 |
| Glu | Val | Glu | Glu | Pro | Asn | Glu | Tyr | Tyr | Cys | Tyr | Val | Ser | Ser | Arg | Gln | |
| | | 275 | | | | | 280 | | | | | 285 | | | | |
| caa | ccc | tca | caa | cct | ttg | ggt | tgt | cgc | ttt | gca | atg | cca | tag | | | 906 |
| Gln | Pro | Ser | Gln | Pro | Leu | Gly | Cys | Arg | Phe | Ala | Met | Pro | | | | |
| | 290 | | | | | 295 | | | | | 300 | | | | | |

<210> SEQ ID NO 53
<211> LENGTH: 301
<212> TYPE: PRT
<213> ORGANISM: Homo sapiens

<400> SEQUENCE: 53

```
Met Phe Ser His Leu Pro Phe Asp Cys Val Leu Leu Leu Leu Leu
1               5                  10                  15

Leu Leu Thr Arg Ser Ser Glu Val Glu Tyr Arg Ala Glu Val Gly Gln
            20                  25                  30

Asn Ala Tyr Leu Pro Cys Phe Tyr Thr Pro Ala Ala Pro Gly Asn Leu
            35                  40                  45

Val Pro Val Cys Trp Gly Lys Gly Ala Cys Pro Val Phe Glu Cys Gly
    50                  55                  60

Asn Val Val Leu Arg Thr Asp Glu Arg Asp Val Asn Tyr Trp Thr Ser
65                  70                  75                  80

Arg Tyr Trp Leu Asn Gly Asp Phe Arg Lys Gly Asp Val Ser Leu Thr
                85                  90                  95

Ile Glu Asn Val Thr Leu Ala Asp Ser Gly Ile Tyr Cys Cys Arg Ile
            100                 105                 110

Gln Ile Pro Gly Ile Met Asn Asp Glu Lys Phe Asn Leu Lys Leu Val
        115                 120                 125

Ile Lys Pro Ala Lys Val Thr Pro Ala Pro Thr Arg Gln Arg Asp Phe
130                 135                 140

Thr Ala Ala Phe Pro Arg Met Leu Thr Thr Arg Gly His Gly Pro Ala
145                 150                 155                 160

Glu Thr Gln Thr Leu Gly Ser Leu Pro Asp Ile Asn Leu Thr Gln Ile
                165                 170                 175

Ser Thr Leu Ala Asn Glu Leu Arg Asp Ser Arg Leu Ala Asn Asp Leu
            180                 185                 190

Arg Asp Ser Gly Ala Thr Ile Arg Ile Gly Ile Tyr Ile Gly Ala Gly
        195                 200                 205

Ile Cys Ala Gly Leu Ala Leu Ala Leu Ile Phe Gly Ala Leu Ile Phe
    210                 215                 220

Lys Trp Tyr Ser His Ser Lys Glu Lys Ile Gln Asn Leu Ser Leu Ile
225                 230                 235                 240

Ser Leu Ala Asn Leu Pro Pro Ser Gly Leu Ala Asn Ala Val Ala Glu
                245                 250                 255

Gly Ile Arg Ser Glu Glu Asn Ile Tyr Thr Ile Glu Glu Asn Val Tyr
```

```
                260                 265                 270
Glu Val Glu Glu Pro Asn Glu Tyr Tyr Cys Tyr Val Ser Ser Arg Gln
                275                 280                 285

Gln Pro Ser Gln Pro Leu Gly Cys Arg Phe Ala Met Pro
        290                 295                 300

<210> SEQ ID NO 54
<211> LENGTH: 426
<212> TYPE: DNA
<213> ORGANISM: Homo sapiens
<220> FEATURE:
<221> NAME/KEY: CDS
<222> LOCATION: (1)..(426)

<400> SEQUENCE: 54 atg gag ttt ggg ctg agc tgg gtt ttc ctc gtt gct ctt tta aga ggt     48
Met Glu Phe Gly Leu Ser Trp Val Phe Leu Val Ala Leu Leu Arg Gly
1               5                   10                  15 gtc cag tgt cag gtg cag ctg gtg gag tct ggg gga ggc gtg gtc cag     96
Val Gln Cys Gln Val Gln Leu Val Glu Ser Gly Gly Gly Val Val Gln
                20                  25                  30 cct ggg agg tcc ctg aga ctc tcc tgt gca gcg tct gga ttc acc ttc    144
Pro Gly Arg Ser Leu Arg Leu Ser Cys Ala Ala Ser Gly Phe Thr Phe
            35                  40                  45 aat agc tat ggc atg cac tgg gtc cgc cag gct cca ggc aag ggg ctg    192
Asn Ser Tyr Gly Met His Trp Val Arg Gln Ala Pro Gly Lys Gly Leu
        50                  55                  60 gag tgg gtg gca gtt ata tgg tat gat gga agt aat aaa tac tat gga    240
Glu Trp Val Ala Val Ile Trp Tyr Asp Gly Ser Asn Lys Tyr Tyr Gly
65                  70                  75                  80 gac tcc gtg aag ggc cga ttc acc atc tcc aga gac aat tcc aag aac    288
Asp Ser Val Lys Gly Arg Phe Thr Ile Ser Arg Asp Asn Ser Lys Asn
                85                  90                  95 acg ctg tat ctg caa atg aac agc ctg aga gcc gag gac acg gct gtg    336
Thr Leu Tyr Leu Gln Met Asn Ser Leu Arg Ala Glu Asp Thr Ala Val
            100                 105                 110 tat tac tgt gcg ata tgg ttc ggg gag atg ttt tcc gaa tac ttc cag    384
Tyr Tyr Cys Ala Ile Trp Phe Gly Glu Met Phe Ser Glu Tyr Phe Gln
        115                 120                 125 cac tgg ggc cag ggc acc ctg gtc acc gtc tcc tca gct agc            426
His Trp Gly Gln Gly Thr Leu Val Thr Val Ser Ser Ala Ser
    130                 135                 140

<210> SEQ ID NO 55
<211> LENGTH: 142
<212> TYPE: PRT
<213> ORGANISM: Homo sapiens

<400> SEQUENCE: 55

Met Glu Phe Gly Leu Ser Trp Val Phe Leu Val Ala Leu Leu Arg Gly
1               5                   10                  15

Val Gln Cys Gln Val Gln Leu Val Glu Ser Gly Gly Gly Val Val Gln
                20                  25                  30

Pro Gly Arg Ser Leu Arg Leu Ser Cys Ala Ala Ser Gly Phe Thr Phe
            35                  40                  45

Asn Ser Tyr Gly Met His Trp Val Arg Gln Ala Pro Gly Lys Gly Leu
        50                  55                  60

Glu Trp Val Ala Val Ile Trp Tyr Asp Gly Ser Asn Lys Tyr Tyr Gly
65                  70                  75                  80

Asp Ser Val Lys Gly Arg Phe Thr Ile Ser Arg Asp Asn Ser Lys Asn
```

```
                85                  90                  95
Thr Leu Tyr Leu Gln Met Asn Ser Leu Arg Ala Glu Asp Thr Ala Val
            100                 105                 110
Tyr Tyr Cys Ala Ile Trp Phe Gly Glu Met Phe Ser Glu Tyr Phe Gln
            115                 120                 125
His Trp Gly Gln Gly Thr Leu Val Thr Val Ser Ser Ala Ser
            130                 135                 140

<210> SEQ ID NO 56
<211> LENGTH: 393
<212> TYPE: DNA
<213> ORGANISM: Homo sapiens
<220> FEATURE:
<221> NAME/KEY: CDS
<222> LOCATION: (1)..(393)

<400> SEQUENCE: 56 atg gac atg agg gtc ccc gct cag ctc ctg ggg ctt ctg ctg ctc tgg      48
Met Asp Met Arg Val Pro Ala Gln Leu Leu Gly Leu Leu Leu Leu Trp
1               5                   10                  15 ctc cca ggt gcc aga tgt gcc atc cag ttg acc cag tct cca tcc tcc      96
Leu Pro Gly Ala Arg Cys Ala Ile Gln Leu Thr Gln Ser Pro Ser Ser
            20                  25                  30 ctg tct gca tct gta gga gac aga gtc acc atc act tgc cgg gca agt     144
Leu Ser Ala Ser Val Gly Asp Arg Val Thr Ile Thr Cys Arg Ala Ser
        35                  40                  45 cag ggc att agc agt gct tta gcc tgg tat cag cag aaa cca ggg aaa     192
Gln Gly Ile Ser Ser Ala Leu Ala Trp Tyr Gln Gln Lys Pro Gly Lys
    50                  55                  60 gct cct aag ctc ctg atc tat gat gcc tcc agt ttg gaa agt ggg gtc     240
Ala Pro Lys Leu Leu Ile Tyr Asp Ala Ser Ser Leu Glu Ser Gly Val
65                  70                  75                  80 cca tca agg ttc agc ggc agt gga tct ggg aca gat ttc act ctc acc     288
Pro Ser Arg Phe Ser Gly Ser Gly Ser Gly Thr Asp Phe Thr Leu Thr
                85                  90                  95 atc agc agc ctg cag cct gaa gat ttt gca act tat tac tgt caa cag     336
Ile Ser Ser Leu Gln Pro Glu Asp Phe Ala Thr Tyr Tyr Cys Gln Gln
            100                 105                 110 ttt aat agt tac cct ctc act ttc ggc gga ggg acc aag gtg gag atc     384
Phe Asn Ser Tyr Pro Leu Thr Phe Gly Gly Gly Thr Lys Val Glu Ile
            115                 120                 125 aaa cgt acg                                                         393
Lys Arg Thr
    130

<210> SEQ ID NO 57
<211> LENGTH: 131
<212> TYPE: PRT
<213> ORGANISM: Homo sapiens

<400> SEQUENCE: 57

Met Asp Met Arg Val Pro Ala Gln Leu Leu Gly Leu Leu Leu Leu Trp
1               5                   10                  15

Leu Pro Gly Ala Arg Cys Ala Ile Gln Leu Thr Gln Ser Pro Ser Ser
            20                  25                  30

Leu Ser Ala Ser Val Gly Asp Arg Val Thr Ile Thr Cys Arg Ala Ser
        35                  40                  45

Gln Gly Ile Ser Ser Ala Leu Ala Trp Tyr Gln Gln Lys Pro Gly Lys
    50                  55                  60

Ala Pro Lys Leu Leu Ile Tyr Asp Ala Ser Ser Leu Glu Ser Gly Val
```

```
              65                  70                  75                  80
Pro Ser Arg Phe Ser Gly Ser Gly Ser Gly Thr Asp Phe Thr Leu Thr
                85                  90                  95

Ile Ser Ser Leu Gln Pro Glu Asp Phe Ala Thr Tyr Tyr Cys Gln Gln
            100                 105                 110

Phe Asn Ser Tyr Pro Leu Thr Phe Gly Gly Gly Thr Lys Val Glu Ile
            115                 120                 125

Lys Arg Thr
        130

<210> SEQ ID NO 58
<211> LENGTH: 432
<212> TYPE: DNA
<213> ORGANISM: Homo sapiens
<220> FEATURE:
<221> NAME/KEY: CDS
<222> LOCATION: (1)..(432)

<400> SEQUENCE: 58 atg gag ttt ggg ctg agc tgg gtt ttc ctt gtt gct att ata aaa ggt       48
Met Glu Phe Gly Leu Ser Trp Val Phe Leu Val Ala Ile Ile Lys Gly
1               5                  10                  15 gtc cag tgt cag gtg cag ctg gtg gag tct ggg gga ggc ttg gtc aag       96
Val Gln Cys Gln Val Gln Leu Val Glu Ser Gly Gly Gly Leu Val Lys
            20                  25                  30 cct gga ggg tcc ctg aga ctc tcc tgt gca gcc tct gga ttc acc ttc      144
Pro Gly Gly Ser Leu Arg Leu Ser Cys Ala Ala Ser Gly Phe Thr Phe
        35                  40                  45 agt gac tac tac atg agc tgg atc cgc cag gct cca ggg aag ggg ctg      192
Ser Asp Tyr Tyr Met Ser Trp Ile Arg Gln Ala Pro Gly Lys Gly Leu
    50                  55                  60 gag tgg gtt tca ttc att agt agt agt ggt agt atc ata tac tac gca      240
Glu Trp Val Ser Phe Ile Ser Ser Ser Gly Ser Ile Ile Tyr Tyr Ala
65                  70                  75                  80 gac tct gtg aag ggc cga ttc acc atc tcc agg gac aac gcc aag aac      288
Asp Ser Val Lys Gly Arg Phe Thr Ile Ser Arg Asp Asn Ala Lys Asn
                85                  90                  95 tca ctg tat ctg caa atg aac agc ctg aga gcc gag gac acg gct gtg      336
Ser Leu Tyr Leu Gln Met Asn Ser Leu Arg Ala Glu Asp Thr Ala Val
            100                 105                 110 tat tac tgt gcg aga gat ggg tat agc agc agt tgg tat tac tac ggt      384
Tyr Tyr Cys Ala Arg Asp Gly Tyr Ser Ser Ser Trp Tyr Tyr Tyr Gly
        115                 120                 125 atg gac gtc tgg ggc caa ggg acc acg gtc acc gtc tcc tca gct agc      432
Met Asp Val Trp Gly Gln Gly Thr Thr Val Thr Val Ser Ser Ala Ser
    130                 135                 140

<210> SEQ ID NO 59
<211> LENGTH: 144
<212> TYPE: PRT
<213> ORGANISM: Homo sapiens

<400> SEQUENCE: 59

Met Glu Phe Gly Leu Ser Trp Val Phe Leu Val Ala Ile Ile Lys Gly
1               5                  10                  15

Val Gln Cys Gln Val Gln Leu Val Glu Ser Gly Gly Gly Leu Val Lys
            20                  25                  30

Pro Gly Gly Ser Leu Arg Leu Ser Cys Ala Ala Ser Gly Phe Thr Phe
        35                  40                  45

Ser Asp Tyr Tyr Met Ser Trp Ile Arg Gln Ala Pro Gly Lys Gly Leu
```

```
                    50                  55                  60
Glu Trp Val Ser Phe Ile Ser Ser Gly Ser Ile Ile Tyr Tyr Ala
 65                  70                  75                  80

Asp Ser Val Lys Gly Arg Phe Thr Ile Ser Arg Asp Asn Ala Lys Asn
                 85                  90                  95

Ser Leu Tyr Leu Gln Met Asn Ser Leu Arg Ala Glu Asp Thr Ala Val
                100                 105                 110

Tyr Tyr Cys Ala Arg Asp Gly Tyr Ser Ser Trp Tyr Tyr Gly
            115                 120                 125

Met Asp Val Trp Gly Gln Gly Thr Thr Val Thr Val Ser Ser Ala Ser
            130                 135                 140

<210> SEQ ID NO 60
<211> LENGTH: 390
<212> TYPE: DNA
<213> ORGANISM: Homo sapiens
<220> FEATURE:
<221> NAME/KEY: CDS
<222> LOCATION: (1)..(390)

<400> SEQUENCE: 60 atg gaa acc cca gcg cag ctt ctc ttc ctc ctg cta ctc tgg ctc cca       48
Met Glu Thr Pro Ala Gln Leu Leu Phe Leu Leu Leu Leu Trp Leu Pro
 1               5                  10                  15 gat acc acc gga gaa att gtg ttg acg cag tct cca ggc acc ctg tct       96
Asp Thr Thr Gly Glu Ile Val Leu Thr Gln Ser Pro Gly Thr Leu Ser
             20                  25                  30 ttg tct cca ggg gaa aga gcc acc ctc tcc tgc agg gcc agt cag agt      144
Leu Ser Pro Gly Glu Arg Ala Thr Leu Ser Cys Arg Ala Ser Gln Ser
         35                  40                  45 gtt agc agc agc tac tta gcc tgg tac cag cag aaa cct ggc cag gct      192
Val Ser Ser Ser Tyr Leu Ala Trp Tyr Gln Gln Lys Pro Gly Gln Ala
     50                  55                  60 ccc agg ctc ctc atc tat ggt gca tcc agc agg gcc act ggc atc cca      240
Pro Arg Leu Leu Ile Tyr Gly Ala Ser Ser Arg Ala Thr Gly Ile Pro
 65                  70                  75                  80 gac agg ttc agt ggc agt ggg tct ggg aca gac ttc act ctc acc atc      288
Asp Arg Phe Ser Gly Ser Gly Ser Gly Thr Asp Phe Thr Leu Thr Ile
                 85                  90                  95 agc aga ctg gag cct gaa gat ttt gca gtg tat tac tgt cag cag tat      336
Ser Arg Leu Glu Pro Glu Asp Phe Ala Val Tyr Tyr Cys Gln Gln Tyr
            100                 105                 110 ggt agc tca ccg ctc act ttc ggc gga ggg acc aag gtg gag atc aaa      384
Gly Ser Ser Pro Leu Thr Phe Gly Gly Gly Thr Lys Val Glu Ile Lys
        115                 120                 125 cgt acg                                                              390
Arg Thr
    130

<210> SEQ ID NO 61
<211> LENGTH: 130
<212> TYPE: PRT
<213> ORGANISM: Homo sapiens

<400> SEQUENCE: 61

Met Glu Thr Pro Ala Gln Leu Leu Phe Leu Leu Leu Leu Trp Leu Pro
 1               5                  10                  15

Asp Thr Thr Gly Glu Ile Val Leu Thr Gln Ser Pro Gly Thr Leu Ser
             20                  25                  30

Leu Ser Pro Gly Glu Arg Ala Thr Leu Ser Cys Arg Ala Ser Gln Ser
```

```
                35                  40                  45
Val Ser Ser Tyr Leu Ala Trp Tyr Gln Gln Lys Pro Gly Gln Ala
    50                  55                  60
Pro Arg Leu Leu Ile Tyr Gly Ala Ser Ser Arg Ala Thr Gly Ile Pro
65                  70                  75                  80
Asp Arg Phe Ser Gly Ser Gly Ser Gly Thr Asp Phe Thr Leu Thr Ile
                85                  90                  95
Ser Arg Leu Glu Pro Glu Asp Phe Ala Val Tyr Tyr Cys Gln Gln Tyr
            100                 105                 110
Gly Ser Ser Pro Leu Thr Phe Gly Gly Gly Thr Lys Val Glu Ile Lys
        115                 120                 125
Arg Thr
    130

<210> SEQ ID NO 62
<211> LENGTH: 414
<212> TYPE: DNA
<213> ORGANISM: Homo sapiens
<220> FEATURE:
<221> NAME/KEY: CDS
<222> LOCATION: (1)..(414)

<400> SEQUENCE: 62 atg gac tgg acc tgg agc atc ctt ttc ttg gtg gca gca aca ggt        48
Met Asp Trp Thr Trp Ser Ile Leu Phe Leu Val Ala Ala Thr Gly
1               5                   10                  15 gcc cac tcc cag gtt cag ctg gtg cag tct gga gct gag gtg aag aag    96
Ala His Ser Gln Val Gln Leu Val Gln Ser Gly Ala Glu Val Lys Lys
            20                  25                  30 cct ggg gcc tca gtg aag gtc tcc tgc aag gct tct ggt tac acc ttt   144
Pro Gly Ala Ser Val Lys Val Ser Cys Lys Ala Ser Gly Tyr Thr Phe
        35                  40                  45 acc agc tat ggt atc agc tgg gtg cga cag gcc cct gga caa ggg ctt   192
Thr Ser Tyr Gly Ile Ser Trp Val Arg Gln Ala Pro Gly Gln Gly Leu
    50                  55                  60 gag tgg atg gga tgg atc agc gct tac aat ggt aac aca aac tat gca   240
Glu Trp Met Gly Trp Ile Ser Ala Tyr Asn Gly Asn Thr Asn Tyr Ala
65                  70                  75                  80 cag aag ctc cag ggc aga gtc acc atg acc aca gac aca tcc acg agc   288
Gln Lys Leu Gln Gly Arg Val Thr Met Thr Thr Asp Thr Ser Thr Ser
                85                  90                  95 aca gcc tac atg gag ctg agg agc ctg aga tct gac gac acg gcc gtg   336
Thr Ala Tyr Met Glu Leu Arg Ser Leu Arg Ser Asp Asp Thr Ala Val
            100                 105                 110 tat tac tgt gcg aga tgg gat agc agc agc tgg tcc ttt gac tac tgg   384
Tyr Tyr Cys Ala Arg Trp Asp Ser Ser Ser Trp Ser Phe Asp Tyr Trp
        115                 120                 125 ggc cag gga acc ctg gtc acc gtc tcc tca                           414
Gly Gln Gly Thr Leu Val Thr Val Ser Ser
    130                 135

<210> SEQ ID NO 63
<211> LENGTH: 138
<212> TYPE: PRT
<213> ORGANISM: Homo sapiens

<400> SEQUENCE: 63

Met Asp Trp Thr Trp Ser Ile Leu Phe Leu Val Ala Ala Thr Gly
1               5                   10                  15

Ala His Ser Gln Val Gln Leu Val Gln Ser Gly Ala Glu Val Lys Lys
```

```
            20                  25                  30
Pro Gly Ala Ser Val Lys Val Ser Cys Lys Ala Ser Gly Tyr Thr Phe
        35                  40                  45

Thr Ser Tyr Gly Ile Ser Trp Val Arg Gln Ala Pro Gly Gln Gly Leu
    50                  55                  60

Glu Trp Met Gly Trp Ile Ser Ala Tyr Asn Gly Asn Thr Asn Tyr Ala
65                  70                  75                  80

Gln Lys Leu Gln Gly Arg Val Thr Met Thr Thr Asp Thr Ser Thr Ser
                85                  90                  95

Thr Ala Tyr Met Glu Leu Arg Ser Leu Arg Ser Asp Asp Thr Ala Val
            100                 105                 110

Tyr Tyr Cys Ala Arg Trp Asp Ser Ser Trp Ser Phe Asp Tyr Trp
        115                 120                 125

Gly Gln Gly Thr Leu Val Thr Val Ser Ser
    130                 135

<210> SEQ ID NO 64
<211> LENGTH: 390
<212> TYPE: DNA
<213> ORGANISM: Homo sapiens
<220> FEATURE:
<221> NAME/KEY: CDS
<222> LOCATION: (1)..(390)

<400> SEQUENCE: 64 atg gac atg agg gtc ctc gct cag ctc ctg ggg ctc ctg ctg ctc tgt    48
Met Asp Met Arg Val Leu Ala Gln Leu Leu Gly Leu Leu Leu Leu Cys
1               5                   10                  15 ttc cca ggt gcc aga tgt gac atc cag atg acc cag tct cca tcc tca    96
Phe Pro Gly Ala Arg Cys Asp Ile Gln Met Thr Gln Ser Pro Ser Ser
                20                  25                  30 ctg tct gca tct gta gga gac aga gtc acc atc act tgt cgg gcg agt   144
Leu Ser Ala Ser Val Gly Asp Arg Val Thr Ile Thr Cys Arg Ala Ser
            35                  40                  45 cag ggt att agc agc tgg tta gcc tgg tat cag cag aaa cca gag aaa   192
Gln Gly Ile Ser Ser Trp Leu Ala Trp Tyr Gln Gln Lys Pro Glu Lys
        50                  55                  60 gcc cct aag tcc ctg atc tat gct gca tcc agt ttg caa agt ggg gtc   240
Ala Pro Lys Ser Leu Ile Tyr Ala Ala Ser Ser Leu Gln Ser Gly Val
65                  70                  75                  80 cca tca agg ttc agc ggc agt gga tct ggg aca gat ttc act ctc acc   288
Pro Ser Arg Phe Ser Gly Ser Gly Ser Gly Thr Asp Phe Thr Leu Thr
                85                  90                  95 atc agc agc ctg cag cct gaa gat ttt gca act tat tac tgc caa cag   336
Ile Ser Ser Leu Gln Pro Glu Asp Phe Ala Thr Tyr Tyr Cys Gln Gln
            100                 105                 110 tat aat agt tac ccg tac act ttt ggc cag ggg acc aag ctg gag atc   384
Tyr Asn Ser Tyr Pro Tyr Thr Phe Gly Gln Gly Thr Lys Leu Glu Ile
        115                 120                 125 aaa cgt                                                            390
Lys Arg
    130

<210> SEQ ID NO 65
<211> LENGTH: 130
<212> TYPE: PRT
<213> ORGANISM: Homo sapiens

<400> SEQUENCE: 65

Met Asp Met Arg Val Leu Ala Gln Leu Leu Gly Leu Leu Leu Leu Cys
```

```
                1               5                      10                     15
              Phe Pro Gly Ala Arg Cys Asp Ile Gln Met Thr Gln Ser Pro Ser Ser
                                20                      25                      30

Leu Ser Ala Ser Val Gly Asp Arg Val Thr Ile Thr Cys Arg Ala Ser
                                35                      40                      45

Gln Gly Ile Ser Ser Trp Leu Ala Trp Tyr Gln Gln Lys Pro Glu Lys
                                50                      55                      60

Ala Pro Lys Ser Leu Ile Tyr Ala Ala Ser Ser Leu Gln Ser Gly Val
               65                      70                      75                      80

Pro Ser Arg Phe Ser Gly Ser Gly Ser Gly Thr Asp Phe Thr Leu Thr
                                85                      90                      95

Ile Ser Ser Leu Gln Pro Glu Asp Phe Ala Thr Tyr Tyr Cys Gln Gln
                                100                     105                     110

Tyr Asn Ser Tyr Pro Tyr Thr Phe Gly Gln Gly Thr Lys Leu Glu Ile
                                115                     120                     125

Lys Arg
                  130

<210> SEQ ID NO 66
<211> LENGTH: 351
<212> TYPE: DNA
<213> ORGANISM: Artificial
<220> FEATURE:
<223> OTHER INFORMATION: HV0 Mouse8213 VH
<220> FEATURE:
<221> NAME/KEY: CDS
<222> LOCATION: (1)..(351)

<400> SEQUENCE: 66 cag gtc caa ctg gtg cag tct ggg gct gaa gtg aag aag cct ggg gct      48
Gln Val Gln Leu Val Gln Ser Gly Ala Glu Val Lys Lys Pro Gly Ala
  1               5                  10                  15 tca gtg aag gtg tcc tgc aag gct tct ggc tac acc ttc acc agc tac      96
Ser Val Lys Val Ser Cys Lys Ala Ser Gly Tyr Thr Phe Thr Ser Tyr
                 20                  25                  30 tgg atg cac tgg gtg cgg cag gcg cct gga caa ggc ctt gag tgg atg     144
Trp Met His Trp Val Arg Gln Ala Pro Gly Gln Gly Leu Glu Trp Met
             35                  40                  45 gga gag att aat cct agc aac ggt cgt act aac tac aat gag aag ttc     192
Gly Glu Ile Asn Pro Ser Asn Gly Arg Thr Asn Tyr Asn Glu Lys Phe
         50                  55                  60 aag acc cgg gtc aca atc act gca gac aca tcc acc agc aca gcc tac     240
Lys Thr Arg Val Thr Ile Thr Ala Asp Thr Ser Thr Ser Thr Ala Tyr
 65                  70                  75                  80 atg gaa ctc agc agc ctg cga tct gag gac act gcg gtc tat tac tgt     288
Met Glu Leu Ser Ser Leu Arg Ser Glu Asp Thr Ala Val Tyr Tyr Cys
                 85                  90                  95 gcg cgg ggt tac tac ctc tac ttt gac tac tgg ggc caa ggc acc ctg     336
Ala Arg Gly Tyr Tyr Leu Tyr Phe Asp Tyr Trp Gly Gln Gly Thr Leu
            100                 105                 110 gtc aca gtc tcc tca                                                 351
Val Thr Val Ser Ser
        115

<210> SEQ ID NO 67
<211> LENGTH: 117
<212> TYPE: PRT
<213> ORGANISM: Artificial
<220> FEATURE:
<223> OTHER INFORMATION: Synthetic Construct
```

<400> SEQUENCE: 67

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Trp Met His Trp Val Arg Gln Ala Pro Gly Gln Gly Leu Glu Trp Met
        35                  40                  45

Gly Glu Ile Asn Pro Ser Asn Gly Arg Thr Asn Tyr Asn Glu Lys Phe
    50                  55                  60

Lys Thr Arg Val Thr Ile Thr Ala Asp Thr Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Gly Tyr Tyr Leu Tyr Phe Asp Tyr Trp Gly Gln Gly Thr Leu
            100                 105                 110

Val Thr Val Ser Ser
        115

<210> SEQ ID NO 68
<211> LENGTH: 321
<212> TYPE: DNA
<213> ORGANISM: Artificial
<220> FEATURE:
<223> OTHER INFORMATION: LV0 Mouse8213 VL
<220> FEATURE:
<221> NAME/KEY: CDS
<222> LOCATION: (1)..(321)

<400> SEQUENCE: 68 gac atc cag atg acc caa tct cca tcc tcc ttg tct gca tct gtg gga      48
Asp Ile Gln Met Thr Gln Ser Pro Ser Ser Leu Ser Ala Ser Val Gly
1               5                   10                  15 gac cga gtc acc atc act tgc cat gca agt cag ggc att agg att aat      96
Asp Arg Val Thr Ile Thr Cys His Ala Ser Gln Gly Ile Arg Ile Asn
            20                  25                  30 ata ggg tgg tat cag cag aag cca ggg aaa gca cct aag ctc ctg atc     144
Ile Gly Trp Tyr Gln Gln Lys Pro Gly Lys Ala Pro Lys Leu Leu Ile
        35                  40                  45 tat cat gga acc aac ttg gaa gat gga gtt cca tca agg ttc agt ggc     192
Tyr His Gly Thr Asn Leu Glu Asp Gly Val Pro Ser Arg Phe Ser Gly
    50                  55                  60 agt gga tct gga aca gat ttc act ctc acc atc agc agc ctg caa cct     240
Ser Gly Ser Gly Thr Asp Phe Thr Leu Thr Ile Ser Ser Leu Gln Pro
65                  70                  75                  80 gaa gat ttt gca acc tat tac tgt gta cag tat ggt cag ttt ccg tgg     288
Glu Asp Phe Ala Thr Tyr Tyr Cys Val Gln Tyr Gly Gln Phe Pro Trp
                85                  90                  95 acg ttc ggt cag ggc acc aag ctg gaa atc aaa                         321
Thr Phe Gly Gln Gly Thr Lys Leu Glu Ile Lys
            100                 105

<210> SEQ ID NO 69
<211> LENGTH: 107
<212> TYPE: PRT
<213> ORGANISM: Artificial
<220> FEATURE:
<223> OTHER INFORMATION: Synthetic Construct

<400> SEQUENCE: 69

Asp Ile Gln Met Thr Gln Ser Pro Ser Ser Leu Ser Ala Ser Val Gly
1               5                   10                  15

Asp Arg Val Thr Ile Thr Cys His Ala Ser Gln Gly Ile Arg Ile Asn
            20                  25                  30

Ile Gly Trp Tyr Gln Gln Lys Pro Gly Lys Ala Pro Lys Leu Leu Ile
        35                  40                  45

Tyr His Gly Thr Asn Leu Glu Asp Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Val Gln Tyr Gly Gln Phe Pro Trp
                85                  90                  95

Thr Phe Gly Gln Gly Thr Lys Leu Glu Ile Lys
            100                 105

<210> SEQ ID NO 70
<211> LENGTH: 22
<212> TYPE: DNA
<213> ORGANISM: Artificial
<220> FEATURE:
<223> OTHER INFORMATION: Primer mTim-3 Fw3

<400> SEQUENCE: 70
ctacacagag ctgtccttgg at                                      22

<210> SEQ ID NO 71
<211> LENGTH: 20
<212> TYPE: DNA
<213> ORGANISM: Artificial
<220> FEATURE:
<223> OTHER INFORMATION: Primer mTim-3 Re3

<400> SEQUENCE: 71
tttctcagtg gctgtggtca                                         20

<210> SEQ ID NO 72
<211> LENGTH: 33
<212> TYPE: DNA
<213> ORGANISM: Artificial
<220> FEATURE:
<223> OTHER INFORMATION: Primer mTim-3 Fw4NotI

<400> SEQUENCE: 72
aattgcggcc gccaccatgt tttcaggtct tac                          33

<210> SEQ ID NO 73
<211> LENGTH: 30
<212> TYPE: DNA
<213> ORGANISM: Artificial
<220> FEATURE:
<223> OTHER INFORMATION: Primer mTim-3 Re4NotI

<400> SEQUENCE: 73
aattgcggcc gctcaggatg gctgctggct                              30

<210> SEQ ID NO 74
<211> LENGTH: 20
<212> TYPE: DNA
<213> ORGANISM: Artificial
<220> FEATURE:
<223> OTHER INFORMATION: Primer hTIM3+mIgV_vecR1

<400> SEQUENCE: 74
ggaccttgta agtagtagca                                         20

<210> SEQ ID NO 75
<211> LENGTH: 22
<212> TYPE: DNA
<213> ORGANISM: Artificial
<220> FEATURE:
<223> OTHER INFORMATION: Primer hTIM3+mIgV_vecF1

<400> SEQUENCE: 75
gccaaggtca cccctgcacc ga                                          22

<210> SEQ ID NO 76
<211> LENGTH: 35
<212> TYPE: DNA
<213> ORGANISM: Artificial
<220> FEATURE:
<223> OTHER INFORMATION: Primer hTIM3+mIgV_insF1

<400> SEQUENCE: 76
ctacttacaa ggtccttgga agatggttat aaggt                            35

<210> SEQ ID NO 77
<211> LENGTH: 35
<212> TYPE: DNA
<213> ORGANISM: Artificial
<220> FEATURE:
<223> OTHER INFORMATION: Primer hTIM3+mIgV_insR1

<400> SEQUENCE: 77
aggggtgacc ttggctgctt tgatgtctaa tttca                            35

<210> SEQ ID NO 78
<211> LENGTH: 909
<212> TYPE: DNA
<213> ORGANISM: Artificial
<220> FEATURE:
<223> OTHER INFORMATION: IgV chimeraTIM-3/pEF6 Myc_HisC
<220> FEATURE:
<221> NAME/KEY: CDS
<222> LOCATION: (1)..(909)

<400> SEQUENCE: 78

| | | | | | | | | | | | | | | | | |
|---|---|---|---|---|---|---|---|---|---|---|---|---|---|---|---|---|---|
| atg | ttt | tca | cat | ctt | ccc | ttt | gac | tgt | gtc | ctg | ctg | ctg | ctg | cta | | | 48 |
| Met | Phe | Ser | His | Leu | Pro | Phe | Asp | Cys | Val | Leu | Leu | Leu | Leu | Leu | | | |
| 1 | | | | 5 | | | | | 10 | | | | | 15 | | | |
| cta | ctt | aca | agg | tcc | ttg | gaa | gat | ggt | tat | aag | gtt | gag | gtt | ggt | aaa | | 96 |
| Leu | Leu | Thr | Arg | Ser | Leu | Glu | Asp | Gly | Tyr | Lys | Val | Glu | Val | Gly | Lys | | |
| | | | 20 | | | | | 25 | | | | | 30 | | | | |
| aat | gcc | tat | ctg | ccc | tgc | agt | tac | act | cta | cct | aca | tct | ggg | aca | ctt | | 144 |
| Asn | Ala | Tyr | Leu | Pro | Cys | Ser | Tyr | Thr | Leu | Pro | Thr | Ser | Gly | Thr | Leu | | |
| | | | | 35 | | | | | 40 | | | | | 45 | | | |
| gtg | cct | atg | tgc | tgg | ggc | aag | gga | ttc | tgt | cct | tgg | tca | cag | tgt | acc | | 192 |
| Val | Pro | Met | Cys | Trp | Gly | Lys | Gly | Phe | Cys | Pro | Trp | Ser | Gln | Cys | Thr | | |
| | | 50 | | | | | 55 | | | | | 60 | | | | | |
| aat | gag | ttg | ctc | aga | act | gat | gaa | aga | aat | gtg | aca | tat | cag | aaa | tcc | | 240 |
| Asn | Glu | Leu | Leu | Arg | Thr | Asp | Glu | Arg | Asn | Val | Thr | Tyr | Gln | Lys | Ser | | |
| 65 | | | | | 70 | | | | | 75 | | | | | 80 | | |
| agc | aga | tac | cag | cta | aag | ggc | gat | ctc | aac | aaa | gga | gat | gtg | tct | ctg | | 288 |
| Ser | Arg | Tyr | Gln | Leu | Lys | Gly | Asp | Leu | Asn | Lys | Gly | Asp | Val | Ser | Leu | | |
| | | | | 85 | | | | | 90 | | | | | 95 | | | |
| atc | ata | aag | aat | gtg | act | ctg | gat | gac | cat | ggg | acc | tac | tgc | tgc | agg | | 336 |
| Ile | Ile | Lys | Asn | Val | Thr | Leu | Asp | Asp | His | Gly | Thr | Tyr | Cys | Cys | Arg | | |
| | | | 100 | | | | | 105 | | | | | 110 | | | | |
| ata | cag | ttc | cct | ggt | ctt | atg | aat | gat | aaa | aaa | tta | gaa | ctg | aaa | tta | | 384 |
| Ile | Gln | Phe | Pro | Gly | Leu | Met | Asn | Asp | Lys | Lys | Leu | Glu | Leu | Lys | Leu | | |

```
                115                 120                 125
gac atc aaa gca gcc aag gtc acc cct gca ccg act cgg cag aga gac      432
Asp Ile Lys Ala Ala Lys Val Thr Pro Ala Pro Thr Arg Gln Arg Asp
    130                 135                 140 ttc act gca gcc ttt cca agg atg ctt acc acc agg gga cat ggc cca      480
Phe Thr Ala Ala Phe Pro Arg Met Leu Thr Thr Arg Gly His Gly Pro
145                 150                 155                 160 gca gag aca cag aca ctg ggg agc ctc cct gat ata aat cta aca caa      528
Ala Glu Thr Gln Thr Leu Gly Ser Leu Pro Asp Ile Asn Leu Thr Gln
                165                 170                 175 ata tcc aca ttg gcc aat gag tta cgg gac tct aga ttg gcc aat gac      576
Ile Ser Thr Leu Ala Asn Glu Leu Arg Asp Ser Arg Leu Ala Asn Asp
            180                 185                 190 tta cgg gac tct gga gca acc atc aga ata ggc atc tac atc gga gca      624
Leu Arg Asp Ser Gly Ala Thr Ile Arg Ile Gly Ile Tyr Ile Gly Ala
        195                 200                 205 ggg atc tgt gct ggg ctg gct ctg gct ctt atc ttc ggc gct tta att      672
Gly Ile Cys Ala Gly Leu Ala Leu Ala Leu Ile Phe Gly Ala Leu Ile
    210                 215                 220 ttc aaa tgg tat tct cat agc aaa gag aag ata cag aat tta agc ctc      720
Phe Lys Trp Tyr Ser His Ser Lys Glu Lys Ile Gln Asn Leu Ser Leu
225                 230                 235                 240 atc tct ttg gcc aac ctc cct ccc tca gga ttg gca aat gca gta gca      768
Ile Ser Leu Ala Asn Leu Pro Pro Ser Gly Leu Ala Asn Ala Val Ala
                245                 250                 255 gag gga att cgc tca gaa gaa aac atc tat acc att gaa gag aac gta      816
Glu Gly Ile Arg Ser Glu Glu Asn Ile Tyr Thr Ile Glu Glu Asn Val
            260                 265                 270 tat gaa gtg gag gag ccc aat gag tat tat tgc tat gtc agc agc agg      864
Tyr Glu Val Glu Glu Pro Asn Glu Tyr Tyr Cys Tyr Val Ser Ser Arg
        275                 280                 285 cag caa ccc tca caa cct ttg ggt tgt cgc ttt gca atg cca tag          909
Gln Gln Pro Ser Gln Pro Leu Gly Cys Arg Phe Ala Met Pro
    290                 295                 300
```

<210> SEQ ID NO 79
<211> LENGTH: 302
<212> TYPE: PRT
<213> ORGANISM: Artificial
<220> FEATURE:
<223> OTHER INFORMATION: Synthetic Construct

<400> SEQUENCE: 79

```
Met Phe Ser His Leu Pro Phe Asp Cys Val Leu Leu Leu Leu Leu
1               5                   10                  15

Leu Leu Thr Arg Ser Leu Glu Asp Gly Tyr Lys Val Glu Val Gly Lys
                20                  25                  30

Asn Ala Tyr Leu Pro Cys Ser Tyr Thr Leu Pro Thr Ser Gly Thr Leu
            35                  40                  45

Val Pro Met Cys Trp Gly Lys Gly Phe Cys Pro Trp Ser Gln Cys Thr
        50                  55                  60

Asn Glu Leu Leu Arg Thr Asp Glu Arg Asn Val Thr Tyr Gln Lys Ser
65                  70                  75                  80

Ser Arg Tyr Gln Leu Lys Gly Asp Leu Asn Lys Gly Asp Val Ser Leu
                85                  90                  95

Ile Ile Lys Asn Val Thr Leu Asp Asp His Gly Thr Tyr Cys Cys Arg
            100                 105                 110

Ile Gln Phe Pro Gly Leu Met Asn Asp Lys Lys Leu Glu Leu Lys Leu
        115                 120                 125
```

-continued

```
Asp Ile Lys Ala Ala Lys Val Thr Pro Ala Pro Thr Arg Gln Arg Asp
            130                 135                 140

Phe Thr Ala Ala Phe Pro Arg Met Leu Thr Thr Arg Gly His Gly Pro
145                 150                 155                 160

Ala Glu Thr Gln Thr Leu Gly Ser Leu Pro Asp Ile Asn Leu Thr Gln
                165                 170                 175

Ile Ser Thr Leu Ala Asn Glu Leu Arg Asp Ser Arg Leu Ala Asn Asp
            180                 185                 190

Leu Arg Asp Ser Gly Ala Thr Ile Arg Ile Gly Ile Tyr Ile Gly Ala
        195                 200                 205

Gly Ile Cys Ala Gly Leu Ala Leu Ala Leu Ile Phe Gly Ala Leu Ile
    210                 215                 220

Phe Lys Trp Tyr Ser His Ser Lys Glu Lys Ile Gln Asn Leu Ser Leu
225                 230                 235                 240

Ile Ser Leu Ala Asn Leu Pro Pro Ser Gly Leu Ala Asn Ala Val Ala
                245                 250                 255

Glu Gly Ile Arg Ser Glu Glu Asn Ile Tyr Thr Ile Glu Glu Asn Val
            260                 265                 270

Tyr Glu Val Glu Glu Pro Asn Glu Tyr Tyr Cys Tyr Val Ser Ser Arg
        275                 280                 285

Gln Gln Pro Ser Gln Pro Leu Gly Cys Arg Phe Ala Met Pro
    290                 295                 300

<210> SEQ ID NO 80
<211> LENGTH: 21
<212> TYPE: DNA
<213> ORGANISM: Artificial
<220> FEATURE:
<223> OTHER INFORMATION: Primer hTIM3+mMucin_vecR2

<400> SEQUENCE: 80
tggtttgatg accaacttca g                                           21

<210> SEQ ID NO 81
<211> LENGTH: 23
<212> TYPE: DNA
<213> ORGANISM: Artificial
<220> FEATURE:
<223> OTHER INFORMATION: Primer hTIM3+mMucin_vecF2

<400> SEQUENCE: 81
ataggcatct acatcggagc agg                                         23

<210> SEQ ID NO 82
<211> LENGTH: 35
<212> TYPE: DNA
<213> ORGANISM: Artificial
<220> FEATURE:
<223> OTHER INFORMATION: Primer hTIM3+mMucin_insF2

<400> SEQUENCE: 82
ttggtcatca aaccagccaa ggtcactcca gctca                            35

<210> SEQ ID NO 83
<211> LENGTH: 35
<212> TYPE: DNA
<213> ORGANISM: Artificial
<220> FEATURE:
<223> OTHER INFORMATION: Primer hTIM3+mMucin_insR2

<400> SEQUENCE: 83
```

<210> SEQ ID NO 84
<211> LENGTH: 876
<212> TYPE: DNA
<213> ORGANISM: Artificial
<220> FEATURE:
<223> OTHER INFORMATION: Mucin chimeraTIM-3/pEF6 Myc_HisC
<220> FEATURE:
<221> NAME/KEY: CDS
<222> LOCATION: (1)..(876)

<400> SEQUENCE: 84

```
atg ttt tca cat ctt ccc ttt gac tgt gtc ctg ctg ctg ctg cta        48
Met Phe Ser His Leu Pro Phe Asp Cys Val Leu Leu Leu Leu Leu
1               5                  10                  15 cta ctt aca agg tcc tca gaa gtg gaa tac aga gcg gag gtc ggt cag    96
Leu Leu Thr Arg Ser Ser Glu Val Glu Tyr Arg Ala Glu Val Gly Gln
            20                  25                  30 aat gcc tat ctg ccc tgc ttc tac acc cca gcc gcc cca ggg aac ctc   144
Asn Ala Tyr Leu Pro Cys Phe Tyr Thr Pro Ala Ala Pro Gly Asn Leu
        35                  40                  45 gtg ccc gtc tgc tgg ggc aaa gga gcc tgt cct gtg ttt gaa tgt ggc   192
Val Pro Val Cys Trp Gly Lys Gly Ala Cys Pro Val Phe Glu Cys Gly
    50                  55                  60 aac gtg gtg ctc agg act gat gaa agg gat gtg aat tat tgg aca tcc   240
Asn Val Val Leu Arg Thr Asp Glu Arg Asp Val Asn Tyr Trp Thr Ser
65                  70                  75                  80 aga tac tgg cta aat ggg gat ttc cgc aaa gga gat gtg tcc ctg acc   288
Arg Tyr Trp Leu Asn Gly Asp Phe Arg Lys Gly Asp Val Ser Leu Thr
                85                  90                  95 ata gag aat gtg act cta gca gac agt ggg atc tac tgc tgc cgg atc   336
Ile Glu Asn Val Thr Leu Ala Asp Ser Gly Ile Tyr Cys Cys Arg Ile
            100                 105                 110 caa atc cca ggc ata atg aat gat gaa aaa ttt aac ctg aag ttg gtc   384
Gln Ile Pro Gly Ile Met Asn Asp Glu Lys Phe Asn Leu Lys Leu Val
        115                 120                 125 atc aaa cca gcc aag gtc act cca gct cag act gcc cat ggg gac tct   432
Ile Lys Pro Ala Lys Val Thr Pro Ala Gln Thr Ala His Gly Asp Ser
    130                 135                 140 act aca gct tct cca aga acc cta acc acg gag aga aat ggt tca gag   480
Thr Thr Ala Ser Pro Arg Thr Leu Thr Thr Glu Arg Asn Gly Ser Glu
145                 150                 155                 160 aca cag aca ctg gtg acc ctc cat aat aac aat gga aca aaa att tcc   528
Thr Gln Thr Leu Val Thr Leu His Asn Asn Asn Gly Thr Lys Ile Ser
                165                 170                 175 aca tgg gct gat gaa att aag gac tct gga gaa acg atc aga ata ggc   576
Thr Trp Ala Asp Glu Ile Lys Asp Ser Gly Glu Thr Ile Arg Ile Gly
            180                 185                 190 atc tac atc gga gca ggg atc tgt gct ggg ctg gct ctg gct ctt atc   624
Ile Tyr Ile Gly Ala Gly Ile Cys Ala Gly Leu Ala Leu Ala Leu Ile
        195                 200                 205 ttc ggc gct tta att ttc aaa tgg tat tct cat agc aaa gag aag ata   672
Phe Gly Ala Leu Ile Phe Lys Trp Tyr Ser His Ser Lys Glu Lys Ile
    210                 215                 220 cag aat tta agc ctc atc tct ttg gcc aac ctc cct ccc tca gga ttg   720
Gln Asn Leu Ser Leu Ile Ser Leu Ala Asn Leu Pro Pro Ser Gly Leu
225                 230                 235                 240 gca aat gca gta gca gag gga att cgc tca gaa gaa aac atc tat acc   768
Ala Asn Ala Val Ala Glu Gly Ile Arg Ser Glu Glu Asn Ile Tyr Thr
                245                 250                 255
```

```
att gaa gag aac gta tat gaa gtg gag gag ccc aat gag tat tat tgc    816
Ile Glu Glu Asn Val Tyr Glu Val Glu Glu Pro Asn Glu Tyr Tyr Cys
        260                 265                 270 tat gtc agc agc agg cag caa ccc tca caa cct ttg ggt tgt cgc ttt    864
Tyr Val Ser Ser Arg Gln Gln Pro Ser Gln Pro Leu Gly Cys Arg Phe
    275                 280                 285 gca atg cca tag                                                    876
Ala Met Pro
    290

<210> SEQ ID NO 85
<211> LENGTH: 291
<212> TYPE: PRT
<213> ORGANISM: Artificial
<220> FEATURE:
<223> OTHER INFORMATION: Synthetic Construct

<400> SEQUENCE: 85

Met Phe Ser His Leu Pro Phe Asp Cys Val Leu Leu Leu Leu Leu Leu
1               5                   10                  15

Leu Leu Thr Arg Ser Ser Glu Val Glu Tyr Arg Ala Glu Val Gly Gln
            20                  25                  30

Asn Ala Tyr Leu Pro Cys Phe Tyr Thr Pro Ala Ala Pro Gly Asn Leu
        35                  40                  45

Val Pro Val Cys Trp Gly Lys Gly Ala Cys Pro Val Phe Glu Cys Gly
    50                  55                  60

Asn Val Val Leu Arg Thr Asp Glu Arg Asp Val Asn Tyr Trp Thr Ser
65                  70                  75                  80

Arg Tyr Trp Leu Asn Gly Asp Phe Arg Lys Gly Asp Val Ser Leu Thr
                85                  90                  95

Ile Glu Asn Val Thr Leu Ala Asp Ser Gly Ile Tyr Cys Cys Arg Ile
            100                 105                 110

Gln Ile Pro Gly Ile Met Asn Asp Glu Lys Phe Asn Leu Lys Leu Val
        115                 120                 125

Ile Lys Pro Ala Lys Val Thr Pro Ala Gln Thr Ala His Gly Asp Ser
    130                 135                 140

Thr Thr Ala Ser Pro Arg Thr Leu Thr Thr Glu Arg Asn Gly Ser Glu
145                 150                 155                 160

Thr Gln Thr Leu Val Thr Leu His Asn Asn Gly Thr Lys Ile Ser
                165                 170                 175

Thr Trp Ala Asp Glu Ile Lys Asp Ser Gly Glu Thr Ile Arg Ile Gly
            180                 185                 190

Ile Tyr Ile Gly Ala Gly Ile Cys Ala Gly Leu Ala Leu Ala Leu Ile
        195                 200                 205

Phe Gly Ala Leu Ile Phe Lys Trp Tyr Ser His Ser Lys Glu Lys Ile
    210                 215                 220

Gln Asn Leu Ser Leu Ile Ser Leu Ala Asn Leu Pro Pro Ser Gly Leu
225                 230                 235                 240

Ala Asn Ala Val Ala Glu Gly Ile Arg Ser Glu Glu Asn Ile Tyr Thr
                245                 250                 255

Ile Glu Glu Asn Val Tyr Glu Val Glu Glu Pro Asn Glu Tyr Tyr Cys
            260                 265                 270

Tyr Val Ser Ser Arg Gln Gln Pro Ser Gln Pro Leu Gly Cys Arg Phe
        275                 280                 285

Ala Met Pro
    290
```

<210> SEQ ID NO 86
<211> LENGTH: 35
<212> TYPE: DNA
<213> ORGANISM: Artificial
<220> FEATURE:
<223> OTHER INFORMATION: Primer hTIM3chimera22-47F1

<400> SEQUENCE: 86
acatctggga cacttgtgcc cgtctgctgg ggcaa                       35

<210> SEQ ID NO 87
<211> LENGTH: 35
<212> TYPE: DNA
<213> ORGANISM: Artificial
<220> FEATURE:
<223> OTHER INFORMATION: Primer hTIM3chimera22-47R1

<400> SEQUENCE: 87
ataaccatct tccaaggacc ttgtaagtag tagca                       35

<210> SEQ ID NO 88
<211> LENGTH: 35
<212> TYPE: DNA
<213> ORGANISM: Artificial
<220> FEATURE:
<223> OTHER INFORMATION: Primer hTIM3chimera22-47F2

<400> SEQUENCE: 88
ctgcagttac actctaccta catctgggac acttg                       35

<210> SEQ ID NO 89
<211> LENGTH: 35
<212> TYPE: DNA
<213> ORGANISM: Artificial
<220> FEATURE:
<223> OTHER INFORMATION: Primer hTIM3chimera22-47R2

<400> SEQUENCE: 89
ttaccaacct caaccttata accatcttcc aagga                       35

<210> SEQ ID NO 90
<211> LENGTH: 35
<212> TYPE: DNA
<213> ORGANISM: Artificial
<220> FEATURE:
<223> OTHER INFORMATION: Primer hTIM3chimera22-47F3

<400> SEQUENCE: 90
aaatgcctat ctgccctgca gttacactct accta                       35

<210> SEQ ID NO 91
<211> LENGTH: 33
<212> TYPE: DNA
<213> ORGANISM: Artificial
<220> FEATURE:
<223> OTHER INFORMATION: Primer hTIM3chimera22-47R3

<400> SEQUENCE: 91
ggcagatagg cattttacc aacctcaacc tta                          33

<210> SEQ ID NO 92
<211> LENGTH: 906
<212> TYPE: DNA
<213> ORGANISM: Artificial
<220> FEATURE:

<223> OTHER INFORMATION: TIM-3 chimera 22-47/pEF6 Myc_HisC
<220> FEATURE:
<221> NAME/KEY: CDS
<222> LOCATION: (1)..(906)

<400> SEQUENCE: 92

```
atg ttt tca cat ctt ccc ttt gac tgt gtc ctg ctg ctg ctg cta        48
Met Phe Ser His Leu Pro Phe Asp Cys Val Leu Leu Leu Leu Leu
1               5                   10                  15 cta ctt aca agg tcc ttg gaa gat ggt tat aag gtt gag gtt ggt aaa    96
Leu Leu Thr Arg Ser Leu Glu Asp Gly Tyr Lys Val Glu Val Gly Lys
            20                  25                  30 aat gcc tat ctg ccc tgc agt tac act cta cct aca tct ggg aca ctt   144
Asn Ala Tyr Leu Pro Cys Ser Tyr Thr Leu Pro Thr Ser Gly Thr Leu
        35                  40                  45 gtg ccc gtc tgc tgg ggc aaa gga gcc tgt cct gtg ttt gaa tgt ggc   192
Val Pro Val Cys Trp Gly Lys Gly Ala Cys Pro Val Phe Glu Cys Gly
    50                  55                  60 aac gtg gtg ctc agg act gat gaa agg gat gtg aat tat tgg aca tcc   240
Asn Val Val Leu Arg Thr Asp Glu Arg Asp Val Asn Tyr Trp Thr Ser
65                  70                  75                  80 aga tac tgg cta aat ggg gat ttc cgc aaa gga gat gtg tcc ctg acc   288
Arg Tyr Trp Leu Asn Gly Asp Phe Arg Lys Gly Asp Val Ser Leu Thr
                85                  90                  95 ata gag aat gtg act cta gca gac agt ggg atc tac tgc tgc cgg atc   336
Ile Glu Asn Val Thr Leu Ala Asp Ser Gly Ile Tyr Cys Cys Arg Ile
            100                 105                 110 caa atc cca ggc ata atg aat gat gaa aaa ttt aac ctg aag ttg gtc   384
Gln Ile Pro Gly Ile Met Asn Asp Glu Lys Phe Asn Leu Lys Leu Val
        115                 120                 125 atc aaa cca gcc aag gtc acc cct gca ccg act cgg cag aga gac ttc   432
Ile Lys Pro Ala Lys Val Thr Pro Ala Pro Thr Arg Gln Arg Asp Phe
    130                 135                 140 act gca gcc ttt cca agg atg ctt acc acc agg gga cat ggc cca gca   480
Thr Ala Ala Phe Pro Arg Met Leu Thr Thr Arg Gly His Gly Pro Ala
145                 150                 155                 160 gag aca cag aca ctg ggg agc ctc cct gat ata aat cta aca caa ata   528
Glu Thr Gln Thr Leu Gly Ser Leu Pro Asp Ile Asn Leu Thr Gln Ile
                165                 170                 175 tcc aca ttg gcc aat gag tta cgg gac tct aga ttg gcc aat gac tta   576
Ser Thr Leu Ala Asn Glu Leu Arg Asp Ser Arg Leu Ala Asn Asp Leu
            180                 185                 190 cgg gac tct gga gca acc atc aga ata ggc atc tac atc gga gca ggg   624
Arg Asp Ser Gly Ala Thr Ile Arg Ile Gly Ile Tyr Ile Gly Ala Gly
        195                 200                 205 atc tgt gct ggg ctg gct ctg gct ctt atc ttc ggc gct tta att ttc   672
Ile Cys Ala Gly Leu Ala Leu Ala Leu Ile Phe Gly Ala Leu Ile Phe
    210                 215                 220 aaa tgg tat tct cat agc aaa gag aag ata cag aat tta agc ctc atc   720
Lys Trp Tyr Ser His Ser Lys Glu Lys Ile Gln Asn Leu Ser Leu Ile
225                 230                 235                 240 tct ttg gcc aac ctc cct ccc tca gga ttg gca aat gca gta gca gag   768
Ser Leu Ala Asn Leu Pro Pro Ser Gly Leu Ala Asn Ala Val Ala Glu
                245                 250                 255 gga att cgc tca gaa gaa aac atc tat acc att gaa gag aac gta tat   816
Gly Ile Arg Ser Glu Glu Asn Ile Tyr Thr Ile Glu Glu Asn Val Tyr
            260                 265                 270 gaa gtg gag gag ccc aat gag tat tat tgc tat gtc agc agc agg cag   864
Glu Val Glu Glu Pro Asn Glu Tyr Tyr Cys Tyr Val Ser Ser Arg Gln
        275                 280                 285
```

```
caa ccc tca caa cct ttg ggt tgt cgc ttt gca atg cca tag          906
Gln Pro Ser Gln Pro Leu Gly Cys Arg Phe Ala Met Pro
290             295                 300
```

<210> SEQ ID NO 93
<211> LENGTH: 301
<212> TYPE: PRT
<213> ORGANISM: Artificial
<220> FEATURE:
<223> OTHER INFORMATION: Synthetic Construct

<400> SEQUENCE: 93

```
Met Phe Ser His Leu Pro Phe Asp Cys Val Leu Leu Leu Leu Leu
1               5                   10                  15

Leu Leu Thr Arg Ser Leu Glu Asp Gly Tyr Lys Val Glu Val Gly Lys
                20                  25                  30

Asn Ala Tyr Leu Pro Cys Ser Tyr Thr Leu Pro Thr Ser Gly Thr Leu
            35                  40                  45

Val Pro Val Cys Trp Gly Lys Gly Ala Cys Pro Val Phe Glu Cys Gly
50                  55                  60

Asn Val Val Leu Arg Thr Asp Glu Arg Asp Val Asn Tyr Trp Thr Ser
65                  70                  75                  80

Arg Tyr Trp Leu Asn Gly Asp Phe Arg Lys Gly Asp Val Ser Leu Thr
                85                  90                  95

Ile Glu Asn Val Thr Leu Ala Asp Ser Gly Ile Tyr Cys Cys Arg Ile
            100                 105                 110

Gln Ile Pro Gly Ile Met Asn Asp Glu Lys Phe Asn Leu Lys Leu Val
        115                 120                 125

Ile Lys Pro Ala Lys Val Thr Pro Ala Pro Thr Arg Gln Arg Asp Phe
130                 135                 140

Thr Ala Ala Phe Pro Arg Met Leu Thr Thr Arg Gly His Gly Pro Ala
145                 150                 155                 160

Glu Thr Gln Thr Leu Gly Ser Leu Pro Asp Ile Asn Leu Thr Gln Ile
                165                 170                 175

Ser Thr Leu Ala Asn Glu Leu Arg Asp Ser Arg Leu Ala Asn Asp Leu
            180                 185                 190

Arg Asp Ser Gly Ala Thr Ile Arg Ile Gly Ile Tyr Ile Gly Ala Gly
        195                 200                 205

Ile Cys Ala Gly Leu Ala Leu Ala Leu Ile Phe Gly Ala Leu Ile Phe
210                 215                 220

Lys Trp Tyr Ser His Ser Lys Glu Lys Ile Gln Asn Leu Ser Leu Ile
225                 230                 235                 240

Ser Leu Ala Asn Leu Pro Pro Ser Gly Leu Ala Asn Ala Val Ala Glu
                245                 250                 255

Gly Ile Arg Ser Glu Glu Asn Ile Tyr Thr Ile Glu Glu Asn Val Tyr
            260                 265                 270

Glu Val Glu Glu Pro Asn Glu Tyr Tyr Cys Tyr Val Ser Ser Arg Gln
        275                 280                 285

Gln Pro Ser Gln Pro Leu Gly Cys Arg Phe Ala Met Pro
290                 295                 300
```

<210> SEQ ID NO 94
<211> LENGTH: 35
<212> TYPE: DNA
<213> ORGANISM: Artificial
<220> FEATURE:
<223> OTHER INFORMATION: Primer hTIM3chimera57-66F

<400> SEQUENCE: 94
acagtgtacc aatgaggtgc tcaggactga tgaaa    35

<210> SEQ ID NO 95
<211> LENGTH: 33
<212> TYPE: DNA
<213> ORGANISM: Artificial
<220> FEATURE:
<223> OTHER INFORMATION: Primer hTIM3chimera57-66R

<400> SEQUENCE: 95
gaccaaggac agaatccttt gccccagcag acg    33

<210> SEQ ID NO 96
<211> LENGTH: 906
<212> TYPE: DNA
<213> ORGANISM: Artificial
<220> FEATURE:
<223> OTHER INFORMATION: TIM-3 chimera 57-66/pEF6 Myc_HisC
<220> FEATURE:
<221> NAME/KEY: CDS
<222> LOCATION: (1)..(906)

<400> SEQUENCE: 96

```
atg ttt tca cat ctt ccc ttt gac tgt gtc ctg ctg ctg ctg cta         48
Met Phe Ser His Leu Pro Phe Asp Cys Val Leu Leu Leu Leu Leu
1               5                   10                  15 cta ctt aca agg tcc tca gaa gtg gaa tac aga gcg gag gtc ggt cag     96
Leu Leu Thr Arg Ser Ser Glu Val Glu Tyr Arg Ala Glu Val Gly Gln
            20                  25                  30 aat gcc tat ctg ccc tgc ttc tac acc cca gcc gcc cca ggg aac ctc    144
Asn Ala Tyr Leu Pro Cys Phe Tyr Thr Pro Ala Ala Pro Gly Asn Leu
        35                  40                  45 gtg ccc gtc tgc tgg ggc aaa gga ttc tgt cct tgg tca cag tgt acc    192
Val Pro Val Cys Trp Gly Lys Gly Phe Cys Pro Trp Ser Gln Cys Thr
    50                  55                  60 aat gag gtg ctc agg act gat gaa agg gat gtg aat tat tgg aca tcc    240
Asn Glu Val Leu Arg Thr Asp Glu Arg Asp Val Asn Tyr Trp Thr Ser
65                  70                  75                  80 aga tac tgg cta aat ggg gat ttc cgc aaa gga gat gtg tcc ctg acc    288
Arg Tyr Trp Leu Asn Gly Asp Phe Arg Lys Gly Asp Val Ser Leu Thr
                85                  90                  95 ata gag aat gtg act cta gca gac agt ggg atc tac tgc tgc cgg atc   336
Ile Glu Asn Val Thr Leu Ala Asp Ser Gly Ile Tyr Cys Cys Arg Ile
            100                 105                 110 caa atc cca ggc ata atg aat gat gaa aaa ttt aac ctg aag ttg gtc   384
Gln Ile Pro Gly Ile Met Asn Asp Glu Lys Phe Asn Leu Lys Leu Val
        115                 120                 125 atc aaa cca gcc aag gtc acc cct gca ccg act cgg cag aga gac ttc   432
Ile Lys Pro Ala Lys Val Thr Pro Ala Pro Thr Arg Gln Arg Asp Phe
    130                 135                 140 act gca gcc ttt cca agg atg ctt acc acc agg gga cat ggc cca gca   480
Thr Ala Ala Phe Pro Arg Met Leu Thr Thr Arg Gly His Gly Pro Ala
145                 150                 155                 160 gag aca cag aca ctg ggg agc ctc cct gat ata aat cta aca caa ata   528
Glu Thr Gln Thr Leu Gly Ser Leu Pro Asp Ile Asn Leu Thr Gln Ile
                165                 170                 175 tcc aca ttg gcc aat gag tta cgg gac tct aga ttg gcc aat gac tta   576
Ser Thr Leu Ala Asn Glu Leu Arg Asp Ser Arg Leu Ala Asn Asp Leu
            180                 185                 190 cgg gac tct gga gca acc atc aga ata ggc atc tac atc gga gca ggg   624
Arg Asp Ser Gly Ala Thr Ile Arg Ile Gly Ile Tyr Ile Gly Ala Gly
```

|  |  |  |  |  |  |  |  |  |  |  |  |  |  |  |  |
|---|---|---|---|---|---|---|---|---|---|---|---|---|---|---|---|
|  | 195 |  |  |  | 200 |  |  |  |  | 205 |  |  |  |  |  |
| atc | tgt | gct | ggg | ctg | gct | ctg | gct | ctt | atc | ttc | ggc | gct | tta | att | ttc | 672 |
| Ile | Cys | Ala | Gly | Leu | Ala | Leu | Ala | Leu | Ile | Phe | Gly | Ala | Leu | Ile | Phe |
|  | 210 |  |  |  | 215 |  |  |  |  | 220 |  |  |  |  |  |
| aaa | tgg | tat | tct | cat | agc | aaa | gag | aag | ata | cag | aat | tta | agc | ctc | atc | 720 |
| Lys | Trp | Tyr | Ser | His | Ser | Lys | Glu | Lys | Ile | Gln | Asn | Leu | Ser | Leu | Ile |
| 225 |  |  |  |  | 230 |  |  |  |  | 235 |  |  |  |  | 240 |
| tct | ttg | gcc | aac | ctc | cct | ccc | tca | gga | ttg | gca | aat | gca | gta | gca | gag | 768 |
| Ser | Leu | Ala | Asn | Leu | Pro | Pro | Ser | Gly | Leu | Ala | Asn | Ala | Val | Ala | Glu |
|  |  |  |  | 245 |  |  |  |  | 250 |  |  |  |  | 255 |  |
| gga | att | cgc | tca | gaa | gaa | aac | atc | tat | acc | att | gaa | gag | aac | gta | tat | 816 |
| Gly | Ile | Arg | Ser | Glu | Glu | Asn | Ile | Tyr | Thr | Ile | Glu | Glu | Asn | Val | Tyr |
|  |  | 260 |  |  |  |  | 265 |  |  |  |  | 270 |  |  |  |
| gaa | gtg | gag | gag | ccc | aat | gag | tat | tat | tgc | tat | gtc | agc | agc | agg | cag | 864 |
| Glu | Val | Glu | Glu | Pro | Asn | Glu | Tyr | Tyr | Cys | Tyr | Val | Ser | Ser | Arg | Gln |
|  |  | 275 |  |  |  |  | 280 |  |  |  |  | 285 |  |  |  |
| caa | ccc | tca | caa | cct | ttg | ggt | tgt | cgc | ttt | gca | atg | cca | tag |  |  | 906 |
| Gln | Pro | Ser | Gln | Pro | Leu | Gly | Cys | Arg | Phe | Ala | Met | Pro |  |  |  |
|  | 290 |  |  |  |  | 295 |  |  |  |  | 300 |  |  |  |  |

<210> SEQ ID NO 97
<211> LENGTH: 301
<212> TYPE: PRT
<213> ORGANISM: Artificial
<220> FEATURE:
<223> OTHER INFORMATION: Synthetic Construct

<400> SEQUENCE: 97

Met Phe Ser His Leu Pro Phe Asp Cys Val Leu Leu Leu Leu Leu Leu
1               5                   10                  15

Leu Leu Thr Arg Ser Ser Glu Val Glu Tyr Arg Ala Glu Val Gly Gln
            20                  25                  30

Asn Ala Tyr Leu Pro Cys Phe Tyr Thr Pro Ala Ala Pro Gly Asn Leu
        35                  40                  45

Val Pro Val Cys Trp Gly Lys Gly Phe Cys Pro Trp Ser Gln Cys Thr
    50                  55                  60

Asn Glu Val Leu Arg Thr Asp Glu Arg Asp Val Asn Tyr Trp Thr Ser
65                  70                  75                  80

Arg Tyr Trp Leu Asn Gly Asp Phe Arg Lys Gly Asp Val Ser Leu Thr
                85                  90                  95

Ile Glu Asn Val Thr Leu Ala Asp Ser Gly Ile Tyr Cys Cys Arg Ile
            100                 105                 110

Gln Ile Pro Gly Ile Met Asn Asp Glu Lys Phe Asn Leu Lys Leu Val
        115                 120                 125

Ile Lys Pro Ala Lys Val Thr Pro Ala Pro Thr Arg Gln Arg Asp Phe
    130                 135                 140

Thr Ala Ala Phe Pro Arg Met Leu Thr Thr Arg Gly His Gly Pro Ala
145                 150                 155                 160

Glu Thr Gln Thr Leu Gly Ser Leu Pro Asp Ile Asn Leu Thr Gln Ile
                165                 170                 175

Ser Thr Leu Ala Asn Glu Leu Arg Asp Ser Arg Leu Ala Asn Asp Leu
            180                 185                 190

Arg Asp Ser Gly Ala Thr Ile Arg Ile Gly Ile Tyr Ile Gly Ala Gly
        195                 200                 205

Ile Cys Ala Gly Leu Ala Leu Ala Leu Ile Phe Gly Ala Leu Ile Phe
    210                 215                 220

Lys Trp Tyr Ser His Ser Lys Glu Lys Ile Gln Asn Leu Ser Leu Ile

```
                    225                 230                 235                 240

Ser Leu Ala Asn Leu Pro Pro Ser Gly Leu Ala Asn Ala Val Ala Glu
                245                 250                 255

Gly Ile Arg Ser Glu Glu Asn Ile Tyr Thr Ile Glu Glu Asn Val Tyr
            260                 265                 270

Glu Val Glu Glu Pro Asn Glu Tyr Tyr Cys Tyr Val Ser Ser Arg Gln
        275                 280                 285

Gln Pro Ser Gln Pro Leu Gly Cys Arg Phe Ala Met Pro
    290                 295                 300

<210> SEQ ID NO 98
<211> LENGTH: 34
<212> TYPE: DNA
<213> ORGANISM: Artificial
<220> FEATURE:
<223> OTHER INFORMATION: Primer hTIM3chimera67-105F

<400> SEQUENCE: 98
ctggatgacc atgggatcta ctgctgccgg atcc                              34

<210> SEQ ID NO 99
<211> LENGTH: 33
<212> TYPE: DNA
<213> ORGANISM: Artificial
<220> FEATURE:
<223> OTHER INFORMATION: Primer hTIM3chimera67-105R

<400> SEQUENCE: 99
atcagttctg agcaacacgt tgccacattc aaa                               33

<210> SEQ ID NO 100
<211> LENGTH: 20
<212> TYPE: DNA
<213> ORGANISM: Artificial
<220> FEATURE:
<223> OTHER INFORMATION: Primer mTIM3chimera67-105F

<400> SEQUENCE: 100
ttgctcagaa ctgatgaaag                                              20

<210> SEQ ID NO 101
<211> LENGTH: 20
<212> TYPE: DNA
<213> ORGANISM: Artificial
<220> FEATURE:
<223> OTHER INFORMATION: Primer mTIM3chimera67-105R

<400> SEQUENCE: 101
cccatggtca tccagagtca                                              20

<210> SEQ ID NO 102
<211> LENGTH: 909
<212> TYPE: DNA
<213> ORGANISM: Artificial
<220> FEATURE:
<223> OTHER INFORMATION: TIM-3 chimera 67-105/pEF6 Myc_HisC
<220> FEATURE:
<221> NAME/KEY: CDS
<222> LOCATION: (1)..(909)

<400> SEQUENCE: 102 atg ttt tca cat ctt ccc ttt gac tgt gtc ctg ctg ctg ctg cta        48
Met Phe Ser His Leu Pro Phe Asp Cys Val Leu Leu Leu Leu Leu
1               5                   10                  15
```

| | | | | | | | | | | | | | | | | |
|---|---|---|---|---|---|---|---|---|---|---|---|---|---|---|---|---|
| cta | ctt | aca | agg | tcc | tca | gaa | gtg | gaa | tac | aga | gcg | gag | gtc | ggt | cag | 96 |
| Leu | Leu | Thr | Arg | Ser | Ser | Glu | Val | Glu | Tyr | Arg | Ala | Glu | Val | Gly | Gln | |
| | | | 20 | | | | 25 | | | | | 30 | | | | |
| aat | gcc | tat | ctg | ccc | tgc | ttc | tac | acc | cca | gcc | gcc | cca | ggg | aac | ctc | 144 |
| Asn | Ala | Tyr | Leu | Pro | Cys | Phe | Tyr | Thr | Pro | Ala | Ala | Pro | Gly | Asn | Leu | |
| | | | 35 | | | | 40 | | | | | 45 | | | | |
| gtg | ccc | gtc | tgc | tgg | ggc | aaa | gga | gcc | tgt | cct | gtg | ttt | gaa | tgt | ggc | 192 |
| Val | Pro | Val | Cys | Trp | Gly | Lys | Gly | Ala | Cys | Pro | Val | Phe | Glu | Cys | Gly | |
| | 50 | | | | | 55 | | | | | 60 | | | | | |
| aac | gtg | ttg | ctc | aga | act | gat | gaa | aga | aat | gtg | aca | tat | cag | aaa | tcc | 240 |
| Asn | Val | Leu | Leu | Arg | Thr | Asp | Glu | Arg | Asn | Val | Thr | Tyr | Gln | Lys | Ser | |
| 65 | | | | | 70 | | | | | 75 | | | | | 80 | |
| agc | aga | tac | cag | cta | aag | ggc | gat | ctc | aac | aaa | gga | gat | gtg | tct | ctg | 288 |
| Ser | Arg | Tyr | Gln | Leu | Lys | Gly | Asp | Leu | Asn | Lys | Gly | Asp | Val | Ser | Leu | |
| | | | | 85 | | | | | 90 | | | | | 95 | | |
| atc | ata | aag | aat | gtg | act | ctg | gat | gac | cat | ggg | atc | tac | tgc | tgc | cgg | 336 |
| Ile | Ile | Lys | Asn | Val | Thr | Leu | Asp | Asp | His | Gly | Ile | Tyr | Cys | Cys | Arg | |
| | | | 100 | | | | 105 | | | | | 110 | | | | |
| atc | caa | atc | cca | ggc | ata | atg | aat | gat | gaa | aaa | ttt | aac | ctg | aag | ttg | 384 |
| Ile | Gln | Ile | Pro | Gly | Ile | Met | Asn | Asp | Glu | Lys | Phe | Asn | Leu | Lys | Leu | |
| | | | 115 | | | | 120 | | | | | 125 | | | | |
| gtc | atc | aaa | cca | gcc | aag | gtc | acc | cct | gca | ccg | act | cgg | cag | aga | gac | 432 |
| Val | Ile | Lys | Pro | Ala | Lys | Val | Thr | Pro | Ala | Pro | Thr | Arg | Gln | Arg | Asp | |
| | 130 | | | | | 135 | | | | | 140 | | | | | |
| ttc | act | gca | gcc | ttt | cca | agg | atg | ctt | acc | acc | agg | gga | cat | ggc | cca | 480 |
| Phe | Thr | Ala | Ala | Phe | Pro | Arg | Met | Leu | Thr | Thr | Arg | Gly | His | Gly | Pro | |
| 145 | | | | | 150 | | | | | 155 | | | | | 160 | |
| gca | gag | aca | cag | aca | ctg | ggg | agc | ctc | cct | gat | ata | aat | cta | aca | caa | 528 |
| Ala | Glu | Thr | Gln | Thr | Leu | Gly | Ser | Leu | Pro | Asp | Ile | Asn | Leu | Thr | Gln | |
| | | | | 165 | | | | | 170 | | | | | 175 | | |
| ata | tcc | aca | ttg | gcc | aat | gag | tta | cgg | gac | tct | aga | ttg | gcc | aat | gac | 576 |
| Ile | Ser | Thr | Leu | Ala | Asn | Glu | Leu | Arg | Asp | Ser | Arg | Leu | Ala | Asn | Asp | |
| | | | 180 | | | | 185 | | | | | 190 | | | | |
| tta | cgg | gac | tct | gga | gca | acc | atc | aga | ata | ggc | atc | tac | atc | gga | gca | 624 |
| Leu | Arg | Asp | Ser | Gly | Ala | Thr | Ile | Arg | Ile | Gly | Ile | Tyr | Ile | Gly | Ala | |
| | | | 195 | | | | 200 | | | | | 205 | | | | |
| ggg | atc | tgt | gct | ggg | ctg | gct | ctg | gct | ctt | atc | ttc | ggc | gct | tta | att | 672 |
| Gly | Ile | Cys | Ala | Gly | Leu | Ala | Leu | Ala | Leu | Ile | Phe | Gly | Ala | Leu | Ile | |
| | 210 | | | | | 215 | | | | | 220 | | | | | |
| ttc | aaa | tgg | tat | tct | cat | agc | aaa | gag | aag | ata | cag | aat | tta | agc | ctc | 720 |
| Phe | Lys | Trp | Tyr | Ser | His | Ser | Lys | Glu | Lys | Ile | Gln | Asn | Leu | Ser | Leu | |
| 225 | | | | | 230 | | | | | 235 | | | | | 240 | |
| atc | tct | ttg | gcc | aac | ctc | cct | ccc | tca | gga | ttg | gca | aat | gca | gta | gca | 768 |
| Ile | Ser | Leu | Ala | Asn | Leu | Pro | Pro | Ser | Gly | Leu | Ala | Asn | Ala | Val | Ala | |
| | | | | 245 | | | | | 250 | | | | | 255 | | |
| gag | gga | att | cgc | tca | gaa | gaa | aac | atc | tat | acc | att | gaa | gag | aac | gta | 816 |
| Glu | Gly | Ile | Arg | Ser | Glu | Glu | Asn | Ile | Tyr | Thr | Ile | Glu | Glu | Asn | Val | |
| | | | 260 | | | | 265 | | | | | 270 | | | | |
| tat | gaa | gtg | gag | gag | ccc | aat | gag | tat | tat | tgc | tat | gtc | agc | agc | agg | 864 |
| Tyr | Glu | Val | Glu | Glu | Pro | Asn | Glu | Tyr | Tyr | Cys | Tyr | Val | Ser | Ser | Arg | |
| | | | 275 | | | | 280 | | | | | 285 | | | | |
| cag | caa | ccc | tca | caa | cct | ttg | ggt | tgt | cgc | ttt | gca | atg | cca | tag | | 909 |
| Gln | Gln | Pro | Ser | Gln | Pro | Leu | Gly | Cys | Arg | Phe | Ala | Met | Pro | | | |
| | 290 | | | | | 295 | | | | | 300 | | | | | |

<210> SEQ ID NO 103
<211> LENGTH: 302
<212> TYPE: PRT
<213> ORGANISM: Artificial
<220> FEATURE:
<223> OTHER INFORMATION: Synthetic Construct

<400> SEQUENCE: 103

```
Met Phe Ser His Leu Pro Phe Asp Cys Val Leu Leu Leu Leu Leu
1               5                   10                  15

Leu Leu Thr Arg Ser Ser Glu Val Glu Tyr Arg Ala Glu Val Gly Gln
            20                  25                  30

Asn Ala Tyr Leu Pro Cys Phe Tyr Thr Pro Ala Ala Pro Gly Asn Leu
            35                  40                  45

Val Pro Val Cys Trp Gly Lys Gly Ala Cys Pro Val Phe Glu Cys Gly
50                  55                  60

Asn Val Leu Leu Arg Thr Asp Glu Arg Asn Val Thr Tyr Gln Lys Ser
65                  70                  75                  80

Ser Arg Tyr Gln Leu Lys Gly Asp Leu Asn Lys Gly Asp Val Ser Leu
                85                  90                  95

Ile Ile Lys Asn Val Thr Leu Asp Asp His Gly Ile Tyr Cys Cys Arg
            100                 105                 110

Ile Gln Ile Pro Gly Ile Met Asn Asp Glu Lys Phe Asn Leu Lys Leu
            115                 120                 125

Val Ile Lys Pro Ala Lys Val Thr Pro Ala Pro Thr Arg Gln Arg Asp
130                 135                 140

Phe Thr Ala Ala Phe Pro Arg Met Leu Thr Thr Arg Gly His Gly Pro
145                 150                 155                 160

Ala Glu Thr Gln Thr Leu Gly Ser Leu Pro Asp Ile Asn Leu Thr Gln
                165                 170                 175

Ile Ser Thr Leu Ala Asn Glu Leu Arg Asp Ser Arg Leu Ala Asn Asp
            180                 185                 190

Leu Arg Asp Ser Gly Ala Thr Ile Arg Ile Gly Ile Tyr Ile Gly Ala
            195                 200                 205

Gly Ile Cys Ala Gly Leu Ala Leu Ala Leu Ile Phe Gly Ala Leu Ile
            210                 215                 220

Phe Lys Trp Tyr Ser His Ser Lys Glu Lys Ile Gln Asn Leu Ser Leu
225                 230                 235                 240

Ile Ser Leu Ala Asn Leu Pro Pro Ser Gly Leu Ala Asn Ala Val Ala
                245                 250                 255

Glu Gly Ile Arg Ser Glu Glu Asn Ile Tyr Thr Ile Glu Glu Asn Val
            260                 265                 270

Tyr Glu Val Glu Glu Pro Asn Glu Tyr Tyr Cys Tyr Val Ser Ser Arg
            275                 280                 285

Gln Gln Pro Ser Gln Pro Leu Gly Cys Arg Phe Ala Met Pro
290                 295                 300
```

<210> SEQ ID NO 104
<211> LENGTH: 35
<212> TYPE: DNA
<213> ORGANISM: Artificial
<220> FEATURE:
<223> OTHER INFORMATION: Primer hTIM3chimera74-81F

<400> SEQUENCE: 104
gtgacatatc agaaatcctc cagatactgg ctaaa    35

<210> SEQ ID NO 105
<211> LENGTH: 35
<212> TYPE: DNA
<213> ORGANISM: Artificial
<220> FEATURE:
<223> OTHER INFORMATION: Primer hTIM3chimera74-81R

<400> SEQUENCE: 105
tttctgatat gtcacattcc tttcatcagt cctga     35

<210> SEQ ID NO 106
<211> LENGTH: 909
<212> TYPE: DNA
<213> ORGANISM: Artificial
<220> FEATURE:
<223> OTHER INFORMATION: TIM-3 chimera 74-81/pEF6 Myc_HisC
<220> FEATURE:
<221> NAME/KEY: CDS
<222> LOCATION: (1)..(909)

<400> SEQUENCE: 106

| | | | | | | | | | | | | | | | | |
|---|---|---|---|---|---|---|---|---|---|---|---|---|---|---|---|---|
| atg | ttt | tca | cat | ctt | ccc | ttt | gac | tgt | gtc | ctg | ctg | ctg | ctg | cta | | 48 |
| Met | Phe | Ser | His | Leu | Pro | Phe | Asp | Cys | Val | Leu | Leu | Leu | Leu | Leu | | |
| 1 | | | | 5 | | | | | 10 | | | | | 15 | | |
| cta | ctt | aca | agg | tcc | tca | gaa | gtg | gaa | tac | aga | gcg | gag | gtc | ggt | cag | 96 |
| Leu | Leu | Thr | Arg | Ser | Ser | Glu | Val | Glu | Tyr | Arg | Ala | Glu | Val | Gly | Gln | |
| | | | 20 | | | | | 25 | | | | | 30 | | | |
| aat | gcc | tat | ctg | ccc | tgc | ttc | tac | acc | cca | gcc | gcc | cca | ggg | aac | ctc | 144 |
| Asn | Ala | Tyr | Leu | Pro | Cys | Phe | Tyr | Thr | Pro | Ala | Ala | Pro | Gly | Asn | Leu | |
| | | 35 | | | | | 40 | | | | | 45 | | | | |
| gtg | ccc | gtc | tgc | tgg | ggc | aaa | gga | gcc | tgt | cct | gtg | ttt | gaa | tgt | ggc | 192 |
| Val | Pro | Val | Cys | Trp | Gly | Lys | Gly | Ala | Cys | Pro | Val | Phe | Glu | Cys | Gly | |
| 50 | | | | | 55 | | | | | 60 | | | | | | |
| aac | gtg | gtg | ctc | agg | act | gat | gaa | agg | aat | gtg | aca | tat | cag | aaa | tcc | 240 |
| Asn | Val | Val | Leu | Arg | Thr | Asp | Glu | Arg | Asn | Val | Thr | Tyr | Gln | Lys | Ser | |
| 65 | | | | | 70 | | | | | 75 | | | | | 80 | |
| tcc | aga | tac | tgg | cta | aat | ggg | gat | ttc | cgc | aaa | gga | gat | gtg | tcc | ctg | 288 |
| Ser | Arg | Tyr | Trp | Leu | Asn | Gly | Asp | Phe | Arg | Lys | Gly | Asp | Val | Ser | Leu | |
| | | | | 85 | | | | | 90 | | | | | 95 | | |
| acc | ata | gag | aat | gtg | act | cta | gca | gac | agt | ggg | atc | tac | tgc | tgc | cgg | 336 |
| Thr | Ile | Glu | Asn | Val | Thr | Leu | Ala | Asp | Ser | Gly | Ile | Tyr | Cys | Cys | Arg | |
| | | | 100 | | | | | 105 | | | | | 110 | | | |
| atc | caa | atc | cca | ggc | ata | atg | aat | gat | gaa | aaa | ttt | aac | ctg | aag | ttg | 384 |
| Ile | Gln | Ile | Pro | Gly | Ile | Met | Asn | Asp | Glu | Lys | Phe | Asn | Leu | Lys | Leu | |
| | | 115 | | | | | 120 | | | | | 125 | | | | |
| gtc | atc | aaa | cca | gcc | aag | gtc | acc | cct | gca | ccg | act | cgg | cag | aga | gac | 432 |
| Val | Ile | Lys | Pro | Ala | Lys | Val | Thr | Pro | Ala | Pro | Thr | Arg | Gln | Arg | Asp | |
| 130 | | | | | 135 | | | | | 140 | | | | | | |
| ttc | act | gca | gcc | ttt | cca | agg | atg | ctt | acc | acc | agg | gga | cat | ggc | cca | 480 |
| Phe | Thr | Ala | Ala | Phe | Pro | Arg | Met | Leu | Thr | Thr | Arg | Gly | His | Gly | Pro | |
| 145 | | | | | 150 | | | | | 155 | | | | | 160 | |
| gca | gag | aca | cag | aca | ctg | ggg | agc | ctc | cct | gat | ata | aat | cta | aca | caa | 528 |
| Ala | Glu | Thr | Gln | Thr | Leu | Gly | Ser | Leu | Pro | Asp | Ile | Asn | Leu | Thr | Gln | |
| | | | | 165 | | | | | 170 | | | | | 175 | | |
| ata | tcc | aca | ttg | gcc | aat | gag | tta | cgg | gac | tct | aga | ttg | gcc | aat | gac | 576 |
| Ile | Ser | Thr | Leu | Ala | Asn | Glu | Leu | Arg | Asp | Ser | Arg | Leu | Ala | Asn | Asp | |
| | | | 180 | | | | | 185 | | | | | 190 | | | |
| tta | cgg | gac | tct | gga | gca | acc | atc | aga | ata | ggc | atc | tac | atc | gga | gca | 624 |
| Leu | Arg | Asp | Ser | Gly | Ala | Thr | Ile | Arg | Ile | Gly | Ile | Tyr | Ile | Gly | Ala | |
| | | 195 | | | | | 200 | | | | | 205 | | | | |
| ggg | atc | tgt | gct | ggg | ctg | gct | ctg | gct | ctt | atc | ttc | ggc | gct | tta | att | 672 |
| Gly | Ile | Cys | Ala | Gly | Leu | Ala | Leu | Ala | Leu | Ile | Phe | Gly | Ala | Leu | Ile | |
| 210 | | | | | 215 | | | | | 220 | | | | | | |
| ttc | aaa | tgg | tat | tct | cat | agc | aaa | gag | aag | ata | cag | aat | tta | agc | ctc | 720 |
| Phe | Lys | Trp | Tyr | Ser | His | Ser | Lys | Glu | Lys | Ile | Gln | Asn | Leu | Ser | Leu | |
| 225 | | | | | 230 | | | | | 235 | | | | | 240 | |
| atc | tct | ttg | gcc | aac | ctc | cct | ccc | tca | gga | ttg | gca | aat | gca | gta | gca | 768 |

```
Ile Ser Leu Ala Asn Leu Pro Pro Ser Gly Leu Ala Asn Ala Val Ala
            245                 250                 255 gag gga att cgc tca gaa gaa aac atc tat acc att gaa gag aac gta    816
Glu Gly Ile Arg Ser Glu Glu Asn Ile Tyr Thr Ile Glu Glu Asn Val
            260                 265                 270 tat gaa gtg gag gag ccc aat gag tat tat tgc tat gtc agc agc agg    864
Tyr Glu Val Glu Glu Pro Asn Glu Tyr Tyr Cys Tyr Val Ser Ser Arg
        275                 280                 285 cag caa ccc tca caa cct ttg ggt tgt cgc ttt gca atg cca tag        909
Gln Gln Pro Ser Gln Pro Leu Gly Cys Arg Phe Ala Met Pro
        290                 295                 300
```

<210> SEQ ID NO 107
<211> LENGTH: 302
<212> TYPE: PRT
<213> ORGANISM: Artificial
<220> FEATURE:
<223> OTHER INFORMATION: Synthetic Construct

<400> SEQUENCE: 107

```
Met Phe Ser His Leu Pro Phe Asp Cys Val Leu Leu Leu Leu Leu Leu
1               5                   10                  15

Leu Leu Thr Arg Ser Ser Glu Val Glu Tyr Arg Ala Glu Val Gly Gln
            20                  25                  30

Asn Ala Tyr Leu Pro Cys Phe Tyr Thr Pro Ala Ala Pro Gly Asn Leu
        35                  40                  45

Val Pro Val Cys Trp Gly Lys Gly Ala Cys Pro Val Phe Glu Cys Gly
    50                  55                  60

Asn Val Val Leu Arg Thr Asp Glu Arg Asn Val Thr Tyr Gln Lys Ser
65                  70                  75                  80

Ser Arg Tyr Trp Leu Asn Gly Asp Phe Arg Lys Gly Asp Val Ser Leu
                85                  90                  95

Thr Ile Glu Asn Val Thr Leu Ala Asp Ser Gly Ile Tyr Cys Cys Arg
            100                 105                 110

Ile Gln Ile Pro Gly Ile Met Asn Asp Glu Lys Phe Asn Leu Lys Leu
        115                 120                 125

Val Ile Lys Pro Ala Lys Val Thr Pro Ala Pro Thr Arg Gln Arg Asp
    130                 135                 140

Phe Thr Ala Ala Phe Pro Arg Met Leu Thr Thr Arg Gly His Gly Pro
145                 150                 155                 160

Ala Glu Thr Gln Thr Leu Gly Ser Leu Pro Asp Ile Asn Leu Thr Gln
                165                 170                 175

Ile Ser Thr Leu Ala Asn Glu Leu Arg Asp Ser Arg Leu Ala Asn Asp
            180                 185                 190

Leu Arg Asp Ser Gly Ala Thr Ile Arg Ile Gly Ile Tyr Ile Gly Ala
        195                 200                 205

Gly Ile Cys Ala Gly Leu Ala Leu Ala Leu Ile Phe Gly Ala Leu Ile
    210                 215                 220

Phe Lys Trp Tyr Ser His Ser Lys Glu Lys Ile Gln Asn Leu Ser Leu
225                 230                 235                 240

Ile Ser Leu Ala Asn Leu Pro Pro Ser Gly Leu Ala Asn Ala Val Ala
                245                 250                 255

Glu Gly Ile Arg Ser Glu Glu Asn Ile Tyr Thr Ile Glu Glu Asn Val
            260                 265                 270

Tyr Glu Val Glu Glu Pro Asn Glu Tyr Tyr Cys Tyr Val Ser Ser Arg
        275                 280                 285
```

```
Gln Gln Pro Ser Gln Pro Leu Gly Cys Arg Phe Ala Met Pro
    290                 295                 300

<210> SEQ ID NO 108
<211> LENGTH: 35
<212> TYPE: DNA
<213> ORGANISM: Artificial
<220> FEATURE:
<223> OTHER INFORMATION: Primer hTIM3chimera88-96F

<400> SEQUENCE: 108
aaaggagatg tgtctctgat catagagaat gtgac                             35

<210> SEQ ID NO 109
<211> LENGTH: 35
<212> TYPE: DNA
<213> ORGANISM: Artificial
<220> FEATURE:
<223> OTHER INFORMATION: Primer hTIM3chimera88-96R

<400> SEQUENCE: 109
agacacatct cctttgttga gatccccatt tagcc                             35

<210> SEQ ID NO 110
<211> LENGTH: 906
<212> TYPE: DNA
<213> ORGANISM: Artificial
<220> FEATURE:
<223> OTHER INFORMATION: TIM-3 chimera 88-96/pEF6 Myc_HisC
<220> FEATURE:
<221> NAME/KEY: CDS
<222> LOCATION: (1)..(906)

<400> SEQUENCE: 110 atg ttt tca cat ctt ccc ttt gac tgt gtc ctg ctg ctg ctg cta        48
Met Phe Ser His Leu Pro Phe Asp Cys Val Leu Leu Leu Leu Leu
1               5                   10                  15 cta ctt aca agg tcc tca gaa gtg gaa tac aga gcg gag gtc ggt cag    96
Leu Leu Thr Arg Ser Ser Glu Val Glu Tyr Arg Ala Glu Val Gly Gln
            20                  25                  30 aat gcc tat ctg ccc tgc ttc tac acc cca gcc gcc cca ggg aac ctc    144
Asn Ala Tyr Leu Pro Cys Phe Tyr Thr Pro Ala Ala Pro Gly Asn Leu
        35                  40                  45 gtg ccc gtc tgc tgg ggc aaa gga gcc tgt cct gtg ttt gaa tgt ggc    192
Val Pro Val Cys Trp Gly Lys Gly Ala Cys Pro Val Phe Glu Cys Gly
    50                  55                  60 aac gtg gtg ctc agg act gat gaa agg gat gtg aat tat tgg aca tcc    240
Asn Val Val Leu Arg Thr Asp Glu Arg Asp Val Asn Tyr Trp Thr Ser
65                  70                  75                  80 aga tac tgg cta aat ggg gat ctc aac aaa gga gat gtg tct ctg atc    288
Arg Tyr Trp Leu Asn Gly Asp Leu Asn Lys Gly Asp Val Ser Leu Ile
                85                  90                  95 ata gag aat gtg act cta gca gac agt ggg atc tac tgc tgc cgg atc    336
Ile Glu Asn Val Thr Leu Ala Asp Ser Gly Ile Tyr Cys Cys Arg Ile
            100                 105                 110 caa atc cca ggc ata atg aat gat gaa aaa ttt aac ctg aag ttg gtc    384
Gln Ile Pro Gly Ile Met Asn Asp Glu Lys Phe Asn Leu Lys Leu Val
        115                 120                 125 atc aaa cca gcc aag gtc acc cct gca ccg act cgg cag aga gac ttc    432
Ile Lys Pro Ala Lys Val Thr Pro Ala Pro Thr Arg Gln Arg Asp Phe
    130                 135                 140 act gca gcc ttt cca agg atg ctt acc acc agg gga cat ggc cca gca    480
Thr Ala Ala Phe Pro Arg Met Leu Thr Thr Arg Gly His Gly Pro Ala
145                 150                 155                 160
```

```
gag aca cag aca ctg ggg agc ctc cct gat ata aat cta aca caa ata    528
Glu Thr Gln Thr Leu Gly Ser Leu Pro Asp Ile Asn Leu Thr Gln Ile
            165                 170                 175 tcc aca ttg gcc aat gag tta cgg gac tct aga ttg gcc aat gac tta    576
Ser Thr Leu Ala Asn Glu Leu Arg Asp Ser Arg Leu Ala Asn Asp Leu
        180                 185                 190 cgg gac tct gga gca acc atc aga ata ggc atc tac atc gga gca ggg    624
Arg Asp Ser Gly Ala Thr Ile Arg Ile Gly Ile Tyr Ile Gly Ala Gly
    195                 200                 205 atc tgt gct ggg ctg gct ctg gct ctt atc ttc ggc gct tta att ttc    672
Ile Cys Ala Gly Leu Ala Leu Ala Leu Ile Phe Gly Ala Leu Ile Phe
210                 215                 220 aaa tgg tat tct cat agc aaa gag aag ata cag aat tta agc ctc atc    720
Lys Trp Tyr Ser His Ser Lys Glu Lys Ile Gln Asn Leu Ser Leu Ile
225                 230                 235                 240 tct ttg gcc aac ctc cct ccc tca gga ttg gca aat gca gta gca gag    768
Ser Leu Ala Asn Leu Pro Pro Ser Gly Leu Ala Asn Ala Val Ala Glu
                245                 250                 255 gga att cgc tca gaa gaa aac atc tat acc att gaa gag aac gta tat    816
Gly Ile Arg Ser Glu Glu Asn Ile Tyr Thr Ile Glu Glu Asn Val Tyr
            260                 265                 270 gaa gtg gag gag ccc aat gag tat tat tgc tat gtc agc agc agg cag    864
Glu Val Glu Glu Pro Asn Glu Tyr Tyr Cys Tyr Val Ser Ser Arg Gln
        275                 280                 285 caa ccc tca caa cct ttg ggt tgt cgc ttt gca atg cca tag            906
Gln Pro Ser Gln Pro Leu Gly Cys Arg Phe Ala Met Pro
    290                 295                 300
```

<210> SEQ ID NO 111
<211> LENGTH: 301
<212> TYPE: PRT
<213> ORGANISM: Artificial
<220> FEATURE:
<223> OTHER INFORMATION: Synthetic Construct

<400> SEQUENCE: 111

```
Met Phe Ser His Leu Pro Phe Asp Cys Val Leu Leu Leu Leu Leu Leu
1               5                   10                  15

Leu Leu Thr Arg Ser Ser Glu Val Glu Tyr Arg Ala Glu Val Gly Gln
            20                  25                  30

Asn Ala Tyr Leu Pro Cys Phe Tyr Thr Pro Ala Ala Pro Gly Asn Leu
        35                  40                  45

Val Pro Val Cys Trp Gly Lys Gly Ala Cys Pro Val Phe Glu Cys Gly
    50                  55                  60

Asn Val Val Leu Arg Thr Asp Glu Arg Asp Val Asn Tyr Trp Thr Ser
65                  70                  75                  80

Arg Tyr Trp Leu Asn Gly Asp Leu Asn Lys Gly Asp Val Ser Leu Ile
                85                  90                  95

Ile Glu Asn Val Thr Leu Ala Asp Ser Gly Ile Tyr Cys Cys Arg Ile
            100                 105                 110

Gln Ile Pro Gly Ile Met Asn Asp Glu Lys Phe Asn Leu Lys Leu Val
        115                 120                 125

Ile Lys Pro Ala Lys Val Thr Pro Ala Pro Thr Arg Gln Arg Asp Phe
    130                 135                 140

Thr Ala Ala Phe Pro Arg Met Leu Thr Thr Arg Gly His Gly Pro Ala
145                 150                 155                 160

Glu Thr Gln Thr Leu Gly Ser Leu Pro Asp Ile Asn Leu Thr Gln Ile
                165                 170                 175
```

```
Ser Thr Leu Ala Asn Glu Leu Arg Asp Ser Arg Leu Ala Asn Asp Leu
            180                 185                 190

Arg Asp Ser Gly Ala Thr Ile Arg Ile Gly Ile Tyr Ile Gly Ala Gly
        195                 200                 205

Ile Cys Ala Gly Leu Ala Leu Ala Leu Ile Phe Gly Ala Leu Ile Phe
    210                 215                 220

Lys Trp Tyr Ser His Ser Lys Glu Lys Ile Gln Asn Leu Ser Leu Ile
225                 230                 235                 240

Ser Leu Ala Asn Leu Pro Pro Ser Gly Leu Ala Asn Ala Val Ala Glu
                245                 250                 255

Gly Ile Arg Ser Glu Glu Asn Ile Tyr Thr Ile Glu Glu Asn Val Tyr
            260                 265                 270

Glu Val Glu Glu Pro Asn Glu Tyr Tyr Cys Tyr Val Ser Ser Arg Gln
        275                 280                 285

Gln Pro Ser Gln Pro Leu Gly Cys Arg Phe Ala Met Pro
    290                 295                 300
```

<210> SEQ ID NO 112
<211> LENGTH: 35
<212> TYPE: DNA
<213> ORGANISM: Artificial
<220> FEATURE:
<223> OTHER INFORMATION: Primer hTIM3chimera96-105F

<400> SEQUENCE: 112
gaatgtgact ctggatgacc atgggatcta ctgct    35

<210> SEQ ID NO 113
<211> LENGTH: 35
<212> TYPE: DNA
<213> ORGANISM: Artificial
<220> FEATURE:
<223> OTHER INFORMATION: Primer hTIM3chimera96-105R

<400> SEQUENCE: 113
tccagagtca cattctttat gatcagggac acatc    35

<210> SEQ ID NO 114
<211> LENGTH: 906
<212> TYPE: DNA
<213> ORGANISM: Artificial
<220> FEATURE:
<223> OTHER INFORMATION: TIM-3 chimera 96-105/pEF6 Myc_HisC
<220> FEATURE:
<221> NAME/KEY: CDS
<222> LOCATION: (1)..(906)

<400> SEQUENCE: 114

```
atg ttt tca cat ctt ccc ttt gac tgt gtc ctg ctg ctg ctg cta       48
Met Phe Ser His Leu Pro Phe Asp Cys Val Leu Leu Leu Leu Leu
1               5                   10                  15 cta ctt aca agg tcc tca gaa gtg gaa tac aga gcg gag gtc ggt cag   96
Leu Leu Thr Arg Ser Ser Glu Val Glu Tyr Arg Ala Glu Val Gly Gln
                20                  25                  30 aat gcc tat ctg ccc tgc ttc tac acc cca gcc gcc cca ggg aac ctc  144
Asn Ala Tyr Leu Pro Cys Phe Tyr Thr Pro Ala Ala Pro Gly Asn Leu
            35                  40                  45 gtg ccc gtc tgc tgg ggc aaa gga gcc tgt cct gtg ttt gaa tgt ggc  192
Val Pro Val Cys Trp Gly Lys Gly Ala Cys Pro Val Phe Glu Cys Gly
        50                  55                  60 aac gtg gtg ctc agg act gat gaa agg gat gtg aat tat tgg aca tcc  240
```

```
Asn Val Val Leu Arg Thr Asp Glu Arg Asp Val Asn Tyr Trp Thr Ser
 65                  70                  75                  80 aga tac tgg cta aat ggg gat ttc cgc aaa gga gat gtg tcc ctg atc      288
Arg Tyr Trp Leu Asn Gly Asp Phe Arg Lys Gly Asp Val Ser Leu Ile
                     85                  90                  95 ata aag aat gtg act ctg gat gac cat ggg atc tac tgc tgc cgg atc      336
Ile Lys Asn Val Thr Leu Asp Asp His Gly Ile Tyr Cys Cys Arg Ile
                100                 105                 110 caa atc cca ggc ata atg aat gat gaa aaa ttt aac ctg aag ttg gtc      384
Gln Ile Pro Gly Ile Met Asn Asp Glu Lys Phe Asn Leu Lys Leu Val
            115                 120                 125 atc aaa cca gcc aag gtc acc cct gca ccg act cgg cag aga gac ttc      432
Ile Lys Pro Ala Lys Val Thr Pro Ala Pro Thr Arg Gln Arg Asp Phe
        130                 135                 140 act gca gcc ttt cca agg atg ctt acc acc agg gga cat ggc cca gca      480
Thr Ala Ala Phe Pro Arg Met Leu Thr Thr Arg Gly His Gly Pro Ala
145                 150                 155                 160 gag aca cag aca ctg ggg agc ctc cct gat ata aat cta aca caa ata      528
Glu Thr Gln Thr Leu Gly Ser Leu Pro Asp Ile Asn Leu Thr Gln Ile
                165                 170                 175 tcc aca ttg gcc aat gag tta cgg gac tct aga ttg gcc aat gac tta      576
Ser Thr Leu Ala Asn Glu Leu Arg Asp Ser Arg Leu Ala Asn Asp Leu
                180                 185                 190 cgg gac tct gga gca acc atc aga ata ggc atc tac atc gga gca ggg      624
Arg Asp Ser Gly Ala Thr Ile Arg Ile Gly Ile Tyr Ile Gly Ala Gly
            195                 200                 205 atc tgt gct ggg ctg gct ctg gct ctt atc ttc ggc gct tta att ttc      672
Ile Cys Ala Gly Leu Ala Leu Ala Leu Ile Phe Gly Ala Leu Ile Phe
210                 215                 220 aaa tgg tat tct cat agc aaa gag aag ata cag aat tta agc ctc atc      720
Lys Trp Tyr Ser His Ser Lys Glu Lys Ile Gln Asn Leu Ser Leu Ile
225                 230                 235                 240 tct ttg gcc aac ctc cct ccc tca gga ttg gca aat gca gta gca gag      768
Ser Leu Ala Asn Leu Pro Pro Ser Gly Leu Ala Asn Ala Val Ala Glu
                245                 250                 255 gga att cgc tca gaa gaa aac atc tat acc att gaa gag aac gta tat      816
Gly Ile Arg Ser Glu Glu Asn Ile Tyr Thr Ile Glu Glu Asn Val Tyr
            260                 265                 270 gaa gtg gag gag ccc aat gag tat tat tgc tat gtc agc agc agg cag      864
Glu Val Glu Glu Pro Asn Glu Tyr Tyr Cys Tyr Val Ser Ser Arg Gln
        275                 280                 285 caa ccc tca caa cct ttg ggt tgt cgc ttt gca atg cca tag              906
Gln Pro Ser Gln Pro Leu Gly Cys Arg Phe Ala Met Pro
    290                 295                 300

<210> SEQ ID NO 115
<211> LENGTH: 301
<212> TYPE: PRT
<213> ORGANISM: Artificial
<220> FEATURE:
<223> OTHER INFORMATION: Synthetic Construct

<400> SEQUENCE: 115

Met Phe Ser His Leu Pro Phe Asp Cys Val Leu Leu Leu Leu Leu Leu
1                5                  10                  15

Leu Leu Thr Arg Ser Ser Glu Val Glu Tyr Arg Ala Glu Val Gly Gln
                20                  25                  30

Asn Ala Tyr Leu Pro Cys Phe Tyr Thr Pro Ala Ala Pro Gly Asn Leu
            35                  40                  45

Val Pro Val Cys Trp Gly Lys Gly Ala Cys Pro Val Phe Glu Cys Gly
```

```
              50                  55                  60
Asn Val Leu Arg Thr Asp Glu Arg Asp Val Asn Tyr Trp Thr Ser
 65                  70                  75                  80

Arg Tyr Trp Leu Asn Gly Asp Phe Arg Lys Gly Asp Val Ser Leu Ile
                 85                  90                  95

Ile Lys Asn Val Thr Leu Asp Asp His Gly Ile Tyr Cys Cys Arg Ile
                100                 105                 110

Gln Ile Pro Gly Ile Met Asn Asp Glu Lys Phe Asn Leu Lys Leu Val
            115                 120                 125

Ile Lys Pro Ala Lys Val Thr Pro Ala Pro Thr Arg Gln Arg Asp Phe
130                 135                 140

Thr Ala Ala Phe Pro Arg Met Leu Thr Thr Arg Gly His Gly Pro Ala
145                 150                 155                 160

Glu Thr Gln Thr Leu Gly Ser Leu Pro Asp Ile Asn Leu Thr Gln Ile
                165                 170                 175

Ser Thr Leu Ala Asn Glu Leu Arg Asp Ser Arg Leu Ala Asn Asp Leu
            180                 185                 190

Arg Asp Ser Gly Ala Thr Ile Arg Ile Gly Ile Tyr Ile Gly Ala Gly
            195                 200                 205

Ile Cys Ala Gly Leu Ala Leu Ala Leu Ile Phe Gly Ala Leu Ile Phe
210                 215                 220

Lys Trp Tyr Ser His Ser Lys Glu Lys Ile Gln Asn Leu Ser Leu Ile
225                 230                 235                 240

Ser Leu Ala Asn Leu Pro Pro Ser Gly Leu Ala Asn Ala Val Ala Glu
                245                 250                 255

Gly Ile Arg Ser Glu Glu Asn Ile Tyr Thr Ile Glu Glu Asn Val Tyr
            260                 265                 270

Glu Val Glu Glu Pro Asn Glu Tyr Tyr Cys Tyr Val Ser Ser Arg Gln
            275                 280                 285

Gln Pro Ser Gln Pro Leu Gly Cys Arg Phe Ala Met Pro
290                 295                 300

<210> SEQ ID NO 116
<211> LENGTH: 121
<212> TYPE: PRT
<213> ORGANISM: Homo sapiens

<400> SEQUENCE: 116

Gln Val Gln Leu Gln Glu Ser Gly Pro Gly Leu Val Lys Pro Ser Glu
 1               5                  10                  15

Thr Leu Ser Leu Thr Cys Thr Val Ser Gly Gly Ser Phe Ser Arg Gly
                 20                  25                  30

Gly Tyr Tyr Trp Asn Trp Ile Arg Gln Pro Pro Gly Lys Gly Leu Glu
             35                  40                  45

Trp Ile Gly Tyr Ile Tyr Tyr Ser Gly Ser Thr Asn Tyr Asn Pro Ser
 50                  55                  60

Leu Lys Ser Arg Val Thr Ile Ser Leu Asp Thr Ser Lys Asn Gln Phe
 65                  70                  75                  80

Ser Leu Lys Leu Ser Ser Val Thr Ala Ala Asp Thr Ala Val Tyr Tyr
                 85                  90                  95

Cys Ala Arg Asp His Tyr Ser Ser Ser Trp Thr Phe Asp Tyr Trp Gly
            100                 105                 110

Gln Gly Thr Leu Val Thr Val Ser Ser
            115                 120
```

<210> SEQ ID NO 117
<211> LENGTH: 107
<212> TYPE: PRT
<213> ORGANISM: Homo sapiens

<400> SEQUENCE: 117

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Tyr
            20                  25                  30

Leu Ala Trp Tyr Gln Gln Lys Pro Gly Gln Ala Pro Arg Leu Leu Ile
        35                  40                  45

Tyr Asp Ala Ser Asn Arg Ala Thr Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Arg Ser Asn Trp Pro Pro
                85                  90                  95

Thr Phe Gly Gln Gly Thr Lys Leu Glu Ile Lys
            100                 105

<210> SEQ ID NO 118
<211> LENGTH: 121
<212> TYPE: PRT
<213> ORGANISM: Homo sapiens

<400> SEQUENCE: 118

Gln Val Gln Leu Gln Glu Ser Gly Pro Gly Leu Val Lys Pro Ser Glu
1               5                   10                  15

Thr Leu Ser Leu Thr Cys Thr Val Ser Gly Gly Ser Ile Ser Ser Tyr
            20                  25                  30

Tyr Trp Ser Trp Ile Arg Gln Pro Pro Gly Lys Gly Leu Glu Trp Ile
        35                  40                  45

Gly Tyr Ile Phe His Ser Gly Ser Thr Asn Tyr Asn Pro Ser Leu Lys
    50                  55                  60

Ser Arg Val Thr Ile Ser Val Asp Thr Ser Lys Asn Gln Phe Ser Leu
65                  70                  75                  80

Lys Leu Ser Ser Val Thr Ala Ala Asp Thr Ala Val Tyr Tyr Cys Ala
                85                  90                  95

Arg Asp Gly Glu Tyr Phe Asp Met Leu Thr Gly Phe Asp Tyr Trp Gly
            100                 105                 110

Gln Gly Thr Leu Val Thr Val Ser Ser
        115                 120

<210> SEQ ID NO 119
<211> LENGTH: 109
<212> TYPE: PRT
<213> ORGANISM: Homo sapiens

<400> SEQUENCE: 119

Arg Cys Asp Ile Gln Met Thr Gln Ser Pro Ser Ser Leu Ser Ala Ser
1               5                   10                  15

Val Gly Asp Arg Val Thr Ile Thr Cys Arg Ala Ser Gln Gly Ile Ser
            20                  25                  30

Ser Trp Leu Ala Trp Tyr Gln Gln Lys Pro Glu Lys Ala Pro Lys Ser
        35                  40                  45

Leu Ile Tyr Ala Ala Ser Ser Leu Gln Ser Gly Val Pro Ser Arg Phe

```
            50                  55                  60
Ser Gly Ser Gly Ser Gly Thr Asp Phe Thr Leu Thr Ile Ser Ser Leu
65                  70                  75                  80

Gln Pro Glu Asp Phe Ala Thr Tyr Tyr Cys Gln Gln Tyr Asn Ser Tyr
                85                  90                  95

Pro Arg Thr Phe Gly Gln Gly Thr Lys Val Glu Ile Lys
                100                 105
```